(12) United States Patent
Colandrea et al.

(10) Patent No.: US 7,605,171 B2
(45) Date of Patent: Oct. 20, 2009

(54) (3,4-DISUBSTITUTED)PROPANOIC CARBOXYLATES AS S1P (EDG) RECEPTOR AGONISTS

(75) Inventors: Vincent J. Colandrea, North Brunswick, NJ (US); George A. Doherty, Superior, CO (US); Jeffrey J. Hale, Westfield, NJ (US); Pei Huo, Millburn, NJ (US); Irene E. Legiec, Mountainside, NJ (US); Leslie Toth, Woodbridge, NJ (US); Petr Vachal, Summit, NJ (US); Lin Yan, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 397 days.

(21) Appl. No.: 10/575,790

(22) PCT Filed: Dec. 13, 2004

(86) PCT No.: PCT/US2004/041887

§ 371 (c)(1),
(2), (4) Date: Apr. 12, 2006

(87) PCT Pub. No.: WO2005/058848

PCT Pub. Date: Jun. 30, 2005

(65) Prior Publication Data

US 2008/0249093 A1    Oct. 9, 2008

Related U.S. Application Data

(60) Provisional application No. 60/530,186, filed on Dec. 17, 2003.

(51) Int. Cl.
*A61K 31/443* (2006.01)
*A61K 31/4245* (2006.01)
*C07D 413/04* (2006.01)
*C07D 271/06* (2006.01)

(52) U.S. Cl. .................... 514/340; 514/364; 546/269.4; 548/131

(58) Field of Classification Search ................ 514/340, 514/364; 546/269.4; 548/131
See application file for complete search history.

(56) References Cited

U.S. PATENT DOCUMENTS

| 3,258,465 A | 6/1966 | Jaunin et al. |
| 6,699,853 B2 | 3/2004 | Harmsen et al. |
| 2004/0058894 A1 | 3/2004 | Doherty et al. |
| 2004/0224941 A1 | 11/2004 | Seko et al. |

FOREIGN PATENT DOCUMENTS

| WO | WO 96/04271 | 2/1996 |
| WO | WO 97/44333 | 11/1997 |
| WO | WO 00/25768 | 5/2000 |
| WO | WO 00/47188 | 8/2000 |
| WO | WO 2004/058149 | 4/2004 |
| WO | WO 2004/103279 | 12/2004 |

*Primary Examiner*—Kamal A Saeed
*Assistant Examiner*—Samantha L Shterengarts
(74) *Attorney, Agent, or Firm*—Yong Zhao; Valerie J. Camera

(57) ABSTRACT

The present invention encompasses compounds of Formula I:

as well as the pharmaceutically acceptable salts thereof. The compounds are $S1P_1/Edg1$ receptor agonists and thus have immunosuppressive, anti-inflammatory and hemostatic activities by modulating leukocyte trafficking, sequestering lymphocytes in secondary lymphoid tissues, and enhancing vascular integrity. The invention is also directed to pharmaceutical compositions containing such compounds and methods of treatment or prevention.

15 Claims, No Drawings

(3,4-DISUBSTITUTED)PROPANOIC CARBOXYLATES AS S1P (EDG) RECEPTOR AGONISTS

CROSS REFERENCE TO RELATED APPLICATIONS

This application is a U.S. National Phase application under 35 U.S.C. § 371 of PCT Application No. PCT/US2004/041887, filed Dec. 13, 2004, which claims priority under 35 U.S.C. 119 to U.S. No. 60/530,186, filed Dec. 17, 2003.

BACKGROUND OF THE INVENTION

The present invention is related to compounds that are $S1P_1$/Edg1 receptor agonists and thus have immunosuppressive, anti-inflammatory and hemostatic activities by modulating leukocyte trafficking, sequestering lymphocytes in secondary lymphoid tissues, and enhancing vascular integrity. The invention is also directed to pharmaceutical compositions containing such compounds and methods of treatment or prevention.

Immunosuppressive and antiinflammatory agents have been shown to be useful in a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves opthalmopathy, atopic dermatitis and asthma, chronic pulmonary disease, acute lung injury, acute respiratory distress syndrome, and sepsis. They have also proved useful as part of chemotherapeutic regimens for the treatment of cancers, lymphomas and leukemias.

Although the underlying pathogenesis of each of these conditions may be quite different, they have in common the activation of the immune system and the appearance of a variety of autoantibodies, self-reactive lymphocytes and/or activation of cells involved in innate immunity. Such self-reactivity may be due, in part, to a loss of the homeostatic controls under which the normal immune system operates. Similarly, following a bone-marrow or an organ transplantation, the host lymphocytes recognize the foreign tissue antigens and begin to produce both cellular and humoral responses including antibodies, cytokines and cytotoxic lymphocytes which lead to graft rejection.

One end result of an autoimmune or a rejection process is increased vascular permeability and tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

Cyclosporin A is a drug used to prevent rejection of transplanted organs. FK-506 is another drug approved for the prevention of transplant organ rejection, and in particular, liver transplantation. Cyclosporin A and FK-506 act by inhibiting the body's immune system from mobilizing its vast arsenal of natural protecting agents to reject the transplant's foreign protein. Cyclosporin A was approved for the treatment of severe psoriasis and has been approved by European regulatory agencies for the treatment of atopic dermatitis.

Though they are effective in delaying or suppressing transplant rejection, Cyclosporin A and FK-506 are known to cause several undesirable side effects including nephrotoxicity, neurotoxicity, and gastrointestinal discomfort. Therefore, an immunosuppressant without these side effects still remains to be developed and would be highly desirable.

The immunosuppressive compound FTY720 is a lymphocyte sequestration agent currently in clinical trials. FTY720 is metabolized in mammals to a compound that is a potent agonist of sphingosine 1-phosphate receptors. Agonism of sphingosine 1-phosphate receptors modulates leukocyte trafficking, induces the sequestration of lymphocytes (T-cells and B-cells) in lymph nodes and Peyer's patches without lymphodepletion, and disrupts splenic architecture, thereby interfering with T cell dependent antibody responses. S1P receptor agonists also have anti-inflammatory properties by enhancing endothelial integrity and inhibiting vascular damage consequent to the activation of the immune system. Such immunosuppression and antiinflammation is desirable to prevent rejection after organ transplantation, in the treatment of autoimmune disorders, and in the treatment of conditions that have an underlying defect in vascular integrity, such as acute lung injury, acute respiratory distress syndrome, and sepsis, —see Groeneveld, A. B. J. 2003. Vascular Pharm. 39:247-256.

Sphingosine 1-phosphate is a bioactive sphingolipid metabolite that is secreted by hematopoietic cells and stored and released from activated platelets. Yatomi, Y., T. Ohmori, G. Rile, F. Kazama, H. Okamoto, T. Sano, K. Satoh, S. Kume, G. Tigyi, Y. Igarashi, and Y. Ozaki. 2000. *Blood.* 96:3431-8. It acts as an agonist on a family of G protein-coupled receptors to regulate cell proliferation, differentiation, survival, and motility. Fukushima, N., I. Ishii, J. J. A. Contos, J. A. Weiner, and J. Chun. 2001. Lysophospholipid receptors. Annu. Rev. Pharmacol. Toxicol. 41:507-34; Hla, T., M.-J. Lee, N. Ancellin, J. H. Paik, and M. J. Kluk. 2001. Lysophospholipids—Receptor revelations. *Science.* 294:1875-1878; Spiegel, S., and S. Milstien. 2000. Functions of a new family of sphingosine-1-phosphate receptors. *Biochim. Biophys. Acta.* 1484:107-16; Pyne, S., and N. Pyne. 2000. Sphingosine 1-phosphate signalling via the endothelial differentiation gene family of G-protein coupled receptors. *Pharm. & Therapeutics.* 88:115-131. Five sphingosine 1-phosphate receptors have been identified ($S1P_1$, $S1P_2$, $S1P_3$, $S1P_4$, and $S1P_5$, also known as endothelial differentiation genes Edg1, Edg5, Edg3, Edg6, Edg8), that have widespread cellular and tissue distribution and are well conserved in human and rodent species (see Table). Binding to S1P receptors elicits signal transduction through $G_q$-, Gi/o, G12-, G13-, and Rho-dependent pathways. Ligand-induced activation of $S1P_1$ and $S1P_3$ has been shown to promote angiogenesis, chemotaxis, and adherens junction assembly through Rac- and Rho-, see Lee, M.-J., S. Thangada, K. P. Claffey, N. Ancellin, C. H. Liu, M. Kluk, M. Volpi, R. I. Sha'afi, and T. Hla. 1999. *Cell.* 99:301-12. S1P enhances endothelial barrier integrity by assembling cortical actin cytoskeletal structures and strengthening cell:cell junctions and cell:extracellular matrix interactions through S1P receptors, primarily S1P1-, see Garcia, J. G. N, F. Liu, A. D. Verin, A. Birukova, M. A. Dechert, W. T. Gerthoffer, J. R. Bamburg, D. English, 2001. J. Clin. Invest. 108:689-701, and S1P receptor agonists, including FTY720, can inhibit vascular permeability induced by VEGF in mice, see Sanchez, T., T. Estrada-Hernandez, J.-H. Paik, M.-T. Wu, K. Venkataraman, V. Brinkmann, K. Claffey, and T. Hla. 2003. J. Biol. Chem. 278:47281-47290.

Administration of sphingosine 1-phosphate to animals induces systemic sequestration of peripheral blood lymphocytes into secondary lymphoid organs, thus resulting in therapeutically useful immunosuppression, see Mandala, S., R. Hajdu, J. Bergstrom, E. Quackenbush, J. Xie, J. Milligan, R. Thornton, G.-J. Shei, D. Card, C. Keohane, M. Rosenbach, J. Hale, C. L. Lynch, K. Rupprecht, W. Parsons, H. Rosen. 2002. *Science.* 296:346-349. However, sphingosine 1-phosphate also has cardiovascular and bronchoconstrictor effects that limit its utility as a therapeutic agent. Intravenous administration of sphingosine 1-phosphate decreases the heart rate, ventricular contraction and blood pressure in rats, see Sugiyama, A., N. N. Aye, Y. Yatomi, Y. Ozaki, and K. Hashimoto. 2000. *Jpn. J. Pharmacol.* 82:338-342. In human airway smooth muscle cells, sphingosine 1-phosphate modulates contraction, cell growth and cytokine production that promote bronchoconstriction, airway inflammation and remodeling in asthma, see Ammit, A. J., A. T. Hastie, L. C. Edsall, R. K. Hoffman, Y. Amrani, V. P. Krymskaya, S. A. Kane, S. P. Peters, R. B. Penn, S. Spiegel, R. A. Panettieri. Jr. 2001, *FASEB J.* 15:1212-1214. The undesirable effects of sphingosine 1-phosphate are associated with its non-selective, potent agonist activity on all S1P receptors.

The present invention encompasses compounds which are agonists of the $S1P_1$/Edg1 receptor having selectivity over the $S1P_3$/Edg3 receptor. An $S1P_1$/Edg1 receptor selective agonist has advantages over current therapies and extends the therapeutic window of lymphocyte sequestration and vascular integrity agents, allowing better tolerability with higher dosing and thus improving efficacy as monotherapy.

While the main use for immunosuppressants and antiinflammatory agents is in treating bone marrow, organ and transplant rejection, other uses for such compounds include the treatment of arthritis, in particular, rheumatoid arthritis, insulin and non-insulin dependent diabetes, multiple sclerosis, psoriasis, inflammatory bowel disease, Crohn's disease, lupus erythematosis, asthma, allergies, chronic pulmonary disease, acute lung injury, acute respiratory disease syndrome, sepsis and the like.

Thus, the present invention is focused on providing immunosuppressant and vascular integrity compounds that are safer and more effective than prior compounds. These and other objects will be apparent to those of ordinary skill in the art from the description contained herein.

Summary of S1P Receptors

| Name | Synonyms | Coupled G proteins | mRNA expression |
|---|---|---|---|
| $S1P_1$ | Edg1, $LP_{B1}$ | $G_{i/o}$ | Widely distributed, endothelial cells |
| $S1P_2$ | Edg5, $LP_{B2}$, AGR16, H218 | $G_{i/o}$, $G_q$, $G_{12/13}$ | Widely distributed, vascular smooth muscle cells |
| $S1P_3$ | Edg3, $LP_{B3}$ | $G_{i/o}$, $G_q$, $G_{12/13}$ | Widely distributed, endothelial cells |
| $S1P_4$ | Edg6, $LP_{C1}$ | $G_{i/o}$ | Lymphoid tissues, lymphocytic cell lines |
| $S1P_5$ | Edg8, $LP_{B4}$, NRG1 | $G_{i/o}$ | Brain, spleen |

SUMMARY OF THE INVENTION

The present invention encompasses compounds of Formula A:

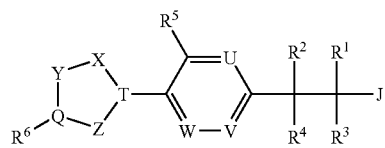

as well as the pharmaceutically acceptable salts thereof. The compounds are $S1P_1$/Edg1 receptor agonists and thus have immunosuppressive, anti-inflammatory and hemostatic activities by modulating leukocyte trafficking, sequestering lymphocytes in secondary lymphoid tissues, and enhancing vascular integrity. The invention is also directed to pharmaceutical compositions containing such compounds and methods of treatment or prevention.

DETAILED DESCRIPTION OF THE INVENTION

The invention encompasses a compound represented by Formula I

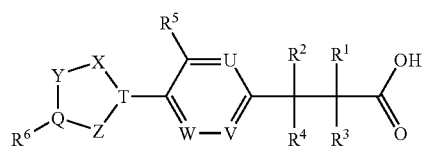

or a pharmaceutically acceptable salt thereof, wherein:
$R^1$, $R^2$, $R^3$ and $R^4$ are each independently selected from the group consisting of: —H, —F, —Cl, —Br, —I, —CN, —OH, $C_{1-6}$alkyl, $C_{2-6}$alkenyl, $C_{2-6}$alkynyl and $C_{1-5}$alkoxy,
wherein said $C_{1-6}$alkyl, $C_{2-6}$alkenyl, $C_{2-6}$alkynyl and $C_{1-5}$alkoxy are each optionally substituted with one to three substituents independently selected from the group consisting of: —F, —Cl, —Br, —I, —OH, $C_{1-8}$alkoxy and —$CO_2H$,
and any two of $R^1$, $R^2$, $R^3$ and $R^4$ may be joined together with the atoms to which they are attached to form a saturated monocyclic ring of 3 to 8 atoms optionally containing 1 or 2 oxygen atoms;
$R^5$ is selected from the group consisting of: —F, —Cl, —Br, —I, —CN, —OH, $C_{1-4}$alkyl, $C_{2-4}$alkenyl, $C_{2-4}$alkynyl and $C_{1-4}$alkoxy,
wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;
$R^6$ is selected from the group consisting of: phenyl, pyridinyl, pyrimidinyl, pyrazinyl, pyridizinyl and thienyl, each optionally substituted with one to three substituents independently selected from the group consisting of: —F, —Cl, —Br, —I, —CN, —OH, —$NR^7R^8$, —$NO_2$, phenyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{2-4}$acyloxy,
wherein said phenyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I, —OH and $C_{1-8}$alkoxy, and $R^6$ may be substituted on two adjacent atoms to form a fused partially aromatic bicyclic ring of 9 to 12 atoms optionally containing one or two oxygen or sulfur groups, or both, and optionally substituted with one to three substituents independently selected from the group consisting of: —F, —Cl, —Br, —I, —CN, —OH, and $C_{1-4}$alkyl;

$R^7$ and $R^8$ are independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy;

U, V and W are independently selected from the group consisting of: —C($R^9$)— and —N—;

each $R^9$ is independently selected from: —H, —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;

For U or V, $R^9$ and $R^1$ or $R^9$ and $R^2$ may be joined together with the atoms to which they are attached to form a 4 to 8 membered ring, optionally containing 1 or 2 oxygen, sulfur or N($R^{10}$) atoms, thus forming a fused partially aromatic bicyclic ring system of 8 to 12 atoms with the 6-membered aromatic ring to which $R^9$ is attached;

X, Y and Z are independently selected from —C($R^{11}$)=, —O—, —N=, —N($R^{12}$)— and —S— such that the resulting ring together with Q and T form an aromatic heterocycle;

Q and T are independently selected from

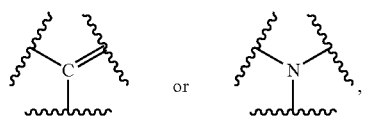

with the proviso that both Q and T are not

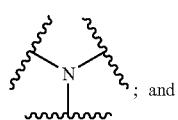

; and $R^{10}$, $R^{11}$ and $R^{12}$ are each independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkyl are each optionally substituted with one to three substituents independently selected from the group consisting of: —F, —Cl, —Br, —I, —OH and $C_{1-5}$alkoxy.

Examples of $R^6$ substituted on two adjacent atoms to form a fused partially aromatic bicyclic ring of 9 to 12 atoms optionally containing one or two oxygen or sulfur groups, or both, includes dihydroquinoline, tetrahydroquinoline, chroman, thiochroman, and the like.

The aromatic heterocycles formed by X, Y, Z, Q and T include, for example, pyrrole, furan, thiophene, pyrazole, imidazole, oxazole, isoxazole, thiazole, isothiazole, triazole, oxadiazole, thiadiazole and tetrazole.

An embodiment of the invention encompasses a compound of Formula I wherein $R^5$ is methyl.

Another embodiment of the invention encompasses a compound of Formula I wherein $R^6$ is selected from the group consisting of: phenyl and pyridinyl, each optionally substituted with one to three substituents independently selected from the group consisting of: —F, —Cl, —Br, —I, —CN, —OH, —NR$^7$R$^8$, —NO$_2$, $C_{1-4}$alkyl, $C_{3-6}$cycloalkyl, $C_{2-4}$alkenyl, $C_{2-4}$alkynyl, $C_{1-4}$alkoxy, $C_{1-4}$alkylthio, $C_{3-6}$cycloalkoxy and $C_{1-4}$acyloxy, wherein said $C_{1-4}$alkyl, $C_{3-6}$cycloalkyl, $C_{2-4}$alkenyl, $C_{2-4}$alkynyl, $C_{1-4}$alkoxy, $C_{1-4}$alkylthio, $C_{3-6}$cycloalkoxy and $C_{1-4}$acyloxy are each optionally substituted from one up to the maximum number of substitutable positions with a substituent independently selected from the group consisting of: —F, —Cl, —Br, —I, —OH and $C_{1-8}$alkoxy; and $R^7$ and $R^8$ are independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy.

Another embodiment of the invention encompasses a compound of Formula I wherein V and W are —CH—.

Another embodiment of the invention encompasses a compound of Formula Ia

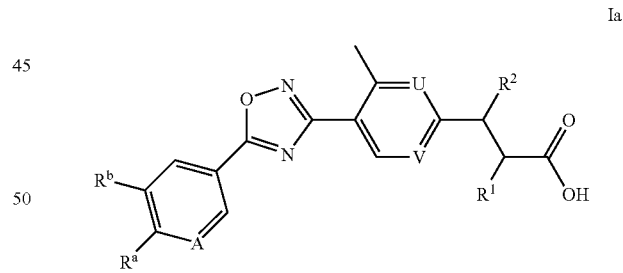

or a pharmaceutically acceptable salt thereof, wherein:

$R^1$ and $R^2$ are independently selected from the group consisting of: —H, —OH and methyl or $R^1$ and $R^2$ may be joined together with the atoms to which they are attached to form cyclopropyl;

U and V are each independently selected from the group consisting of: —C($R^9$)— and —N—;

each $R^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy, and For U or V, $R^9$ and $R^1$ or $R^9$ and $R^2$ may be joined together with the atoms to which they are attached to form a 5 membered ring, thus forming a fused partially aromatic bicyclic ring system of 9 atoms with the 6-membered aromatic ring to which $R^9$ is attached;

A is selected from the group consisting of: —N— and —C($R^{13}$)—, wherein $R^{13}$ is selected from the group consisting of: —H, —F, —Cl, —Br, —I, —CN, —$CH_3$, —$OCH_3$, —$CF_3$, ethynyl, —$NO_2$ and —$NH_2$;

$R^a$ is selected from the group consisting of: $NR^7R^8$, $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy, wherein said $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I and —OH;

$R^7$ and $R^8$ are independently selected from the group consisting of: —H and $C_{1-6}$alkyl, optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy; and $R^b$ is selected from the group consisting of: —H, —F, —Cl, —Br, —I, —CN, —$CH_3$, —$OCH_3$, —$CF_3$, ethynyl, —$NO_2$ and —$NH_2$.

Another embodiment of the invention encompasses a compound of Formula Ib

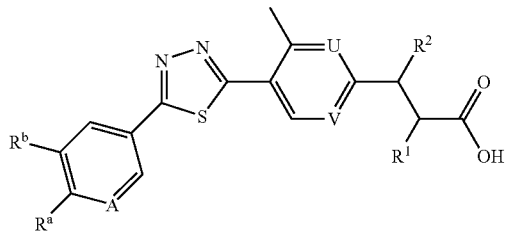

Ib or a pharmaceutically acceptable salt thereof, wherein:

$R^1$ is selected from the group consisting of: —H, —OH and methyl;

A is selected from the group consisting of: —N— and —C($R^{13}$)—, wherein $R^{13}$ is selected from the group consisting of: —H, —F, —Cl, —Br, —I, —CN, —$CH_3$, —$OCH_3$, —$CF_3$, ethynyl, —$NO_2$ and —$NH_2$;

$R^a$ is selected from the group consisting of: $NR^7R^8$, $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy, wherein said $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I and —OH;

$R^7$ and $R^8$ are independently selected from the group consisting of: —H and $C_{1-6}$alkyl, optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy; and $R^b$ is selected from the group consisting of: —H, —F, —Cl, —Br, —I, —CN, —$CH_3$, —$OCH_3$, —$CF_3$, ethynyl, —$NO_2$ and —$NH_2$.

Another embodiment of the invention encompasses a compound of Formula Ic

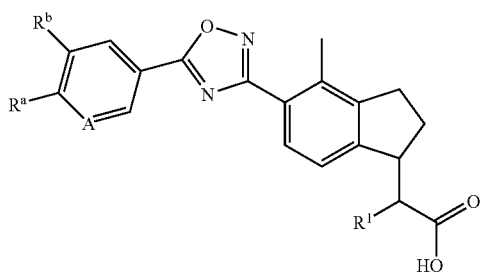

Ic or a pharmaceutically acceptable salt thereof, wherein:

$R^1$ and $R^2$ are independently selected from the group consisting of: —H, —OH and methyl or $R^1$ and $R^2$ may be joined together with the atoms to which they are attached to form cyclopropyl;

U and V are each independently selected from the group consisting of: —C($R^9$)— and —N—;

each $R^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy, and For U or V, $R^9$ and $R^1$ or $R^9$ and $R^2$ may be joined together with the atoms to which they are attached to form a 5 membered ring, thus forming a fused partially aromatic bicyclic ring system of 9 atoms with the 6-membered aromatic ring to which $R^9$ is attached;

A is selected from the group consisting of: —N— and —C($R^{13}$)— wherein $R^{13}$ is selected from the group consisting of: —H, —F, —Cl, —Br, —I, —CN, —$CH_3$, —$OCH_3$, —$CF_3$, ethynyl, —$NO_2$ and —$NH_2$;

$R^a$ is selected from the group consisting of: $NR^7R^8$, $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy, wherein said $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I and —OH;

$R^7$ and $R^8$ are independently selected from the group consisting of: —H and $C_{1-6}$alkyl, optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy; and $R^b$ is selected from the group consisting of: —H, —F, —Cl, —Br, —I, —CN, —CH$_3$, —OCH$_3$, —CF$_3$, ethynyl, —NO$_2$ and —NH$_2$.

Another embodiment of the invention encompasses a compound of Formula Id

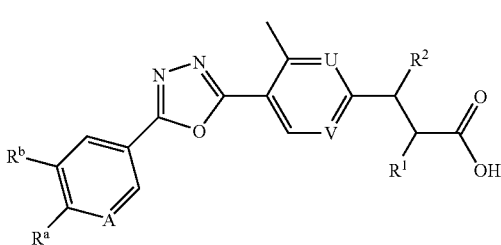

Id or a pharmaceutically acceptable salt thereof, wherein:

$R^1$ and $R^2$ are independently selected from the group consisting of: —H, —OH and methyl or $R^1$ and $R^2$ may be joined together with the atoms to which they are attached to form cyclopropyl;

U and V are each independently selected from the group consisting of: —C($R^9$)— and —N—;

each $R^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{1-4}$alkenyl, $C_{1-4}$alkynyl and $C_{1-4}$alkoxy are each optionally substituted with one to three substituents independently selected from the group consisting of: —F, —Cl, —Br, —I, —OH and $C_{1-8}$alkoxy, and $R^9$ and $R^1$ or $R^9$ and $R^2$ may be joined together with the atoms to which they are attached to form a 5 membered ring, thus forming a fused partially aromatic bicyclic ring system of 9 atoms with the 6-membered aromatic ring to which $R^9$ is attached;

A is selected from the group consisting of: —N— and —C($R^{13}$)—, wherein $R^{13}$ is selected from the group consisting of: —H, —F, —Cl, —Br, —I, —CN, —CH$_3$, —OCH$_3$, —CF$_3$, ethynyl, —NO$_2$ and —NH$_2$;

$R^a$ is selected from the group consisting of: $NR^7R^8$, $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy, wherein said $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I and —OH;

$R^7$ and $R^8$ are independently selected from the group consisting of: —H and $C_{1-6}$alkyl, optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy; and $R^b$ is selected from the group consisting of: —H, —F, —Cl, —Br, —I, —CN, —CH$_3$, —OCH$_3$, —CF$_3$, ethynyl, —NO$_2$ and —NH$_2$.

The invention is further exemplified in the examples that follow.

The invention also encompasses a method of treating an immunoregulatory abnormality in a mammalian patient in need of such treatment comprising administering to said patient a compound of Formula I or Formula A in an amount that is effective for treating said immunoregulatory abnormality.

Within this embodiment is encompassed the above method wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

Also within this embodiment is encompassed the above method wherein the immunoregulatory abnormality is bone marrow or organ transplant rejection or graft-versus-host disease.

Also within this embodiment is encompassed the above method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also within this embodiment is encompassed the above method wherein the immunoregulatory abnormality is selected from the group consisting of:
1) multiple sclerosis,
2) rheumatoid arthritis,
3) systemic lupus erythematosus,
4) psoriasis,
5) rejection of transplanted organ or tissue,
6) inflammatory bowel disease,
7) a malignancy of lymphoid origin,
8) acute and chronic lymphocytic leukemias and lymphomas and
9) insulin and non-insulin dependent diabetes.

The invention also encompasses a method of suppressing the immune system in a mammalian patient in need of immunosuppression comprising administering to said patient an immunosuppressing effective amount of a compound of Formula I or Formula A.

The invention also encompasses a pharmaceutical composition comprised of a compound of Formula I or Formula A in combination with a pharmaceutically acceptable carrier.

The invention also encompasses a method of treating a respiratory disease or condition in a mammalian patient in need of such treatment comprising administering to said patient a compound of Formula I or Formula A in an amount that is effective for treating said respiratory disease or condition. Within this embodiment is encompasses the above method wherein the respiratory disease or condition is selected from the group consisting of: asthma, chronic bronchitis, chronic obstructive pulmonary disease, adult respiratory distress syndrome, infant respiratory distress syndrome, cough, eosinophilic granuloma, respiratory syncytial virus bronchiolitis, bronchiectasis, idiopathic pulmonary fibrosis, acute lung injury and bronchiolitis obliterans organizing pneumonia.

The invention also encompasses a method for treating a disease or condition related to vascular integrity in a patient in need thereof, wherein the disease or condition is selected from the group consisting of: angioedemas, vasculitis, vascular damage caused by ischemic diseases and thrombosis, ischemic bowel diseases, inflammatory bowel diseases, necrotizing enterocolitis, intestinal lesions associated with thermal burns, arteriosclerosis, athersosclerosis, aortitis syndrome, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, sepsis, pancreatitis, disease caused by histamine or leukotriene-C4 release, necrosis caused by toxin, viral hepatitis, shock or anoxia, senile dementia, and trauma, comprising administering to the patient a compound of Formula I or Formula A in an amount that is effective to treat the disease or condition.

The invention also encompasses a method for treating a disease or condition associated with cerebral or pulmonary edema in a patient in need thereof, comprising administering to the patient a compound of Formula I or Formula A in an amount that is effective to treat the disease or condition. Within this embodiment is encompassed a disease or condition selected from the group consisting of: shock, sepsis, acute respiratory distress syndrome and brain edema.

Also, within this embodiment is encompassed the above method wherein the patient also has a respiratory disease or condition.

Also, within this embodiment is encompassed the above method wherein the patient is also suffering from a cardiovascular disease or condition.

The invention is described using the following definitions unless otherwise indicated.

When a nitrogen atom appears in a formula of the present specification, it is understood that sufficient hydrogen atoms or substituents are present to satisfy the valency of the nitrogen atom.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propenyl, 1-methylethenyl, butenyl and the like.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, cyclobutylmethyl cyclopropylmethyl and the like.

The term "cycloalkoxy" means cycloalkyl as defined above attached to a molecule by an oxygen atom (cycloalkyl-O) and includes, for example, cyclopentyloxy, cyclopropylmethyloxy and the like.

The term "acyl" means an organic radical derived from an organic acid by the removal of a hydroxyl group and having the general formula R—C(O)— wherein R is a linear or branched alkyl chain which together with the carbonyl carbon atom has the indicated number of carbon atoms. For example, $C_{2-4}$acyl, includes acetyl, propionyl and butyryl. The term "acyloxy" means acyl as defined above attached to a molecule by an oxygen atom (acyl-O) and includes, for example, acetyloxy and the like.

For purposes of this specification, the following abbreviations have the indicated meanings:

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

The term "treating" encompasses not only treating a patient to relieve the patient of the signs and symptoms of the disease or condition but also prophylactically treating an asymptomatic patient to prevent the onset or progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The invention described herein includes pharmaceutically acceptable salts and hydrates. Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I or Formula A.

For purposes of this Specification, "pharmaceutically acceptable hydrate" means the compounds of the instant invention crystallized with one or more molecules of water to form a hydrated form.

Compounds of Formula I or Formula A may contain one or more asymmetric centers and can thus occur as racemates and racemic mixtures, single enantiomers, diastereomeric mixtures and individual diastereomers. The present invention is meant to comprehend all such isomeric forms of the compounds of Formula I or Formula A.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I or Formula A.

Compounds of the Formula I or Formula A may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Formula A may be obtained by stereospecific synthesis using optically pure starting materials or reagents of known configuration.

The invention also includes the compounds falling within Formula I or Formula A in the form of one or more stereoisomers, in substantially pure form or in the form of a mixture of stereoisomers. All such isomers are encompassed within the present invention.

By virtue of their $S1P_1$/Edg1 agonist activity, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves opthalmopathy and asthma. The compounds of the invention are also useful for enhancing vascular integrity.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremnic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The compounds of the present invention are also useful for treating or preventing Alzheimer's Disease.

Also embodied within the present invention is a method of preventing or treating resistance to transplantation or transplantation rejection of organs or tissues in a mammalian patient in need thereof, which comprises administering a therapeutically effective amount of the compound of Formula I or Formula A.

A method of suppressing the immune system in a mammalian patient in need thereof, which comprises administering to the patient an immune system suppressing amount of the compound of Formula I or Formula A is yet another embodiment.

Most particularly, the method described herein encompasses a method of treating or preventing bone marrow or organ transplant rejection which is comprised of administering to a mammalian patient in need of such treatment or prevention a compound of Formula I or Formula A, or a pharmaceutically acceptable salt or hydrate thereof, in an amount that is effective for treating or preventing bone marrow or organ transplant rejection.

The compounds of the present invention are also useful for treating a respiratory diseases or condition, such as asthma, chronic bronchitis, chronic obstructive pulmonary disease, adult respiratory distress syndrome, infant respiratory distress syndrome, cough, eosinophilic granuloma, respiratory syncytial virus bronchiolitis, bronchiectasis, idiopathic pulmonary fibrosis, acute lung injury and bronchiolitis obliterans organizing pneumonia.

Furthermore, the compounds of the present invention are selective agonists of the $S1P_1$/Edg1 receptor having selectivity over $S1P_3$/Edg3 receptor. An Edg1 selective agonist has advantages over current therapies and extends the therapeutic window of lymphocytes sequestration agents, allowing better tolerability with higher dosing and thus improving efficacy as monotherapy.

The present invention also includes a pharmaceutical formulation comprising a pharmaceutically acceptable carrier and the compound of Formula I or Formula A or a pharmaceutically acceptable salt or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506, rapamycin, FFY720 and ISAtx247 (Isotechnika). Methods of co-administering a compound of Formula I or Formula A with a second immunosuppressive agent, including one or more of the above, is also encompassed within the invention.

The present compounds, including salts and hydrates thereof, are useful in the treatment of autoimmune diseases, including the prevention of rejection of bone marrow transplant, foreign organ transplants and/or related afflictions, diseases and illnesses.

The compounds of this invention can be administered by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 1 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I or Formula A in suitable propellants, such as fluorocarbons or hydrocarbons.

For ocular administration, an ophthalmic preparation may be formulated with an appropriate weight percent solution or suspension of the compounds of Formula I or Formula A in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Methods of Synthesis

A convenient method to prepare 4-(1,2,4-oxadiazol-3-yl) arylpropionic acid compounds of general structure i in the present invention is shown in Scheme 1. Methods to prepare an N-hydroxyamidine intermediates of general structure ii are known to those skilled in the art and representative methods of their preparation can be found in WO 03/061567 A2. Such intermediates can be treated with an activated carboxylic acid in the presence of a suitable base and solvent to give an N-acyloxyamidine of general structure iii. The carboxylic acid in this reaction can be activated for acylation with a reagent such as N,N'-dicyclohexylcarbodiimide, 1-(3-dimethylaminopropyl)-3-ethylcarbodiimide, 1,1'-carbonyldiimidazole, or bis(2-oxo-3-oxazolidinyl)phosphinic chloride in the presence of a suitable base (if necessary) such as triethylamine, N,N-diisopropylethylamine, or sodium bicarbonate in a solvent such as 1,2-dichloroethane, toluene, xylenes, THF, acetonitrile, N,N-dimethylformamide or N-methyl pyrrolidinone. Alternatively, an acid chloride, acid anhydride, acyl imidazole could also be used in the presence of the aforementioned bases and solvents to give iii. Intermediate iii can be isolated using methods known to those skilled in the art (e.g., crystallization, silica gel chromatography, HPLC) and in a subsequent step, cyclized/dehydrated by warming in a suitable solvent (e.g., 1,2-dichloroethane, toluene, xylenes, THF, acetonitrile, N,N-dimethylformamide or N-methylpyrrolidinone) to give a 1,2,4-oxadiazole of structure iv. Conversion of iii to iv may require added base, in which case reagents such as pyridine, N,N-diisopropylethylamine or tetrabutylammonium fluoride can be used. It may be more convenient or desirable to not isolate N-acyloxyamidine iii, in which case the transformation of ii to iv can be carried out as a continuous process. Other methods to prepare 1,2,4-oxadiazoles are potentially pertinent to the present invention and are known to those skilled in the art and have been reviewed in the literature (see, Clapp, L. B., "1,2,3- and 1,2,4-Oxadiazoles", pp. 366-91 in *Comprehensive Heterocyclic Chemistry, Volume 6*, Potts, K. T., Editor, Pergamon Press, 1984).

The final compound i can be obtained from iv by ester cleavage (i.e., —CO$_2$A→—CO$_2$H) which can be accomplished under basic, acidic, or reductive conditions depending on the chemical structure of —CO$_2$A. Representative examples of this would include (but are not limited to): if -A is —CH$_3$ or —CH$_2$CH$_3$, treating iv with aqueous lithium, sodium or potassium hydroxide in the presence of a suitable cosolvent such as methanol, ethanol, dioxane or THF at or above room temperature can give i; if -A is —C(CH$_3$)$_3$, treating iv with trifluoroacetic acid or hydrochloric acid in a suitable solvent, such as methanol, ethanol, ethyl acetate or THF can give i; if -A is —CH$_2$Ph, stirring a solution of iv in a suitable solvent, such as methanol, ethanol, ethyl acetate or THF, and a palladium catalyst, such as palladium on carbon or palladium hydroxide on carbon, in the presence of hydrogen gas at or above atmospheric pressure can give i.

Scheme 1

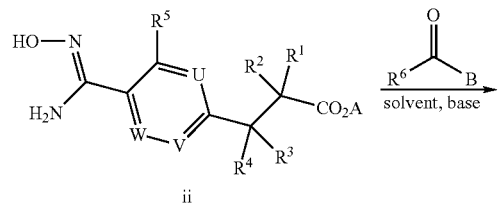

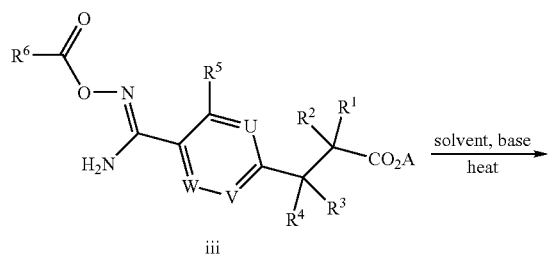

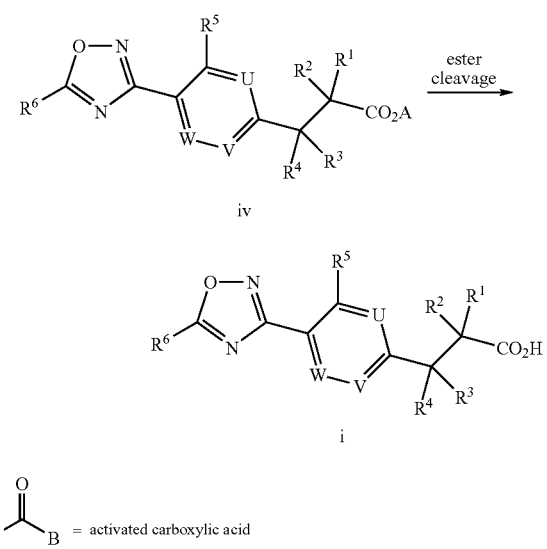

A related convenient method to prepare 4-(1,2,4-oxadiazol-3-yl)arylpropionic acid compounds of general structure viii in the present invention is shown in Scheme 2. N-Hydroxyamidine v can be first converted to 1,2,4-oxadiazole intermediate vi using procedures analogous to those described in Scheme 1 to convert ii to iv. Coupling of vi (where C=Cl, Br, I or OSO$_2$CF$_3$) and an α,β-unsaturated carboxylate ester can be carried out under Heck conditions, i.e. by treating a mixture of the coupling partners with a catalytic amount of palladium(II) salt (palladium(II) acetate, palladium(II) chloride) or a palladium(0) source (tris(dibenzylideneacetone)palladium(0), tetrakis(triphenylphosphine)palladium(0) with or without added ligand (e.g., triphenylphosphine, 1.1'-biphenyl-2-yl(di-tert-butyl)phosphine) and a tertiary amine base (triethylamine, N,N-diisopropylethylamine, N-methyldicyclohexylamine) in a suitable solvent (dimethylformamide, N-methylpyrrolidinone) at or above room temperature to give vii. The double bond of vii can be reduced via catalytic hydrogenation (stirring a solution of vii in a suitable solvent, such as methanol, ethanol, ethyl acetate or THF, and a palladium catalyst, such as palladium on carbon or palladium hydroxide on carbon, in the presence of hydrogen gas at or above atmospheric pressure) or by treating vii with lithium tri(sec-butyl)borohydride in THF at −78° C. or with magnesium methoxide in methanol at room temperature. Final compound viii is obtained by ester cleavage using methods analogous to those described in Scheme 1 to convert iv to i.

Scheme 2

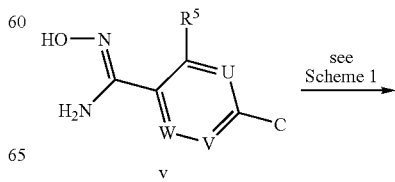

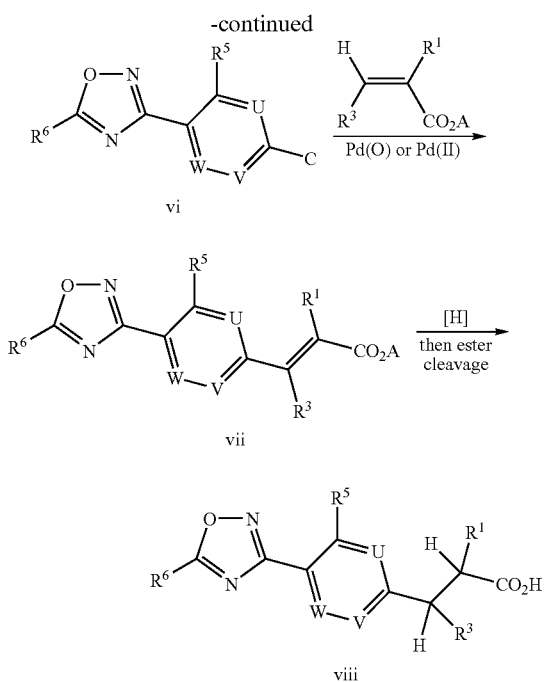

—C≡ —Cl, —Br, —I, —OSO₃CF₃

Intermediate vii can also be further functionalized to afford other compounds that fall within the scope of the present invention (Scheme 3). Conversion of vii to the corresponding cyclopropylcarboxylate ix can be accomplished by treating vii with trimethylsulfoxonium iodide and a strong base (sodium hydride, potassium t-butoxide) in dimethylsulfoxide or with diazomethane in the presence of a catalytic amount of palladium acetate in a suitable solvent (diethyl ether, dimethoxyethane, tetrahydrofuran). Ester cleavage to give x can be accomplished using methods analogous to those described in Scheme 1 to convert iv to i. Treating vii with an oxidant such as N-methylmorpholine N-oxide in the presence of catalytic osmium tetraoxide in a suitable solvent can give diol xi and again ester cleavage would give xii. Intermediate xi could also be treated with a ketone or a masked ketone in the presence of a catalytic amount of an acid (boron trifluoride etherate, toluene fulfonic acid, phosphorus pentoxide) in a suitable solvent (dichloromethane, 1,2-dichloroethane, toluene) at or above room temperature to give cyclized 1,3-dioxolanes of structure xiii. Ester cleavage as previously described would give xliii.

Scheme 3

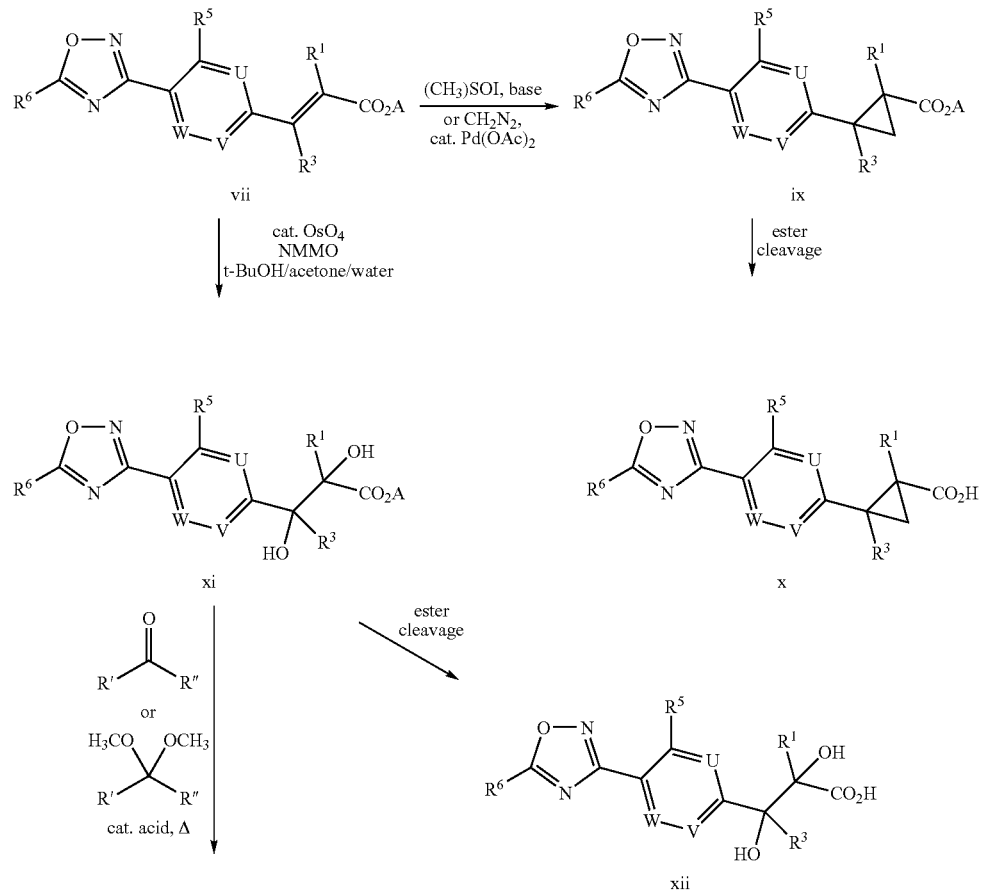

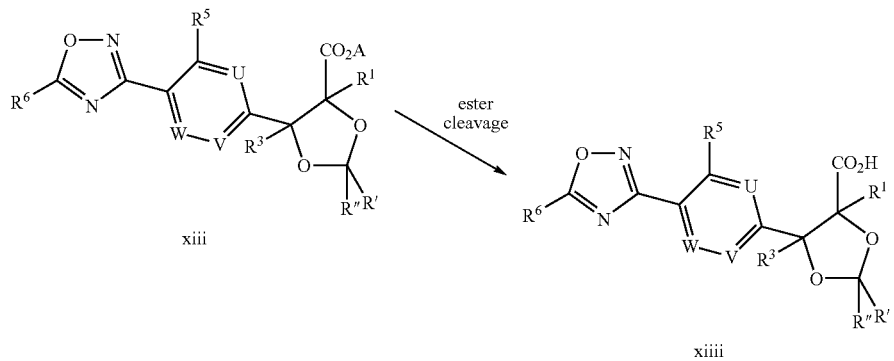

Intermediate vi can be elaborated in other manners to afford compounds that fall within the scope of the present invention (Scheme 4). Treating vi with a functionalized oragnozinc reagent such as xiii in the presence of a nickel(0) or palladium(0) catalyst in an appropriate solvent (dimethoxyethane, tetrahydrofuran, dioxane, toluene) at or above room temperature followed by ester cleavage (as described in Scheme 1 for the conversion of vi to i) can afford xiv. Stille coupling of vi and vinyltributyltin followed by oxidation of the resulting styrene can afford aldehyde xv which can be used to prepare several different compound classes within the scope of the present invention. These would include (but are not limited to): 1)

Treatment of xv with bis(2,2,2-trifluoroethyl)(methoxycarbonyl-methyl)phosphonate to give the cis α,β-unsaturated ester xvi. This intermediate can then be elaborated to cyclopropyl carboxylate xvii or diol xviii using conditions analogous to those described in Scheme 3 to convert vii to x or vii to xii, respectively. 2) Treatment of aldehyde xv with a Reformatsky reagent followed by conversion of the hydroxy of the resulting product to functional group (e.g. oxalate ester, xanthate, aryl thiocarbamate) that will allow for subsequent a radical formation/reduction reaction. Ester cleavage using conditions analogous to those described in Scheme 1 to convert vi to i can afford xx.

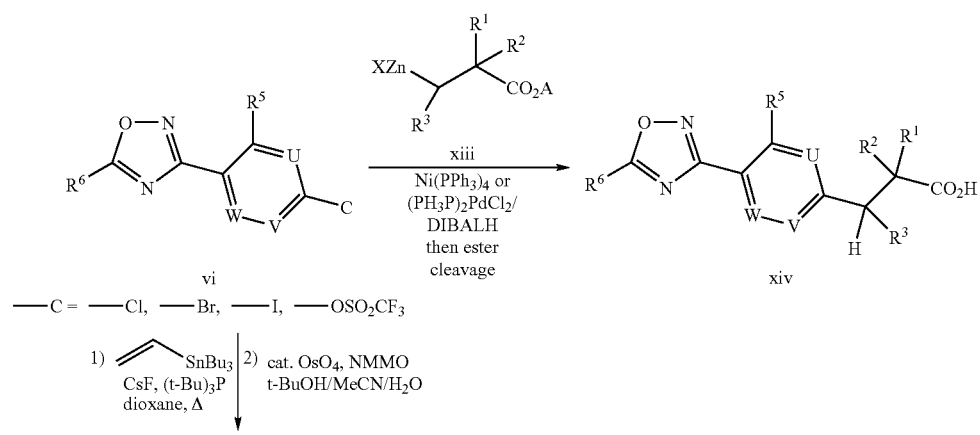

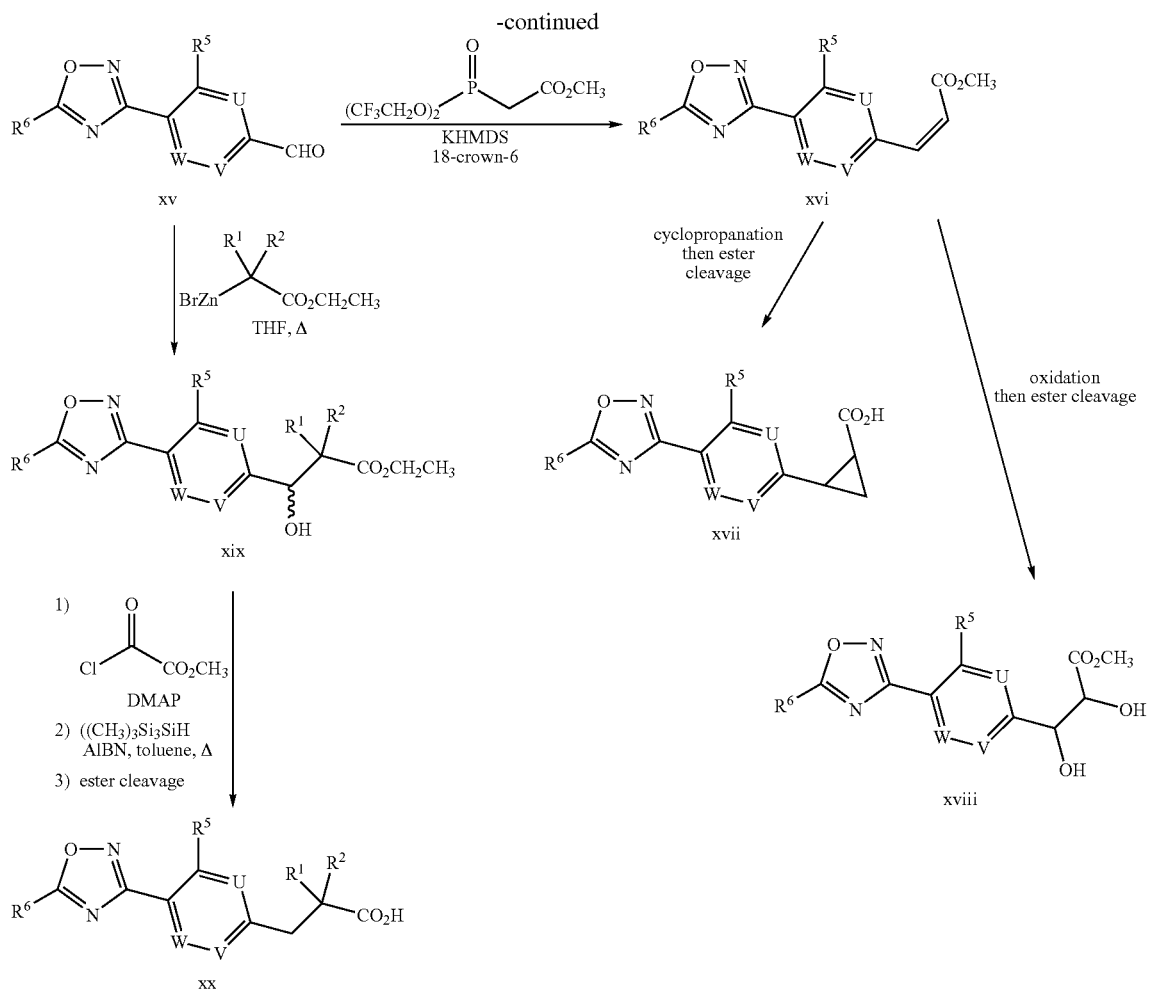

A convenient method to prepare 5-(1,2,4-oxadiazol-3-yl)-4-substituted indan-1-yl acetic acid compounds of general structure xxvii in the present invention is shown in Scheme 5. A benzoyl chloride xxi is first be treated with the potassium salt of ethyl malonic acid in the presence of magnesium chloride and triethylamine in acetonitrile to afford a β-keto ester which can subsequently be reduced via catalytic hydrogenation ($H_2$ at or above atmospheric pressure in the presence of a palladium metal catalyst in an alcohol solvent) or chemically (triethylsilane/trifluoroacetic acid) to an aryl propionic acid ester xxii. Ester saponification and acid chloride formation followed by an intramolecular Friedel-Crafts reaction can then give indanone xxiii. This intermediate can be elaborated to indane acetic acid ester xxiv by a variety of methods that include, but are not limited to Wittig, Horner-Wadsworth-Emmons or Reformatsky homologation followed by reduction of the resulting α,β-unsaturated ester or β-hydroxy ester to give xxiv. Conversion of the 5-methoxy group of xxiv to the nitrile of xxv can be acconmplished in a three step sequence: 1) demethylation using a strong Lewis acid ($BCl_3$, $BBr_3$) in a suitable solvent (dichloromethane, dichloroethane) to give a phenol; 2) formation of a trifluoromethylsulfonate ester using trifluoromethylsulfonic anhydride in the presence of base (pyridine, collidine) in a suitable solvent (dichloromethane, dichloroethane); 3) treatment of the triflate with zinc cyanide or copper cyanide in the presence of a palladium(0) catalyst in a suitable solvent (tetrahydrofuran, dioxane, N-methylpyrrolidinone, N,N-dimethylformamide) at or above room temperature. Nitrile xxv is treated with hydroxyamine in an alcoholic solvent (MeOH, EtOH) at or above room temperature to give N-hydroxyamidine xxvi. This compound can be converted to the final product xxvii using procedures analogous to those described in Scheme 1 to convert ii to i.

Scheme 5

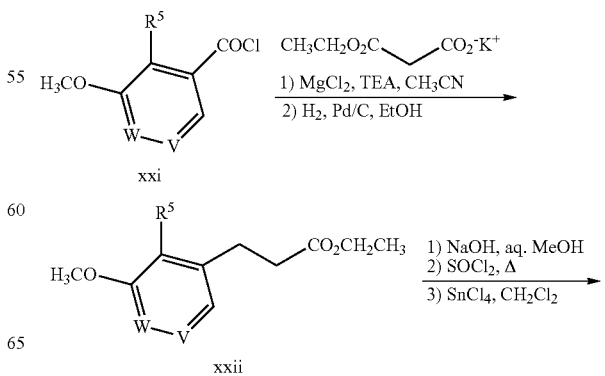

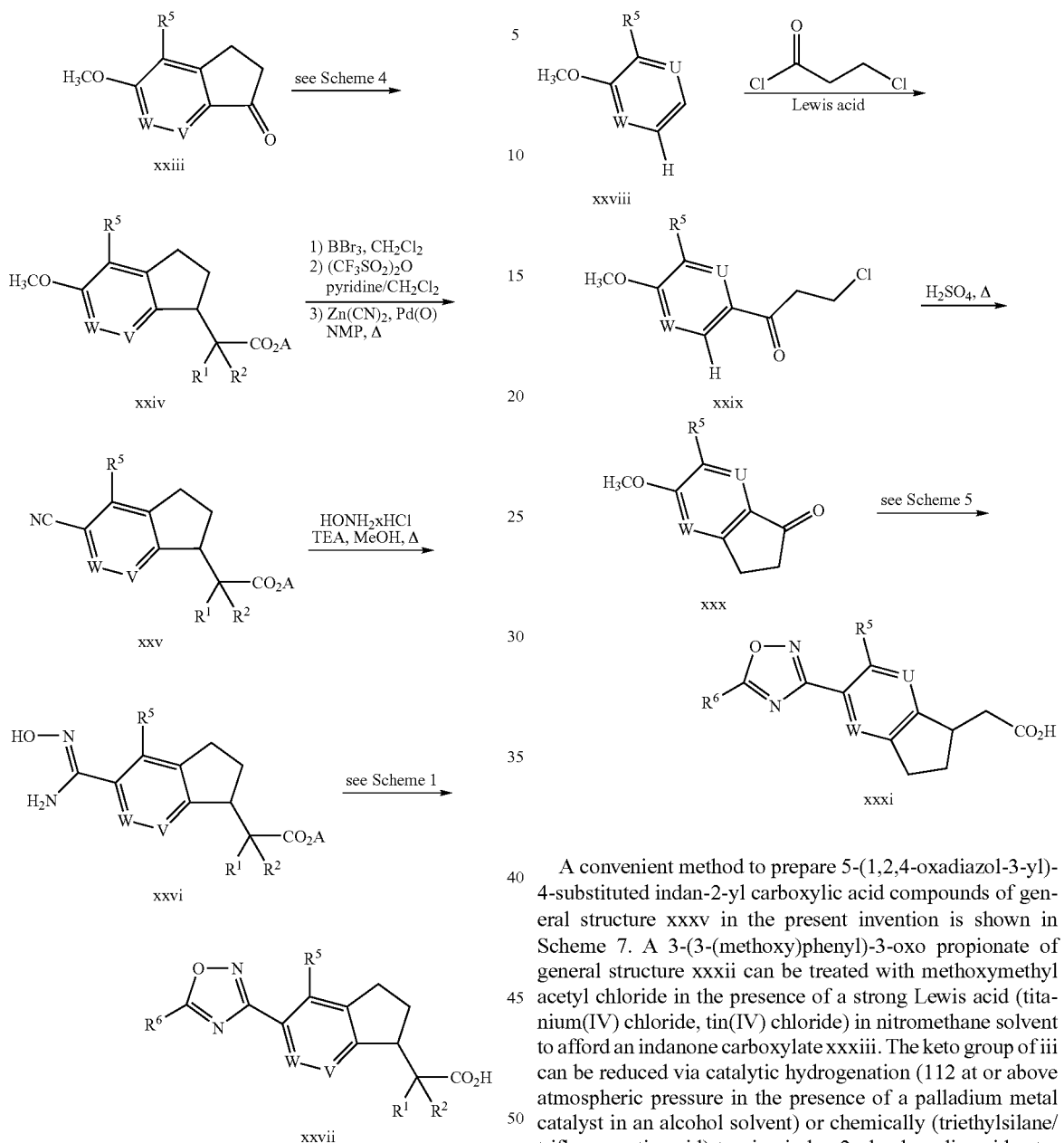

A convenient method to prepare 5-(1,2,4-oxadiazol-3-yl)-6-substituted indan-1-yl acetic acid compounds of general structure xxxi in the present invention is shown in Scheme 6. A substituted anisole of the structure xxviii can be treated with 3-chloropropionyl chloride in the presence of a strong Lewis acid (titanium(IV) chloride, tin(IV) chloride) in a suitable solvent (dichloromethane, 1,2-dichloroethane, nitrobenzene) at or below room temperate to give ketone xxix. Heating xxix in sulfuric acid can then give indanone xxx. Subjecting these indanone intermediates to reaction conditions analogous to those described in Scheme 5 to convert xxiii to xxvii will give the final compound of general structure xxxi.

A convenient method to prepare 5-(1,2,4-oxadiazol-3-yl)-4-substituted indan-2-yl carboxylic acid compounds of general structure xxxv in the present invention is shown in Scheme 7. A 3-(3-(methoxy)phenyl)-3-oxo propionate of general structure xxxii can be treated with methoxymethyl acetyl chloride in the presence of a strong Lewis acid (titanium(IV) chloride, tin(IV) chloride) in nitromethane solvent to afford an indanone carboxylate xxxiii. The keto group of iii can be reduced via catalytic hydrogenation (112 at or above atmospheric pressure in the presence of a palladium metal catalyst in an alcohol solvent) or chemically (triethylsilane/trifluoroacetic acid) to give indan-2-ylcarboxylic acid ester xxxiv. Intermediates of this general structure can be converted to target compounds xxxv using a sequence of reactions analogous to those used to prepare xxviii from xxiv as described in Scheme 5.

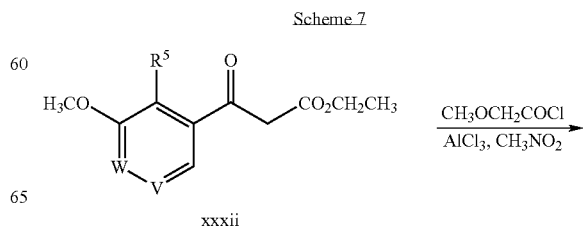

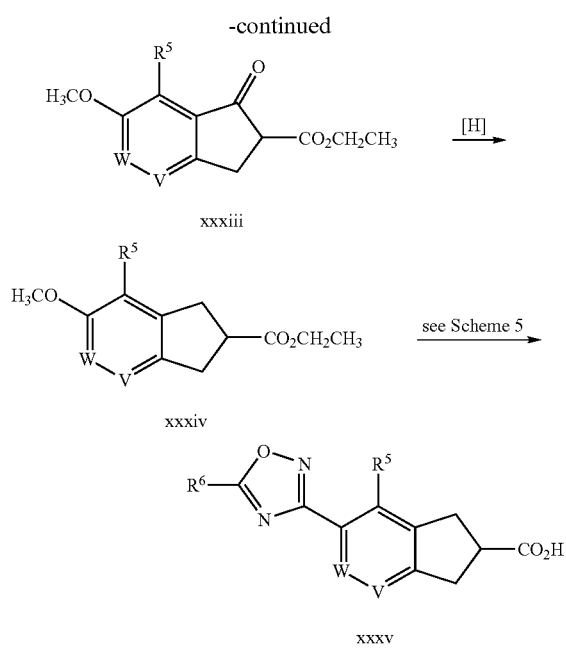

Convenient methods to prepare 5-(1,3,4-thiadiazol-2-yl) arylpropionic acid and 5-(1,3,4-oxadiazol-2-yl)arylpropionic acid compounds of general structures xxxix and xli, respectively, in the present invention are shown in Scheme 8. An acyl hydrazide of structure xxxvi be treated with an activated carboxylic acid in the presence of a suitable base and solvent to give an N,N'diacylhydrazide of general structure xxxvii. The carboxylic acid in this reaction can be activated for acylation with a reagent such as N,N'-dicyclohexylcarbodiimide, 1-(3-dimethylaminopropyl)-3-ethylcarbodiimide, 1,1'-carbonyldiimidazole, or bis(2-oxo-3-oxazolidinyl)phosphinic chloride in the presence of a suitable base (if necessary) such as triethylamine, N,N-diisopropylethylamine, or sodium bicarbonate in a solvent such as 1,2-dichloroethane, toluene, xylenes, N,N-dimethylformamide or N-methylpyrrolidinone. Alternatively, an acid chloride, acid anhydride, acyl imidazole could also be used in the presence of the aforementioned bases and solvents to give xxxvii. These compounds can be converted to 1,3,4-thiadiazole intermediates xxxviii by heating them with Lawesson's reagent in pyridine followed by heating with phosphorous pentasulfide. Alternatively, xxxvii can be converted to 1,3,4-oxadiazole intermediates xl by heating them with phosphorous oxychloride. Both xxxviii and xl can be elaborated to the final carboxylic acids xxxix and xli, respectively, using methods described to do this with the corresponding 1,2,4-oxadiazole analogs described in Schemes 2, 3 and 4.

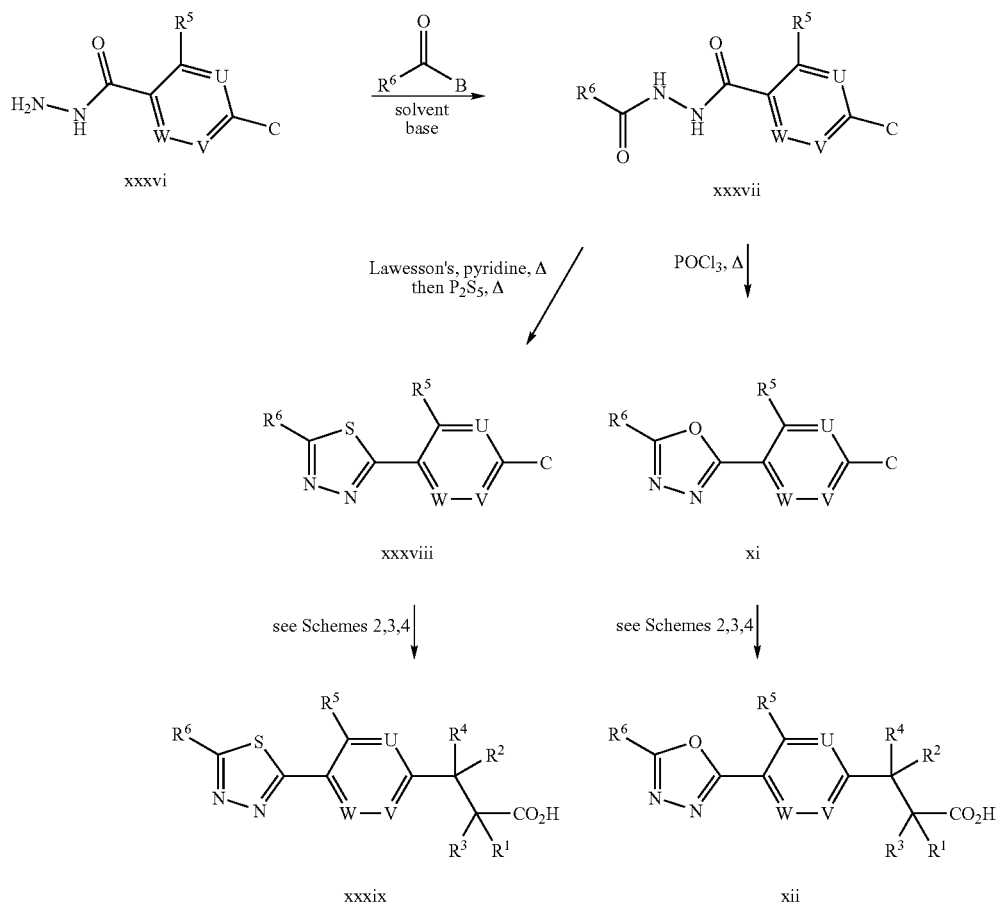

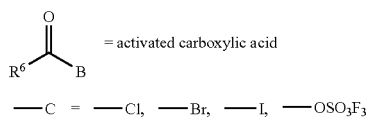
= activated carboxylic acid

—C = —Cl, —Br, —I, —OSO₃F₃

In Scheme 9, heteropentalene derivatives of a general structure I in this invention are defined as follows: derivatives of furan: X=O, Z=Y=CH; derivatives of thiophene: X=S, Z=Y=CH; derivatives of pyrrole: X=NH, Z=Y=CH; derivatives of N-substituted pyrrole: X=NR, Z=Y=CH; derivativesof 1,3-oxazole: X=O, Z=CH, Y=N, or X=O, Z=N, Y=CH or X=NH, Y=O, Z=CH; derivatives of 1,3-thiazole: X=S, Z=CH, Y=N or X=S, Z N, Y=CH or X=NH, Y=S, Z=CH; derivatives of 1,3-imidazole X=NH, Z=CH, Y=NH or X=NH, Z=NH, Y=CH in which each of the nitrogen may be alkylated; derivatives of 1,3,4-triazole in which each one of the nitrogens may be alkylated.

A convergent method to prepare heteropentalene derivatives l is shown in Scheme 9. Organometallic reagents xliv are either commercially available or can be prepared from an appropriate heteroaryl halide by well precedented methods dependent on the nature of such organometallic reagent; similarly, xlv are either commercially available or accessible by methods well established in the published literature. Reaction of xliv and xlv is accomplished by palladium(0) or nickel(0) mediated couplings also known as Stille, Suzuki, Kumada, Negishi reactions and their modifications depending on the nature of xliv and xlv. According to the nature of xliv and xlv, use of various ligands for palladium(0) or nickel(0) may be needed to influence the aforementioned transformations efficiently. Structures and use of such ligands and/or palladium (0) or nickel(0) complexes with these ligands is precedented and includes (but is not limited to) work of Hartwig, Buchwald, Fu, and Knochel. Formation of heteroaryl halide xlviii can be accomplished by a wide range of methods including (but not limited to) use of N-iodosuccinimide, N-bromosuccinimide, N-chlorosuccinimide and bromine or iodine in various solvents such as methanol, ethanol, methylene chloride, chloroform, acidic acid, typically under acidic conditions in the presence of salts such as sodium or potassium acetate. Subsequent coupling of xlvii with R⁶M may be accomplished under conditions analogous to these for coupling of xliv and xlv. Arylhalide il is converted to the desired propionic acid derivative l via a sequence of steps depicted in Schemes 2-4 above.

Scheme 9

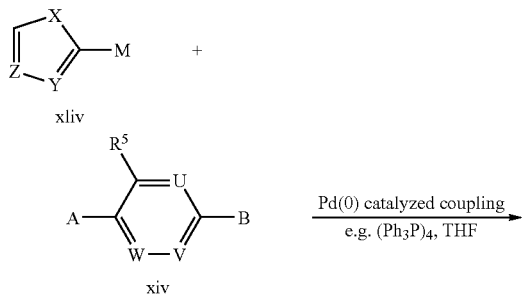

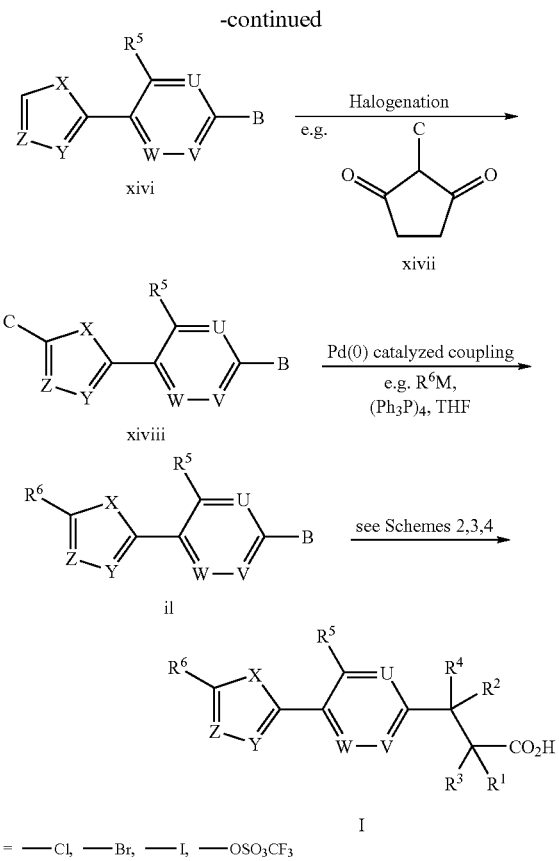

-A = —Cl, —Br, —I, —OSO₃CF₃
-B = —Cl, —Br, —I, —OSO₃CF₃
-C = —Cl, —Br, —I
-M = B(OR)₂, B(OH)₂, SnR₃, ZnA, MgA, Li
-X = O, S, NH, NR
-Y = CH, N
-Z = CH, N

A method for the preparation of 1,3,4-oxadiazole and 1,3,4-thiadiazole derivatives is described in Scheme 10. Starting material xxv can be synthesized according to a procedure described in Scheme 5. A two stage reduction of xxv ensures a selective transformation of methyl ester to the primary alcohol in the presence of aryl nitrile. DIBAlLH reduction may be conducted in variety of solvents including dichloromethane, dichloroethatne and toluene, while sodium borohydride reduction is best to be accomplished in a protic solvents such as methanol or ethanol. Free alcohol resulting from the two-stage reduction is protected as a benzylether li using a benzylic electrophile, such as benzyl bromide and a base, such as sodium hydride, potassium tert-butoxide or sodium hydroxide. Although a direct hydrolysis of li under both acidic and basic conditions provides desired acid lii, higher yield may be obtained using a two stage reduction/oxidation sequence such as (but not limited to) DIBAl reduction/chromium(IV) oxide-mediated oxidation shown. N,N'- diarylhydarzide liii, derived from a variety of R⁶-monoarylhydrazides, is isolated implementing a standard, well precedented sequence via an appropriate acyl chloride followed by coupling under Schotten-Baumann conditions. N,N'-Diarylhydrazides liii may be converted to either 1,3,4-thiadiazoles or 1,3,4-oxadiazoles liv under by synthetic strategy described in Scheme 8. Deprotection of a terminal alcohol using for example reductive cleavage of the benzylic ether with hydrogen catalyzed with palladium on activated carbon yields lv. Although the final oxidation of lv may be accomplished in one step, a two-step sequence such as (but not limited to) Swern Oxidation/chromium(I) oxide-mediated oxidation was found to be more effective for the preparation of the desired carboxylic acid lvi.

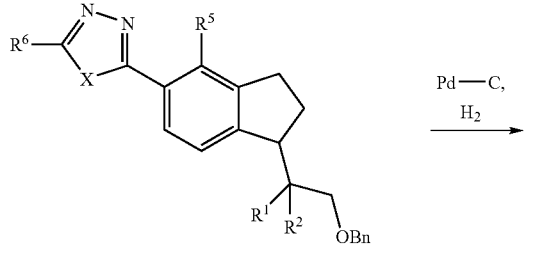

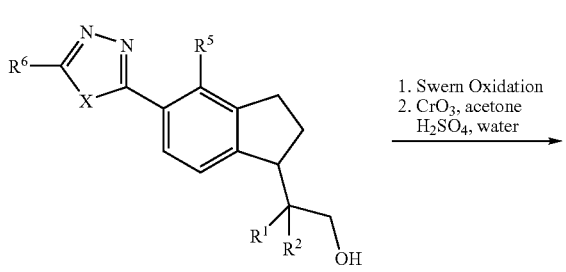

Scheme 10

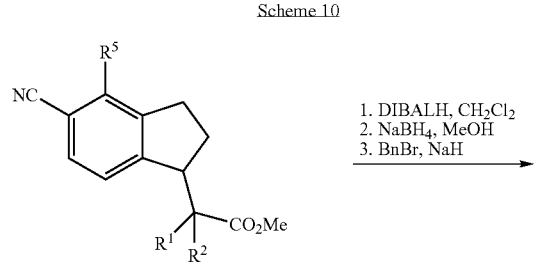

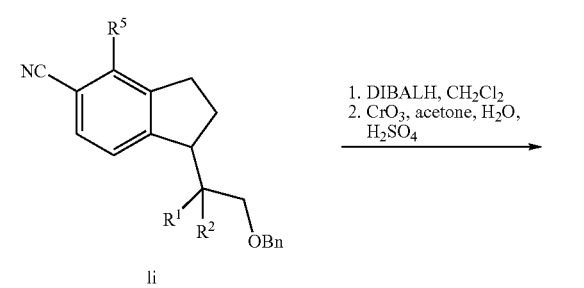

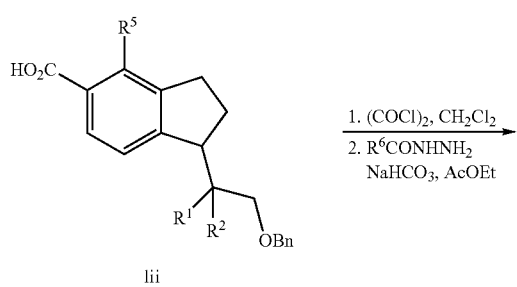

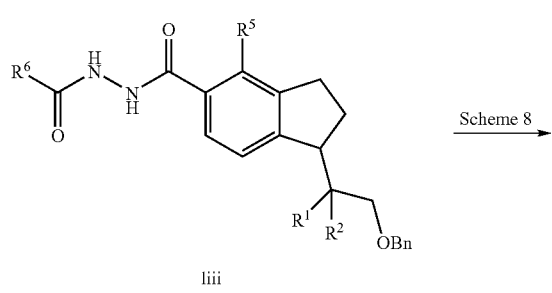

A convenient method to prepare 1-(1,3-imidazo-4-yl)arylpropionic acid compounds of general structure lxi in the present invention is shown in Scheme 11. The functionalized zincate lvii, prepared by Jetter (*Synthesis*, 1998, 829-831) can be selectively cross-oupled with a dihalogenated aromatic, such as lviii (J=I) and catalytic amounts of Pd(0) to afford a 4-substituted imidazole of general structure lix. This material can be subsequently N-arylated with an appropriately substituted aryl boronic acid with the aid of a Cu(II) catalyst and an amine base, such as pyridine or triethylamine according to the method of Lam (*Tetrahedron Lett.* 1998, 39, 2941-2944). Further manipulations, as documented in Schemes 2, 3 and 4 would enable the isolation of corresponding 1-(1,3-imidazo-4-yl)arylpropionic acids lxi.

Scheme 11

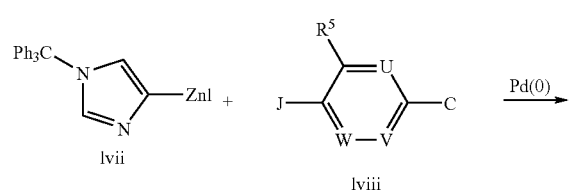

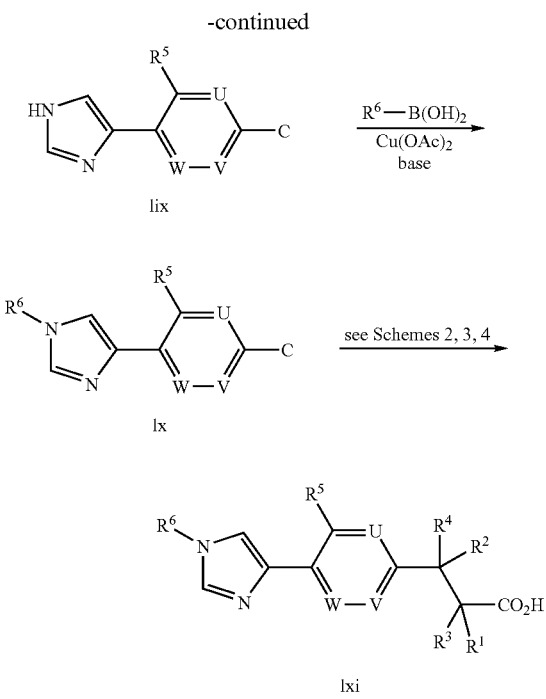

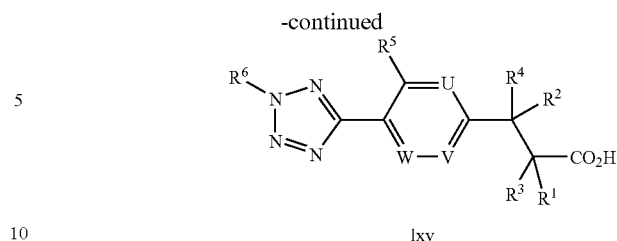

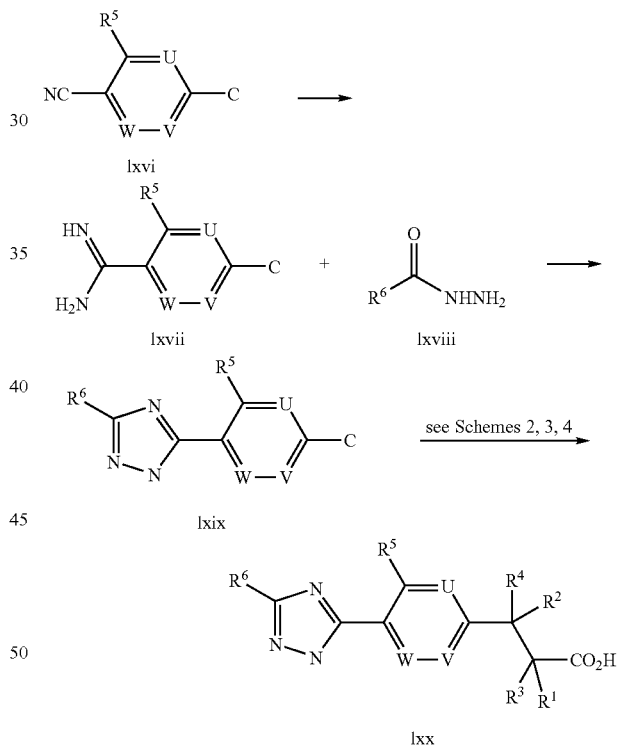

The synthesis of (2-aryl-tetrazol-5-yl)propionic acid compounds of type lxv detailed in the present invention are displayed in Scheme 12. Reaction of a nitrile of type lxii with sodium azide and a zinc salt, as demonstrated by Sharpless (*J. Org. Chem.* 2001, 66, 7945-7950) can generate the 5-substituted tetrazole lxiii. This material can be N-arylated with a boronic acid utilizing the aforementioned Cu(II) conditions in Scheme 11 to yield compounds of type lxiv. Additional transformations detailed in Schemes 2, 3 and 4 would furnish the corresponding (2-aryl-tetrazol-5-yl)propionic acids of type lxv.

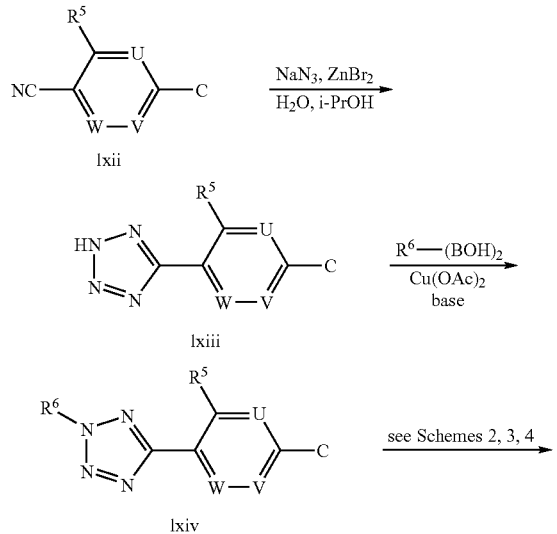

A convenient method to synthesize 5-(1,2,4-triazol-3-yl) propionic acids of type lxx is detailed in Scheme 13. Nitrile lxvi can be treated with chloromethylaluminum amide as detailed by Garigipati (*Tetrahedron Lett.* 1991, 31, 1969-1972) to afford amidine lxvii. An acyl hydrazide of type lxviii can be condensed with amidine lxvii according to the method of Meckler (*Tetrahedron Lett.* 1987, 28, 5133-516) in an alcoholic solvent such as ethanol to give the triazole lxix. Additional steps outlined in Schemes 2, 3, and 4 would provide 3-(1,2,4-triazol-5-yl)propionic acids of type lxx.

It will be understood by those skilled in the art that it may be desirable or necessary to carry out the reactions as described above to prepare the compounds in the present invention in different sequences depending on the identities of the functional groups present. It will also be understood by those skilled in the art that the identities of the functional groups compounds in the present invention may create asymmetric centers in final compounds or the intermediates used to prepare them. Individual stereoisomers can obtained by methods known to those skilled in the art which include (but are not limited to): stereospecific synthesis, resolution of salts of final compounds or any of the intermediates used in their preparation with enantiopure acids or bases, resolution of final compounds or any of the intermediates used in their preparation by HPLC employing enantiopure stationary phases.

REPRESENTATIVE EXAMPLES

Compounds of the invention are exemplified as follows:

General

Concentration of solutions was carried out on a rotary evaporator under reduced pressure. Conventional flash chromatography was carried out on silica gel (230-400 mesh). Flash chromatography was also carried out using a Biotage Flash Chromatography apparatus (Dyax Corp.) on silica gel (32-63 mM, 60 Å pore size) in pre-packed cartridges of the size noted. NMR spectra were obtained in CDCl$_3$ solution unless otherwise noted. Coupling constants (3) are in hertz (Hz). Abbreviations: diethyl ether (ether), triethylamine (IEA), N,N-diisopropylethylamine (DIEA) sat'd aqueous (sat'd), rt (rt), hour(s) (h), minute(s) (min).

HPLC Conditions

HPLC A: YMC ODS A, 5µ, 4.6×50 mm column, gradient 10:90-95:5 v/v CH$_3$CN:H$_2$O+0.05% TFA over 4.5 min, then hold at 95:5 v/v CH$_3$CN:H$_2$O+0.05% TFA for 1.5 min; flow rate 2.5 mL/min, diode array detection 200-400 nM.

HPLC B: Advantage ARMOR C18 5 µm 250×20 mm column (Analytical Sales and Services, Inc.); gradient from 10:90 to 95:5 v/v CH$_3$CN:H$_2$O+0.05% TFA over 10 min, isocratic at 95:5 v/v CH$_3$CN:H$_2$O+0.05% TFA over 15 min, isocratic at 10:90 v/v CH$_3$CN:H$_2$O+0.05% TFA over 10 min; flow rate 10 mL/min; UV detection at 254 nm.

Preparation of N-Hydroxyamide Intermediates

N-Hydroxyamidine 1

N-Hydroxy 3-methyl-4-(2-(tert-butoxycarbonyl) ethyl)benzamidine

Step A: tert-Butyl 3-(3-methyl-4-cyanophenyl)acrylate

A solution of 10.0 g (51.0 mmol) of 4-bromo-2-methylbenzonitrile in 80 mL of 1,4-dioxane was treated with 7.19 g (56.1 mmol) of tert-butyl acrylate, 10.96 g (56.1 mol) of N-methyldicyclohexylamine, 228 mg (0.76 mol) of 2-(di-tert-butylphosphino) biphenyl, and 396 mg (0.38 mol) of tris(dibenzylideneacetone)dipalladium(0)-chloroforin adduct. The resulting mixture was heated at 70° C. for 16 h and cooled to rt. The reaction mixture was filtered though a filter paper, and the filtrate was concentrated. The crude product was partitioned into four portions. Chromatography on four Biotage 40M cartridges using 19:1 v/v hexanes/EtOAc as the eluant followed by pooling of product fractions afforded 10.0 g of the title compound: $^1$H NMR (500 MHz, CDCl$_3$) δ 1.55 (s, 9H), 2.58 (s, 3H), 6.44 (d, J=16.0, 1H), 7.41 (d, J=8.0, 1H), 7.45 (s, 1H), 7.53 (d, J=16.0, 1H), 7.61 (d, J=8.0, 1H).

Step B: tert-Butyl 3-(3-methyl-4-cyanophenyl)propionate

A mixture of 5.0 g (20.6 mmol) of tert-butyl 3-(3-methyl-4-cyanophenyl)acrylate (from Step A) and 500 mg of 10% palladium on carbon in 200 mL of EtOAc was stirred under 1 atm of hydrogen at rt for 16 h. The catalyst was removed by filtration. The filtrate was concentrated to afford 5.04 g of the title compound: $^1$H NMR (500 MHz, CDCl$_3$) δ 1.42 (s, 9H), 2.53 (s, 3H), 2.55 (t, J=7.6, 2H), 2.93 (t, J=7.6, 2H), 7.12 (d, J=7.8, 1H), 7.17 (s, 1H), 7.51 (d, J=7.8, 1H).

Step C: N-Hydroxy 3-methyl-4-(2-(tert-butoxycarbonyl)ethyl)benzamidine

A mixture of 2.5 g (10.2 mmol) of tert-butyl 3-(3-methyl-4-cyanophenyl) propionate (from Step B), 0.85 g (12.2 mmol) of hydroxylamine hydrochloride and 2.57 g (30.6 mmol) of sodium bicarbonate in 30 mL of methanol was heated in a sealed tube at 100° C. for 16 h. The reaction mixture was cooled to rt, then concentrated. The residue was partitioned between EtOAc (50 mL) and water (50 mL). The organic layer was separated and washed with sat'd NaCl (3×50 mL), dried over MgSO$_4$, and concentrated. Chromatography on a Biotage 40M cartridge using 7:3 v/v hexanes/EtOAc as the eluant afforded 1.65 g (58%) of the title compound as a white solid: $^1$H NMR (500 MHz, CDCl$_3$) δ 1.45 (s, 9H), 2.40 (s, 3H), 2.54 (t, J=7.8, 2H), 2.90 (t, J=7.8, 2H), 5.05 (s, 2H), 7.04 (d, J=7.8, 1H), 7.08 (s, 1H), 7.27 (d, J=7.8, 1H).

N-Hydroxyamidine 2

(R/S)—N-Hydroxy 3-methyl-4-(2-(tert-butoxycarbonyl)propyl)benzamidine

The title compound was prepared using procedures analogous to those described for N-HYDROXYAMIDINE 1 substituting tert-butyl methacrylate for tert-butyl acrylate in Step A. 50% Aqueous hydroxylamine was substituted for hydroxylamine hydrochloride and triethylamine and the reaction mixture was heated for 15 min at 180° C. in a microwave reactor in Step C: $^1$H NMR (500 MHz, CDCl$_3$) δ 1.11 (d, J=6.2, 3H), 1.40 (s, 9H), 2.41 (s, 1.5H), 2.47 (s, 1.5H), 2.62 (m, 2H), 2.95 (m, 1H), 4.88 (bs, 2H), 5.90 (bs, 0.5H), 6.48 (bs, 0.5H), 7.04 (m, 2H), 7.28 (m, 0.5H), 7.37 (m, 0.5H).

N-Hydroxyamine 3

(R/S)—N-Hydroxy 3-methyl-4-(1-methyl-2-(tert-butoxycarbonyl)ethyl)benzamidine

The title compound was prepared using procedures analogous to those described for N-HYDROXYAMIDINE 1 substituting tert-butyl crotonate for tert-butyl acrylate in Step A. 50% Aqueous hydroxylamine was substituted for hydroxylamine hydrochloride and triethylamine and the reaction mixture was heated for 15 min at 180° C. in a microwave reactor in Step C: $^1$HNMR (500 MHz, CDCl$_3$) δ 1.28 (d, J=1.1, 3H), 1.39 (s, 9H), 2.42 (s, 1.5H), 2.50 (m, 3.5H), 3.23 (m, 1H), 5.09 (bs, 2H), 5.80 (bs, 0.5H), 5.92 (bs, 0.5H), 7.09 (m, 2H), 7.29 (m, 0.5H), 7.41 (m, 0.5H).

N-Hydroxyamidine 4

(1R,2R/1S,2S)—N-Hydroxy 3-methyl-4-(2-(tert-butoxycarbonyl)cycloprop-1-yl)benzamidine Step A: tert-Butyl (1R,2R/1S,2S)-2-(4-cyano-3 methylphenyl)cyclopropanecarboxylate To a suspension of 0.89 g (37.0 mmol) of sodium hydride (60% dispersion in mineral oil) in 20 mL of DMSO at rt was added 8.14 g (37.0 mmol) of trimethylsulfoxonium iodide in several portions over a period of 30 min. The mixture was stirred at rt for 1 h, and then tert-butyl 3-(3-methyl-4-cyanophenyl)acrylate (from N-HYDROXYAMIDINE 1, Step A) was added as solid in several portions. The suspension was stirred at rt for 2 h and heated at 50° C. for 1 h. The reaction mixture was cooled to rt, diluted with 30 mL of water and extracted with ether (5×75 mL). The organic phase was washed with water (3×50 mL), saturated NaCl (3×50 mL), dried over MgSO$_4$, and concentrated. Chromatography on a Biotage 40M cartridge using 17:3 v/v hexanes/EtOAc as the eluant afforded 1.80 g of the title compound: $^1$H NMR (500 MHz, CDCl$_3$) δ 1.27 (m, 1H), 1.50 (s, 9H), 1.63 (m, 1H), 1.88 (m, 1H), 2.44 (m, 1H), 2.54 (s, 1H), 6.98 (d, J=8.0, 1H), 7.04 (s, 1H), 7.52 (d, J=8.0, 1H).

Step B: (1R,2R/1S,2S)—N-Hydroxy 3-methyl-4-(2-(tert-butoxycarbonyl)cycloprop-1-yl)benzamidine The title compound was prepared using a procedure analogous to that described for N-HYDROXYAMIDINE 1 substituting 50% aqueous hydroxylamine for hydroxylamine hydrochloride in Step C. The reaction mixture was heated for 15 min at 180° C. in a microwave reactor: $^1$H NMR (500 MHz, CDCl$_3$) δ 1.24 (m, 1H), 1.48 (s, 9H), 1.55 (m, 1H), 1.84 (m, 1H), 2.41 (s, 3H), 2.43 (m, 1H), 4.83 (bs, 2H), 6.91 (dd, J=1.6, 6.4, 1H), 6.95 (s, 1H), 7.29 (d, J=2.5, 1H).

N-hydroxyamidine 5

N-Hydroxy 2-methyl-6-(2-(tert-butoxycarbonyl)ethyl)nicotinamidine

Step A: 2-Methyl-3-hydroxy-6-iodopyridine

To a suspension of 1.05 g (9.62 mmol) of 2-methyl-3-hydroxypyridine and 2.04 g (19.24 mmol) of sodium carbonate in 10 mL of H$_2$O and 5 mL of CH$_3$OH was added 2.44 g (9.62 mmol) of iodine in several portions. After stirring at rt for 30 min, the reaction mixture was acidified using 5.0 N HCl until pH=3. The mixture was extracted with EtOAc (3×20 mL). Organic layers were combined, dried over MgSO$_4$ and concentrated. Chromatography on a Biotage 40M cartridge using 1:9 v/v EtOAc/hexanes as the eluant afforded 1.04 g of the title compound: $^1$H NMR (500 MHz, CDCl$_3$) δ 2.28 (s, 3H), 6.76 (d, J=8.2, 1H), 7.34 (d, J=8.7, 1H).

Step B: 2-Methyl-3-benzyloxy-6-iodopyridine

A suspension of 810 mg (3.45 mmol) of 2-methyl-3-hydroxy-6-iodopyridine (from Step A), 533 µL (4.48 mmol) of benzyl bromide, 953 mg (6.89 mmol) of potassium carbonate and catalytic amount of tetrabutylammonium iodide in 10 mL of acetone was refluxed for 3 h and cooled to rt. Solid was filtered off through a cake of Celite and washed with EtOAc, and the filtrate was concentrated. Chromatography on a Biotage 40M cartridge using 1:19 v/v EtOAc/hexanes as the eluant afforded 1.03 g of the title compound: $^1$H NMR (500 MHz, CDCl$_3$) δ 2.48 (s, 3H), 5.04 (s, 2H), 6.79 (d, J=8.4, 1H), 7.32-7.42 (m, 6H).

Step C: tert-Butyl (2E)-3-(5-benzyloxy-6-methylpyridin-2-yl)acrylate

To a solution of 828 mg (2.55 mmol) of 2-methyl-3-benzyloxy-6-iodopyridine (from Step B), 746 µL (5.09 mmol) of tert-butyl acrylate, 535 mg (6.37 mmol) of sodium bicarbonate, 708 mg (255 mmol) of tetrabutylammonium chloride, and 20 mg of crushed 4 A molecular sieve in 10 mL of DMF was added 29 mg (0.13 mmol) of palladium acetate. After stirring at 60° C. for 5 h, the reaction mixture was cooled to rt, diluted with EtOAc (20 mL), and filtered through a cake of Celite. The filtrate was washed with brine (100 mL), H$_2$O (3×100 mL), and brine (100 mL). The organic layer was dried over Na$_2$SO$_4$ and concentrated. Chromatography on a Biotage 40M cartridge using 2:23 v/v EtOAc/hexanes as the eluant afforded 703 mg of the title compound: $^1$H NMR (500 MHz, CDCl$_3$) δ 1.52 (s, 9H), 2.53 (s, 3H), 5.09 (s, 2H), 6.70 (d, J=15.6, 2H), 7.06 (d, J=8.5, 1H), 7.18 (d, J=8.5, 1H), 7.37-7.42 (m, 5H), 7.52 (d, J=15.8, 2H).

Step D: tert-Butyl 3-(5-hydroxy-6-methylpyridin-2-yl)propanoate

A solution of 700 mg (2.15 mmol) of tert-butyl (2E)-3-(5-benzyloxy-6-methylpyridin-2-yl)acrylate (from Step C) and 100 mg of 20% palladium hydroxide on carbon in 20 mL of EtOH was stirred under 1 atm of H$_2$ overnight. The catalyst was filtered off through a cake of Celite and washed extensively with EtOAc. The filtrate was concentrated. Chromatography on a Biotage 40M cartridge using 7:13 v/v EtOAc/hexanes as the eluant afforded 450 mg of the title compound: $^1$H NMR (500 MHz, CDCl$_3$) δ 1.41 (s, 9H), 2.49 (s, 3H), 2.63 (d, J=7.4, 2H), 2.98 (d, J=7.4, 2H), 6.90 (d, J=8.3, 1H), 7.05 (d, J=8.3, 1H).

Step E: tert-Butyl 3-(5-trifluoromethylsulfonyloxy-6-methylpyridin-2-yl)propanoate To a solution of 450 mg (1.90 mmol) of tert-butyl 3-(5-hydroxy-6-methylpyridin-2-yl)propanoate (from Step D) and 881 mg (2.47 mmol) of N-phenyl-bis(trifluoromethanesulfonimide) in 10 mL of CH$_2$Cl$_2$ was added 661 µL (3.79 mmol) of N,N-diisopropylethylamine. The mixture was stirred at rt overnight and then concentrated. Chromatography on a Biotage 40M cartridge using 2:23 v/v EtOAc/hexanes as the eluant afforded 664 mg of the title compound: $^1$H NMR (500 MHz, CDCl$_3$) δ 1.41 (s, 9H), 2.57 (s, 3H), 2.70 (d, J=7.3, 2H), 3.05 (d, J=7.4, 2H), 7.10 (d, J=8.5, 1H), 7.45 (d, J=8.5, 1H).

Step F: tert-Butyl 3-(5-cyano-6-methylpyridin-2-yl)propanoate

To a solution of 729 mg (1.97 mmol) of tert-butyl 3-(5-trifluoromethylsulfonyloxy-6-methylpyridin-2-yl)propanoate (from Step E) and 464 mg (3.95 mmol) of zinc cyanide in 10 mL of DMF was added 137 mg (0.12 mmol) of tetrakis(triphenylphosphine)palladium(0). After stirring at 85° C. for 4 h, the reaction mixture was diluted with 10 mL of EtOAc and filtered through a cake of Celite. Solid was washed with EtOAc (3×10 mL) and the filtrate was concentrated. Chromatography on a Biotage 40M cartridge using 3:17 v/v EtOAc/hexanes as the eluant afforded 487 mg of the title compound: $^1$H NMR (500 MHz, CDCl$_3$) δ 1.42 (s, 9H), 2.71 (d, J=7.4, 2H), 2.73 (s, 3H), 3.09 (d, J=7.3, 2H), 7.12 (d, J=8.0, 1H), 7.77 (d, J=8.0, 1H).

Step G: N-Hydroxy 2-methyl-6-(2-(tert-butoxycarbonyl)ethyl)nicotinamidine

The title compound was prepared using a procedures analogous to that described for N-HYDROXYAMIDINE 1 substituting tert-butyl 3-(3-methyl-4-cyanophenyl)propionate for tert-butyl 3-(5-cyano-6-methylpyridin-2-yl)propanoate (from Step F) in N-HYDROXYAMIDINE 1, Step C: $^1$H NMR (500 MHz, CDCl$_3$) δ 1.41 (m, 9H), 2.60-2.69 (m, 5H), 3.04 (d, J=7.5, 2H), 4.92 (br. s, 1H), 6.05-6.60 (m, 1H), 7.01-7.04 (m, 1H), 7.56-7.66 (m, 1H).

N-Hydroxyamidine 6

(R/S)—N-Hydroxy 2-methyl-6-(2-(tert-butoxycarbonyl)propyl)nicotinamidine

The title compound was prepared using procedures analogs to those described for N-HYDROXYAMIDINE 5 substituting tert-butyl crotonate for tert-butyl acrylate in Step C.

Preparation of Carboxylic Acid Intermediates

Carboxylic Acid 1

3-Cyano-4-isopropyloxybenzoic acid

Step A: Methyl 3-bromo-4-hydroxybenzoate

A solution of 3.9 g (18.0 mmol) of 3-bromo-4-hydroxybenzoic acid in 20 mL of 3:1 v/v CH$_2$Cl$_2$/CH$_3$OH was treated with 10.8 mL of 2.0 M (trimethylsilyl)diazomethane solution in hexanes. The mixture was stirred at rt for 2 h, then concentrated to give 4.6 g of the title compound: $^1$H NMR (500 MHz, CDCl$_3$) δ 3.90 (s, 3H), 5.93 (bs, 1H), 7.05 (d, J=8.5, 1H), 7.92 (dd, J=2.1, 8.5, 1M), 8.19 (d, J=2.0, 1H).

Step B: Methyl 3-bromo-4-isopropyloxybenzoate

A mixture of 4.6 g (19.9 mmol) of methyl 3-bromo-4-hydroxybenzoate (from Step A), 2.2 mL (21.9 mmol) of 2-iodopropane and 5.5 g (39.8 mmol) of potassium carbonate in 10 mL of DMF was stirred at 65° C. for 3 h. The mixture was diluted with 20 mL of EtOAc and washed with sat'd NaCl, H$_2$O (3×), and sat'd NaCl. The organic layer was dried over MgSO$_4$ and concentrated. Chromatography on a Biotage 40M cartridge using 24:1 v/v hexanes/EtOAc gave 4.3 g of the title compound: $^1$H NMR (500 MHz, CDCl$_3$) δ 1.44 (d, J=6.2, 6H), 3.91 (s, 3H), 4.71-4.79 (m, 1H), 6.99 (d, J=8.9, 1H), 8.18 (dd, J=2.2, 8.8, 1H), 8.24 (d, J=2.1, 1H).

Step C: Methyl 3-cyano-4-isopropyloxybenzoate

A mixture of 1.32 g (4.83 mmol) of methyl 3-bromo-4-isopropyloxybenzoate (from Step B), 341 mg (2.90 mmol) of zinc cyanide, 67 mg (0.12 mmol) of 1,1'-bis(diphenylphosphino)ferrocene, 44 mg (0.05 mmol) of tris(dibenzylideneacetone) dipalladium(0)-chloroform complex and 50 μL of H$_2$O in 5.0 mL of DMF was stirred at 120° C. for 48 h. The mixture was cooled, then partitioned between EtOAc and sat'd NaCl. The aqueous layer was separated and extracted with 3× EtOAc. The organic layers were combined, dried over MgSO$_4$ and concentrated. Chromatography on a Biotage 40M cartridge using 9:1 v/v hexanes/EtOAc gave 802 mg of the title compound: $^1$H NMR (500 MHz, CDCl$_3$) δ 1.44 (d, J=6.2, 6H), 3.91 (s, 3H), 4.71-4.79 (m, 1H), 6.99 (d, J=8.9, 1H), 8.18 (dd, J=2.2, 8.8, 1H), 8.24 (d, J=2.1, 1H).

Step D: 3-Cyano-4-isopropoxybenzoic acid

A solution of 802 mg (3.66 mmol) of methyl 3-cyano-4-isopropyloxybenzoate (from Step C) in 5.0 mL EtOH was treated with 770 μL of 5.0 N NaOH. The mixture was stirred at rt for 16 h and then concentrated. The residue was partitioned between EtOAc and aqueous HCl. The organic layer was separated, dried over Na$_2$SO$_4$, and concentrated to give 706 mg of the title compound: $^1$H NMR (500 M, CDCl$_3$) δ 1.46 (d, J=6.0, 6H), 4.74-4.81 (m, 1H), 7.02 (d, J=9.0, 1H), 8.24 (dd, J=2.3, 8.9, 1H), 8.32 (d, J=2.0, 1H).

Carboxylic Acid 2

3-Chloro-4-isopropyloxybenzoic acid

Step A: Methyl 3-chloro-4-isopropyloxybenzoate

A solution of 1.42 g (7.63 mmol) of methyl 3-chloro-4-hydroxybenzoate, 585 μL (7.63 mmol) of 2-propanol and 3.0 g (11.45 mmol) of triphenylphosphine in 20 mL of THF at 0° C. was treated with 2.25 mL (11.45 mmol) of diisopropyl azodicarboxylate. The mixture was stirred for 16 h at rt, then concentrated. Chromatography on a Biotage 40M cartridge using 19:1 v/v hexanes/EtOAc as the eluant afforded 1.77 g of the title compound: $^1$H NMR (500 MHz, CDCl$_3$) δ 1.41 (d, J=6.2, 6H), 4.63-4.70 (m, 1H), 6.93 (d, J=8.7, 1H), 7.89 (dd, J=2.2, 8.6, 1H), 8.05 (d, J=2.0, 1H).

Step B: 3-Chloro-4-isopropyloxybenzoic acid

The title compound was prepared using a procedure analogous to that described in CARBOXYLIC ACID 1, Step D, substituting methyl 3-chloro-4-isopropoxybenzoate (from Step A) for methyl 3-cyano-4-isopropyloxybenzoate: $^1$H NMR (500 M, CDCl$_3$) δ 1.43 (d, J=5.9, 6H), 4.66-4.73 (m, 1H), 6.96 (d, J=8.9, 1H), 7.97 (dd, J=2.1, 8.7, 1H), 8.12 (d, J=2.0, 1H), 11.7 (bs, 1H).

Carboxylic Acids 3-6

The following carboxylic acid intermediates were prepared using procedures analogous to those described for CARBOXYLIC ACID 2 substituting the appropriate benzoate ester for methyl 3-chloro-4-hydroxybenzoate in Step A.

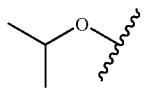

| CARBOXYLIC ACID | $R^c$ | $R^d$ | $^1$H NMR (500 MHz, CDCl$_3$) δ |
|---|---|---|---|
| 3 |  | 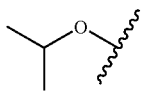 | 1.43 (d, J = 5.9, 6 H), 4.65-4.73 (m, 1 H), 6.92 (d, J = 8.9, 1 H), 8.01 (dd, J = 2.1, 8.7, 1 H), 8.30 (d, J = 2.1, 1 H), 10.9 (br. s, 1 H) |
| 4 |  | 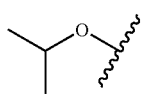 | 1.44 (d, J = 6.1, 6 H), 3.95 (s, 3 H), 4.70 (m, 1 H), 6.94 (d, J = 8.7, 1 H), 7.62 (s, 1 H), 7.76 (m, 1 H) |
| 5 |  | 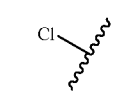 | 1.40 (d, J = 6.0, 6 H), 2.61 (s, 3 H), 4.68 (m, 1 H), 6.87 (d, J = 8.7, 1H), 7.93 (s, 1 H), 7.96 (m, 1 H) |
| 6 | Cl | 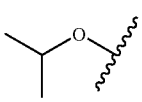 | 1.41 (d, J = 6.2, 6 H), 4.67 (spt, J = 6.1, 1 H), 7.46 (d, J = 8.3, 1 H), 7.62-7.66 (m, 2 H) |

Carboxylic Acid 7

3-Fluoro-4-isopropoxybenzoic acid

Step A: 1-Isopropyloxy-2-fluoro-4-bromobenzene

The title compound was prepared using a procedure analogous to that described in CARBOXYLIC ACID 2, Step A, substituting 2-fluoro-4-bromophenol for methyl 3-chloro-4-hydroxybenzoate: $^1$H NMR (500 MHz, CDCl$_3$) δ 1.35 (d, J=6.0, 6H), 4.46-4.53 (m, 1H), 6.85 (t, J=8.7, 1H), 7.16 (dt, J=2.0, 8.7, 1H), 7.22 (dd, J=2.5, 10.5, 1H).

Step B: 3-Fluoro-4-isopropoxybenzoic acid

A solution of 639 mg (2.74 mmol) 1-isopropyloxy-2-fluoro-4-bromobenzene (from Step A) in 10 mL of THF at −78° C. was treated with 1.64 mL of 2.0 M n-butyllithium in heptane. After stirring at −78° C. for 30 min, the mixture was poured onto 300 g of crushed dry ice and allowed to warm up to rt. The mixture was partitioned between 100 mL of 2.0 N NaOH and 100 mL of Et$_2$O. The aqueous layer was separated, acidified using 5.0 N HCl to pH 2, and extracted with CH$_2$Cl$_2$ (3×50 mL). The organic layers were combined, dried over MgSO$_4$, and concentrated to afford 380 mg of the title compound: $^1$H NMR (500 MHz, CDCl$_3$) δ 1.41 (d, J=6.2, 6H), 4.65-4.73 (m, 1H), 7.00 (t, J=8.5, 1H), 7.79-7.87 (m, 2H).

Carboxylic Acid 8

3-Trifluoromethyl-4-(2-(S)-butoxy)benzoic acid

Step A: 3-Trifluoromethyl-4-(2-(S)-butoxy)benzonitrile

A solution of 1.1 g (5.9 mmol) of 4-fluoro-3-trifluoromethylbenzonitrile and 485 mg (6.5 mmol) of (S)-(+)-2-butanol in 10 mL of THF at −10° C. was treated with 235 mg (5.9 mmol) of sodium hydride. The resulting mixture was stirred cold for 2 h, then quenched with 10 mL of H$_2$O. The quenched solution was extracted with 30 mL of Et$_2$O, dried over MgSO$_4$ and concentrated. Chromatography on a Biotage 40M cartridge using 4:1 v/v hexanes/Ethyl acetate as the eluant afforded 550 mg of the title compound: $^1$H NMR (500 MHz) δ 0.99 (t, J=7.6, 3H), 1.35 (d, J=6.2, 3H), 1.58-1.83 (m, 2H), 4.51 (septet, 1H), 7.04 (d, J=8.7, 1H), 7.75 (d, J=8.7, 1H), 7.85 (s, 1H).

Step B: 3-Trifluoromethyl-4-(2-(S)-butoxy)benzoic acid

A solution of 550 mg (2.2 mmol) of 3-trifluoromethyl-4-(2-(S)-methylpropyloxy)benzonitrile (from Step A) in 5 mL of ethanol was treated with 1.5 mL of 5.0 N NaOH and was heated to 80° C. for 3 h. The reaction was then concentrated, treated with 2 N HCl, extracted with 30 mL of EtOAc, dried and concentrated to afford 600 mg of the title compound: $^1$H NMR (500 Mhz) δ 0.99 (t, J=7.3, 3H), 1.43 (d, J=5.9, 3H), 1.73-1.83 (m, 2H), 4.54 (septet, 1H), 7.02 (d, J=8.9, 1H), 8.21 (d, J=8.9, 1H), 8.32 (s, 1H).

Carboxylic Acid 9

3-Trifluoromethyl-4-(isopropyloxy)benzoic acid

The title compound was prepared using procedures analogous to those described in CARBOXYLIC ACID 8, substituting the isopropanol for (S)-2-butanol in Step A: $^1$H NMR (500 Mhz) δ 8.36 (s, 1H), 8-26 (d, J=8.7, 1H), 7.08 (d, J=8.7, 1H), 4.75-4.82 (m, 1H), 1.44 (d, J=5.9, 6H).

Carboxylic Acid 10

(R/S)-3-Trifluoromethyl-4-(1-(trifluoromethyl)ethoxy)benzoic acid

The title compound was prepared using procedures analogous to those described in CARBOXYLIC ACID 8, substituting the 1,1,1-trifluoro-2-propanol for (S)-2-butanol in Step A: $^1$H NMR (500 Mhz) δ 8.41 (d, J=2.1, 1H), 8.31 (dd, J=2.1, 6.6, 1H), 7.14 (d, J=8.7, 1H), 4.89-4.96 (m, 1H), 1.63 (d, J=6.4, 3H).

Carboxylic Acid 11

3-Cyano-4-(2,2,2-trifluoro-1-methylethoxy)benzoic acid

Step A: 5-Formyl-2-(2,2,2-trifluoro-1-methylethoxy)benzonitrile

To a solution of 0.50 g (4.38 mmol) of 1,1,1-trifluoro-2-propanol in 15 mL of DMF at 0° C. was added 0.13 g (5.26 mmol) of sodium hydride (60% dispersion in mineral oil). After stirring for 10 min, 0.65 g (4.38 mmol) of 2-fluoro-5-formylbenzonitrile was added. The reaction mixture was gradually warmed up to rt and stirred overnight. The mixture was diluted with 20 mL of EtOAc and washed with brine (10 mL), H$_2$O (3×10 mL), and brine (10 mL L). The organic layer was dried over MgSO$_4$ and concentrated. Chromatography on a Biotage 40M cartridge using 4:1 v/v hexanes/EtOAc as the eluant gave 0.44 g of the title compound: $^1$H NMR (500 MHz, CDCl$_3$) δ 1.67 (d, J=6.4, 3H), 4.95 (m, 1H), 7.22 (d, J=8.9, 1H), 8.12 (dd, J=2.0, 6.7, 1H), 8.16 (s, 1H), 9.96 (s, 1H).

Step B: 3-Cyano-4-(2,2,2-trifluoro-1-methylethoxy)benzoic acid

To a solution of 440 mg (1.81 mmol) of 5-formyl-2-(2,2,2-trifluoro-1-methylethoxy)benzonitrile (from Step A) in 20 mL of acetone at 0° C. was added dropwise a solution of Jones reagent, which was prepared by dissolving 0.27 g (2.71 mmol) of chromium (VI) oxide in 0.25 mL of concentrated sulfuric acid and diluted with 2 mL of water at 0° C. The reaction mixture was gradually warmed up to rt, stirred overnight, and concentrated. The residue was diluted with 20 mL of EtOAc and washed with brine (10 mL), H$_2$O (3×10 mL), and brine (10 mL). The organic layer was dried over MgSO$_4$ and concentrated to give 0.44 g of the title compound: $^1$H NMR (500 Mhz, CDCl$_3$) δ 1.69 (d, J=6.4, 3H), 4.94 (m, 1H), 7.16 (d, J=9.1, 1H), 8.34 (dd, J=2.0, 6.9, 1H), 8.42 (d, J=2.1, 1H).

Carboxylic Acids 12-14

The following carboxylic acid intermediates were prepared using procedures analogous to those described for CARBOXYLIC ACID 11 substituting the appropriate alcohol for 2,2,2-trifluoroethanol in Step A.

| CARBOXYLIC ACID | R$^e$ | $^1$H NMR (500 MHz, CDCl$_3$) δ |
|---|---|---|
| 12 | F$_3$C–CH$_2$–O– | 4.63 (m, 1 H), 7.12 (d, J = 8.9, 1 H), 8.36 (dd, J = 2.0, 6.9, 1 H), 8.43 (d, J = 2.0, 1 H) |
| 13 | F$_3$C–CH(CF$_3$)–O– | 5.13 (m, 1 H), 7.26 (d, J = 8.9, 1 H), 8.42 (dd, J = 2.1, 6.8, 1 H), 8.48 (d, J = 2.1, 1 H) |
| 14 | CH$_3$CH$_2$–CH(CH$_3$)–O– (S) | 1.05 (t, J = 7.5, 3 H), 1.42 (d, J = 6.2, 3 H), 1.78 (m, 1 H), 1.88 (m, 1 H), 4.56 (m, 1 H), 7.04 (d, J = 9.2, 1 H), 8.25 (dd, J = 2.3, 6.7, 1 H), 8.32 (d, J = 2.0, 1 H) |

Carboxylic Acid 15

3,5-Dichloro-4-isopropoxybenzoic acid

Step A: Methyl 3,5-dichloro-4-isopropoxybenzoate

To a solution of 2.0 g (9.05 mmol) of methyl 3,5-dichloro-4-hydroxybenzonate in 15 mL DMF at rt was added 2.3 g (13.57 mmol) of 2-iodopropane and 3.75 g (27.14 mmol) of potassium carbonate. After stirring at rt overnight, the mixture was diluted with 50 mL of EtOAc and washed with brine (30 mL), H$_2$O (3×30 mL), and brine (30 mL). The organic layer was dried over MgSO$_4$ and concentrated. Chromatography on a Biotage 40M cartridge using 9:1 v/v hexanes/EtOAc as the eluant gave 1.88 g of the title compound: $^1$H NMR (500 MHz, CDCl$_3$) δ 1.41 (d, J=6.2, 6H), 3.94 (s, 3H), 4.75 (m, 1H), 8.00 (s, 2H).

Step B: 3,5-Dichloro-4-isopropoxybenzoic acid

To a solution of 1.88 g (7.15 mmol) of methyl 3,5-dichloro-4-isopropoxybenzoate (from Step A) in 20 mL of methanol was added 4 mL of 5.0 N sodium hydroxide solution. The mixture was stirred at rt overnight and concentrated. The residue was partitioned between EtOAc (30 mL) and 1 N NaOH (30 mL). The aqueous layer was separated, washed with EtOAc (2×30 mL), acidified using 5.0 N HCl until pH=1, and then extracted with EtOAc (3×30 mL). Organic layers were combined, dried over MgSO$_4$, and concentrated to give 1.51 g of the title compound: $^1$H NMR (500 MHz, CDCl$_3$) δ 1.43 (d, J=6.2, 6H), 4.79 (m, 1H), 8.07 (s, 2H).

Carboxylic Acids 16-19

The following carboxylic acid intermediates were prepared using procedures analogous to those described for CARBOXYLIC ACID 15 substituting the appropriate benzoate ester and alkyl halide for methyl 3,5-dichloro-4-hydroxybenzonate and 2-iodopropane, respectively, in Step A.

Step B: Methyl 5-chloro-6-(2,2,2-trifluoro-1-methylethoxy)nicotinate

To a solution of 630 mg (3.06 mmol) of methyl 5,6-dichloronicotinate (from Step A) and 349 μL (3.06 mmol) of 1,1,1-trifluoro-2-propanol in 10 mL of THF at −78° C. was added 3.1 mL (3.06 mmol) of sodium bis(trimethylsilyl)amide (1.0 M in THF). After stirring at −78° C. for 30 min and at 0° C. for 5 h, the reaction was quenched by adding 10 mL of saturated NH$_4$Cl. The mixture was poured into brine and extracted with CH$_2$Cl$_2$ (3×20 mL). Organic layers were combined, dried over MgSO$_4$, and concentrated. Chromatography on a

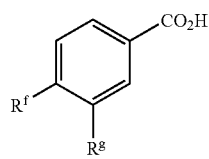

| CARBOXYLIC ACID | R$^f$ | R$^g$ | $^1$H NMR (500 MHz, CDCl$_3$) δ |
|---|---|---|---|
| 16 | cyclopropylmethoxy | Cl | 0.45 (m, 2 H), 0.72 (m, 2 H), 1.37 (m, 1 H), 4.00 (d, J = 6.6, 2 H), 6.96 (d, J = 8.7, 1 H), 8.00 (dd, J = 2.2, 6.5, 1 H), 8.15 (d, J = 2.1, 1 H) |
| 17 | F$_3$C-CH(CH$_3$)-O | NO$_2$ | 1.65 (d, J = 6.4, 3 H), 4.92 (m, 1 H), 7.22 (d, J = 8.9, 1 H), 8.31 (d, J = 8.2, 1 H), 8.58 (dd, J = 1.9, 5.0, 1 H) |
| 18 | cyclopentyloxy | Cl | 1.65-1.97 (m, 8 H), 4.90 (m, 1 H), 6.96 (d, J = 8.7, 1 H), 7.96 (dd, J = 1.8, 8.7, 1 H), 8.10 (d, J = 2.1, 1 H) |
| 19 | isobutyloxy | Cl | 1.08 (d, J = 6.8, 6 H), 2.19 (m, 1 H), 3.85 (d, J = 6.6, 1 H), 7.97 (dd, J = 2.0, 8.7, 1 H), 8.11 (d, J = 2.1, 1 H) |

Carboxylic Acid 20

5-Cyano-6-(2,2,2-trifluoro-1-methylethoxy)nicotinic acid

Step A: Methyl 5,6-dichloronicotinate

To a solution of 2.15 g (11.2 mmol) of 5,6-dichloronicotinic acid in 10 mL of v:v 1:1 CHCl$_2$/CH$_3$OH at rt was added dropwise 8.4 mL (16.8 mmol) of (trimethylsilyl)diazomethane (2.0 M in hexanes). The mixture was stirred at rt for 30 min and then concentrated. Chromatography on a Biotage 40M cartridge using 1:19 v/v EtOAc/hexanes as the eluant gave 1.85 g of the title compound: $^1$H NMR (500 MHz, CDCl$_3$) δ 3.98 (s, 3H), 8.35 (d, J=1.8, 1H), 8.88 (d, J=1.8, 1H).

Biotage 40M cartridge using 3:97 v/v Et$_2$O/hexanes as the eluant gave 627 mg of the title compound: $^1$H NMR (500 MHz, CDCl$_3$) δ 1.56 (d, J=6.4, 3H), 3.93 (s, 3H), 5.86 (m, 1H), 8.27 (d, J=2.1, 1H), 8.67 (d, J=2.0, 1H).

Step C: Methyl 5-cyano-6-(2,2,2-trifluoro-1-methylethoxy)nicotinate

To a solution of 627 mg (2.21 mmol) of methyl 5-chloro-6-(2,2,2-trifluoro-1-methylethoxy)nicotinate (from Step B), 123 mg (0.22 mmol), 156 mg (1.33 mmol) of zinc cyanide, and 29 mg (0.44 mmol) of zinc dust in 5.0 ml of DMF was added 101 mg (0.11 mmol) of tris(dibenzylideneacetone)dipalladium(0). After stirring at 120° C. overnight, the mixture was filtered through a cake of Celite and washed with EtOAc. The filtrate was washed with brine (10 mL), H$_2$O (3×10 mL), and brine (10 mL). The organic layer was dried over MgSO$_4$ and concentrated. Chromatography on a Biotage 40M cartridge using 1:9 v/v EtOAc/hexanes as the eluant gave 498 mg of the title compound: $^1$H NMR (500 MHz, CDCl$_3$) δ 1.59 (d, J=6.6, 3H), 3.97 (s, 3H), 5.93 (m, 1H), 8.54 (d, J=2.2, 1H), 8.96 (d, J=2.3, 1H).

Step D: 5-Cyano-6-(2,2,2-trifluoro-1-methylethoxy) nicotinic acid

To a solution of 363 mg (1.32 mmol) of methyl 5-cyano-6-(2,2,2-trifluoro-1-methylethoxy)nicotinate (from Step C) and 5.0 mL of 1,1,1-trifluoro-2-propanol in 5.0 mL of Et$_2$O was added 530 μL (2.65 mmol) of 5.0 N NaOH. After stirring at rt overnight, the mixture was diluted with Et$_2$O (20 mL), washed with diluted HCl (2×10 mL), dried over Na$_2$SO$_4$, and concentrated to give 327 mg of the title compound: $^1$H NMR (500 MHz, CD$_3$OD) δ 1.46 (d, J=6.4, 3H), 5.92 (m, 1H), 8.52 (d, J=2.1, 1H), 8.86 (d, J=2.0, 1H).

Carboxylic Acid 21

5-Cyano-6-ethoxynicotinic acid

To a solution of 498 mg (1.82 mmol) of methyl 5-cyano-6-(2,2,2-trifluoro-1-methylethoxy)nicotinate (from CARBOXYLIC ACID 20, Step C) in 10 mL of EtOH was added 1.8 mL of 5.0 N NaOH. After stirring at rt overnight, the mixture was acidified using Dowex H cation exchange resin until pH=3. The resin was filtered off and the filtrate was concentrated to give 160 mg of the title compound: $^1$H NMR (500 MHz, CD$_3$OD) δ 1.37 (t, J=7.1, 3H), 4.50 (d, J=7.1, 2H), 8.43 (d, J=2.1, 1H), 8.85 (d, J=2.3, 1H).

Carboxylic Acid 22

5-Cyano-6-isobutylnicotinic acid

Step A: Ethyl 5-cyano-6-hydroxynicotinate

To a solution of 716 mg (2.44 mmol) of ethyl 6-hydroxy-5-iodonicotinate and 573 mg (4.88 mmol) of zinc cyanide in 10 mL of DMF was added 169 mg (0.15 mmol) of tetrakis (triphenylphosphine)palladium(0). After stirring at 80° C. overnight, the mixture was filtered through a cake of Celite. The filtrate was washed with brine (10 mL), H$_2$O (3×10 mL), and brine (10 μL), dried over MgSO$_4$, and concentrated. Chromatography on a Biotage 40M cartridge using 4:1 v/v EtOAc/hexanes as the eluant gave 222 mg of the title compound: $^1$H NMR (500 MHz, CD$_3$OD) δ 1.29 (d, J=7.1, 3H), 4.28 (q, J=7.1, 2H), 8.31 (d, J=2.5, 1H), 8.42 (d, J=2.8, 1H).

Step B: Ethyl 6-chloro-5-cyanonicotinate

To a solution of 222 mg (1.16 mmol) of ethyl 5-cyano-6-hydroxynicotinate (from Step A) in 5 mL of SOCl$_2$ was added 500 μL of DMF. After refluxing overnight, the mixture was cooled to rt and concentrated. The residue was dissolved in EtOAc (20 mL) and washed with brine (10 mL), saturated NaHCO$_3$ (10 mL), and brine (10 mL), dried over Na$_2$SO$_4$, and concentrated. Chromatography on a Biotage 40M cartridge using 1:9 v/v EtOAc/hexanes gave 145 mg of the title compound: $^1$H NMR (500 MHz, CDCl$_3$) δ 1.44 (d, J=7.1, 3H), 4.46 (q, J=7.1, 2H), 8.58 (d, J=2.1, 1H), 9.15 (d, J=2.1, 1H).

Step C: Ethyl 5-cyano-6-isobutylnicotinate

To a solution of 145 mg (0.69 mmol) of ethyl 6-chloro-5-cyanonicotinate (from Step B), 1.65 mL (0.83 mmol) of isobutylzinc bromide (0.5 M in THF), and 100 mL of 1-methyl-2-pyrrolidinone was added 18 mg (0.03 mmol) bis(tri-tert-butylphosphine)palladium(0). After stirring at 65° C. overnight, the reaction mixture was cooled to rt and filtered through a cake of Celite. The filtrate was concentrated. Chromatography on a Biotage 40S cartridge using 1:19 v/v EtOAc/hexanes as the eluant gave 75 mg of the title compound: $^1$H NMR (500 MHz, CDCl$_3$) δ 0.99 (d, J=6.7, 6H), 1.43 (t, J=7.1, 3H), 2.27 (m, 1H), 2.99 (d, J=7.3, 2H), 4.45 (q, J=7.1, 2H), 8.50 (d, J=2.1, 1H), 9.28 (d, J=2.3, 1H).

Step D: 5-Cyano-6-isobutylnicotinic acid

The title compound was prepared using the procedure analogous to that described for CARBOXYLIC ACID 11, Step D substituting ethyl 5-cyano-6-isobutylnicotinate for methyl 3-cyano-4-isopropoxybenzoate: $^1$H NMR (500 MHz, CD$_3$OD) δ 0.98 (d, J=6.8, 6H), 2.23 (m, 1H), 2.95 (d, J=7.3, 2H), 8.57 (d, J=2.0, 1H), 9.20 (d, J=2.0, 1H).

Carboxylic Acid 23

4-(1,1-Difluoro-2-methylpropyl)benzoic acid

Step A: Ethyl 4-(1-hydroxy-2-methylpropyl)benzoate

To a solution of 3.19 g (11.6 mmol) of ethyl 4-iodobenzoate in 10 mL of THF at −40° C. was added 6.4 mL (12.7 mmol) of isopropylmagnesium chloride (2.0 M in THF). After stirring at −40° C. for 1 h, 1.26 mL (13.9 mmol) of isobutylaldehyde was added. After stirring at −40° C. for 1 h, the reaction was quenched by adding 10 mL of saturated NaHCO$_3$. The mixture was warmed to rt and poured into brine (20 mL). The aqueous layer was extracted with CH$_2$Cl$_2$ (3×20 mL). Organic layers were combined, dried over Na$_2$SO$_4$, and concentrated. Chromatography on a Biotage 40M cartridge using 1:9 v/v EtOAc/hexanes as the eluant gave 2.08 g of the title compound: $^1$H NMR (500 MHz, CDCl$_3$) δ 0.82 (d, J=6.9, 3H), 0.96 (d, J=6.6, 3H), 1.39 (t, J=7.1, 3H), 1.95 (m, 1H), 2.09 (br. s, 1H), 4.36 (q, J=7.1, 2H), 4.45 (d, J=6.4, 1H), 7.37 (d, J=8.2, 2H), 7.99 (d, J=8.3, 2H).

Step B: Ethyl 4-isobutyrylbenzoate

To a solution of 2.08 g (9.36 mmol) of ethyl 4-(1-hydroxy-2-methylpropyl)benzoate (from Step A) and 1.64 g (14.04 mmol) of 4-methylmorpholine N-oxide in 20 mL of CH$_2$Cl$_2$ were added 164 mg (0.47 mmol) of tetrapropylammonium perruthenate and few specks of ground 4 A molecular sieves. After stirring at rt for 2 h, the mixture was filtered through a cake of Celite and the filtrate was concentrated. Chromatography on a Biotage 40M cartridge using 1:19 v/v EtOAc/hexanes as the eluant gave 2.0 g of the title compound: $^1$H NMR (500 MHz, CDCl$_3$) δ 1.23 (t, J=6.9, 6H), 1.41 (t, J=7.1, 3H), 3.56 (m, 1H), 4.41 (q, J=7.1, 2H), 7.99 (dd, J=1.7, 6.5, 2H), 8.13 (dd, J=1.9, 6.7, 2H).

Step C: Ethyl 4-(1,1-difluoro-2-methylpropyl)benzoate

To a solution of 2.34 mL (12.7 mmol) of bis((2-methoxyethyl)amino)sulfur trifluoride in 5 mL of toluene at 0° C. was added 115 μL (0.91 mmol) of boron trifluoride diethyl etherate. After the mixture was stirred at 0° C. for 1 h, 2.0 g (9.08 mmol) of ethyl 4-isobutyrylbenzoate (from Step B) in 10 mL of toluene was added. After stirring at 50° C. for overnight, the reaction mixture was cooled to rt and 20 mL of saturated NaHCO$_3$ was added. The mixture was extracted with CH$_2$Cl$_2$ (3×20 mL). Organic layers were combined, dried over MgSO$_4$, and concentrated. Chromatography on a Biotage 40M cartridge using 1.0 L of 3:97 v/v Et$_2$O/hexanes and 1.0 L of 1:9 v/v Et$_2$O/hexanes as the eluant gave 896 mg of the starting material (the polar fraction) and 1.14 g of the title compound: $^1$H NMR (500 MHz, CDCl$_3$) δ 0.99 (d, J=6.9, 6H), 1.41 (t, J=7.1, 3H), 2.33 (m, 1H), 4.40 (q, J=7.1, 2H), 7.50 (d, J=8.2, 2H), 8.09 (d, J=8.4, 2H).

Step D: 4-(1,1-Difluoro-2-methylpropyl)benzoic acid

The title compound was prepared using the procedure analogous to that described for CARBOXYLIC ACID 11, Step D substituting ethyl 4-(1,1-difluoro-2-methylpropyl)benzoate for methyl 3-cyano-4-isopropoxybenzoate: $^1$H NMR (500 MHz, CDCl$_3$) δ 1.00 (d, J=6.8, 6H), 2.34 (m, 1H), 7.56 (d, J=8.4, 2H), 8.17 (d, J=8.5, 2H).

Carboxylic Acid 24

5-Iodo-6-(2,2,2-trifluoro-1-methylethoxy)nicotinic acid

Step A: Ethyl 6-chloro-5-iodonicotinate

To a solution of 2.03 g (7.66 mmol) of 6-hydroxy-5-iodonicotinic acid in 15 mL of SOCl$_2$ was added 1 mL of DMF. After refluxing overnight, the mixture was concentrated. The residue was treated with 10 mL of EtOH and concentrated. This process was repeated three times. Chromatography on a Biotage 40M cartridge using 1:19 v/v EtOAc/hexanes as the eluant gave 2.34 g of the title compound: $^1$H NMR (500 MHz, CDCl$_3$) δ 1.41 (d, J=7.1, 3H), 4.41 (q, J=7.1, 2H), 8.71 (d, J=2.1, 1H), 8.93 (d, J=2.1, 1H).

Step B: Ethyl 5-iodo-6-(2,2,2-trifluoro-1-methylethoxy)nicotinate

To a solution of 120 mg (0.39 mmol) of ethyl 6-chloro-5-iodonicotinate (from Step A) and 52 μL (0.58 mmol) of 1,1,1-trifluoro-2-propanol in 5 mL of THF at rt was added 578 μL (0.58 mmol) of sodium bis(trimethylsilyl)amide (1.0 M in THF). After refluxing overnight, the reaction mixture was concentrated. Chromatography on a Biotage 40S cartridge using 1:49 v/v Et$_2$O/hexanes as the eluant gave 73 mg of the title compound: $^1$H NMR (500 MHz, CDCl$_3$) δ 1.39 (t, J=7.1, 3H), 1.55 (d, J=6.6, 3H), 4.38 (q, J=7.1, 2H), 5.79 (m, 1H), 8.66 (d, J=2.1, 1H), 8.73 (d, J=2.0, 1H).

Step C: 5-Iodo-6-(2,2,2-trifluoro-1-methylethoxy)nicotinic acid

The title compound was prepared using the procedure analogous to that described for CARBOXYLIC ACID 20, Step D substituting ethyl 5-iodo-6-(2,2,2-trifluoro-1-methylethoxy)nicotinate (from Step C) for methyl 5-cyano-6-(2,2,2-trifluoro-1-methylethoxy)nicotinate: $^1$H NMR (500 MHz, CDCl$_3$) δ 1.57 (d, J=6.4, 3H), 5.81 (m, 1H), 8.72 (d, J=2.0, 1H), 8.81 (d, J=2.1, 1H).

Carboxylic Acid 25

4-(Trifluoromethyl)-6-(2,2,2-trifluoro-1-methylethoxy)nicotinic acid

To a solution of 180 mg (1.56 mmol) of 1,1,1-trifluoro-2-propanol in 10 mL of THF at −78° C. was added 1.56 mL (1.56 mmol) of sodium bis(trimethylsilyl)amide (1.0M in THF). After 30 min at −78° C., 250 mg (1.04 mmol) of methyl 6-chloro-4-(trifluoromethyl)nicotinate was added. The reaction mixture was gradually warmed up to rt and stirred over night. The mixture was diluted with 10 mL of EtOAc and washed with brine. The organic layer was dried over MgSO$_4$ and concentrated. Purification using HPLC B gave 160 mg of the title compound: $^1$H NMR (500 MHz, CDCl$_3$) δ 1.57 (d, J=6.6, 3H), 5.91 (m, 1H), 7.26 (s, 1H), 8.98 (s, 1H).

Carboxylic Acid 26

5-Iodo-6-isopropoxynicotinic acid

Step A: Ethyl 6-hydroxy-5-iodonicotinate

A suspension of 4.6 g (17.36 mmol) of 5-iodo-6-hydroxynicotinic acid and 7.0 mL of concentrated sulfuric acid in 40 mL of ethanol was refluxed for 16 h. The reaction mixture was cooled to rt and filtered to afford 3.0 g of a white solid as the title compound: $^1$H NMR (500 MHz, DMSO) δ 1.25 (t, J=6.9, 3H), 4.21 (q, J=6.6, 2H), 8.05 (d, J=1.4, 1H), 8.33 (d, J=1.3, 1H).

Step B: Ethyl 5-iodo-6-isopropoxynicotinate

To a solution of 500 mg (1.71 mmol) of ethyl 6-hydroxy-5-iodonicotinate (from Step A) in 10 mL of DMF were added 330 mg (1.96 mmol) of 2-iodopropane and 1.67 g (5.11 mmol) of cesium carbonate. After stirring at 50° C. for 16 h, the reaction mixture was partitioned between EtOAc (20 mL) and water (20 mL). The organic layer was washed with brine (3×20 mL), dried over MgSO$_4$, and concentrated. Chromatography on a Biotage 25+M cartridge using 4:1 v/v hexanes/EtOAc as the eluant to afford 210 mg (37%) of a white solid as the title compound: $^1$H NMR (500 MHz, CDCl$_3$) δ 1.40 (m, 9H), 4.37 (q, J=7.1, 2H), 5.37 (m, 1H), 8.59 (d, J=2.1, 1H), 8.74 (d, J=2.0, 1H).

Step C: 5-Iodo-6-isopropoxynicotinic acid

To a solution of 210 mg (0.63 mmol) of ethyl 5-iodo-6-isopropoxynicotinate (from Step B) in 2.5 mL isopropanol was added 250 μL of 5.0 N NaOH. After stirring at rt for S h, the reaction mixture was partitioned between EtOAc (10 mL) and 1.0 N HCl (10 mL). The organic layer was separated, washed with brine (3×5 mL), dried over MgSO$_4$, and concentrated to give 190 mg of the title compound: $^1$H NMR (500 MHz, CDCl$_3$) δ 1.44 (d, J=6.4, 6H), 5.44 (m, 1H), 8.66 (d, J=2.1, 1H), 8.83 (d, J=2.1, 1H).

Carboxylic Acid 27

5-Trifluoromethyl-6-(morpholin-4-yl)nicotinic acid

Step A: 2-Hydroxy-3-trifluoromethyl-5-bromopyridine

A solution of 1.95 g (12 mmol) of 2-hydroxy-3-trifluoromethyl-pyridine and 0.8 mL of bromine in 10 mL of MeOH was stirred at rt for 20 h. The solution was concentrated and the residue partitioned between 100 mL of EtOAc and 25 mL of H$_2$O. The layers were separated and the organic layer was washed with 25 mL of 5% Na$_2$S$_2$O$_3$, 25 mL of sat'd NaCl, dried and concentrated. Chromatography on a Biotage 40 M cartridge using 3:1 hexanes/acetone as the eluant afforded 1.84 g of the title compound: ESI-MS (m/z) 242.1, 244.1; HPLC A: 2.22 min.

Step B: 2-Chloro-3-trifluoromethyl-5-bromopyridine

A mixture of 1.83 g (7.6 mmol) of 2-hydroxy-3-trifluoromethyl-5-bromopyridine (from Step A) in 15 mL of POCl₃ was heated at reflux for 3 h. The mixture was cooled and poured onto 200 g of ice. The resulting mixture was extracted with 200 mL of CH₂Cl₂. The extract was dried and concentrated. Chromatography on a Biotage 40 M cartridge using hexanes as the eluant afforded 1.11 g of the title compound: ¹H NMR (500 MHz, CDCl₃) δ 8.14 (d, J=2.0, 1H), 8.64 (d, J=2.0, 1H).

Step C: 2-(Morpholin-4-yl)-3-trifluoromethyl-5-bromopyridine

A mixture of 260 mg (1.0 mmol) of 2-chloro-3-trifluoromethyl-5-bromopyridine (from Step B) and 3 mL of morpholine was heated at 80° C. for 1 h. The mixture was cooled and concentrated. The residue was partitioned between 50 mL of CH₂Cl₂ and 1.0 N NaOH and the layers were separated. The organics were dried and concentrated. Chromatography on a Biotage 40S cartridge using 19:1 v/v hexanes/ether as the eluant afforded 290 mg of the title compound: ¹H NMR (500 MHz, CDCl₃) δ 3.29 (app t, J=5.5, 4H), 3.82 (app t, J=5.5, 4H); 7.95 (d, J=2.0, 1H), 8.45 (d, J=2.0, 1H.

Step D: 2-(Morpholin-4-yl)-3-trifluoromethyl-5-cyanopyridine

A mixture of 160 mg (0.63 mmol) of 2-(morpholin-4-yl)-3-trifluoromethyl-5-bromopyridine (from Step C), 117 mg (1.0 mmol) of zinc cyanide, 20.1 mg (0.22 mmol) of tris(dibenzylideneacetone)dipalladium(0) and 48.7 mg (0.088) mmol of 1,1'-bis(diphenylphosphino)ferrocene in 2 mL of N-methylpyrrolidinone under argon was stirred at 100° C. for 1 h. The mixture was cooled and partitioned between ether and water. The organic layer was dried and concentrated. Chromatography on a Biotage 40S cartridge using 9:1 v/v hexanes/ether then 17:3 v/v hexanes/ether as the eluant afforded 87 mg of the title compound: ESI-MS (m/z) 258.2; HPLC A: 3.04 min.

Step E: 5-Trifluoromethyl-6-(morpholin-4-yl)-nicotinic acid

A solution of 249 mg (0.97 mmol) of 2-(morpholin-4-yl)-3-trifluoromethyl-5-cyanopyridine (from Step D) in 5 mL 1:1 v/v 5 N NaOH/EtOH was heated at reflux for 1 h. The mixture was cooled and partitioned between 20 mL of ether and 20 mL of water. The aqueous layer was separated and adjusted to pH=4 with conc. HCl. The precipitated solid was filtered, rinsed with water and dried to afford 138 mg of the title compound: ¹H NMR (500 MHz, CD₃OD) δ 3.52 (app t, J=5.0, 4H), 3.78 (app t, J=5.0, 4H), 8.40 (d, J=2.0, 1H), 8.90 (d, J=2.0, 1H); ESI-MS (m/z) 277.3; HPLC A: 2.71 min.

PREPARATION OF EXAMPLES

Example 1

3-(4-(5-(3-Cyano-4-isopropyloxyphenyl)-1,2,4-oxadiazol-3-yl)-3-methylphenyl)propanoic acid

Step A: tert-Butyl 3-(4-(5-(3-cyano-4-isopropyloxyphenyl)-1,2,4-oxadiazol-3-yl)-3-methylphenyl)propanoate A mixture of 25 mg (0.09 mmol) of N-HYDROXYAMIDINE 1, 21 mg (0.10 mmol) of CARBOXYLIC ACID 1 and 26 mg (0.14 mmol) of N-(3-dimethylamino-propyl)-N'-ethylcarbodiimide in 5 mL of acetonitrile was stirred at rt for 2 h then at 120° C. for 16 h. The reaction mixture was cooled to rt and concentrated. Chromatography on a Biotage 40S cartridge using 17:3 v/v hexanes/EtOAc as the eluant gave 23 mg of the title compound: ¹H NMR (500 MHz, CDCl₃) δ 1.43 (s, 9H), 1.47 (d, J=6.2, 6H), 2.57 (t, J=7.7, 2H), 2.65 (s, 3H), 2.95 (t, J=7.7, 2H), 4.76-4.83 (m, 1H), 7.11 (d, J=8.9, 1H), 7.17-7.19 (m, 2H), 7.99 (d, J=8.2, 1H), 8.33 (dd, J=2.3, 9.0, 1H), 8.42 (d, J=2.0, 1H).

Step B: 3-(4-(5-(3-Cyano-4-isopropyloxyphenyl)-1,2,4-oxadiazol-3-yl)-3-methylphenyl)propanoic acid A solution of 23 mg (0.05 mmol) of tert-butyl 3-(4-(5-(3-cyano-4-isopropyloxyphenyl)-1,2,4-oxadiazol-3-yl)-3-methylphenyl)propanoate (from Step A) in 4:1 v/v CH₂Cl₂/TFA was stirred at rt for 30 min. The mixture was concentrated. Purification by HPLC B gave 17 mg of the title compound: ¹H NMR (500 MHz, CDCl₃) δ 1.47 (d, J=6.2, 6H), 2.66 (s, 3H), 2.74 (t, J=7.8, 2H), 3.01 (t, J=7.8, 2H), 4.76-4.82 (m, 1H), 7.11 (d, J=9.0, 1H), 7.19-7.21 (m, 2H), 8.01 (d, J=8.3, 1H), 8.33 (dd, J=2.3, 8.9, 11H), 8.42 (d, J=2.1, 1H).

Examples 2-7

The following examples were prepared using procedures analogous to those described for EXAMPLE 1 substituting the appropriate carboxylic acid for CARBOXYLIC ACID 1 in Step A.

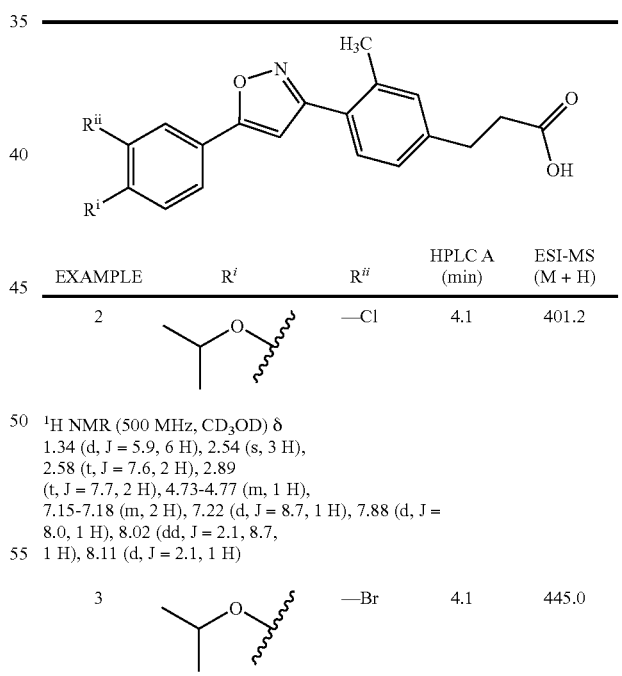

| EXAMPLE | R$^i$ | R$^{ii}$ | HPLC A (min) | ESI-MS (M + H) |
|---|---|---|---|---|
| 2 | ![isopropoxy] | —Cl | 4.1 | 401.2 |
| ¹H NMR (500 MHz, CD₃OD) δ 1.34 (d, J = 5.9, 6 H), 2.54 (s, 3 H), 2.58 (t, J = 7.6, 2 H), 2.89 (t, J = 7.7, 2 H), 4.73-4.77 (m, 1 H), 7.15-7.18 (m, 2 H), 7.22 (d, J = 8.7, 1 H), 7.88 (d, J = 8.0, 1 H), 8.02 (dd, J = 2.1, 8.7, 1 H), 8.11 (d, J = 2.1, 1 H) | | | | |
| 3 | ![isopropoxy] | —Br | 4.1 | 445.0 |
| ¹H NMR (500 MHz, CDCl₃) δ 1.45 (d, J = 6.0, 6 H), 2.65 (s, 3 H), 2.73 (t, J = 7.8, 2 H), 3.01 (t, J = 7.7, 2 H), 4.69-4.73 (m, 1 H), 7.02 (d, J = 8.7, 1 H), 7.18-7.21 (m, 2 H), 8.00 (d, J = 8.4, 1 H), 8.09 (dd, J = 2.2, 8.6, 1 H), 8.41 (d, J = 2.0, 1 H) | | | | |

-continued

| EXAMPLE | $R^i$ | $R^{ii}$ | HPLC A (min) | ESI-MS (M + H) |
|---|---|---|---|---|
| 4 | isopropoxy | —OCH₃ | 3.7 | 397.2 |

¹H NMR (500 MHz, CD₃OD) δ
1.38 (d, J = 6.0, 6 H), 2.62 (s, 3 H),
2.66 (t, J = 7.8, 2 H), 2.97
(t, J = 7.8, 2 H), 3.95 (s, 3 H), 4.75 (m,
1 H), 7.15 (d, J = 8.0, 1 H), 7.23 (d, J = 8.0, 1 H), 7.26 (s,
1 H), 7.73 (s, 1 H), 7.80 (m, 1 H), 7.94 (d, J = 8.0, 1 H)

| 5 | isopropoxy | —CH₃ | 4.1 | 381.2 |

¹H NMR (500 MHz, CD₃OD) δ
1.38 (d, J = 6.1, 6 H), 2.26 (s, 3 H), 2.61 (s, 3 H), 2.65 (t, J =
7.8, 2 H), 2.96 (t, J = 7.8, 2 H), 4.75 (m,
1 H), 7.08 (d, J = 8.7, 1 H), 7.21 (d, J = 8.0, 1 H), 7.24
(s, 1 H), 7.95 (m, 2 H), 7.98 (m, 1 H)

| 6 | isopropoxy | —F | 3.9 | 385.4 |

¹H NMR (500 MHz, CD₃OD) δ
1.40 (d, J = 5.9, 6 H), 2.61 (s, 3 H), 2.66 (t, J = 7.8, 2 H), 2.96
(t, J = 7.8, 2 H), 4.80, (m, 1 H), 7.24 (m,
2 H), 7.31 (m, 1 H), 7.89 (m, 1 H), 7.96 (m, 2 H)

Example 7

3-(4-(5-(5-(2-Methylpropyl)pyridin-2-yl)-1,2,4-oxadiazol-3-yl)-3-methylphenyl)propanoic acid Step A: tert-Butyl 3-(4-(5-(5-(2-methylpropyl)pyridin-2-yl)-1,2,4-oxadiazol-3-yl)-3-methylphenyl)propanoic acid The title compound was prepared using the procedure analogous to that described for EXAMPLE 1 substituting 5-(2-methylpropyl)picolinic acid for CARBOXYLIC ACID 1 in Step A: ¹H NMR (500 MHz, CD₃OD) δ 1.43 (s, 9H), 2.57 (t, J=7.8, 2H), 2.67 (s, 3H), 2.95 (t, J=7.7, 2H), 7.17-7.19 (m, 2H), 8.06-8.09 (m, 2H), 8.19 (d, J=8.5, 1H), 8.91 (d, J=2.1, 1H).

Step B: 3-(4-(5-(5-(2-Methylpropyl)pyridin-2-yl)-1,2,4-oxadiazol-3-yl)-3-methylphenyl)propanoic acid The title compound was prepared from tert-butyl 3-(4-(5-(5-(2-methylpropyl)pyridin-2-yl)-1,2,4-oxadiazol-3-yl)-3-methylphenyl)propanoic acid (from Step A) using a procedure analogous to that described in EXAMPLE 1, Step B: ¹H NMR (500 MHz, CD₃OD) δ 0.87 (d, J=6.7, 6H), 1.84-1.92 (m, 1H), 2.54-2.57 (m, 7H), 2.87 (t, J=7.7, 2H), 7.13-7.17 (m, 2H), 7.83 (dd, J=2.0, 8.1, 1H), 7.91 (d, J=7.8, 1H), 8.20 (d, J=8.1, 1H), 8.51 (s, 1H).

Example 8

(1S,2S/1R,2R)-2-(4-(5-(4-Isopropoxy-3-(trifluoromethyl)phenyl)-1,2,4-oxadiazol-3-yl)-3-methylphenyl)cyclopropanecarboxylic acid Step A: 3-(4-Bromo-2-methylphenyl)-5-(4 isopropoxy-3-(trifluoromethyl)phenyl)-1,2,4-oxadiazole The title compound was prepared using procedures analogous to those described in EXAMPLE 1, Step A substituting 2-methylbromobenzamidine for N-HYDROXYAMIDINE 1 and CARBOXYLIC ACID 9 for CARBOXYLIC ACID 1: ¹H NMR (500 MHz, CD₃OD) δ 1.44 (d, J=5.9, 6H), 2.67 (s, 3H), 4.78 (spt, J=6.2, 1H), 7.15 (d, J=8.9, 1H), 7.48 (dd, J=2.0, 8.4, 1H), 7.51 (s, 1H), 7.97 (d, J=8.2, 1H), 8.30 (dd, J=2.2, 8.8, 1H), 8.43 (d, J=2.3, 11H).

Step B: tert-Butyl (2E)-3-(4-(5-(4-isopropoxy-3-(trifluoromethyl)phenyl)-1,2,4-oxadizol-3-yl)-3-methylphenyl)acrylate To a solution of 181 mg (0.41 mmol) of 3-(4-bromo-2-methylphenyl)-5-(4-isopropoxy-3-(trifluoromethyl)phenyl)-1,2,4-oxadiazole (from Step A), 66 μL (0.45 mmol) of tert-butyl acrylate, 6.1 mg (0.02 mmol) of 1,1'-biphenyl-2-yl(di-tert-butyl)phosphine, and 132 μL (0.62 mmol) of N-methyldicyclohexylamine in 5.0 mL of 1,4-dioxane was added 9.4 mg (0.01 mmol) of tris(dibenzylideneacetone)dipalladium(0)-chloroform complex. The reaction mixture was stirred at 70° C. for 16 h, cooled to rt, and filtered though a cake of Celite. The filtrate was concentrated. Chromatography on a Biotage 40S cartridge using 1:19 v/v EtOAc/hexanes as the eluant afforded 116 mg of the title compound: ¹H NMR (500 MHz, CDCl₃) δ 1.44 (d, J=5.9, 6H), 1.55 (s, 9H), 2.70 (s, 3H), 4.78 (spt, J=6.2, 1H), 6.46 (d, J=16.0, 1H), 7.15 (d, J=8.9, 1H), 7.47-7.49 (m, 2H), 7.60 (d, J=16.0, 1H), 8.11 (d, J=8.0, 1H), 8.31 (dd, J=2.1, 8.8, 1H), 8.43 (d, J=2.0, 1H).

Step C: tert-Butyl (1S,2S/1R,2R)-2-(4-(5-(4-isopropoxy-3-(trifluoromethyl)phenyl)-1,2,4-oxadiazol-3-yl)-3-methylphenyl)cyclopropanecarboxylate To a suspension of 30 mg (0.14 mmol) of trimethylsulfoxonium iodide in 5.0 mL of DMSO was added 30 mg (0.14 mmol, 60% in mineral oil) of sodium hydride. The mixture was stirred at rt for 1 h. To the reaction mixture was added 61 mg (0.12 mmol) of tert-butyl (2E)-3-(4-(5-(4-isopropoxy-3-(trifluoromethyl)phenyl)-1,2,4-oxadizol-3-yl)-3-methylphenyl)acrylate (from Step B. After stirring at rt for 15 min and then at 50° C. for 1 h, the reaction mixture was cooled down to rt and partitioned between 50 mL of EtOAc and 50 mL of H₂O. Aqueous layer was separated and extracted with EtOAc three times. Organic layers were combined, washed with brine, dried over MgSO₄, and concentrated. Chromatography on a Biotage 40S cartridge using 3:17 v/v EtOAc/hexanes as the eluant afforded 37 mg of the title compound: ¹H NMR (500 MHz, CDCl₃) δ 1.26-1.31 (m, 1H), 1.43 (d, J=5.9, 6H), 1.48 (s, 9H), 1.56-1.61 (m, 1H), 1.88-1.92 (m, 1H), 2.44-2.49 (m, 1H), 2.65 (s, 3H), 4.75-4.80 (m, 1H), 7.03-7.06 (m, 2H), 7.13 (d, J=8.9, 1H), 8.00 (d, J=8.0, 1H), 8.30 (dd, J=2.0, 8.7, 1H), 8.42 (d, J=2.1, 1H).

Step D: (1S,2S/1R,2R)-2-(4-(5-(4-Isopropoxy-3-(trifluoromethyl)phenyl)-1,2,4-oxadiazol-3-yl)-3-methylphenyl)cyclopropanecarboxylic acid The title compound was prepared a procedure analogous to that described in EXAMPLE 1, Step B substituting tert-butyl (1S,2S/1R,2R)-2-(4-(5-(4-isopropoxy-3-(trifluoromethyl)phenyl)-1,2,4-oxadiazol-3-yl)-3-methylphenyl)cyclopropanecarboxylate for tert-butyl 3-(4-(5-(3-cyano-4-isopropyloxyphenyl)-1,2,4-oxadiazol-3-yl)-3-methylphenyl)propanoate: $^1$H NMR (500 MHz, CDCl$_3$) δ 1.43-1.49 (m, 7H), 1.70-1.74 (m, 1H), 1.97-2.01 (m, 1H), 2.62-2.66 (m, 4H), 4.76-4.79 (m, 1H), 7.06-7.09 (m, 2H), 7.14 (d, J=8.7, 1H), 8.02 (d, J=8.0, 1H), 8.30 (dd, J=2.2, 8.8, 1H), 8.42 (d, J=2.0, 1H).

Examples 9-11

The following examples were prepared using procedures analogous to those described for EXAMPLE 1 substituting N-HYDROXYAMIDINE 2 for N-HYDROXYAMIDINE 1 in Step A.

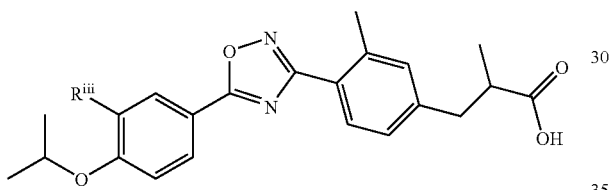

| EXAMPLE | R$^{iii}$ | HPLC A (min) | ESI-MS (M + H) |
|---|---|---|---|
| 9 | —CF$_3$ | 4.6 | 449.3 |

$^1$HNMR (500 MHz, CD$_3$OD) δ 1.18 (d, J = 6.9, 3 H), 1.41 (d, J = 6, 6 H), 2.62 (s, 3 H), 2.75 (m, 2 H), 3.02 (m, 1 H), 4.92 (m, 1 H), 7.20 (d, J = 8.0, 1 H), 7.23 (s, 1 H), 7.41 (d, J = 9.4, 1 H), 7.95 (d, J = 8.0, 1 H), 8.38 (m, 2 H)

| | 10 | —CN | 4.3 | 406.3 |

$^1$HNMR (500 MHz, CD$_3$OD) δ 1.19 (d, J = 6.9, 3 H), 1.47 (d, J = 5.9, 6 H), 2.64 (s, 3 H), 2.77 (m, 2 H), 3.05 (m, 1 H), 4.96 (m, 1 H), 7.22 (d, J = 8.0, 1 H), 7.25 (s, 1 H), 7.43 (d, J = 8.7, 1 H), 7.97 (d, J = 8.0, 1 H), 8.43 (m, 2 H)

| | 11 | —CH$_3$ | 4.7 | 395.3 |

$^1$HNMR (500 MHz, CD$_3$OD) δ 1.19 (d, J = 6.6, 3 H), 1.39 (d, J = 6.0, 6 H), 2.27 (s, 3 H), 2.62 (s, 3 H), 2.78 (m, 2 H), 3.04 (m, 1 H), 4.76 (m, 1 H), 7.09 (d, J = 8.7, 1 H), 7.20 (d, J = 7.8, 1 H), 7.23 (s, 1 H), 7.95 (m, 2 H) 8.00 (m, 1 H)

Examples 12-14

The following examples were prepared using procedures analogous to those described for EXAMPLE 1 substituting N-HYDROXYAMIDINE 3 for N-HYDROXYAMIDINE 1 in Step A.

| EXAMPLE | R$^{iv}$ | HPLC A (min) | ESI-MS (M + H) |
|---|---|---|---|
| 12 | —CF$_3$ | 4.9 | 449.3 |

$^1$HNMR (500 MHz, CD$_3$OD) δ 1.33 (d, J = 7.1, 3 H), 1.41 (d, J = 5.9, 6 H), 2.63 (m, 5 H), 3.29 (m, 1 H), 4.91 (m, 1 H), 7.24 (m, 2 H), 7.41 (m, 1 H), 7.97 (m, 1 H), 8.35 (m, 2 H)

| | 13 | —CN | 4.5 | 406.3 |

$^1$HNMR (500 MHz, CD$_3$OD) δ 1.33 (d, J = 7.1, 3 H), 1.41 (d, J = 5.9, 6 H), 2.62 (m, 5 H), 3.28 (m, 1 H), 4.92 (m, 1 H), 7.24 (m, 2 H), 7.39 (d, J = 8.9, 1 H), 7.96 (d, J = 8.1, 1 H), 8.38 (m, 1 H)

| | 14 | —CH$_3$ | 4.9 | 395.3 |

$^1$HNMR (500 MHz, CD$_3$OD) δ 1.32 (d, J = 6.9, 3 H), 1.37 (d, J = 5.9, 6 H), 2.24 (s, 3 H), 2.60 (m, 5 H), 3.27 (m, 1 H), 4.73 (m, 1 H), 7.05 (d, J = 8.5, 1 H), 7.22 (m, 2 H), 7.95 (m, 3 H)

Example 15

3-(4-(5-(5-Chloro-6-isopropoxypyridin-3-yl)-1,24-oxadiazol-3-yl)-3-methylphenyl)propanoic acid Step A: tert-Butyl 3-(4-(5-(5,6-dichloropyridin-3-yl)-1,2,4-oxadiazol-3-yl)-3-methylphenyl)propanoate To a solution of 200 mg (1.04 mmol) of 5,6-dichloronicotinic acid in 5.0 mL of CH$_2$Cl$_2$ was added 273 μL (3.13 mmol) of oxalyl chloride and one drop of DMF. After stirring at rt overnight, the mixture was concentrated and dried azeotropically using toluene (3×5 mL). The residue was dissolved in 5.0 mL of dichloroethane and added to a solution of 242 mg (0.87 mmol) of N-HYDROXYAMIDINE 1 and 182 μL (1.30 mmol) of triethylamine in 5.0 mL of dichloroethane. After stirring at rt for 1 hr and at 120° C. overnight, the reaction mixture was cooled to rt and concentrated. Chromatography on a Biotage 40S cartridge using 1:19 v/v EtOAc/hexanes as the eluant gave 303 mg of the title compound: $^1$H NMR (500 MHz, CDCl$_3$) δ 1.44 (s, 9H), 2.58 (t, J=7.8, 2H), 2.65 (s, 3H), 2.95 (t, J=7.7, 2H), 7.17-7.19 (m, 2H), 8.00 (d, J=8.5, 1H), 8.53 (d, J=2.0, 1H), 9.08 (d, J=2.0, 1H).

Step B: tert-Butyl 3-(4-(5-(5-chloro-6-isopropoxypyridin-3-yl)-1,2,4-oxadiazol-3-yl)-3-methylphenyl)propanoate To a solution of 138 mg (0.32 mmol) of tert-butyl 3-(4-(5-(5,6-dichloropyridin-3-yl)-1,2,4-oxadiazol-3-yl)-3-methylphenyl)propanoate and 36.5 μL (0.48 mmol) of 2-propanol in 10 mL of THF was added 477 μL (0.48 mmol) of sodium bis(trimethylsilyl)amide (1.0 M in THF). The mixture was refluxed overnight, cooled to rt and concentrated. Chromatography on a Biotage 40S cartridge using 1:19 v/v EtOAc/hexanes as the eluant gave 106 mg of the title compound: $^1$H NMR (500 MHz, CDCl$_3$) δ 1.43 (s, 9H), 1.44 (d, J=6.2, 6H), 2.58 (t, J=7.8, 2H), 2.65 (s, 3H), 2.95 (t, J=7.7, 2H), 5.49 (m, 1H), 7.17-7.18 (m, 2H), 8.00 (d, J=8.4, 1H), 8.38 (d, J=2.0, 1H), 8.86 (d, J=2.3, 1H).

Step C: 3-(4-(5-(5-Chloro-6-isopropoxypyridin-3-yl)-1,2,4-oxadiazol-3-yl)-3-methylphenyl)propanoic acid The title compound was prepared using a procedure analogous to that described for EXAMPLE 1, Step B substituting tert-butyl 3-(4-(5-(5-chloro-6-isopropoxypyridin-3-yl)-1,2,4-oxadiazol-3-yl)-3-methylphenyl)propanoate for tert-butyl 3-(4-(5-(3-cyano-4-isopropoxyphenyl)-1,2,4-oxadiazol-3-yl)-3-methyl-phenyl)propanoate: $^1$H NMR (500 MHz, CD$_3$OD) δ 1.35 (d, J=6.2, 6H), 2.55 (s, 3H), 2.58 (t, J=7.7, 2H), 2.89 (t, J=7.7, 2H), 5.44 (m, 1H), 7.15-7.19 (m, 2H), 7.90 (d, J=8.0, 1H), 8.38 (d, J=2.0, 1H), δ 80 (d, J=2.3, 1H).

Example 16

3-(4-(5-(5-Chloro-6-isopropylaminopyridin-3-yl)-1,2,4-oxadiazol-3-yl)-3-methylphenyl)propanoic acid Step A: tert-Butyl 3-(4-(5-(5-chloro-6-isopropylaminopyridin-3-yl)-1,2,4-oxadiazol-3-yl)-3-methylphenyl)propanoate A solution of 31 mg (0.07 mmol) of tert-butyl 3-(4-(5-(5,6-dichloropyridin-3-yl)-1,2,4-oxadiazol-3-yl)-3-methylphenyl)propanoate (from EXAMPLE 15, Step A) and 120 μL (1.4 mmol) of 2-propylamine in 5.0 mL of THF was heated to 100° C. in a sealed tube overnight. The mixture was cooled to rt and concentrated. Chromatography on a Biotage 40S cartridge using 1:9 v/v Et$_2$O/hexanes as the eluant gave 28 mg of the title compound: $^1$H NMR (500 MHz, CDCl$_3$) δ 1.32 (d, J=6.4, 6H), 1.43 (s, 9H), 2.57 (t, J=7.7, 2H), 2.64 (s, 3H), 2.94 (t, J=7.7, 2H), 4.41 (m, 1H), 5.32 (d, J=7.5, 1H), 7.16-7.17 (m, 2H), 7.99 (d, J=8.5, 1H), 8.18 (d, J=1.8, 1H), 8.85 (d, J=1.8, 1H).

Step B: 3-(4-(5-(5-Chloro-6-isopropylaminopyridin-3-yl)-1,2,4-oxadiazol-3-yl)-3-methylphenyl)propanoic acid The title compound was prepared using the procedure analogous to that described for EXAMPLE 1, Step B substituting tert-butyl 3-(4-(5-(5-chloro-6-isopropylaminopyridin-3-yl)-1,2,4-oxadiazol-3-yl)-3-methylphenyl)propanoate (from Step A) for tert-butyl 3-(4-(5-(3-cyano-4-(2-propyloxy)phenyl)-1,2,4-oxadiazol-3-yl)-3-methyl-phenyl)propanoate: $^1$H NMR (500 MHz, CD$_3$OD) δ 1.31 (d, J=6.4, 6H), 2.61 (s, 3H), 2.65 (t, J=7.6, 2H), 2.96 (t, J=7.7, 2H), 4.42 (m, 1H), 7.22-7.25 (m, 2H), 7.94 (d, J=8.0, 1H), 8.24 (d, J=2.1, 1H), 8.77 (d, J=1.8, 1H).

Examples 17-20

The following examples were prepared using procedures analogous to those described for EXAMPLE 15 substituting appropriate alcohol for 2-propanol in Step B or EXAMPLE 16 substituting the appropriate amine for 2-propylamine in Step A.

| EXAMPLE | R$^v$ | HPLC A (min) | ESI-MS (M + H) |
|---|---|---|---|
| 17 | (CF$_3$, CHF, O-CH$_3$ group) | 4.1 | — |
| 18 | (pyrrolidinyl) | 4.0 | 413.2 |
| 19 | (morpholinyl) | 3.6 | 429.2 |
| 20 | (isopropyl-N-methyl) | 4.1 | 415.2 |

Examples 21-24

The following examples were prepared using procedures analogous to those described for EXAMPLE 15 substituting N-HYDROXYAMIDINE 3 for N-HYDROXYAMIDINE 1 in Step A and the appropriate alcohol for 2-propanol in Step B or EXAMPLE 16 substituting the appropriate amine for 2-propylamine in Step A.

| EXAMPLE | R$^{vi}$ | HPLC A (min) | ESI-MS (M + H) |
|---|---|---|---|
| 21 | (CF$_3$-CH$_2$-O) | 4.0 | 457.4 |
| 22 | (CF$_2$H-CH(CH$_3$)-O) | 4.0 | — |

-continued

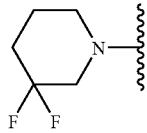

| EXAMPLE | R$^{vi}$ | HPLC A (min) | ESI-MS (M + H) |
|---|---|---|---|
| 23 | 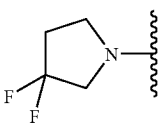 | 4.1 | 477.2 |
| 24 | 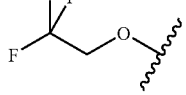 | 4.0 | 463.2 |

Example 25

3-(4-(5-(5-Trifluoromethyl-6-(morpholin-4-yl)pyridin-3-yl)-1,2,4-oxadiazol-3-yl)-3-methylphenyl) butanoic acid The following examples were prepared using procedures analogous to those described for EXAMPLE 15 substituting N-HYDROXYAMINE 3 for N-HYDROXYAMIDINE 1 and 5-trifluoromethyl-6-(morpholin-4-yl)nicotinic acid for CARBOXYLIC ACID 1 in Step A: $^1$H NMR (500 MHz, CD$_3$OD) δ 1.34 (d, J=6.8, 3H), 2.58-2.67 (m, 5H), 3.30 (m, 1H), 3.63 (t, J=4.6, 4H), 3.81 (t, J=4.6, 4H), 7.25-7.28 (m, 2H), 7.99 (d, J=7.8, 1H), 8.61 (d, J=2.1, 1H), 9.12 (d, J=2.1, 1H).

Examples 26-30

The following examples were prepared using procedures analogous to those described for EXAMPLE 15 substituting HYDROXYAMIDINE 4 for HYDROXYAMIDINE 1 in Step A and appropriate alcohols or amines for 2-propanol in Step B.

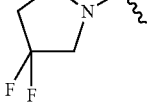

| EXAMPLE | R$^{vii}$ | HPLC A (min) | ESI-MS (M + H) |
|---|---|---|---|
| 26 | 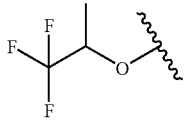 | 4.0 | 461.1 |
| 27 | 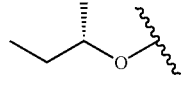 | 4.0 | 454.1 |
| 28 | 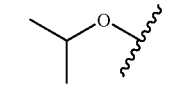 | 4.2 | 468.1 |
| 29 | | 4.4 | 428.1 |
| 30 | | 4.2 | 414.2 |

Example 31

3-(4-(5-(5-Chloro-6-isobutylpyridin-3-yl)-1,2,4-oxadiazol-3-yl)-3-methylphenyl)propanoic acid Step A: tert-Butyl 3-(4-(5-(5-chloro-6-isobutylpyridin-3-yl)-1,2,4-oxadiazol-3-yl)-3-methylphenyl) propanoate To a solution of 86 mg (0.20 mmol) of tert-butyl 3-(4-(5-(5,6-dichloropyridin-3-yl)-1,2,4-oxadiazol-3-yl)-3-methylphenyl)propanoate (from EXAMPLE 15, Step A), 5.1 mg (0.01 mmol) of bis(tri-tert-butylphosphine)palladium(0), and 200 μL of 1-methyl-2-pyrrolidinone in 5.0 mL of THF was added 475 μL (0.24 mmol) of isobutylzinc bromide (0.5 M in THF). The reaction mixture was refluxed for 4 h, cooled to rt, and filtered through a cake of Celite. The filtrate was concentrated. Chromatography on Biotage 40S cartridge using 7:93 v/v Et$_2$O/hexanes as the eluant afforded 55 mg of the title compound: $^1$H NMR (500 MHz, CD$_3$OD) δ 0.99 (d, J=6.7, 6H), 1.44 (s, 9H), 2.28 (m, 1H), 2.58 (t, J=7.7, 2H), 2.66 (s, 3H), 2.93-2.97 (m, 4H), 7.18-7.20 (m, 2H), 8.01 (d, J=8.5, 1H), 8.42 (d, J=1.8, 1H), 9.22 (d, J=1.9, 1H).

Step B: 3-(4-(5-(5-Chloro-6-isobutylpyridin-3-yl)-1,2,4-oxadiazol-3-yl)-3-methylphenyl)propanoic acid The title compound was prepared using the procedure analogous to that described for EXAMPLE 1, Step B substituting tert-butyl 3-(4-(5-(5-chloro-6-isobutylpyridin-3-yl)-1,2,4-oxadiazol-3-yl)-3-methylphenyl)propanoate (from Step A) for tert-butyl 3-(4-(5-(3-cyano-4-isopropoxyphenyl)-1,2,4-oxadiazol-3-yl)-3-methyl-phenyl)propanoate: $^1$H NMR (500 MHz, CD$_3$OD) δ 0.93 (d, J=6.7, 6H), 2.21 (m, 1H), 2.57

(s, 3H), 2.59 (t, J=7.7, 2H), 2.87-2.91 (m, 4H), 4.42 (m, 1H), 7.17-7.20 (m, 2H), 7.93 (d, J=7.8, 1H), 8.48 (d, J=1.9, 1H), 9.12 (d, J=1.8, 1H).

Example 32

3-(4-(5-(5-Iodo-6-(N-isopropyl-N-methylamino)pyridin-3-yl)-1,2,4-oxadiazol-3-yl)-3-methylphenyl)propanoic acid The title compound was prepared using a procedure analogous to those described for EXAMPLE 16 substituting 6-hydroxy-5-iodonicotinic acid for 5,6-dichloronicotinic acid and N-isopropyl-N-methylamine for 2-propylamine: $^1$H NMR (500 MHz, CDCl$_3$) δ 1.26 (d, J=6.6, 6H), 2.64 (s, 3H), 2.73 (t, J=7.7, 2H), 2.96 (s, 3H), 3.00 (t, J=7.7, 2H), 4.46 (m, 1H), 7.18-7.20 (m, 2H), 7.99 (d, J=8.5, 1H), 8.75 (d, J=1.8, 1H), 8.94 (d, J=1.9, 1H).

Example 33

3-(4-(5-(5-Cyano-6-(N-isopropyl-N-methylamino)pyridin-3-yl)-1,2,4-oxadiazol-3-yl)-3-methylphenyl)propanoic acid

Step A: tert-Butyl 3-(4-(5-(5-cyano-6-(N-isopropyl-N-methylamino)pyridin-3-yl)-1,2,4-oxadiazol-3-yl)-3-methylphenyl)propanoate To a solution of 250 mg (0.44 mmol) of tert-butyl 3-(4-(5-iodo-(6-(N-isopropyl-N-methylamino)pyridin-3-yl)-1,2,4-oxadiazol-3-yl)-3-methylphenyl)propanoate (from EXAMPLE 32) and 104 mg (0.89 mmol) of zinc cyanide in 5.0 mL of DMF was added 31 mg (0.03 mmol) of tetrakis(triphenylphosphine)palladium(0). The mixture was stirred at 80° C. overnight, cooled to rt, and filtered through a cake of Celite. The filtrate was washed with brine (20 mL), H$_2$O (2×20 mL), and brine (20 mL). The organic layer was dried over Na$_2$SO$_4$ and concentrated. Chromatography on Biotage 40S cartridge using 1:9 v/v EtOAc/hexanes as the eluant afforded 129 mg of the title compound: $^1$H NMR (500 MHz, CDCl$_3$) δ 1.30 (d, J=6.6, 6H), 1.43 (s, 9H), 2.58 (t, J=7.7, 2H), 2.64 (s, 3H), 2.95 (t, J=7.7, 2H), 3.23 (s, 3H), 5.14 (m, 1H), 7.17-7.18 (m, 2H), 7.99 (d, J=8.5, 1H), 8.48 (d, J=2.5, 1H), 9.02 (d, J=2.5, 1H).

Step B: 3-(4-(5-(5-Cyano-6-(N-isopropyl-N-methylamino)pyridin-3-yl)-1,2,4-oxadiazol-3-yl)-3-methylphenyl)propanoic acid The title compound was prepared using the procedure analogous to that described for EXAMPLE 1, Step B substituting tert-butyl 3-(4-(5-(5-cyano-6-(N-isopropyl-N-methylamino)pyridin-3-yl)-1,2,4-oxadiazol-3-yl)-3-methylphenyl)propanoate (from Step A) for tert-butyl 3-(4-(5-(3-cyano-4-isopropoxyphenyl)-1,2,4-oxadiazol-3-yl)-3-methyl-phenyl)propanoate: $^1$H NMR (500 MHz, CD$_3$OD) δ 1.31 (d, J=6.7 6H), 2.61 (s, 3H), 2.65 (t, J=7.6, 2H), 2.96 (t, J=7.7, 2H), 3.24 (s, 3H), 5.14 (m, 1H), 7.22-7.26 (m, 2H), 7.95 (d, J=8.0, 1H), 8.55 (d, J=2.5, 1H), 9.02 (d, J=2.5, 1H).

Example 34

3-(4-(5-(6-(3,3-Difluoropyrrolidin-1-yl)-5-iodopyridin-3-yl)-1,2,4-oxadiazol-3-yl)-3-methylphenyl)propanoic acid The title compound was prepared using the procedure analogous to that described for EXAMPLE 32 substituting 3,3-difluoropyrrolidine for N-isopropyl-N-methylamine: $^1$H NMR (500 MHz, DMSO) δ 2.48-2.59 (m, 7H), 2.86 (t, J=7.6, 2H), 3.40 (t, J=7.3, 2H), 4.17 (t, J=13, 2H), 7.25 (d, J=8.0, 1H), 7.28 (s, 1H), 9.92 (d, J=7.8, 1H), 8.70 (d, J=2.1, 1H), 8.87 (d, J=2.1, 1).

Example 35

3-(4-(5-(6-(3,3-Difluoropyrrolidin-1-yl)-5-ethynylpyridin-3-yl)-1,2,4-oxadiazol-3-yl)-3-methylphenyl)propanoic acid

Step A: tert-Butyl 3-(4-(5-(6-(3,3-difluoropyrrolidin-1-yl)-5-(trimethylsilyl)ethynylpyridin-3-yl)-1,2,4-oxadiazol-3-yl)-3-methylphenyl)propanoate To a solution of 61 mg (0.10 mmol) of tert-butyl 3-(4-(5-(6-(3,3-difluoropyrrolidin-1-yl)-5-iodopyridin-3-yl)-1,2,4-oxadiazol-3-yl)-3-methylphenyl)propanoate (from EXAMPLE 34) in 5.0 mL of 1,4-dioxane were added 1 mg (0.005 mmol) of copper(II) iodide, 20 mg (0.21 mmol) of (trimethylsilyl)acetylene, 12 mg (0.12 mmol) of diisopropylamine, and 2.6 mg (0.005 mmol) of bis(tri-tert-butylphosphine)palladium(0). The mixture was stirred at rt for 16 h and concentrated. Chromatography on a Biotage 25S cartridges using 9:1 v/v hexanes/EtOAc as the eluant afforded 43 mg of a yellow solid as the title compound: $^1$HNMR (500 MHz, CDCl$_3$) δ 0.26 (s, 9H), 1.45 (s, 9H), 2.46 (m, 2H), 2.58 (t, J=7.8, 2H), 2.66 (s, 3H), 2.96 (t, J=7.8, 2H), 4.15 (t, J=7.3, 2H), 4.32 (t, J=13, 2H), 7.18 (s, 1H), 7.19 (s, 1H), 8.01 (m, 1H), 8.34 (d, J=2.3, 1H), 8.88 (d, J=2.3, 1H).

Step B: 3-(4-(5-(6-(3,3-Difluoropyrrolidin-1-yl)-5-(trimethylsilyl)ethynylpyridin-3-yl)-1,2,4-oxadiazol-3-yl)-3-methylphenyl)propanoic acid The title compound was prepared using the procedure analogous to that described for EXAMPLE 1, Step B substituting tert-butyl 3-(4-(5-(6-(3,3-difluoropyrrolidin-1-yl)-5-(trimethylsilyl)ethynylpyridin-3-yl)-1,2,4-oxadiazol-3-yl)-3-methylphenyl)propanoate (from Step A) for tert-butyl 3-(4-(5-(3-cyano-4-isopropoxyphenyl)-1,2,4-oxadiazol-3-yl)-3-methyl-phenyl)propanoate: $^1$HNMR (500 MHz, DMSO) δ 0.24 (s, 9H), 2.49 (m, 4H), 2.86 (t, J=7.5, 2H), 4.06 (t, J=7.3, 2H), 4.27 (t, J=13, 2H), 7.24 (d, J=8.3, 1H), 7.28 (s, 1H), 7.92 (d, J=7.8, 1H), 8.21 (d, J=2.3, 1H), 8.84 (d, J=2.3, 1H).

Step C: 3-(4-(5-(6-(3,3-Difluoropyrrolidin-1-yl)-5-ethynylpyridin-3-yl)-1,2,4-oxadiazol-3-yl)-3-methylphenyl)propanoic acid A solution of 5 mg of 3-(4-(5-(6-(3,3-difluoropyrrolidin-1-yl)-5-(trimethylsilyl)ethynylpyridin-3-yl)-1,2,4-oxadiazol-3-yl)-3-methylphenyl)propanoic acid in 200 μL of tetrabutylammonium fluoride (1.0 M in THF) was stirred at rt for 2 h. Purification by HPLC B afforded the title compound: $^1$HNMR (500 MHz, DMSO) δ 2.48 (m, 4H), 2.86 (t, J=7.3, 2H), 4.09 (t, J=7.3, 2H), 4.24 (t, J=13, 2H), 7.24 (d, J=8.4, 1H), 7.28 (s, 1), 7.92 (d, =8.0, 1H), 8.27 (d, J=2.3, 1H), 8.86 (d, J=2.3, 1H).

Example 36

(1R,2R/1S,2S)-2-(4-(5-(4-isopropoxy-3-cyanophenyl)-1,2,4-oxadiazol-3-yl)-3-methylphenyl)cyclopropanecarboxylic acid Step A: tert-Butyl (1R,2R/1S,2S)-2-(4-(5-(4-isopropoxy-3-cyanophenyl)-1,2,4-oxadiazol-3-yl)-3-methylphenyl)cyclopropanecarboxylate The title compound was prepared using the procedure analogous to that described for EXAMPLE 1 substituting N-HYDROXYAMINE 4 for N-HYDROXYAMIDINE 1 in Step A: ¹H NMR (500 MHz, CD₃OD) δ 1.41-1.46 (m, 7H), 1.59 (m, 1H), 1.94 (m, 1H), 2.50 (m, 1H), 2.61 (s, 3H), 4.93 (m, 1H), 7.10 (dd, J=1.5, 8.2, 1H), 7.14 (s, 1H), 7.40 (d, J=8.9, 1H), 7.96 (d, J=8.0, H), 8.36-8.39 (m, 2H).

Examples 37-44

The following examples were prepared using procedures analogous to that described for EXAMPLE 36 substituting the appropriate acid for CARBOXYLIC ACID 1.

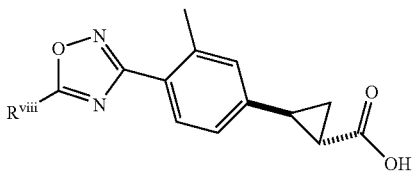

| EXAMPLE | R^viii | HPLC A (min) | ESI-MS (M + H) |
|---|---|---|---|
| 37 | (F₃C-CH(CH₃)-O-phenyl-CN) | 5.0 | 458.3 |
| 38 | (isopropoxy-phenyl-OCH₃) | 3.7 | 409.2 |
| 39 | (F₃C-CH₂-O-phenyl-CN) | 3.6 | 444.2 |
| 40 | ((CF₃)₂CH-O-phenyl-CN) | 3.8 | 512.2 |
| 41 (Enantiomer 1) | (isopropoxy-phenyl-CN) | 3.7 | 404.3 |
| 42 (Enantiomer 2) | (isopropoxy-phenyl-CN) | 3.7 | 404.3 |
| 43 | (sec-butoxy-phenyl-CN) | 3.8 | 418.3 |
| 44 | (F₃C-CH(CH₃)-O-pyridyl-CN) | 3.8 | 459.3 |

Example 45

(1R,2R/1S,2S)-2-(4-(5-(5-(5-Iodo-6-isopropoxypyridin-3-yl)-1,2,4-oxadiazol-3-yl)-3-methylphenyl)cyclopropanecarboxylic acid The title compound was prepared using the procedure analogous to that described for EXAMPLE 15 substituting N-HYDROXYAMIDINE 4 for N-HYDROXYAMIDINE 1 and 5-iodo-6-chloronicotinoyl chloride for 5,6-dichloronicotinoyl chloride in Step A: ¹H NMR (500 MHz, CD₃OD) δ 1.42 (m, 7H), 1.60 (m, 1H), 1.93 (m, 1H), 2.49 (m, 1H), 2.61 (s, 3H), 5.45 (m, 1H), 7.10 (d, J=8.2, 1H), 7.15 (s, 1H), 7.29 (m, 1H), 7.96 (t, J=8.0, 1H), 8.78 (d, J=2.3, 1H), 8.89 (d, J=2.3, 1H).

Example 46

(1R,2R/1S,2S)-2-(4-(5-(5-(4-Iodo-6-isopropoxypyridin-3-yl)-1,24-oxadiazol-3-yl)-3-methyl)phenyl)cyclopropanecarboxylic acid Step A: tert-Butyl (1R,2R/1S,2S)-2-(4-(5-(5-(4-fluorophenyl)-6-isopropoxypyridin-3-yl)-1,2,4-oxadiazol-3-yl)-3-methylphenyl)cyclopropanecarboxylate To a solution of 60 mg (0.11 mmol) of tert-butyl (1R,2R/1S,2S)-2-(4-(5-(5-iodo-6-isopropoxypyridin-3-yl)-1,2,4-oxadiazol-3-yl)-3-methylphenyl)cyclopropane carboxylate (from EXAMPLE 45) in 10 mL of THF were added 19 mg (0.32 mmol) of potassium fluoride, 22 mg (0.16 mmol) of 4-fluorophenylboronic acid, and 2.73 mg (0.005 mmol) of bis(tri-tert-butylphosphine)palladium(0). The mixture was stirred at 80° C. for 16 h and concentrated. Chromatography on a Biotage 25S cartridges using 19:1 v/v hexanes/EtOAc as the eluant afforded 45 mg of the title compound: $^1$H NMR (500 MHz, CDCl$_3$) δ 1.32 (m, 1H), 1.41 (d, J=6.2, 6H), 1.51 (s, 9H), 1.62 (m, 1H), 1.92 (m, 1H), 2.57 (m, 1H), 2.68 (s, 3H), 5.55 (m, 1H), 7.10 (m, 2H), 7.19 (m, 2H), 7.62 (m, 2H), 8.03 (m, 1H), 8.34 (d, J=2.3, 1H), 8.98 (d, J=2.3, 1H).

Step B: (1R,2R/1S,2S)-2-(4-(5-(5-(4-fluorophenyl)-6-isopropoxypyridin-3-yl)-1,2,4-oxadiazol-3-yl)-3-methylphenyl)cyclopropanecarboxylic acid The title compound was prepared using the procedure analogous to that described for EXAMPLE 1 substituting tert-butyl (1R,2R/1S,2S)-2-(4-(5-(5-(4-fluorophenyl)-6-isopropoxypyridin-3-yl)-1,2,4-oxadiazol-3-yl)-3-methylphenyl)cyclopropanecarboxylate (from Step A) for tert-butyl 3-(4-(5-(3-cyano-4-isopropoxyphenyl)-1,2,4-oxadiazol-3-yl)-3-methyl-phenyl)propanoate in Step B: $^1$HNMR (500 MHz, CD$_3$OD) δ 1.35 (d, J=6.2, 6H), 1.40 (m, 1H) 1.57 (m, 1H), 1.91 (m, 1H), 2.47 (m, 1H), 2.57 (s, 3H), 5.48 (m, 1H), 7.04 (m, 1H), 7.09 (m, 1H), 7.15 (m, 2H), 7.58 (m, 2H), 7.91 (d, J=8.0, 1H), 8.22 (d, J=2.3, 1H), 8.81 (d, J=2.3, 1H).

Examples 47-64

The following examples were prepared using procedures analogous to that described for EXAMPLE 1 substituting appropriate acids for CARBOXYLIC ACID 1 in Step A.

| EXAMPLE | R$^{ix}$ | HPLC A (min) | ESI-MS (M + H) |
|---|---|---|---|
| 47 | [5-(2-fluoro-2-methylpropyl)pyridin-2-yl] | 3.6 | 402.2 |
| 48 | [5-cyano-6-ethoxypyridin-3-yl] | 3.6 | — |
| 49 | [5-cyano-6-(1,1,1-trifluoropropan-2-yloxy)pyridin-3-yl] | 3.7 | 447.2 |
| 50 | [5-cyano-6-isobutylpyridin-3-yl] | 3.8 | 391.2 |
| 51 | [4-(2-fluoro-2-methylpropyl)phenyl] | 4.1 | 401.2 |
| 52 | [5-iodo-6-(1,1,1-trifluoropropan-2-yloxy)pyridin-3-yl] | 4.1 | 547.9 |
| 53 | [3-chloro-4-cyclopentyloxyphenyl] | 5.0 | 429.3 |
| 54 | [3-chloro-4-isobutoxyphenyl] | 5.0 | 415.2 |
| 55 | [3-cyano-4-(1,1,1-trifluoropropan-2-yloxy)phenyl] | 4.7 | 446.3 |

-continued

| EXAMPLE | R$^{ix}$ | HPLC A (min) | ESI-MS (M + H) |
|---|---|---|---|
| 56 | 4-(1-trifluoromethylethoxy)-3-chlorophenyl | 4.9 | 455.2 |
| 57 | 3,5-dichloro-4-isopropoxyphenyl | 5.2 | 435.2 |
| 58 | 3-chloro-4-(cyclopropylmethoxy)phenyl | 5.0 | 413.2 |
| 59 | 5-propoxypyridin-2-yl | 5.2 | 368.3 |
| 60 | 4-(1-trifluoromethylethoxy)-3-nitrophenyl | 3.7 | 466.2 |
| 61 | 4-(2,2,2-trifluoroethoxy)-3-cyanophenyl | 3.6 | 432.2 |

-continued

| EXAMPLE | R$^{ix}$ | HPLC A (min) | ESI-MS (M + H) |
|---|---|---|---|
| 62 | 4-(1-trifluoromethyl-2,2,2-trifluoroethoxy)-3-cyanophenyl | 3.8 | 500.3 |
| 63 | 4-(sec-butoxy)-3-cyanophenyl | 3.8 | 406.2 |
| 64 | 4-trifluoromethyl-6-(1-trifluoromethylethoxy)pyridin-3-yl | 4.1 | 490.1 |

Example 65

2-(4-(5-(5-(4-Amino-6-(2,2,2-trifluoro-1-methylethoxy)phenyl)-1,2,4-oxadiazol-3-yl)-3-methylphenyl)propanoic acid A solution of 24 mg (0.046 mmol) of tert-butyl 2-(4-(5-(5-(4-nitro-6-(2,2,2-trifluoro-1-methylethoxy)phenyl)-1,2,4-oxadiazol-3-yl)-3-methylphenyl)propanoate (from EXAMPLE 60) in 5.0 mL of ethanol was added 50 mg (0.23 mmol) of tin(II) chloride dihydrate. The mixture was heated at 70° C. for 16 h, and cooled to rt, partitioned between EtOAc (10 mL) and 1.0 N NaOH (10 mL). The organic layer was separated, washed with brine (3×5 mL), dried over MgSO$_4$, and concentrated. The residue was dissolved in CH$_2$Cl$_2$ and added 200 mL of trifluoroacetic acid to give 11.5 mg of the title compound: $^1$H NMR (500 MHz, CD$_3$OD) δ 1.56 (d, J=9.5, 3H), 2.61 (s, 3H), 2.66 (t, J=7.5, 2H), 2.97 (t, J=7.5, 2H), 5.16 (m, 1H), 7.23 (m, 3H), 7.66 (dd, J=2.1, 6.4, 1H), 7.71 (d, J=2.1, 1H), 7.93 (d, J=7.7, 1H).

Examples 66-68

The following examples were prepared using procedures analogous to those described for EXAMPLE 1 substituting N-HYDROXYAMIDINE 3 for N-HYDROXYAMIDINE 1 in Step A.

3.07 (s, 3H), 3.31 (m, 2H), 4.96 (m, 1H), 7.45 (d, J=9.1, 1H), 7.84 (d, J=8.2, 1H), 8.44 (dd, J=2.3, 8.9, 1H), 8.48 (d, J=2.3, 1H), 8.92 (d, J=8.2, 1H).

Examples 70-72

The following examples were prepared using procedures analogous to those described for EXAMPLE 69 substituting the appropriate carboxylic acid for CARBOXYLIC ACID 1 in Step A.

| EXAMPLE | R$^x$ | HPLC A (min) | ESI-MS (M + H) |
|---|---|---|---|
| 66 | (S)-sec-butoxy-cyanophenyl | 3.9 | 420.3 |
| 67 | (1,1,1,3,3,3-hexafluoroisopropoxy)-cyanophenyl | 3.8 | 514.1 |
| 68 | (2,2,2-trifluoroethoxy)-cyanophenyl | 3.6 | 446.2 |

| EXAMPLE | R$^{xi}$ | HPLC A (min) | ESI-MS (M + H) |
|---|---|---|---|
| 70 | cyano-isopropoxy-pyridyl | 2.9 | 448.1 |
| 71 | (2,2,2-trifluoroethoxy)-cyanophenyl | 2.7 | 433.1 |
| 72 | (1,1,1,3,3,3-hexafluoroisopropoxy)-cyanophenyl | 3.0 | 501.4 |

Example 69

3-(5-(5-(3-Cyano-4-isopropoxyphenyl)-1,2,4-oxadiazol-3-yl)-6-methylpyridin-2-yl)propanoic acid Step A: tert-Butyl 3-(5-(5-(3-cyano-4-isopropoxyphenyl)-1,2,4-oxadiazol-3-yl)-6-methylpyridin-2-yl)propanoate The title compound was prepared using the procedure analogous to that described for EXAMPLE 1 substituting N-HYDROXYAMIDINE 5 for N-HYDROXYAMIDINE 1 in Step A: $^1$H NMR (500 MHz, CDCl$_3$) δ 1.44 (s, 9H), 1.48 (d, J=6.2, 6H), 2.75 (t, J=7.6, 2H), 2.89 (s, 3H), 3.13 (t, J=7.4, 2H), 4.80 (m, 1H), 7.12 (d, J=8.9, 1H), 7.18 (d, J=8.0, 1H), 8.27 (d, J=8.0, 1H), 8.33 (dd, J=2.1, 9.0, 1H), 8.42 (d, J=2.3, 1H).

Step B: 3-(5-(5-(3-Cyano-4-isopropyloxyphenyl)-1,2,4-oxadiazol-3-yl)-6-methylpyrindin-2-yl)propanoic acid The title compound was prepared using a procedure analogous to that described for EXAMPLE 1, Step B substituting tert-butyl 3-(5-(5-(3-cyano-4-isopropoxyphenyl)-1,2,4-oxadiazol-3-yl)-6-methylpyrindin-2-yl)propanoate (from Step A) for tert-butyl 3-(4-(5-(3-cyano-4-isopropoxyphenyl)-1,2,4-oxadiazol-3-yl)-3-methyl-phenyl)propanoate: $^1$H NMR (500 MHz, CD$_3$OD) δ 1.46 (d, J=6.2, 6H), 2.92 (t, J=7.2, 2H),

Example 73

3-(5-(5-(3-Cyano-4-(2,2,2-trifluoroethoxy)phenyl)-1,2,4-oxadiazol-3-yl)-6-methylpyrindin-2-yl)butanoic acid The title compound was prepared using the procedure analogous to that described for EXAMPLE 69 substituting CARBOXYLIC ACID 5 and N-HYDROXYAMIDINE 6 for CARBOXYLIC ACID 1 and N-HYDROXYAMIDINE 5, respectively, in Step A: $^1$H NMR (500 MHz, CD$_3$OD) δ 1.47 (d, J=8.9, 3H), 2.86 (dd, J=6.1, 17.1, 1H), 2.99 (dd, J=8.9, 17.1, 1H), 3.09 (s, 3H), 3.63 (m, 1H), 4.92 (q, J=8.2, 2H), 7.55 (d, J=8.9, 1H), 7.89 (d, J=8.4, 1H), 8.51 (dd, J=2.3, 8.9, 1H), 8.58 (d, J=2.0, 1H), 8.95 (d, J=8.5, 1H).

Example 74

3-(5-(5-(5-Cyano-6-(2,2,2-trifluoro-1-methylethoxy)pyridin-3-yl)-1,2,4-oxadiazol-3-yl)-6-methylpyrindin-2-yl)butanoic acid The title compound was prepared using the procedure analogous to that described for EXAMPLE 73 substituting CARBOXYLIC ACID 10 for CARBOXYLIC ACID 1: $^1$H NMR (500 MHz, CD$_3$OD) δ 1.47 (d, J=7.1, 3H), 1.63 (d, J=6.6, 3H), 2.86 (dd, J=6.1, 17.1, 1H), 3.00 (dd, J=8.9, 17.2, 1H), 3.10 (s, 3H), 3.64 (m, 1H), 6.11 (m, 1H), 7.91 (d, J=8.4, 1H), 8.97 (d, J=8.4, 1H), 8.99 (d, J=2.2, 1H), 9.27 (d, J=2.3, 1H).

Example 75

3-(4-(3-(4-(Isopropoxy)-3-(trifluoromethyl)phenyl)-1,2,4-oxadiazol-5-yl)-3-methylphenyl)propanoic acid Step A: Benzyl 4-bromo-2-methylbenzoate To a suspension of 1.26 g (5.86 mmol) of 4-bromo-2-methylbenzoic acid in 10 mL of CH$_2$Cl$_2$ was added 1.5 mL (17.6 mmol) of oxalyl chloride and two drops of DMF. After stirring at rt overnight, the reaction mixture was concentrated. The residue was dried azeotropically using toluene (3×5 mL) and then dissolved in 10 mL of CH$_2$Cl$_2$, to which 667 μL (6.45 mmol) of benzyl alcohol, 1.23 mL (8.79 mmol) of triethylamine, and catalytic amount of 4-dimethylaminopyridine were added. After stirring at rt for 1 h, the reaction mixture was poured into 20 mL brine. The aqueous layer was extracted with CH$_2$Cl$_2$ (3×10 mL). Organic layers were combined, dried over MgSO$_4$, and concentrated. Chromatography on Biotage 40S cartridge using 1:19 v/v EtOAc/hexanes as the eluant afforded 1.58 g of the title compound: $^1$H NMR (500 MHz, CDCl$_3$) δ 2.58 (s, 3H), 5.33 (s, 2H), 7.33-7.44 (m, 7H), 7.81 (d, J=8.5, 1H).

Step B: Methyl (E/Z)-3-(4-benzyloxycarbonyl-3-methyl)propenoate

A solution of 1.58 g (5.18 mmol) of benzyl 4-bromo-2-methylbenzoate (from Step A), 1.66 mL (7.77 mmol) of in 80 mL of N-methyldicyclohexylamine, and 77.2 mg (0.26 mmol) of 2-(di-tert-butylphosphino)biphenyl in 10 mL of 1,4-dioxane was treated with 513 μL (5.70 mmol) of methyl acrylate and 119 mg (0.13 mol) of tris(dibenzylideneacetone) dipalladium(0)-chloroform adduct. The resulting mixture was heated at 70° C. for 3 h and then cooled to rt. The reaction mixture was filtered though a cake of Celite and washed with EtOAc, and the filtrate was concentrated. Chromatography on a Biotage 40M cartridge using 3:7 v/v EtOAc/hexanes as an eluant afforded 657 mg of the title compound: $^1$H NMR (500 MHz, CDCl$_3$) δ 2.61 (s, 3H), 3.80 (s, 3H), 5.34 (s, 2H), 6.46-7.96 (m, 10H).

Step C: Methyl (4-carboxy-3-methyl)propanoate

To a solution of 437 mg (1.41 mmol) of methyl (E/Z)-3-(4-benzyloxycarbonyl-3-methyl)propenoate (from Step B) in 10 mL of EtOAc was added 50 mg of 10 wt % Pd/C. After stirring at rt under one atm of H$_2$, the catalyst was filtered off through a cake of Celite and washed with EtOAc. The filtrate was concentrated to give the title compound as a white solid: $^1$H NMR (500 MHz, CDCl$_3$) δ 2.63 (s, 3H), 2.66 (d, J=7.7, 2H), 2.97 (d, J=7.8, 2H), 3.68 (s, 3H), 7.10-7.26 (m, 2H), 8.00 (d, J=8.7, 1H).

Step D: Methyl 3-(4-(3-(4-(isopropoxy)-3-(trifluoromethyl)phenyl)-1,2,4-oxadiazol-5-yl)-3-methylphenyl)propanoate The title compound was prepared using the procedure analogous to that described for EXAMPLE 1 substituting methyl (4-carboxy-3-methyl)propanoate (from Step C) and N-Hydroxy (4-isopropoxy-3-trifluoromethyl)benzamidine for CARBOXYUC ACID 1 and N-HYDROXYAMIDINE 1, respectively, in Step A: $^1$H NMR (500 MHz, CDCl$_3$) δ 1.42 (d, J=6.0, 6H), 2.68 (t, J=7.7, 2H), 2.75 (s, 3H), 3.01 (t, J=7.7, 2H), 3.69 (s, 3H), 4.75 (m, 1H), 7.11 (d, J=9.0, 1H), 7.19-7.27 (m, 2H), 8.09 (d, J=8.7, 1H), 8.27 (dd, J=2.1, 8.7, 1H), 8.38 (d, 3=2.0, 1H).

Step E: 3-(4-(3-(4-(Isopropoxy)-3-(trifluoromethyl)phenyl)-1,2,4-oxadiazol-5-yl)-3-methylphenyl)propanoic acid To a solution of 33 mg (0.07 mmol) of methyl 3-(4-(3-(4-isopropoxy-3-(trifluoromethyl)phenyl)-1,2,4-oxadiazol-5-yl)-3-methylphenyl)propanoate (from Step D) in 2.0 mL of EtOH was added 200 μL (1.0 mmol) of 5.0 N NaOH. The mixture was stirred at rt overnight. Purification by HPLC B gave 22 mg of the title compound: $^1$H NMR (500 MHz, CD$_3$OD) δ 1.40 (d, J=6.0, 6H), 2.66 (t, J=7.7, 2H), 2.74 (s, 3H), 2.99 (t, J=7.6, 2H), 4.87 (m, 1H), 7.28-7.37 (m, 3H), 8.06 (d, J=8.0, 1H), 8.30-8.31 (m, 2H).

Example 76

2,2-Difluoro-3-hydroxy-3-(4-(4-(4-isopropoxy-3-(trifluoromethyl)phenyl)-1,2,4-oxadiazol-3-yl)-3-methylphenyl)propanoic acid Step A: 5-(4-Isopropoxy-3-(trifluoromethyl)phenyl)-3-(2-methyl-4-vinylphenyl)-1,2,4-oxadiazole To a solution of 1.12 g (2.54 mmol) of 3-(4-bromo-2-methylphenyl)-5-(4-isopropoxy-3-(trifluoromethyl)phenyl)-1,2,4-oxadiazole (EXAMPLE 12), 816 μL (2.79 mmol) of tributyl(vinyl)tin, and 848 mg (5.58 mmol) of cesium fluoride in 20 mL of 1,4-dioxane was added 32 mg (0.06 mmol) of bis(tri-tert-butylphosphine)palladium(0). After stirring at 100° C. for 2 h, the mixture was filtered through a cake of Celite and concentrated. Chromatography on Biotage 40M cartridge using 1:19 v/v EtOAc/hexanes as the eluant afforded 873 mg of the title compound.

Step B: 1-(4-(5-(4-Isopropoxy-3-(trifluoromethyl)phenyl)-1,2,4-oxadiazol-3-yl)-3-methylphenyl)ethane-1,2-diol To a solution of 215 mg (0.55 mmol) of 5-(4-isopropoxy-3-(trifluoromethyl)phenyl)-3-(2-methyl-4-vinylphenyl)-1,2,4-oxadiazole and 78 mg (0.66 mmol) of 4-methylmorpholine N-oxide in 12 mL of 3:1 v:v THF/H$_2$O mix solvent was added 347 μL (0.03 mmol) osmium tetraoxide (2.5 wt %). After stirring at rt overnight, the mixture was poured into brine and extracted with EtOAc (3×20 mL). Organic layers were combined, dried over Na$_2$SO$_4$, and concentrated. Chromatography on Biotage 40S cartridge using 7:3 v/v EtOAc/hexanes as the eluant afforded 143 mg of the title compound: $^1$H NMR (500 MHz, CDCl$_3$) δ 1.43 (d, J=5.9, 6H), 2.30 (br. s, 2H), 2.67 (s, 3H), 3.68 (dd, J=8.1, 11.4, 1H), 3.80 (dd, J=3.6, 11.3, 1H), 4.78 (m, 1H), 4.86 (dd, J=3.5, 8.0, 1H), 7.13 (d, J=8.7, 1H), 7.32-7.34 (m, 2H), 8.05 (d, J=8.0, 1H), 8.29 (dd, J=2.2, 8.8, 1H), 8.41 (d, J=2.1, 1H).

Step C: 4-(5-(4-Isopropoxy-3-(trifluoromethyl)phenyl)-1,2,4-oxadiazol-3-yl)-3-methylbenzaldehyde A solution of 49 mg (0.12 mmol) of 1-(4-(5-(4-isopropoxy-3-(trifluoromethyl)phenyl)-1,2,4-oxadiazol-3-yl)-3-methylphenyl)ethane-1,2-diol and 37 mg (0.17 mmol) of sodium periodate in 9 mL of 2:1 v:v THF/H$_2$O mix solvent. After stirring at rt for 4 h, the mixture was poured into brine and extracted with EtOAc (3×10 mL). Organic layers were combined, dried over MgSO$_4$, and concentrated. Chromatography on Biotage 40S cartridge using 1:9 v/v EtOAc/hexanes as the eluant afforded 40 mg of the title compound: $^1$H NMR (500 MHz, CDCl$_3$) δ 1.44 (d, J=5.9, 6H), 2.78 (s, 3H), 4.79 (m, 1H), 7.16 (d, J=9.0, 1H), 7.84-7.86 (m, 2H), 8.28 (d, J=8.5, 1H), 8.32 (dd, J=2.2, 8.9, 1H), 8.44 (d, J=2.1, 1H), 10.09 (s, 1H).

Step D: Ethyl 2,2-difluoro-3-hydroxy-3-(4-(4-(4-isopropoxy-3-(trifluoromethyl)phenyl)-1,2,4-oxadiazol-3-yl)-3-methylphenyl)propanoate A suspension of 37 mg (0.56 mmol) of zinc powder and 5 µL (0.06 mmol) of dibromoethane in 5.0 mL of THF was heated to 65° C. for 1 min and cooled to rt. To this suspension was added 4 µL (0.03 mmol) of chlorotrimethylsilane and the resulting mixture was stirred at rt for 15 min and then cooled down to 0° C. To this mixture was added 53 µL (0.41 mmol) of ethyl bromodifluoroacetate, then 40 mg of 4-(5-(4-isopropoxy-3-(trifluoromethyl)phenyl)-1,2,4-oxadiazol-3-yl)-3-methylbenzaldehyde (from Step C) in 1 mL of THF. After stirring at 0° C. for 10 min and rt overnight, the mixture was concentrated. Chromatography on Biotage 40S cartridge using 1:4 v/v EtOAc/hexanes as the eluant afforded 42 mg of the title compound: $^1$H NMR (500 MHz, CDCl$_3$) δ 1.32 (t, J=7.2, 3H), 1.44 (d, J=6.0, 6H), 2.70 (s, 3H), 4.34 (q, J=7.1, 2H), 4.78 (m, 1H), 5.22 (dd, J=7.6, 15.4, 1H), 7.15 (d, J=8.9, 1H), 7.41-7.43 (m, 2H), 8.10 (d, J=8.0, 1H), 8.30 (dd, J=2.1, 8.7, 1H), 8.42 (d, J=2.0, 1H).

Step E: 2,2-Difluoro-3-hydroxy-3-(4-(4-(4-isopropoxy-3-(trifluoromethyl)phenyl)-1,2,4-oxadiazol-3-yl)-3-methylphenyl)propanoic acid The title compound was prepared using the procedure analogous to that described for EXAMPLE 75, Step E substituting ethyl 2,2-difluoro-3-hydroxy-3-(4-(4-(4-isopropoxy-3-(trifluoromethyl)phenyl)-1,2,4-oxadiazol-3-yl)-3-methylphenyl)propanoate (from Step D) for methyl 3-(4-(3-(4-isopropoxy-3-(trifluoromethyl)phenyl)-1,2,4-oxadiazol-5-yl)-3-methylphenyl)propanoate: $^1$H NMR (500 MHz, CD$_3$OD) δ 1.34 (d, J=6.2, 6H), 2.60 (s, 3H), 4.85 (m, 1H), 5.09 (dd, J=7.7, 17.0, 1H), 7.35-7.42 (m, 3H), 7.99 (d, J=8.1, 1H), 8.31-8.33 (m, 2H).

Example 77

2,2-Difluoro-3-(4-(4-(4-isopropoxy-3-(trifluoromethyl)phenyl)-1,2,4-oxadiazol-3-yl)-3-methylphenol-propanoic acid

Step A: Ethyl 2,2-difluoro-3-(4-(4-(4-isopropoxy-3-(trifluoromethyl)phenyl)-1,2,4-oxadiazol-3-yl)-3-methylphenyl)propanoate To a solution of 29 mg (0.06 mmol) of ethyl 2,2-difluoro-3-hydroxy-3-(4-(4-(4-(isopropoxy)-3-(trifluoromethyl)phenyl)-1,2,4-oxadiazol-3-yl)-3-methylphenyl)propanoate (from EXAMPLE 75, Step D) and 21 mg (0.17 mmol) of 4-dimethylaminopyridine in 5.0 mL of CH$_2$Cl$_2$ at ° C. was added 10 µL (0.11 mmol) of methyl chlorooxoacetate. After stirring at 0° C. for 10 min and rt for 20 min, the reaction mixture was diluted with 20 mL of EtOAc and washed with diluted HCl (10 mL), saturated NaHCO$_3$ (10 mL), and brine (10 mL). The organic layer was dried over MgSO$_4$ and concentrated to give the crude ester product.

To a solution of aforementioned ester (0.06 mmol) and 35 mL (0.11 mmol) of tris(trimethylsilyl)silane in 5.0 mL of toluene was added 2 mg (0.01 mmol) of 2,2'-azobisisobutyronitrile (AIBN). After refluxed over night, 3 mg of AIBN was added and the mixture was refluxed for 5 h and concentrated. Chromatography on Biotage 40S cartridge using 1:9 v/v EtOAc/hexanes as the eluant afforded 11 mg of the title compound: $^1$H NMR (500 MHz, CDCl$_3$) δ 1.29 (t, J=7.1, 3H), 1.44 (d, J=6.0, 6H), 2.67 (s, 3H), 3.42 (t, J=16.3, 2H), 4.28 (q, J=7.1, 2H), 4.78 (m, 1H), 7.14 (d, J=9.0, 1H), 7.24-7.26 (m, 2H), 8.05 (d, J=8.5, 1H), 8.30 (dd, J=2.1, 8.8, 1H), 8.42 (d, J=2.1, 1H).

Step B: 2,2-Difluoro-3-(4-(4-(4-isopropoxy-3-(trifluoromethyl)phenyl)-1,2,4-oxadiazol-3-yl)-3-methylphenyl)propanoic acid The title compound was prepared using the procedure analogous to that described for EXAMPLE 75 substituting ethyl 2,2-difluoro-3-(4-(4-(4-isopropoxy-3-(trifluoromethyl)phenyl)-1,2,4-oxadiazol-3-yl)-3-methylphenyl)propanoate (from Step A) for methyl 3-(4-(3-(4-isopropoxy-3-(trifluoromethyl)phenyl)-1,2,4-oxadiazol-5-yl)-3-methylphenyl)propanoate in Step E: $^1$H NMR (500 MHz, CD$_3$OD) δ 1.41 (d, J=5.9, 6H), 2.64 (s, 3H), 3.45 (t, J=16.7, 2H), 4.92 (m, 1H), 7.29-7.32 (m, 2H), 7.43 (d, J=8.4, 1H), 8.01 (d, J=7.8, 1H), 8.38-8.40 (m, 2H).

Example 78

(1R,2S/1S,2R)-2-(4-(5-(3-cyano-4-isopropoxyphenyl)-1,2,4-oxadiazol-3-yl)-3-methylphenyl)cyclopropanecarboxylic acid

Step A: Methyl (2Z)-3-(4-(5-(3-cyano-4-isopropoxyphenyl)-1,2,4-oxadiazol-3-yl)-3-methylphenyl)propenoate To a solution of 85 mg (0.24 mmol) of 4-(5-(4-isopropoxy-3-(trifluoromethyl)phenyl)-1,2,4-oxadiazol-3-yl)-3-methylbenzaldehyde (EXAMPLE 76, Step C) and 322 mg (1.22 mmol) of 18-crown-6 in 5.0 mL of THF at −78° C. was added 487 µL (0.24 mmol) of potassium bis(trimethylsilyl)amide (0.5 M in toluene). After stirring at −78° C. for 30 min, the reaction quenched by 10 mL of saturated NaHCO$_3$, and the mixture was extracted with CH$_2$Cl$_2$ (3×10 mL). The organic layers were combined, dried over MgSO$_4$, and concentrated. Purification by HPLC B gave 64 mg of the title compound: $^1$H NMR (500 MHz, CDCl$_3$) δ 1.29 1.48 (d, J=6.0, 6H), 2.69 (s, 3H), 3.74 (s, 3H), 4.80 (m, 1H), 6.04 (d, J 12.6, 1H), 6.99 (d, J=12.6, 11H), 7.14 (d, J=8.2, 1H), 7.53 (d, J=8.0, 1H), 8.07 (d, J=8.0, 1H), 8.34 (dd, J=2.3, 8.9, 1H), 8.43 (d, J=2.2, 1H).

Step B: Methyl (1R,2S/1S,2R)-2-(4-(5-(3-cyano-4-isopropoxyphenyl)-1,2,4-oxadiazol-3-yl)-3-methylphenyl)cyclopropanecarboxylate To a solution of 47 mg (0.12 mmol) of methyl (2Z)-3-(4-(5-(3-cyano-4-isopropoxyphenyl)-1,2,4-oxadiazol-3-yl)-3- methylphenyl)propenoate (from Step A) and diazomethane (2.33 mmol, prepared from 343 mg of 1-methyl-3-nitro-1-nitrosoguanidine) in 10 mL of 1:2 v:v CH$_2$Cl$_2$/Et$_2$O at 0° C. was added one speck of palladium(II) acetate. After stirring for 30 min, the reaction was quenched by adding three drops of acetic acid. The mixture was concentrated. Chromatography on Biotage 40S cartridge using 1:4 v/v EtOAc/hexanes as the eluant afforded 20 mg of the title compound: $^1$H NMR (500 MHz, CDCl$_3$) δ 1.41 (m, 1H), 1.47 (d, J=5.9, 6H), 1.76 (m, 1H), 2.15 (m, 1H), 2.60 (m, 1H), 2.65 (s, 3H), 3.48 (s, 3H), 4.79 (m, 1H), 7.11 (d, J=9.0, 1H), 7.22-7.26 (m, 2H), 7.99 (d, J=8.0, 1H), 8.33 (dd, J=2.1, 9.0, 1H), 8.41 (d, J=2.1, 1H).

Step C: (1R,2S/1S,2R)-2-(4-(5-(3-cyano-4-isopropoxyphenyl)-1,2,4-oxadiazol-3-yl)-3-methylphenyl) cyclopropanecarboxylic acid The title compound was prepared using the procedure analogous to that described for EXAMPLE 75, Step E substituting methyl (1R,2S/1S,2R)-2-(4-(5-(3-cyano-4-isopropoxyphenyl)-1,2,4-oxadiazol-3-yl)-3-methylphenyl)cyclopropanecarboxylate (from Step B) for methyl 3-(4-(3-(4-isopropoxy-3-(trifluoromethyl)phenyl)-1,2,4-oxadiazol-5-yl)-3-methylphenyl)propanoate: $^1$H NMR (500 MHz, CD$_3$OD) δ 1.42-1.48 (m, 7H), 2.15 (m, 1H), 2.63-2.72 (m, 4H), 4.79 (m, 1H), 7.11 (d, J=9.2, 1H), 7.23-7.26 (m, 2H), 7.98 (d, J=7.8, 1H), 8.33 (dd, J=2.1, 9.0, 1H), 8.41 (d, J=2.1, 1H).

Example 79

Erythro (+/−)-2,3-dihydroxy-3-(4-(4-(3-cyano-4-isopropoxyphenyl)-1,2,4-oxadiazol-3-yl)-3-methylphenyl)propanoic acid

Step A: Methyl erythro(+/−)-2,3-dihydroxy-3-(4-(4-(3-cyano-4-isopropoxyphenyl)-1,2,4-oxadiazol-3-yl)-3-methylphenyl)propanoate To a solution of 388 mg (0.96 mmol) of methyl (2Z)-3-(4-(5-(3-cyano-4-isopropoxyphenyl)-1,2,4-oxadiazol-3-yl)-3-methylphenyl)acrylate (EXAMPLE 19) and 135 mg (1.15 mmol) of 4-methylmorpholine N-oxide in 12.0 mL of 3:1 v:v THF/H$_2$O mix solvent was added 603 µL (0.05 mmol) of osmium tetraoxide (2.5 wt %). After stirring at rt overnight, the mixture was poured into brine and extracted with CH$_2$Cl$_2$ (3×20 mL). Organic layers were combined, dried over Na$_2$SO$_4$, and concentrated. Chromatography on Biotage 40M cartridge using 4:1 v/v EtOAc/hexanes as the eluant afforded 217 mg of the title compound: $^1$H NMR (500 MHz, CDCl$_3$) δ 1.48 (d, J=6.0, 6H), 2.67 (s, 3H), 3.72 (s, 3H), 4.54 (d, J=4.3, 1H), 4.80 (m, 1H), 5.06 (d, J=4.1, 1H), 7.12 (d, J=8.9, 1H), 7.26-7.31 (m, 2H), 8.05 (d, J=7.7, 1H), 8.32 (dd, J=2.3, 9.0, 1H), 8.40 (d, J=2.1, 1H).

Step B: Erythro (+/−)-2,3-dihydroxy-3-(4-(4-(3-cyano-4-isopropoxyphenyl)-1,2,4-oxadiazol-3-yl)-3-methylphenyl)propanoic acid The title compound was prepared using the procedure analogous to that described for EXAMPLE 75, Step E substituting methyl erythro(+/−)-2,3-dihydroxy-3-(4-(4-(3-cyano-4-isopropoxyphenyl)-1,2,4-oxadiazol-3-yl)-3-methylphenyl)propanoate (from Step A) for methyl 3-(4-(3-(4-isopropoxy-3-(trifluoromethyl)phenyl)-1,2,4-oxadiazol-5-yl)-3-methylphenyl)propanoate: $^1$H NMR (500 MHz, CD$_3$OD) δ 1.45 (d, J=6.2, 6H), 2.65 (s, 3H), 4.37 (d, J=5.3, 1H), 4.93-4.96 (m, 2M), 7.40-7.44 (m, 3H), 8.00 (d, J=8.2, 1H), 8.42 (dd, J=2.1, 9.0, 1H), 8.44 (d, J=2.1, 11H).

Example 80

Threo(+/−)-2,3-dihydroxy-3-(4-(4-(3-cyano-4 isopropoxyphenyl)-1,2,4-oxadiazol-3-yl)-3-methylphenyl)propanoic acid The title compound was prepared using the procedure analogous to that described for EXAMPLE 79 substituting methyl (2E)-3-(4-(5-(3-cyano-4-isopropoxyphenyl)-1,2,4-oxadiazol-3-yl)-3-methylphenyl)acrylate for methyl (2Z)-3-(4-(5-(3-cyano-4-isopropoxyphenyl)-1,2,4-oxadiazol-3-yl)-3-methylphenyl)acrylate in Step A: $^1$H NMR (500 MHz, CD$_3$OD) δ 1.47 (d, J=7.0, 6H), 2.66 (s, 1H), 2.67 (s, 3H), 3.37 (s, 1H), 4.35 (d, J=3.0, 1H), 4.95 (m, 1H), 5.12 (d, J=2.8, 1H), 7.46 (m, 3H), 8.05 (m, 1H), 8.42 (m, 2H).

Example 81

(4R,5R/4S,5S)-5-(4-(5-(3-Cyano-4-isopropoxyphenyl)-1,2,4-oxadiazol-3-yl)-3-methylphenyl)-1,3-dioxolane-4-carboxylic acid

Step A: Methyl (4R,5R/4S,5S)-5-(4-(5-(3-cyano-4-isopropoxyphenyl)-1,2,4-oxadiazol-3-yl)-3-methylphenyl)-1,3-dioxolane-4-carboxylate A suspension of 77 mg (0.18 mmol) of methyl erythro (+/−)-2,3-dihydroxy-3-(4-(4-(3-cyano-4-isopropoxyphenyl)-1,2,4-oxadiazol-3-yl)-3-methylphenyl)propanoate (EXAMPLE 79, Step A), 156 mL (1.77 mmol) of dimethoxymethane, and 1.5 g (5.28 mmol) of phosphorus pentoxide in 10 mL of CH$_2$Cl$_2$ was stirred at rt overnight. The reaction was quenched using H$_2$O (10 mL) and poured into 20 mL of saturated NaHCO$_3$. The mixture was extracted with CH$_2$Cl$_2$ (3×10 mL). Organic layers were combined, dried over MgSO$_4$, and concentrated. Chromatography on Biotage 40S cartridge using 1:3 v/v EtOAc/hexanes as the eluant afforded 41 mg of the title compound: $^1$H NMR (500 MHz, CDCl$_3$) δ 1.48 (d, J=6.2, 6H), 2.68 (s, 3H), 3.30 (s, 3H), 4.80 (m, 1H), 4.84 (d, J=7.6, 1H), 5.19 (s, 1H), 5.29 (d, J=7.5, 1H), 5.67 (s, 1H), 7.12 (d, J=9.1, 1H), 7.29-7.32 (m, 2H), 8.07 (d, J=8.0, 1H), 8.33 (dd, J=2.1, 8.9, 1H), 8.42 (d, J=2.0, 1H).

Step B: (4R,5R/4S,5S)-5-(4-(5-(3-Cyano-4-isopropoxyphenyl)-1,2,4-oxadiazol-3-yl)-3-methylphenyl)-1,3-dioxolane-4-carboxylic acid The title compound was prepared using the procedure analogous to that described for EXAMPLE 75, Step E substituting methyl (4R,5R/4S,5S)-5-(4-(5-(3-cyano-4-isopropoxyphenyl)-1,2,4-oxadiazol-3-yl)-3-methylphenyl)-1,3-dioxolane-4-carboxylate (from Step A) for methyl 3-(4-(3-(4-isopropoxy-3-(trifluoromethyl)phenyl)-1,2,4-oxadiazol-5-yl)-3-methylphenyl)propanoate: $^1$H NMR (500 MHz, CD$_3$OD) δ 1.45 (d, J=6.1, 6H), 2.63 (s, 3H), 4.83 (d, J=7.8, 1H), 4.94 (m, 1H), 5.12 (s, 1H), 5.34 (d, J=7.5, 1H), 5.57 (s, 1H), 7.36-7.39 (m, 2H), 7.43 (d, J=9.2, 1H), 8.01 (d, J=8.1, 1H), 8.41 (dd, J=2.3, 8.9, 1H), 8.44 (d, J=2.0, 1H).

Example 82

(4R,5S/4S,5R)-5-(4-(5-(3-Cyano-4-isopropoxyphenyl)-1,2,4-oxadiazol-3-yl)-3-methylphenyl)-1,3-dioxolane-4-carboxylic acid The title compound was prepared using the procedure analogous to that described for EXAMPLE 79 substituting threo(+/−)-2,3-dihydroxy-3-(4-(4-(3-cyano-4-isopropoxyphenyl)-1,2,4-oxadiazol-3-yl)-3-methylphenyl)propanoate (from EXAMPLE 80) for erythro(+/−)-2,3-dihydroxy-3-(4-(4-(3-cyano-4-isopropoxyphenyl)-1,2,4-oxadiazol-3-yl)-3-methylphenyl)propanoate in Step A: $^1$H NMR (500 MHz, CD$_3$OD) δ 1.47 (d, J=6.2, 6H), 2.66 (s, 3H), 2.70 (s, 1H), 3.37 (s, 1H), 4.41 (d, J=5.4, 1H), 4.95 (m, 1H), 5.12 (d, J=5.5, 1H), 7.44 (m, 3H), 8.13 (m, 1H), 8.39 (m, 2H).

Examples 83-86

The following examples were prepared using procedures analogous to those described for EXAMPLE 1 substituting the appropriate carboxylic acid for CARBOXYLIC ACID 1 in Step A.

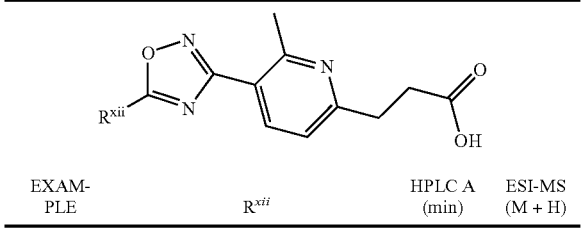

| EXAMPLE | R$^{xii}$ | HPLC A (min) | ESI-MS (M + H) |
|---------|-----------|--------------|----------------|
| 83 | 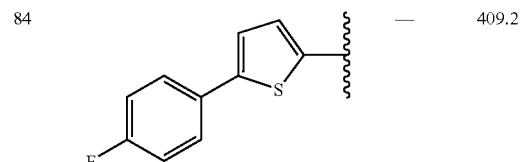 | — | 391.2 |

$^1$H NMR (500 MHz, CDCl$_3$) δ 2.66 (s, 3 H), 2.74 (t, 2 H), 3.01 (t, 2 H), 7.19 (m, 4 H,), 7.38-7.48 (m, 4 H), 7.68 (d, 2 H, J = 7), 7.91 (d, 1 H, J = 4), 8.01 (d, 1 H, J = 8)

| 84 | 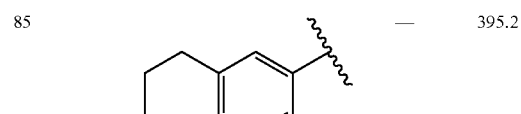 | — | 409.2 |

$^1$H NMR (500 MHz, CDCl$_3$) δ 2.66 (s, 3 H), 2.74 (t, 2 H), 3.01 (t, 2 H), 7.14 (t, 2 H,), 7.19 (m, 2 H), 7.33 (d, 1 H, J = 4), 7.65 (m, 2 H, J = 7), 7.90 (d, 1 H, J = 4), 8.01 d, 1 H, J = 8 Hz)

| 85 | | — | 395.2 |

$^1$H NMR (500 MHz, CDCl$_3$) δ 1.42 (d, 3 H, J = 7) 2.25-1.76 (m, 2 H), 2.64 (s, 3 H), 2.73 (t, 2 H, J = 8), 2.96 (m, 3 H), 3.00 (t, 2 H, J = 8), 3.47 (m, 1 H), 7.16-7.19 (m, 2 H), 7.21 (d, 1 H, J = 8), 7.84 (d, 1 H, J = 8), 7.87 (d, 1 H, J = 1), 8.00 (d, 1 H, J = 8)

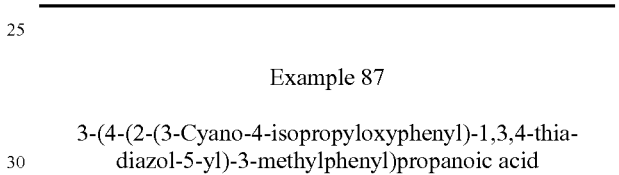

| EXAMPLE | R$^{xii}$ | HPLC A (min) | ESI-MS (M + H) |
|---------|-----------|--------------|----------------|
| 86 | | — | 417.2 |

$^1$H NMR (500 MHz, CDCl$_3$) δ 1.44 (d, 3 H, J = 6), 2.61 (s, 3 H), 2.73 (t, 2 H, J = 8); 3.00 (t, 2 H, J = 8); 3.78 (m, 1 H); 7.16-7.19 (m, 2 H,), 7.28 (m, 2 H, J = 8); 7.98 (d, 1 H, J = 8); 8.12 (4, 1 H, J = 2,8); 8.20 (d, 1 H, J = 2)

Example 87

3-(4-(2-(3-Cyano-4-isopropyloxyphenyl)-1,3,4-thiadiazol-5-yl)-3-methylphenyl)propanoic acid Step A: N'-(3-Cyano-4-isopropyloxyphenylcarbonyl)-4-bromo-2-methylbenzhydrazide A solution of 170 mg (0.83 mmol) of 3-cyanoisopropyloxybenzoic acid in 10 mL of anhydrous CH$_2$Cl$_2$ and 10 μL of DMF was treated with 1.0 mL of oxalyl chloride. The reaction mixture was heated to 50° C. for 10 minutes, cooled to rt and the solvents were removed under reduced pressure. The resulting crude material was dissolved in 10 mL of EtOAc and added in one portion to a vigorously stirring biphasic mixture of 209 mg of 4-bromo-2-methylbenzhydrazide (0.91 mmol), 20 mL of EtOAc, and 20 mL of saturated aqueous solution of sodium bicarbonate. After 30 minutes, the precipitate was collected by filtration and rinsed with 2×10 mL of water and dried in a desiccator overnight. Product (299 mg) was found to be >95% pure by $^1$H NMR and used in subsequent cyclization step without further purification: $^1$H NMR (500 MHZ, temp.=50° C., CDCl$_3$) δ 1.55 (d, J=6.5, 6H), 2.51 (s, 3H), 4.78 (sep, J=6.5, 1H), 7.04 (d, J=9.0, 1H), 7.42 (s, 2H), 7.48 (s, 1H), 8.02 (dd, J=9.0, 2.0, 1H), 8.10 (d, J=2.0, 1H), 8.66 (d, J=2.0, 1H), 9.18 (d, J=2.0, 1H).

Step B: 2-(3-Cyano-4-isopropyloxy-phenyl)-5-(4-bromo-2-methyphenyl)-1,3,4-thiadiazole In an oven-dried high-pressure tube, 240 mg (0.58 mmol) of N'-(3-cyano-4-isopropyloxyphenylcarbonyl)-4-bromo-2-methylbenzhydrazide (from Step A) was combined with 40 mL of anhydrous toluene, 300 mg of Lawesson's Reagent (0.74 mmol), and 100 μL of pyridine. The tube was sealed with a plastic/teflon cap and the reaction mixture was heated to 125° C. for 2 h. The resulting mixture was cooled down to rt, solvents were removed under reduced pressure and residual solids were dissolved in 10 mL of pyridine. To this mixture, 0.5 g of phosphorous pentasulfide was added and the mixture heated to 110° C. The reaction mixture was combined with ice-water and extracted 2×100 mL of EtOAc. Combined organic layers were dried over sodium sulfate, and solvents removed under reduced pressure. Pure title compound was isolated by flash chromatography using Biotage 40S (eluant: hexanes/EtOAc-4/1) to yield 239 mg: $^1$H NMR (500 MHZ, CDCl$_3$) δ 1.49 (d, J=6.5, 6H), 2.65 (s, 3H), 4.79 (sep, J=6.5, 1H), 7.13 (dd, J=9.0, 2.0, 1H), 7.50 (dd, J=9.0, 2.0, 1H), 7.56 (d, J=2.0, 1H), 7.63 (d, J=8.0, 1H), 8.17 (d, J=2.0, 1H), 8.24 (dd, J=8.0, 2.0, 1H).

Step C: tert-Butyl 3-(4-(5-(3-Cyano-4-isopropyloxyphenyl)-1,2,4-thiadiazol-3-yl)-3-methylphenyl)-2-propenoate In an oven-dried flask, under an atmosphere of argon, 10 mg of 2-(di-tert-butylphosphino)biphenyl (0.03 mmol) and 13 mg of tris(dibenzylideneacetone)-dipalladium-chloroform complex (0.015 mmol) were dissolved in 10 mL of anhydrous dioxane and the solution was degassed with argon. To this mixture, 100 µL of N,N-dicyclohexylmethylamine (0.45 mmol), 55 µL of tert-butyl acrylate (0.38 mmol), and a dioxane (1 mL) solution of 125 mg (0.30 mmol) of 2-(3-cyano-4-isopropyloxyphenyl)-5-(4-bromo-2-methyphenyl)-1,3,4-thiadiazole (from Step B) were added sequentially via syringe. The resulting mixture was heated under argon atmosphere at 95° C. for 2 h. The reaction mixture was diluted with 20 mL of EtOAc, filtered trough a disposable frit and concentrated. Pure product was isolated by a column chromatography, using Biotage 40S column (eluent: hexanes/EtOAc=4/1) as a mixture of (E)- and (Z)-stereoisomers: $^1$H NMR (500 MHZ, CDCl$_3$, major, (E)-stereoisomer) δ 1.46 (d, J=6.5, 6H), 2.69 (s, 3H), 4.79 (sep, J=6.5, 1H), 6.47 (d, J=15.5, 1H), 7.12 (d, J=9.0, 1H), 7.51 (d, J=9.0, 1H), 7.52 (s, 1H), 7.61 (d, J=15.5, 1H), 7.80 (d, J=8.0, 1H), 8.18 (d, J=2.0, 1H), 8.25 (dd, J=8.0, 2.0, 1H).

Step D: tert-butyl 3-(4-(5-(3-cyano-4-isopropyloxyphenyl)-1,2,4-thiadiazol-3-yl)-3-methylphenyl) propanoate A mixture of 120 mg (0.26 mmol) of tert-butyl 3-(4-(5-(3-cyano-4-isopropyloxyphenyl)-1,2,4-thiadiazol-3-yl)-3-methylphenyl)-2-propenoate (from Step C) and 41 mg of palladium on activated carbon (10% w/w; 0.025 mmol) in 15 mL of methanol/EtOAc (1/1) was hydrogenated under atmospheric pressure of hydrogen for 2 h. The heterogeneous mixture was filtered through a disposable frit to remove palladium and the filtrate was concentrated. The crude product was found to be pure by ESI-MS and $^1$H NMR analyses and used in subsequent step without purification: $^1$H NMR (500 MHZ, CDCl$_3$) δ 1.46 (s, 9H), 1.49 (d, J=6.5, 6H), 2.61 (t, J=7.5, 2H), 2.65 (s, 3H), 2.97 (t, J=7.5, 2H), 4.79 (sep, J=6.5, 1H), 7.11 (d, J=9.0, 1H), 7.18 (d, J=9.0, 1H), 7.23 (s, 1H), 7.69 (d, J=8.0, 1H), 8.18 (d, J=2.0, 1H), 8.24 (dd, J=8.0, 2.0, 1H).

Step E: 3-(4-(5-(3-Cyano-4-isopropyloxyphenyl)-1, 2,4-thiadiazol-3-yl)-3-methylphenyl)propanoic acid tert-Butyl 3-(4-(5-(3-Cyano-4 isopropyloxyphenyl)-1,2,4-thiadiazol-3-yl)-3-methylphenyl)propanoate (110 mg, 0.23 mmol, from Step D) was treated with 20% solution of trifluoroacetic acid in dichloromethane (10 mL) for 3 h at rt. The solvents were removed under reduced pressure, residual solids dissolved in toluene and concentrated again. Pure product was isolated by a column chromatography using a Biotage 40S column (eluent: dichloromethane/methanol=9/1): $^1$H NMR (500 MHZ, CDCl$_3$) δ 1.49 (d, J=6.5, 6H), 2.65 (s, 3H), 2.77 (t, J=8.0, 2H), 3.03 (t, J=8.0, 2H), 4.79 (sep, J=6.5, 1H), 7.11 (d, J=9.0, 1H), 7.21 (d, J=9.0, 1H), 7.24 (s, 1H), 7.70 (d, J=8.0, 1H), 8.17 (d, J=2.0, 1H), 8.25 (dd, J=8.0, 2.0, 1H).

Examples 88-89

The following examples were prepared using procedures analogous to those described in EXAMPLE 87 substituting the appropriate carboxylic acid for 3-cyano-4-isopropyloxybenzoic acid in Step A.

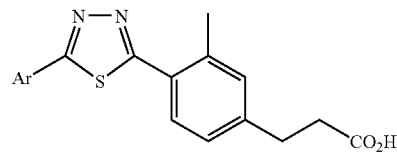

| EXAMPLE | Ar | Characterization |
|---|---|---|
| 88 | 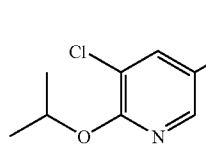 | $^1$H NMR (500 MHZ, CDCl$_3$) δ 1.46(d, J = 6.5, 6H), 2.65 (s, 3H), 2.75(t, J = 7.5, 2H), 3.03(t, J = 7.5, 2H), 5.47 (sep, J = 6.5, 1H), 7.21(d, J = 8.0, 1H), 7.24(s, 1H), 7.69(d, J = 7.5, 1H), 8.35(d, J = 2.5, 1H), 8.62(d, J = 2.5, 1H). |
| 89 | 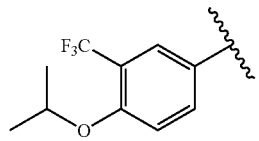 | $^1$H NMR (500 MHZ, CDCl$_3$) δ 8.19-8.21(m, 2H), 7.71 (d, J = 7.8, 1H), 7.25(s, 1H), 7.21(d, J = 7.8, 1H), 7.15 (d, J = 8.7, 1H), 4.78-4.81(m, 1H), 3.00-3.04(m, 2H), 2.77(t, J = 7.6, 2H), 2.66(s, 3H), 1.46(d, J = 6.0, 6H); ESI-MS (m/z) = 451.2; HPLC A = 2.95 min |

Example 90

(R/S)-3-(4-(5-(3-Cyano-4-isopropyloxyphenyl)-1,2,4-thiadiazol-3-yl)-3-methylphenyl)butanoic acid The title compound was prepared using procedures analogous to those described in EXAMPLE 87 substituting tert-butyl crotonate for tert-butyl acrylate in Step C: $^1$H NMR (500 MHZ, CDCl$_3$) δ 1.49 (d, J=6.5, 6H), 1.50 (d, J=7.0, 3H), 2.65 (s, 3H), 2.75 (m, 1H), 3.36 (m, 2H), 4.79 (sep, J=6.5, 1H), 7.13 (d, J=9.0, 1H), 7.23 (dd, J=9.0, 1.0, 1H), 7.26 (d, J=1.0, 1H), 7.71 (d, J=8.0, 1H), 8.17 (d, J=2.0, 1H), 8.25 (dd, J=8.0, 2.0, 1H).

Example 91

3-(4-(5-(3-Cyano-4-isopropylthiophenyl)-1,2,4-thiadiazol-3-yl)-3-methylphenyl)propanoic acid

Step A: N'-(3-Cyano-4-fluorophenyl)-4-bromo-2-methylbenzhydrazide

The title compound was prepared using procedures analogous to those described in EXAMPLE 87, Step A substituting 3-cyano-4-fluorobenzoic acid for 3-cyano-4-isopropyloxy-benzoic acid: $^1$H NMR (500 ME, DMSO) δ 8.42 (d, J=4.6, 1H), 8.28-8.29 (m, 1H), 7.70 (t, J=8.9, 1H), 7.55 (s, 1H), 7.47-7.51 (m, 1H), 7.37 (d, J=8.0, 1H), 2.41 (s, 3H).

Step B: N'-(3-Cyano-4-isopropylthiophenyl)-4-bromo-2-methylbenzhydrazide

Sodium hydride (95%) (0.8 mmol, 0.025 g) was added to a solution of 2-propanethiol (0.8 mmol, 0.09 mL) in DMF (4 mL) in an oven dried high pressure tube. This reaction mixture was stirred for 10 minutes at room temperature after which N'-(3-cyano-4-fluorophenylcarbonyl)-4-bromo-2-methylbenzhydrazide (0.53 mmol, 0.2 g) was added. The reaction mixture was heated at 100° C. for 16 h, cooled to room temperature, and combined with water. The resulting precipitate was collected by filtration and washed with water to yield 0.1 g (44%) of the title compound. $^1$H NMR (500 MHZ, DMSO) δ 8.28 (s, 1H), 8.14 (d, J=8.0, 1H), 7.76 (d, J=8.2, H), 7.55 (s, 1H), 7.49 (d, J=7.8, 1H), 7.36 (d, J=8.0, 1H), 3.80-3.90 (m, 1H), 2.40 (s, 3H), 1.34 (d, J=6.2, 6H)

Step C: 2-(3-Cyano-4-isopropylthiophenyl)-5-(4-bromo-2-methyphenyl)-1,3,4-thiadiazole The title compound was prepared using a procedure analogous to that described in EXAMPLE 87, Step B substituting N'-(3-cyano-4-isopropylthiophenyl)-4-bromo-2-methylbenzhydrazide (from Step B) for N'-(3-Cyano-4-isopropyloxyphenyl)-4-bromo-2-methylbenzhydrazide: ESI-MS (m/z) 432.0; HPLC A: 3.30 min.

Step D: Ethyl 3-(4-(5-(3-cyano-4-isopropylthiophenyl)-1,3,4-thiadiazol-3-yl)-3-methylphenyl)propanoate Bis(tri-tert-butylphosphine)palladium (0) (5 mg) was added to a solution of 2-(3-cyano-4-isopropylthiophenyl)-5-(4-bromo-2-methyphenyl)-1,3,4-thiadiazole (0.15 mmol, 0.066 g, from Step C) in 3-ethoxy-3-oxopropylzinc bromide (0.5M in TI-IF) (0.31 mmol, 0.61 mL) which had been degassed with argon. The reaction mixture was stirred under an atmosphere of argon at rt for 5 h after which it was concentrated in vacuo. Silica gel chromatography eluting with 20% EtOAc/hexane yielded the desired product. ESI-MS (m/z) 452.3; HPLC A: 2.85 min.

Step E: 3-(4-(5-(3-Cyano-4-isopropylthiophenyl)-1,3,4-thiadiazol-3-yl)-3-methylphenyl)propanoic acid Sodium hydroxide (5 N) (0.44 mmol, 0.1 mL) was added to a solution of ethyl 3-(4-(5-(3-cyano-4-isopropylthiophenyl)-1,3,4-thiadiazol-3-yl)-3-methylphenyl)propanoate (0.09 mmol, from Step D) in ethanol (2 mL). The reaction mixture was stirred at 50° C. for 1 h. The reaction was acidified to a pH<7 with 2 N HCl and the product was extracted with EtOAc (20 mL). The organics were dried over magnesium sulfate, filtered and concentrated in vacuo. Silica gel chromatography eluting with 10% methanol/methylene chloride yielded 12 mg of the title compound: $^1$H NMR (500 MHZ, CDCl$_3$) δ 8.26 (s, 1H), 8.24 (d, J=8.3, H), 7.74 (d, J=7.7, 1H), 7.62 (d, J=8.3, 1H), 7.28 (s, 1H), 7.24 (d, J=8.0, 1H), 3.70-3.78 (m, 1H), 3.02-3.10 (m, 2H), 2.76-2.82 (m, 2H), 2.68 (s, 3H), 1.47 (d, J=6.4, 6H); ESI-MS (m/z) 423.9; HPLC A: 3.79 min.

Example 92

3-(4-(5-(3-Cyano-4-(1-methylpropyloxy)phenyl)-1,2,4-thiadiazol-3-yl)-3-methylphenyl)propanoic acid

Step A: 2-(3-Iodo-4-isopropyloxyphenyl)-5-(4-bromo-2-methyphenyl)-1,3,4-thiadiazole The title compound was prepared using procedures analogous to those described in EXAMPLE 87, Steps A and B substituting 3-iodo-4-isopropyloxybenzoic acid for 3-cyano-4-isopropyloxybenzoic acid in Step A: $^1$H NMR (500 MHZ, DMSO) δ 8.36 (s, 1H), 7.95 (dd, J=7.3, 1.4, 1H), 7.56 (s, 1H), 7.52 (d, J=8.3, 1H), 7.38 (d, J=8.9, 1H), 7.15 (d, J=8.9, 1H), 4.76-4.84 (m, 1H), 2.51 (s, 3H), 1.34 (d, J=6.0, 6H).

Step B: 2-(3-Cyano-4-isopropyloxyphenyl)-5-(4-bromo-2-methyphenyl)-1,3,4-thiadiazole 2-(3-Iodo-4-isopropyloxyphenyl)-5-(4-bromo-2-methyphenyl)-1,3,4-thiadiazole (0.78 mmol; 0.4 g, from Step A), zinc cyanide (0.47 mmol, 0.55 g), tris(dibenzylideneacetone)-dipalladium(0) (0.039 mmol, 0.036 g) and 1,1'-bis (diphenylphosphino)-ferrocene (0.094 mmol, 0.052 g) were dissolved in DMF (5 mL) and heated at 120° C. for 3 h. The reaction was concentrated in vacuo. Silica gel chromatography eluting with 10% EtOAc/hexanes yielded 0.25 g of the desired product. ESI-MS (m/z) 416.1; HPLC A: 4.22 min.

Step C: Ethyl 3-(4-(5-(3-cyano-4-isopropyloxyphenyl)-1,3,4-thiadiazol-3-yl)-3-methylphenyl)propanoate The title compound was prepared using a procedure analogous to that described in EXAMPLE 91, Step D substituting 2-(3-cyano-isopropyloxyphenyl)-5-(4-bromo-2-methylphenyl)-1,3,4-thiadiazole (from Step B) for ethyl 3-(4-(5-(3-cyano-4 isopropylthiophenyl)-1,3,4-thiadiazol-3-yl)-3-methylphenyl)propanoate: ESI-MS (m/z) 436.3; HPLC A: 4.08 min.

Step D: Ethyl 3-(4-(5-(3-cyano-4-hydroxyphenyl)-1,3,4-thiadiazol-3-yl)-3-methylphenyl)propanoate Boron trichloride (1 M in CH$_2$Cl$_2$, 3 mL was added to a solution of ethyl 3-(4-(5-(3-cyano-4-isopropyloxyphenyl)-1,3,4-thiadiazol-3-yl)-3-methylphenyl)propanoate (0.6 mmol, from Step C) in methylene chloride (40 mL) at 0° C. The reaction mixture was allowed to warm to rt over 4 h and then was stirred at rt for 16 h. The reaction mixture was diluted with methylene chloride (50 mL) and washed with water (50 mL). The organics were dried over magnesium sulfate, filtered and concentrated in vacuo. Silica gel chromatography eluting with EtOAc yielded 0.12 g of the title compound. $^1$H NMR (500 MHZ, CDCl$_3$) δ $^1$H NMR (500 MHZ, CDCl$_3$) δ 8.17 (s, 1H), 8.13 (s, 1H), 7.68 (s, 1H), 7.24 (s, 1H), 7.20-7.24 (m, 2H), 4.14-4.23 (m, 2H), 2.98-3.08 (m, 2H), 2.68-2.78 (m, 2H), 2.64 (s, 3H), 1.30 (t, J=7.1, 3H); ESI-MS (m/z) 394.2; HPLC A: 2.71 min.

Step E: (R/S)-Ethyl 3-(4-(5-(3-cyano-4-(1-methylpropyloxyphenyl)-1,3,4-thiadiazol-3-yl)-3-methylphenyl)propanoate 2-Iodobutane (0.9 mmol; 0.14 g) was added to a solution of ethyl 3-(4-(5-(3-cyano-4-hydroxyphenyl)-1,3,4-thiadiazol-3-yl)-3-methylphenyl)propanoate (0.03 mmol, 0.01 g, from Step D) and potassium carbonate (0.9 mmol, 0.011 g) in DMF (1 mL). The reaction mixture was heated at 70° C. for 1 h. Silica gel chromatography eluting with 25% EtOAc/hexanes yielded desired product: ESI-MS (n7/z) 450.2; 3.16 min.

Step F: (R/S)-3-(4-(5-(3-cyano-4-(1-methylpropyloxyphenyl)-1,3,4-thiadiazol-3-yl)-3-methylphenyl)propanoic acid The title compound was prepared using a procedure analogous to that described in EXAMPLE 91, Step E substituting (R/S)-ethyl 3-(4-(5-(3-cyano-4-(1-methylpropyloxyphenyl)-1,3,4-thiadiazol-3-yl)-3-methylphenyl)propanoate (from Step E) for 3-(4-(5-(3-cyano-4-isopropylthiophenyl)-1,3,4-thiadiazol-3-yl)-3-methylphenyl)propanoic acid: $^1$H NMR (500 MHZ, CDCl$_3$) δ 8.25 (d, J=8.7, 1H), 8.19 (s, 1H), 7.71 (d, J=7.8, 1H), 7.26 (s, 1H), 7.22 (d, J=7.8, 1H), 7.11 (d, J=8.7, 1H), 4.52-4.60 (m, 1H), 3.04 (t, J=7.6, 2H), 2.77 (t, J=7.7, 2H), 2.66 (s, 3H), 1.85-1.95 (m, 1H), 1.76-1.84 (m, 1H), 1.45 (d, J=6.0, 3H), 1.08 (t, J=7.3, 3H); ESI-MS (m/z) 422.2; 2.82 min.

Examples 93-101

The following examples were prepared using procedures analogous to those described for EXAMPLE 92 substituting the appropriate alkyl halide for 2-iodobutane in Step E.

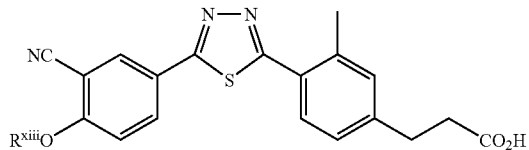

| EXAMPLE | R$^{xiii}$ | Characterization |
|---|---|---|
| 93 | CH$_3$CH$_2$— | $^1$H NMR (500 MHZ, CDCl$_3$) δ 8.26(d, J = 8.9, 1H); 8.20 (s, 1H), 7.70(d, J = 8.0, 1H), 7.25(s, 1H), 7.21(d, J = 7.8, 1H), 7.12(d, J = 8.7, 1H), 4.26-4.32(m, 2H), 3.03 (t, 2H), 2.76(t, 2H), 2.65(s, 3H), 1.57(t, J = 6.9, 3H); ESI-MS (m/z) 393.9; HPLC A: 3.41 min |
| 94 | CH$_3$CH$_2$CH$_2$— | $^1$H NMR (500 MHZ, CDCl$_3$) δ 8.27(dd, J = 7.1, 1.7, 1H), 8.21(s, 1H), 7.72(d, J = 7.8, 1H), 7.27(s, 1H), 7.23 (d, J = 8.0, 1H), 7.14(d, J = 8.9, 1H), 4.18(t, J = 6.5, 2H), 3.03-3.07(m, 2H), 2.78(t, J = 7.6, 2H), 2.67(s, 3H), 1.96-2.00(m, 2H), 1.16(t, J = 7.5, 3H); ESI-MS (m/z) 408.2; HPLC A: 2.77 min |
| 95 | (CH$_3$)$_2$CHCH$_2$— | $^1$H NMR (500 MHZ, CDCl$_3$) δ 8.26(d, J = 8.4, 1H), 8.20(s, 1H), 7.71(d, J = 7.8, 1H), 7.26(s, 1H), 7.22(d, J = 7.6, 1H), 7.13(d, J = 8.9, 1H), 3.97(d, J = 6.2, 2H), 3.00-3.09(m, 2H), 2.74-2.82(m, 1H), 2.66(s, 3H), 2.23-2.31(m, 1H), 1.15(d, J = 6.4, 6H); ESI-MS (m/z) 422.2; HPLC A: 2.86 min |
| 96 | cyclopropyl-CH$_2$— | $^1$H NMR (500 MHZ, CDCl$_3$) δ 8.25(dd, J = 6.8, 1.9, 1H), 8.24(s, 1H), 7.70(d, J = 7.8, 1H), 7.25(s, 1H), 7.22 (d, J = 8.0, 1H), 7.10(d, J = 8.9, 1H), 4.07(d, J = 6.8, 2H), 3.04(t, J = 7.6, 2H), 2.77(t, J = 7.6, 2H), 2.66(s, 3H), 1.38-1.43(m, 1H), 0.75(d, J = 7.8, 2H), 0.47(d, J = 4.8, 2H); ESI-MS (m/z) 420.2; HPLC A: 2.75 min |
| 97 | cyclobutyl-CH$_2$— | $^1$H NMR (500 MHz, CDCl$_3$) δ 8.24(dd, J = 6.9, 2.0, 1H), 8.23(s, 1H), 7.70(d, J = 7.7, 1H), 7.25(s, 1H), 7.21(d, J = 8.0, 1H), 7.10(d, J = 9.0, 1H), 4.06(d, J = 6.9, 2H), 3.04(t, J = 7.6, 2H), 2.77(t, J = 7.7, 2H), 2.65(s, 3H), 0.74(d, J = 7.8, 2H), 0.47(d, J = 5.0, 2H); ESI-MS (m/z) 420.2; HPLC A: 3.56 min |
| 98 | FCH$_2$CH$_2$— | $^1$H NMR (500 MHZ, CDCl$_3$) δ 8.27(d, J = 6.7, 1H), 8.21 (d, J = 9.6, 1H), 7.70(d, J = 8.0, 1H), 7.25(s, 1H), 7.21 (d, J = 7.8, 1H), 7.16(d, J = 9.0, 1H), 4.80-4.98(m, |

-continued

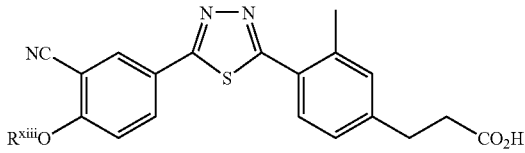

| EXAMPLE | R^xiii | Characterization |
|---|---|---|
| | | 2H), 4.41-4.51(m, 2H), 3.04(m, 2H), 2.76(t, J = 7.6, 2H), 2.65(s, 3H); ESI-MS (m/z) 412.2; HPLC A: 2.56 min |
| 99 | $CF_3CH_2$— | $^1$H NMR (500 MHZ, $CDCl_3$) δ 8.32(d, J = 8.5, 1H), 8.27 (s, 1H), 7.71(d, J = 7.7, 1H), 7.26(s, 1H), 7.22(d, J = 7.8, 1H), 7.17(d, J = 8.7, 1H), 4.58-4.67(m, 2H), 3.04(t, J = 7.5, 2H), 2.77()t, J = 7.5, 2H), 2.66(s, 3H); ESI-MS (m/z) 448.0; HPLC A: 3.52 min |
| 100 | $CF_3CH_2CH_2$— | $^1$H NMR (500 MHZ, $CDCl_3$) δ 8.29(dd, J = 7,.1, 1.9, 1H), 8.22(s, 1H), 7.70(d, J = 7.7, 1H), 7.25(s, 1H), 7.22 (d, J = 8.0, 1H), 7.14(d, J = 8.9, 1H), 4.43(t, J = 6.7, 2H), 3.03(t, 2H), 2.78-2.87(m, 2H), 2.76(t, J = 7.7, 2H), 2.65(s, 3H); ESI-MS (m/z) 462.1; HPLC A: 2.70 min |
| 101 | $(CF_3)_2CH$— | ESI-MS (m/z) 517.7 (2.93 min) |

Example 102

3-(4-(5-(3-Cyano-4-isopropyloxyphenyl)-1,3,4-oxadiazol-3-yl)-5-methylphenyl)propanoic acid Step A: 2-(3-Cyano-4-isopropyloxyphenyl)-5-(4-bromo-2-methylphenyl)-1,3,4-oxadiazole In an oven-dried round bottom flask 145 mg (0.35 mmol) of N'-(3-cyano-4-isopropyloxyphenylcarbonyl)-4-bromo-2-methylbenzhydrazide (from EXAMPLE 87, Step A) was combined with 10 mL of anhydrous xylenes and 5 mL of phosphorus oxychloride and the heterogeneous reaction mixture was heated to reflux for 6 h. The resulting homogeneous mixture was cooled down to rt and combined with 200 mL of ice-water, neutralized to pH>10 and extracted with EtOAc (2×150 mL). The combined organic layers were dried with sodium sulfate and solvents were removed under reduced pressure. The crude compound was purified by flash chromatography using Biotage 40S (eluent: hexanes/EtOAc—4/1) to yield 121 mg of title compound: $^1$H NMR (500 MHZ, $CDCl_3$) δ 1.50 (d, J=7.0, 6H), 2.78 (s, 3H), 4.80 (sep, J=7.0, 1H), 7.14 (d, J=9.0, 1H), 7.54 (dd, J=9.0, 2.0, 1H), 7.58 (d, J=2.0, 1H), 7.91 (d, J=8.5, 1H), 8.30 (d, J=2.0, 1H), 8.33 (dd, J=8.5, 2.0, 1H).

Step B: 2-(4-(5-(3-Cyano-4-isopropyloxyphenyl)-1,3,4-oxadiazol-3-yl)-5-methylphenyl)propanoic acid The title compound was prepared from 2-(3-cyano-4-isopropyloxy phenyl)-5-(4-bromo-2-methylphenyl)-1,3,4-oxadiazole (from Step A) using procedures analogous to those described in EXAMPLE 87, Steps C-E: $^1$H NMR (500 MEZ, $CDCl_3$) δ 1.48 (d, J=6.0, 6H), 2.60 (t, J=7.5, 2H), 2.75 (s, 3H), 2.98 (t, J=7.5, 2H), 4.80 (sep, J=6.0, 1H), 7.13 (d, J=9.0, 1H), 7.21 (m, 2H), 7.95 (d, J=8.0, 1H), 8.28 (d, J=2.5, 1H), 8.31 (dd, J=8.5, 2.5, 1H).

Example 103

3-(4-(5-(5-Chloro-6-isopropoxy-pyridin-3-yl)-1,3,4-oxadiazol-3-yl)-5-methylphenyl)propanoic acid The title compound was prepared from 5-chloro-6-isopropoxynicotinic acid using procedures analogous to those described in EXAMPLE 87, Step A and EXAMPLE 102: $^1$H NMR (500 MHZ, $CDCl_3$) δ 1.47 (d, J=6.5, 6H), 2.78 (s, 3H), 2.80 (t, J=7.5, 2H), 3.05 (t, J=7.5, 2H), 5.50 (sep, J=6.0, 1H), 7.25 (m, 2H), 7.99 (d, J=7.5, 1H), 8.36 (d, J=2.5, 1H), 8.81 (d, J=2.5, 1H).

Example 104

3-(4-(5-(3-Cyano-4-(2-methylpropyl)phenyl)-1,3,4-thiadiazol-3-yl)-5-methylphenyl)propanoic acid Step A: 2-Amino-5-(4-bromo-3-methylphenyl)-1,2,4-thiadiazole In an oven-dried round bottom flask, 7.0 g of 4-bromo-3-methylbenzoic acid (32.6 mmol) was dissolved in 10 mL of dichloromethane, 30 mL of dimethyl formamide was added to the solution and the resulting mixture was treated with 7.0 mL of oxalyl chloride at 50° C. for 30 min. The reaction mixture was cooled to rt and solvents were removed under reduced pressure. The residual white solids were dissolved in 50 mL of EtOAc and added over 10 minutes to a stirring biphasic system consisting of 150 mL of EtOAc, 150 mL of saturated solution of sodium bicarbonate, and 7.5 g of thiosemicarbazide (81.4 mmol). The resulting reaction mixture was allow to stir at rt for 3 h, organic layer was separated and aqueous was extracted with 2×250 mL of EtOAc. Combined organic extracts were dried over sodium sulfate and concentrated to yield a crude product, contaminated with thiosemicarbazide. This crude material was treated with 25 mL of neat sulfuric acid at rt for 30 minutes. The reaction mixture was diluted with 500 mL of ice-water mixture and basified with solid sodium hydroxide to pH>13, controlling the isotherm by an external ice-bath. The basic heterogeneous solution was extracted 3×300 mL of EtOAc, organic extracts dried over sodium sulfate and concentrated. The crude product was purified by column chromatography using Biotage 40L cartridge (eluant hexanes/EtOAc=1/1) yielding 3.7 g of the title compound: $^1$H NMR (500 MHZ, CDCl$_3$) δ 2.56 (s, 3H), 5.28 (s, 2H), 7.42 (d, J=6.5, 1H), 7.44 (d, J=6.5, 1H), 7.49 (s, 1H).

Step B: tert-Butyl 4-(2-Amino-1,3,4-thiadiazol-5-yl)-3-methylphenylpropenoate In an oven-dried flask, under an atmosphere of argon, 232 mg of 2-(di-tert-butylphosphino)biphenyl (0.78 mmol) and 400 mg of tris(dibenzylideneacetone) dipalladium-chloroform complex (0.39 mmol) were dissolved in 40 mL of anhydrous dioxane and the solution was degassed with argon. To this mixture, 3.30 mL of dicyclohexylmethylamine (1.56 mmol), 1.11 mL of tert-butyl acrylate (9.72 mmol), and a solution of 2.10 g of 2-amino-5-(4-bromo-3-methylphenyl)-1,2,4-thiadiazole (7.78 mmol, from Step A) in 10 mL of dioxane were added sequentially via syringe. The resulting mixture was degassed with argon and heated under argon atmosphere at 100° C. for 30 min. The reaction mixture was filtered through a frit and concentrated. The title compound was isolated by a column chromatography using Biotage 40L column (eluent hexanes/EtOAc) as a white solid (2.62 g): $^1$H NMR (500 MHZ, CDCl$_3$) δ 1.57 (s, 9H), 2.61 (s, 3H), 6.44 (d, J=17.5, 1H), 7.42 (d, J=6.5, 1H), 7.45 (s, 1H), 7.59 (m, 2H).

Step C: tert-Butyl 4-(2-Amino-1,3,4-thiadiazol-5-yl)-3-methylphenylpropanoate tert-Butyl 4-(2-amino-1,3,4-thiadiazol-5-yl)-3-methylphenyl)propenoate (2.62 g, from Step B) was dissolved in 150 mL of mixture of methanol/EtOAc (1/1), 1.40 g of palladium on activated carbon (10% w/w, 13 mmol) was added and the resulting mixture was hydrogenated under 55 psi of hydrogen for 36 h. The heterogeneous mixture was filtered through a filter paper under reduced pressure and subsequently through a disposable frit to remove traces of palladium and the filtrate was concentrated. The crude product was used in subsequent step without purification: $^1$H NMR (500 MHZ, CDCl$_3$) δ 1.47 (s, 9H), 2.57 (s, 3H), 2.59 (t, J=8.0, 2H), 2.95 (t, J=8.0, 2H), 5.16 (s, 2H), 7.13 (d, J=7.5, 1H), 7.18 (s, 1H), 7.51 (d, J=7.5, 1H).

Step D: tert-Butyl 4-(2-Bromo-1,3,4-thiadiazol-5-yl)-3-methylphenylpropanoate tert-Butyl 4-(2-Amino-1,3,4-thiadiazol-5-yl)-3-methylphenyl)propanoate (from Step C) was dissolved in 100 mL of acetonitrile and 3.2 g of copper(II) bromide and 1.5 mL of isoamyl nitrite were added sequentially. The mixture was stirred at rt for 40 min, diluted with 500 mL of EtOAc and combined with 300 mL of water. The organic layer was separated, aqueous was washed with 200 mL of EtOAc, and combined organic extracts were washed with brine and dried over sodium sulfate before concentrated. Pure product was isolated by column chromatography using Biotage 40L column: $^1$H NMR (500 MHZ, CDCl$_3$) δ 1.46 (s, 9H), 2.59 (s, 3H), 2.60 (t, J=8.0, 2H), 2.97 (t, J=8.0, 2H), 5.16 (s, 2H), 7.19 (d, J=8.0, 1.5, 1H), 7.22 (d, J=1.0, 1H), 7.60 (d, J=8.0, 1H); $^{13}$C NMR {H} (500 MHZ, CDCl$_3$) δ 21.4, 28.0, 30.74, 36.5, 80.6, 126.3, 126.4, 130.7, 131.8, 137.3, 138.4, 144.2, 171.3, 171.8; ESI-MS (m/z) obsd. 382/384 (intensity=1/1).

Step E: 2-(2-Methylpropyl)-5-bromobenzonitrile

5-Bromo-2-iodobenzonitrile (3.25 mmol) was combined with 6.5 mL of 0.5 M solution of iso-butylzinc bromide, the solution was degassed with argon, 100 mg of tetrakis(triphenylphosphine) palladium was added in one portion and the solution was stirred at rt under argon for 48 h. The solvents were removed under reduced pressure and the residual mixture was purified by column chromatography using Biotage 40L cartridge to obtain the title compound: $^1$H NMR (500 MHZ, CDCl$_3$) δ 0.97 (d, J=8.5, 6H), 2.00 (m, 1H), 2.71 (d, J=7.5, 2H), 7.19 (d, J=8.5, 1H), 7.65 (dd, J=8.5, 2.0, 1H), 7.76 (d, J=2.0, 1H).

Step F: (3-Cyano-4-(2-methylphenyl)phenyl)boronic acid, pinacol ester 2-(2-Methylpropyl)-5-bromobenzonitrile (120 mg, 0.50 mmol, from Step E) was combined with 140 mg of bis(pinacolato)diboron (0.55 mmol), 150 mg of potassium acetate (1.50 mmol), and 5 mL of dimethyl sulfoxide. The resulting solution was degassed with argon and 50 mg of [1,1'-bis(diphenylphosphino)ferrocene]dichloropalladium(II)-dichloromethane complex was added to the solution. The mixture was heated to 80° C. for 1 h, cooled to rt and the product was isolated by column chromatography using Biotage 40L cartridge (eluent: hexanes/EtOAc=10/1) as a mixture of the desired product and starting material (approx. 60% of product in the mixture). The mixture was used without further purification.

Step G: tert-Butyl 3-(4-(5-(3-Cyano-4-(2-methylpropyl)phenyl)-1,2,4-thiadiazol-3-yl)-3-methylphenyl)propanoate A stirred solution of 33 mg (0.086 mmol) of tert-butyl 4-(2-bromo-1,3,4-thiadiazol-5-yl)-3-methylphenyl)propanoate (from Step D), 50 mg of (3-cyano-4-(2-methylphenyl)phenyl)boronic acid, pinacol ester (from Step F), 123 mg of sodium carbonate decahydrate (0.43 mmol), 100 μL of water, and 2 mL of dimethylformamide was degassed with argon. To this solution, 10 mg of tetrakis(triphenylphosphine) palladium (0.009 mmol) was added, the solution was degassed with argon and heated under argon to 80° C. for 0.5 h. The solvents were removed under reduced pressure, and the crude concentrate was purified by preparative TLC (eluent: hexanes/EtOAc=4/1) to obtain 22 mg of title compound: $^1$H NMR (500 MHZ, CDCl$_3$) δ 1.03 (d, J=7.0, 6H), 1.47 (s, 9H), 2.09 (m, 1H), 2.61 (t, J=7.5, 2H), 2.66 (s, 3H), 2.83 (d, J=7.5, 2H), 2.98 (t, J=8.0, 2H), 7.21 (d, J=8.0, 1.5, 1H), 7.24 (s, 1H), 7.46 (d, J=8.5, 1H), 7.71 (d, J=8.0, 1H), 8.21 (dd, J=8.0, 1.5, 1H), 8.26 (d, J=1.5, 1H).

Step H: 2-(4-(5-(3-Cyano-4-(2-methylpropyl)phenyl-1,3,4-thiadiazol-3-yl)-5-methylphenyl)propanoic acid tert-Butyl 2-(4-(5-(3-cyano-4-(2-methylpropyl)phenyl-1,3,4-thiadiazol-3-yl)-5-methylphenyl)propanoate (20 mg, 0.043 mmol, from Step F) was treated with 20% solution of trifluoroacetic acid in dichloromethane (10 mL) for 3 h at rt. The solvents were removed under reduced pressure, residual solids dissolved in toluene and solvents removed to afford the title compound: $^1$H NMR (500 MHZ, CDCl$_3$) δ 1.03 (d, J=7.0, 6H), 2.10 (m, 1H), 2.68 (s, 3H), 2.78 (t, J=7.5, 2H), 2.84 (d, J=7.5, 2H), 3.06 (t, J=8.0, 2H), 7.24 (d, J=8.5, 1.5, 1H), 7.28 (s, 1H), 7.48 (d, J=8.5, 1H), 7.73 (d, J=8.0, 1H), 8.21 (dd, J=8.0, 2.0, 1H), 8.27 (d, J=2.0, 1H).

Example 105

3-(4-(2-(3-Cyano-4-cyanomethoxyphenyl)-1,3,4-thiadiazol-5-yl)-3-methylphenyl)propanoic acid Step A: 3-Cyano-4-fluorobenzoic acid Chromium oxide (14.77 mmol; 1.48 g) was dissolved in a solution of sulfuric acid (1.1 mL) and water (3.4 mL) at 0° C. To this solution was added to a mixture of 3-cyano-4-fluorobenzaldehyde (13.4 mmol; 2.0 g) in acetone (17 mL) at 0° C. The reaction mixture was warmed to rt and stirred for 6 h. The reaction was then quenched with methanol (20 mL) and water (50 mL) and the product was extracted with EtOAc (2×50 mL). The combined organics were washed with brine (50 mL), dried over magnesium sulfate, filtered and concentrated in vacuo to yield 2.25 g of product: $^1$H NMR (500 MHZ, CDCl$_3$) δ 8.39 (d, J=5.0, 1H), 8.28-8.29 (m, 1H), 7.64 (t, J=8.9, 1H).

Step B: tert-Butyl 3-(4-(3-(3-Cyano-4-fluorophenyl)-1,3,4-thiadiazol-5-yl)-3-methylphenyl)propanoate The title compound was prepared from 3-cyano-4-fluorobenzoic acid (from Step A) using procedures analogous to those described in EXAMPLE 87, Steps A-C.

Step C: tert-Butyl 3-(4-(3-(3-Cyano-4-cyanomethoxyphenyl)-1,3,4-thiadiazol-5-yl)-3-methylphenyl)propanoate Glycolonitrile (0.013 mmol, 0.1 mL) was added to a solution of tert-butyl 3-(4-(3-(3-cyano-4-fluorophenyl)-1,3,4-thiadiazol-5-yl)-3-methylphenyl)propanoate (0.012 mmol, 0.005 g, from Step B) in THF (1 mL). Sodium hydride (95%, 5 mg) was added to the reaction mixture which was heated at 75° C. for 16 h. The reaction was diluted with EtOAc (20 mL) and washed with water (20 mL). The organics were dried over magnesium sulfate, filtered and concentrated in vacuo. Silica gel chromatography eluting with 25% EtOAc/hexanes yielded the title compound: ESI-MS (m/z) 461.2; HPLC A: 3.94 min.

Step D: 3-(4-(3-(3-Cyano-4-cyanomethoxyphenyl)-1,3,4-thiadiazol-5-yl)-3-methylphenyl)propanoic acid The title compound was prepared from tert-butyl 3-(4-(3-(3-Cyano-4-cyanomethoxyphenyl)-1,3,4-thiadiazol-5-yl)-3-methylphenyl)propanoate using a procedure analogous to that described in EXAMPLE 87, Step E: $^1$H NMR (500 MHZ, CDCl$_3$) δ 8.30-8.38 (m, 2H), 7.72 (d, J=7.7, 1H), 7.26 (s, 1H), 7.20-7.24 (m, 2H), 4.15 (d, J=7.1, 2H), 3.04 (t, 2H), 2.77 (t, J=7.4, 2H), 2.66 (s, 3H). ESI-MS (m/z) 405.1; HPLC A: 3.12 min.

Examples 106-109

The following examples were prepared using procedures analogous to those described in EXAMPLE 105 substituting the appropriate alcohol for glycolonitrile in Step C.

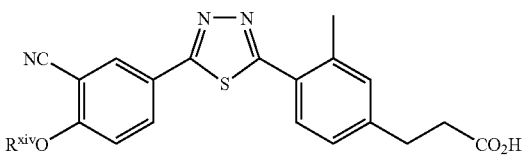

| EXAMPLE | R$^{xiv}$ | Characterization |
|---|---|---|
| 106 | CF$_3$CH(CH$_3$)— | $^1$H NMR (500 MHZ, CDCl$_3$) δ 8.31(dd, J = 6.8, 2.0, 1H), 8.25(s, 1H), 7.72(d, J = 7.8, 1H), 7.27(s, 1H), 7.23 (d, J = 8.7, 1H), 4.38-4.95(m, 1H), 3.05(t, J = 7.6, 2H), 2.77(t, J = 7.6, 2H), 2.67(s, 3H), 1.70(d, J = 6.4, 3H); ESI-MS (m/z) 462.1; HPLC A: 2.75 min |
| 107 | (FCH$_2$)$_2$CH— | $^1$H NMR (500 MHZ, CDCl$_3$) δ 8.27(dd, J = 7.1, 1.7, 1H), 8.24(s, 1H), 7.70(d, J = 7.8, 1H), 7.27(s, 1H), 7.25 (s, 1H), 7.22(d, J = 8.0, 1H), 4.92-5.04(m, 1H), 4.84(t, J = 4.8, 2H), 4.74(d, J = 4.6, 2H), 3.04(t, J = 7.6, 2H), 2.77(t, J = 7.6, 2H), 2.65(s, 3H); ESI-MS (m/z) 444.2; HPLC A: 3.28 min |
| 109 | HCF$_2$CH$_2$— | $^1$H NMR (500 MHZ, CDCl$_3$) δ 8.30(d, J = 8.7, 1H), 8.25(s, 1H), 7.71(d, J = 7.8, 1H), 7.26(s, 1H), 7.22(d, J = 7.8, 1H), 7.16(d, J = 8.9, 1H), 4.40-4.48(m, 2H), 3.04 (t, J = 7.6, 2H), 2.77(t, J = 7.6, 2H), 2.66(s, 3H); ESI-MS (m/z) 430.2; HPLC A: 3.31 min |

Example 110

(R)-(5-(5-(5-Chloro-6-isopropoxypyridin-3-yl)-1,2,4-oxadiazol-3-yl)-4-methyl-2,3-dihydro-1-H-inden-1-yl)methyl formate Step A: Ethyl 3-(3-methoxy-2-methylphenyl)-3-oxopropanoate Thionyl chloride (118 mL) was added to 3-methoxy-2-methyl benzoic acid (98.8 g, 595 mmol) and heated to reflux. After 2 hr, the reaction mixture was cooled to ambient temperature and concentrated in vacuo. The residue was azeotroped with toluene (2×300 mL) and the resultant solid set aside. A suspension of ethyl malonate potassium salt (208 g, 1.22 mol) in acetonitrile (1.50 L) cooled to 5° C., triethylamine (166 mL, 1.49 mol) were added followed by MgCl$_2$ (142 g, 1.49 mol). The cooling bath was removed and the mixture stirred for 3.5 hr at ambient temperature. The mixture was re-cooled to 5° C., and a solution of the aforementioned acid chloride in acetonitrile (100 mL) was added over 10 min. The mixture was warmed to ambient temperature, stirred for 15 hr, concentrated in vacuo and azeotroped with toluene (2×mL). The residue was suspended in EtOAc (750 mL) and toluene (750 mL), cooled in an ice bath and 4 N HCl (750 mL) was added slowly. The cooling bath was removed and the biphasic mixture was stirred vigorously for 30 min. The layers were separated, and the organic layer was washed with sat NaHCO$_3$ (2×1.0 L) and dried over MgSO$_4$. The mixture was filtered, concentrated in vacuo, and purified by flash chromatography (5, 10% EtOAc/heptane) on SiO$_2$ to afford 138 g of the title compound as a pale yellow liquid: $^1$H NMR (500 MHz, CDCl$_3$) indicated a mixture of keto ester and enol in a 2.5 1 ratio. For keto ester: δ 1.23 (t, 3H, J=7.2 Hz), 2.34 (s, 3H), 3.85 (s, 3H), 3.89 (s, 2H), 4.17 (q, 2H, J=7.1 Hz), 6.97 (d, 1H, J=7.8 Hz), 7.14 (d, 1H, J=8.7 Hz), 7.22 (d, 1H, J=7.9 Hz).

Step B: Ethyl 3-(3-methoxy-2-methylphenyl)propanoate

To a solution ethyl 3-(3-methoxy-2-methylphenyl)-3-oxo-propanoate (137.2 g, 595 mmol, from Step A) in ethyl alcohol (924 mL), 10% Pd—C (13.7 g) was added and 3 atm of hydrogen were applied. The mixture was heated to 60° C. for 20 hr, cooled to ambient temperature and filtered through Celite®. The filtrate was concentrated in vacuo and the residue purified by flash chromatography (2% EtOAc/hexanes) on SiO$_2$ to afford 110.8 g of the title compound as a pale yellow liquid: $^1$H NMR (500 MHz, CDCl$_3$) δ 1.25 (t, 3H, J=7.1 Hz), 2.19 (s, 3H), 2.55 (t, 2H, J=8.0 Hz), 2.95 (t, 2H, J=8.0 Hz), 3.82 (s, 3H), 4.14 (q, 2H, J=7.1 Hz), 6.73 (d, 1H, J=8.2 Hz), 6.78 (d, 1H, J=7.6 Hz), 7.10 (d, 1H, J=7.9 Hz).

Step C: 3-Methoxy-2-methylphenylpropionic acid

A solution of ethyl 3-(3-methoxy-2-methylphenyl)propanoate (36.3 g, 165 mmol, from Step B) in abs. EtOH (200 mL) and 5 N NaOH (99 mL) was heated to reflux for 30 min and cooled to ambient temperature. The reaction mixture was concentrated in vacuo, and the resultant solid mass was dissolved in H$_2$O (100 mL) and cooled in an ice bath. Concentrated HCl (50 mL) was then added dropwise. At pH=4, an additional 300 mL H$_2$O was added to facilitate stirring. The acidified mixture was stirred for 30 min, filtered, and the solids washed with H$_2$O (2×100 mL) and Et$_2$O (2×100 mL). After 3 hr, the solids were dried over P$_2$O$_5$ in vacuo overnight to give 29.3 g of the title compound as a white solid: $^1$H NMR (500 MHz, CD$_3$OD) δ 2.15 (s, 3H), 2.50 (t, 2H, J=7.9 Hz), 2.90 (t, 2H, J=7.9 Hz), 3.78 (s, 3H), 6.75 (d, 2H, J=8.0 Hz), 7.05 (t, 1H, J=8.0 Hz).

Step D: 5-Methoxy-4-methylindan-1-one

SOCl$_2$ (144 mL) was added to 3-methoxy-2-methylphenylpropionic acid (from Step C) and the mixture was heated to reflux. After 2 hr, the reaction mixture was concentrated in vacuo and azeotroped with dichloroethane (2×50 mL). The resultant acid chloride was dissolved in dichloromethane (250 mL), cooled in an ice bath and a 1.0 M solution of SnCl$_4$ in dichloromethane (155 mL, 155 mmol) was added dropwise. The purple reaction mixture was warmed to ambient temperature for 1 hr and quenched into 300 mL H$_2$O/300 g crushed ice. The layers were separated and the organic layer was washed with 2N HCl (2×150 mL) H$_2$O (2×150 mL) brine (2×150 mL), dried over MgSO$_4$, filtered and concentrated in vacuo. Purification of the residue by flash chromatography (10, 30% EtOAc/heptane), on SiO$_2$ gave an amber solid that was triturated with hexanes (100 mL) at 0° C. to give 16.6 g of the title compound as an off-white powder. The hexanes filtrate was purified further purified by flash chromatography as above to afford an additional 1.00 g of an off-white solid: $^1$H NMR (500 MHz, CDCl$_3$) δ 2.18 (s, 3H), 2.67-2.69 (m, 2H), 2.98-3.01 (m, 2H), 3.92 (s, 3H), 6.89 (d, 1H, J=8.5 Hz), 7.63 (d, 1H, J=8.5 Hz).

Step E: Ethyl (5-methoxy-4-methyl-2,3-dihydro-1H-1-inden-1-ylidene)acetate

To a mixture of activated Zn dust (556 mg, 8.51 mmol) in THF (2.5 mL), a solution of 5-methoxy-4-methylindan-1-one (1.00 g, 5.68 mmol, from Step D) and ethyl bromoacetate (819 μL, 7.38 mmol) in THF (5 mL) were added dropwise via cannula. The reaction was initiated by immersing in a 60° C. oil bath for 1 min. After 10 min, the reaction was quenched into 2 N HCl (10 mL) and extracted with EtOAc (10 mL). The organic layer was washed with H$_2$O (1×10 mL), brine (1×10 mL), dried over MgSO$_4$, and filtered. Solvents were removed in vacuo, and the residue was purified by flash chromatography (2, 5% EtOAc/hexanes) on SiO$_2$ to afford 1.26 g that was recrystallized from hexanes to afford 1.01 g of the title compound as a white solid: $^1$H NMR (500 MHz, CDCl$_3$) δ 1.32 (t, 3H, J=7.1 Hz), 2.15 (s, 3H), 2.94-2.97 (m, 2H), 3.29-3.32 (m, 2H), 3.87 (s, 3H), 4.20, (q, 2H, J=7.1 Hz), 6.17 (t, 1H, J=2.5 Hz), 6.79 (d, 1H, J=8.8 Hz), 7.43 (d, 1H, J=8.5 Hz).

Step F: (2E-)-(5-methoxy-4-methyl-2,3-dihydro-1H-inden-1-ylidene)acetic acid

To solution of ethyl (5-methoxy-4-methyl-2,3-dihydro-1H-1-inden-1-ylidene)acetate (8.28 g, 33.6 mmol, from Step E) in 3:2:1 THF:CH$_3$OH:H$_2$O (83 mL) 5.0 N NaOH (14.8 mL, 74.0) was added and the resultant solution was heated to reflux. After 2 hr, the reaction mixture was concentrated in vacuo, dissolved in H$_2$O (150 mL) and cooled to 0° C. The aqueous layer was made acidic (pH<2) by the addition of concentrated HCl and the resultant precipitate was filtered, washed with H$_2$O (150 mL) and dried over P$_2$O$_5$ in vacuo. A total of 6.75 g of the title compound was isolated as a white solid: $^1$H NMR (500 MHz, CD$_3$OD) δ 2.18 (s, 3H), 3.22-3.29 (m, 2H), 3.50-3.52 (m, 2H), 3.80 (s, 3H), 6.26 (s, 1H), 6.82 (d, 1H, J=8.2 Hz), 7.12 (d, 1H, J=8.3 Hz).

Step G: Methyl (R)-(5-methoxy-4-methyl-indan-1-yl)acetate

To a solution of (2E-)-(5-methoxy-4-methyl-2,3-dihydro-1H-inden-1-ylidene)acetic acid (1.0 g, 4.58 mmol, from Step F) in methanol (10 mL) was added [(S)-(−)-2,2'bis(diphenylphosphino)-1,1'-binaphthyl]ruthenium (II) (36.0 mg, 0.0458 mmol) and triethylamine (64 μL, 0.458 mmol). The resultant mixture was subjected to 3 atm H$_2$ and was shaken at ambient temperature for 24 hr. The reaction mixture was filtered through Celite®, and concentrated in vacuo. The residue was dissolved in THF (5 mL) and methanol (5 mL) and treated with TMSCHN$_2$ (6.51 mL, 13.0 mmol) at ambient temperature. After 1 hr, the reaction mixture was concentrated in vacuo and purified by flash chromatography (3% EtOAc/hexanes) on SiO$_2$ to give 828 mg of the title compound as a colorless liquid: $^1$H NMR (500 MHz, CDCl$_3$) δ 1.71-1.78 (m, 1H), 2.15 (s, 3H), 2.37-2.46 (m, 2H), 2.73-2.81 (m, 2H), 2.86-2.92 (m, 1H), 3.53-3.59 (m, 1H), 3.73 (s, 3H), 3.82 (s, 3H), 6.69 (d, 1H, J=8.2 Hz), 6.96 (d, 1H, J=8.2 Hz).

Step H: Methyl (R)-(5-hydroxy-4-methyl-indan-1-yl)acetate

A 1.0 M solution of boron tribromide in dichloromethane (16.2 mL, 16.2 mmol) was added to an ice-cold solution methyl (R or S)-(5-methoxy-4-methyl-indan-1-yl)acetate (1.52 g, 6.49 mmol, from Step F) in dichloromethane (5 mL). The cooling bath was removed and the reaction mixture stirred at ambient temperature. After 1 hr, the reaction mixture was slowly transferred to an ice-cold solution of methanol (50 mL). Methanol was removed in vacuo, and the residue was partitioned between EtOAc and sat. NaH$_2$PO$_4$. The organic layer was washed with H$_2$O, brine, and dried over MgSO$_4$. The mixture was filtered, concentrated in vacuo and purified by flash chromatography (5, 10% EtOAc/hexanes) on SiO$_2$ to afford 1.22 g of the title compound as a white solid: $^1$H NMR (500 MHz, CDCl$_3$) δ 1.71-1.78 (m, 1H), 2.16 (s, 3H), 2.35-2.44 (m, 2H), 2.71-2.79 (m, 2H), 2.86-2.90 (m, 1H), 3.54 (p, 1H, J=7.3 Hz), 3.72 (s, 3H), 4.83 (s, 1H), 6.61 (d, 1H, J=8.0 Hz), 6.85 (d, 1H, J=8.0 Hz).

Step I: Methyl (R)-(5-trifluoromethylsulfonyloxy-4-methyl-indan-1-yl)acetate To a solution of pyridine (440 μL, 5.45 mmol) in dichloromethane (5.0 mL) cooled to 0° C. trifluoromethanesulfonic anhydride (840 μL, 4.99 mmol) was added. The resultant mixture was stirred for 5 min, and methyl (R or S)-(5-hydroxy-4-methyl-indan-1-yl)acetate (1.00 g, 1.34 mmol, from Step H) was added as a solid. The reaction mixture was warmed to ambient temperature, stirred for 1 hr and diluted with dichloromethane. The organic layer was washed with H$_2$O, brine and dried over MgSO$_4$. The mixture was filtered and concentrated in vacuo. Purification by flash chromatography (10% EtOAc/hexanes) on SiO$_2$ gave 1.46 g of the title compound as a pale yellow liquid: $^1$H NMR (500 MHz, CDCl$_3$) δ 1.69-1.91 (m, 1H), 2.33 (s, 3H), 2.38-2.56 (m, 2H), 2.69-2.79 (m, 1H), 2.79-3.01 (m, 2H), 3.49-3.65 (m, 1H), 3.76 (s, 3H), 7.09 (s, 2H).

Step J: Methyl (R)-(5-Cyano-4-methyl-indan-1-yl)acetate

To a solution of methyl (R or S)-(5-Trifluoromethylsulfonyloxy-4-methyl-indan-1-yl)acetate (1.00 g, 2.84 mmol, from Step I) in N-methylpyrrolidinone (13 mL) under argon, zinc cyanide (267 mg, 2.27 mmol), Pd$_2$dba$_3$ (13.0 mg, 14.2 μmol) and dppf (19.0 mg, 34.1 μmol) and the reaction mixture was heated to 100° C. After 16 hr, the reaction mixture was concentrated in vacuo and partitioned between EtOAc and H$_2$O. The layers were separated and the organic layer was washed with H$_2$O, brine and dried over MgSO$_4$. The mixture was filtered, the filtrate concentrated in vacuo, and the residue purified by flash chromatography (5, 10% EtOAc/hexanes) on SiO$_2$ to give 553 mg of the title compound as a white solid: $^1$H NMR (500 MHz, CDCl$_3$) δ 1.76-1.80 (m, 1H), 2.41-2.50 (m, 5H), 2.73 (dd, 1H, J=5.8, 15.8 Hz), 2.78-2.84 (m, 1H), 2.91 (ddd, 1H, J=4.8, 8.7, 13.5 Hz) 3.61-3.67 (m, 1H), 3.71, (s, 3H), 7.07 (d, 1H, J=7.8 Hz), 7.43 (d, 1H, J=7.7 Hz).

Step K: Methyl (R)-(5-(N-hydroxycarboxamidinyl)-4-methyl-indan-1-yl)acetate

To a solution of methyl (R or S)-(5-Cyano-4-methyl-indan-1-yl)acetate (724 mg, 3.16 mmol, from Step J) in methanol (10 mL), hydroxylamine hydrochloride (285 mg, 4.11 mmol) and triethylamine (660 μL, 474 mmol) were added and heated to reflux. After 14 hr, the reaction mixture was cooled to ambient temperature and concentrated in vacuo. The residue was purified by flash chromatography (10, 30, 50% EtOAc/hexanes) on SiO$_2$ to give 318 mg of starting material and 352 mg of the title compound, as an inseparable 2:1 mixture of the amidoxime and primary amide by $^1$H NMR. For amidoxime: $^1$H NMR (500 MHz, CDCl$_3$) δ 1.72-1.84 (m, 1H), 2.37 (s, 3H), 2.43-2.51 (m, 2H), 2.76-2.87 (m, 2H), 2.90-2.96 (m, 1H), 3.64 (p, 1H, J=7.2 Hz), 3.76 (s, 3H), 4.85, (br, s, 2H), 7.05 (d, 1H, J=7.5 Hz), 7.31 (d, 1H, J=8.0 Hz).

Step L: Methyl (R)-(5-(5-(5-chloro-6-isopropoxypyridin-3-yl))-1,2,4-oxadiazol-3-yl)-4-methyl-indan-1-yl)acetate To a solution of 5-chloro-6-isopropoxynicotinic acid (289 mg, 1.34 mmol) in acetonitrile (5.0 mL), EDC-HCl (257 mg, 1.34 mmol) was added. The resultant solution was stirred at ambient temperature for 30 min and methyl (R or S)-(5-(N-hydroxycarboxamidinyl)-4-methyl-indan-1-yl)acetate (352 mg, from Step K) was added. After 1 hr, the reaction mixture was concentrated in vacuo. The residue was dissolved in EtOAc and washed with H$_2$O, brine, and dried over MgSO$_4$. The mixture was filtered, concentrated in vacuo and dissolved in THF (1.5 mL). A solution of TBAF 1.0 M in THF (1.34 mL) was added and the resultant yellow solution was stirred at ambient temperature for 1.5 hr. The reaction mixture was concentrated in vacuo, dissolved in EtOAc and washed with H$_2$O, brine, and dried over MgSO$_4$. The mixture was filtered, concentrated in vacuo and purified by flash chromatography (10% EtOAc/hexanes) on SiO$_2$ to give 277 mg of the title compound as white solid. This material was recrystallized from hexanes to give 176 mg that was >99% ee: $^1$H NMR (500 MHz, CDCl$_3$) δ 1.44 (d, 6H, J=6.2 Hz), 1.78-1.85 (m, 1H), 2.43-2.46 (m, 1H), 2.49 (dd, 1H, J=9.3, 15.6 Hz), 2.56 (s, 3H), 2.81 (dd, 1H, J=5.5, 15.5 Hz), 2.86-2.93 (m, 1H), 3.73 (s, 3H), 5.49, (septet, 1H, J=6.2 Hz), 7.14 (d, 1H, J=7.8 Hz), 7.85 (d, 1H, J=7.8 Hz), 8.38 (d, 1H, J=2.3 Hz), 8.85 (d, 1H, J=2.3 Hz).

Step M: (R or S)-(5-(5-(5-chloro-6-isopropoxypyridin-3-yl))-1,2,4-oxadiazol-3-yl)-4-methyl-indan-1-yl)acetic acid To a solution of methyl (R or S)-(5-(5-(5-chloro-6-isopropoxypyridin-3-yl))-1,2,4-oxadiazol-3-yl)-4-methyl-indan-1-yl)acetate (176 mg, 0.398 mmol, from Step L) in THF (3 mL) and H$_2$O (1 mL) lithium hydroxide monohydrate (167 mg, 3.98 mmol) was added. The reaction mixture was heated to 50° C. for 3 hr, cooled to ambient temperature and partitioned between EtOAc and 5% citric acid. The organic layer was washed with H$_2$O, brine, dried over MgSO$_4$, filtered and concentrated in vacuo. Purification of the residue by flash chromatography (2% CH$_3$OH/CH$_2$Cl$_2$/0.2% HCO$_2$H) on SiO$_2$ afforded 154 mg of the title compound as a white solid:

¹H NMR (500 MHz, DMSO-d₆) δ 1.37 (d, 6H, J=6.2 Hz), 1.69-1.73 (m, 1H), 2.31-2.38 (m, 2H), 2.49 (s, 3H), 2.72 (dd, 1H, J=5.6, 15.6 Hz), 2.81-2.85 (m, 1H), 2.92-2.96 (m, 1H), 3.50-3.52 (m, 1H), 5.43 (septet, 1H, J=6.1 Hz), 7.30 (d, 1H, J=8.0 Hz), 7.77 (d, 1H, J=7.8 Hz), 8.48 (s, 1H), 8.89 (s, 1H); HPLC A: rt=4.32 min, m/z=428.2 (M+H)⁺.

Examples 111-113

The following examples were prepared using procedures analogous to those described in EXAMPLE 110 except the substrate in Step G was reduced using 10% Pd—C as the catalyst and methanol as the solvent.

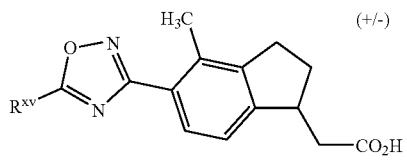

| EX. | R^xv | HPLC A (min) | ESI-MS (M + H)⁺ |
|---|---|---|---|
| 111 | (4-(1,1,1-trifluoropropan-2-yloxy)-3-(trifluoromethyl)phenyl) | 4.18 | 515.2 |

¹H NMR (500 MHz, DMSO-d₆) δ 1.34(d, 6H, J = 6.0 Hz), 1.71-1.75(m, 1H), 2.34-2.40(m, 2H), 2.47(d, 3H), 2.75(dd, 1H, J = 5.5, 15.8 Hz), 22.80-2.85(m, 1H), 2.94-2.96(m, 1H), 3.39-3.54(m, 1H), 4.96(septet, 1H, J = 6.1 Hz), 7.25(d, 1H, J = 8.0 Hz), 7.57(d, 1H, J = 9.6 Hz), 7.78(d, 1H, J = 7.8 Hz), 8.29(s, 1H), 8.37(dd, 1H, J = 2.0, 8.6 Hz)

| 112 | (4-isopropoxy-3-(trifluoromethyl)phenyl) | 4.25 | 461.2 |

¹H NMR (500 MHz, DMSO-d₆) δ 1.51(d, 3H, J = 6.2 Hz), 1.72-1.75(m, 1H), 2.35-2.40(m, 2H), 2.48(s, 3H), 2.74(dd, 1H, J = 5.5, 16.0 Hz), 2.82-2.93(m, 1H), 2.94-2.98(m, 1H), 3.51-3.54(m, 1H), 5.69-5.71(m, 1H), 7.26(d, 1H, J = 7.5 Hz), 7.78(d, 2H, J = 8.8 Hz), 8.35(s, 1H), 8.45(d, 1H, J = 8.7 Hz)

| 113 | (3-chloro-2-morpholinopyridin-5-yl) | 3.87 | 455.1 |

¹H NMR (500 MHz, DMSO-d₆) δ 1.70-1.75(m, 1H), 2.34-2.40(m, 2H), 2.47(s, 3H), 2.73-2.85(m, 2H), 2.83-2.95(m, 1H), 3.38-3.55(m, 5H), 3.74-3.76(m, 4H), 7.25(d, 1H, J = 7.8 Hz), 7.76(d, 1H, J = 8.5 Hz), 8.38(d, 1H, J = 2.1 Hz), 8.92(d, 1H, J = 2.1 Hz)

Example 114

(R/S)-5-[5-(5-Chloro-6-isopropoxypyridin-3-yl)-1,2,4-oxadiazol-3-yl]-4-methylindane-2-carboxylic acid

Step A: Ethyl 5-methoxy-4-methylindane-3-oxo-2-carboxylate

To a solution of ethyl 3-(3-methoxy-2-methylphenyl)-3-oxopropanoate (5.31 g, 20.1 mmol, from EXAMPLE 110, Step A) in nitromethane (150 mL) AlCl$_3$, methoxymethylacetyl chloride (24.1 mmol, 2.20 mL) in nitromethane (40 mL) was added dropwise. The reaction was then heated to 80° C. for 2 hr, cooled to room temperature and poured into 100 mL 10% aqueous oxalic acid. 100 mL Et$_2$O was added and the layers were separated. The organic layer was washed with sat. NaHCO$_3$ (1×100 mL, brine (1×100 mL) and dried over Na$_2$SO$_4$. The mixture was filtered and concentrated in vacuo. was purified by The residue flash chromatography (0, 2, 5% EtOAc/hexanes) on SiO$_2$ to give 4.10 g of the title compound as an off-white solid: $^1$H NMR (500 MHz, CDCl$_3$) δ 1.31 (t, 3H, J=7.2 Hz), 2.51 (s, 3H), 3.23, (dd, 1H, J=8.5, 16.7 Hz), 3.40 (dd, 1H, J=5.0 16.7 Hz), 3.69 (dd, 1H, J=4.4, 8.5 Hz), 3.86, (s, 3H), 4.24 (q, 2H, J=7.0 Hz), 7.10 (d, 1H, J=8.5 Hz), 7.25 (d, 1H, J=8.7 Hz); HPLC/MS: m/z 249 (M+H)$^+$.

Step B: Ethyl 5-methoxy-4-methylindane-2-carboxylate

To a solution ethyl 5-methoxy-4-methylindane-3-oxo-2-carboxylate (1.01 g, 4.07 mmol, from Step A) in trifluoroacetic acid (10 mL) cooled to 0° C., triethylsilane (1.95 mL, 12.2 mmol) was added dropwise. The reaction mixture was allowed to warm to ambient temperature, stirred for 17 hr and concentrated in vacuo. The residue was purified by flash chromatography (0, 2, 3% EtOAc/hexanes) on SiO$_2$ to give 0.910 g of the title compound as a colorless liquid: $^1$H NMR (500 MHz, CDCl$_3$) δ 1.29 (t, 3H, J=7.2 Hz), 2.13 (s, 3H), 3.14-3.20 (m, 4H), 3.31 (quintet, 1H, J=8.8 Hz), 3.80, (s, 3H), 4.18 (q, 2H, J=7.2 Hz), 6.68 (d, 1H, J=8.3 Hz), 6.98 (d, 1H, J=8.1 Hz); HPLC/MS: m/z 235 (M+H)$^+$.

Step C: Ethyl 5-hydroxy-4-methylindane-2-carboxylate

To a solution of ethyl 5-methoxy-4-methylindane-2-carboxylate (896 mg, 3.82 mmol, from Step B) in dichloromethane (10 mL) cooled to 0° C., BBr$_3$ (1.0 M in CH$_2$Cl$_2$, 19.1 mL, 19.1 mmol) was added dropwise. The reaction mixture was stirred for 30 min at 0° C. and warmed to ambient temperature. After 2 hr, the reaction mixture was slowly transferred to an ice-old solution of methanol (10 mL). The resulting solution was warmed to ambient temperature, concentrated in vacuo, and azeotroped with methanol (2×5 mL). The residue was partitioned between EtOAc (15 mL) and sat. NaH$_2$PO$_4$ (5 mL). The layers were separated, and the EtOAc layer was washed with H$_2$O (1×5 mL), brine (1×5 mL) and dried (MgSO$_4$). The mixture was filtered, concentrated in vacuo and purified by flash chromatography (10, 20% EtOAc/hexanes) on SiO$_2$ to afford 560 mg of the title compound: $^1$H NMR (500 MHz, CDCl$_3$) δ 2.15 (s, 3H), 3.13-3.22 (m, 4H), 3.35 (quintet, 1H, J=8.6 Hz), 3.73, (s, 3H), 4.66 (s, 1H), 6.61 (d, 1H, J=8.1 Hz), 6.89 (d, 1H, J=8.1 Hz).

Step D: Ethyl 5-trifluorosulfonyloxy-4-methylindane-2-carboxylate

Trifluoromethnanesulfonic anhydride (492 µL, 2.92 mmol) was added to a solution of pyridine (258 µL, 3.19 mmol) and dichloromethane (3 mL) at 0° C. After 5 min, a solution of ethyl 5-hydroxy-4-methylindane-2-carboxylate (548 mg, 2.66 mmol, from Step C) in dichloromethane (3 mL) was added. The resulting solution was stirred for 30 min at 0° C., and at ambient temperature for 1 hr. The reaction mixture was diluted with dichloromethane (10 mL), washed with H$_2$O (1×10 mL), brine (1×10 mL), and dried over MgSO$_4$. The mixture was filtered and the filtrate concentrated in vacuo. The residue was purified by flash chromatography (5% EtOAc/hexanes) on SiO$_2$ to give 907 mg of the title compound as a colorless liquid: $^1$H NMR (500 MHz, CDCl$_3$) δ 2.26 (s, 3H), 3.20-3.29 (m, 4H), 3.37-3.44 (m, 1H), 3.74, (s, 3H), 7.04 (d, 1H, J=8.2 Hz), 7.07 (d, 1H, J=8.4 Hz).

Step E: Ethyl 5-cyano-4-methylindane-2-carboxylate

To a solution of ethyl 5-trifluorosulfonyloxy-4-methylindane-2-carboxylate (905 mg, 2.68 mmol, Step D) in N-methylpyrrolidinone (7 mL), zinc cyanide (251 mg, 2.14 mmol), Pd$_2$dba$_3$ (12.2 mg, 0.0134 mmol) and dppf (17.8 mg, 0.0321 mmol) were added and the reaction mixture was heated to 100° C. After 16 hr, the reaction mixture was concentrated in vacuo and partitioned between Et$_2$O (10 mL) and H$_2$O (10 mL). The layers were separated and the aqueous layer was back-extracted with Et$_2$O (2×10 mL). The combined Et$_2$O layers were washed with H$_2$O (1×15 mL), brine (1×15 mL) and dried over MgSO$_4$. The mixture was filtered, the filtrate concentrated in vacuo, and the residue purified by flash chromatography (5, 10% EtOAc/hexanes) on SiO$_2$ to give 409 mg of the title compound as a white solid: $^1$H NMR (500 MHz, CDCl$_3$) δ 2.42 (s, 3H), 3.19-3.39 (m, 5H), 3.73, (s, 3H), 7.11 (d, 1H, J=8.8 Hz), 7.41 (d, 1H, J=8.8 Hz); $^{13}$C NMR (500 MHz, CDCl$_3$) δ 17.6, 34.9, 36.7, 42.5, 52.1, 110.8, 118.5, 122.3, 131.5, 137.5, 141.7, 146.7, 175.1.

Step F: Methyl 5-(N-hydroxycarboxamidinyl)-4-methylindane-2-carboxylate

To a solution of ethyl 5-cyano-4-methylindane-2-carboxylate (239 mg, 1.11 mmol, from Step E) in methanol (5 mL), hydroxylamine hydrochloride (100 mg, 1.44 mmol) and triethylamine (232 µL, 1.67 mmol) were added and heated to reflux. After 14 hr, the reaction mixture was cooled to ambient temperature and concentrated in vacuo. The residue was purified by flash chromatography (10, 30, 50% EtOAc/hexanes) on SiO$_2$ to give 85 mg of starting material and 105 mg of the title compound, as an inseparable 2:1 mixture of the amidoxime and primary amide by $^1$H NMR. For amidoxime: $^1$H NMR (500 MHz, CDCl$_3$) δ 2.33 (s, 3H), 3.17-3.39 (m, 5H), 4.77, (br, s, 2H), 7.06 (d, 1H, J=7.8 Hz), 7.21 (d, 1H, J=7.8 Hz).

Step G: Methyl 5-(5-(5-chloro-6-isopropoxypyridin-3-yl)-1,2,4-oxadiazol-3-yl)-4-methylindane-2-carboxylate To a solution of methyl 5-(N-hydroxycarboxamidinyl)-4-methylindane-2-carboxylate (36 mg, 0.145 mmol, from Step F) and 5-chloro-6-isopropoxynicotinic acid (31.2 mg, 0.145 mmol) in acetonitrile (1.0 mL), EDC-HCl was added. The resulting solution was heated to 50° C. for 3 hr and then heated to 120° C. (sealed tube). After 15 hr, the reaction mixture was cooled to ambient temperature and concentrated in vacuo. The residue was purified by flash chromatography (5, 10% EtOAc/hexanes) on SiO$_2$ to give 17 mg of the title compound as white solid: $^1$H NMR (500 MHz, CDCl$_3$) δ 1.43 (d, 6H, J=6.2 Hz), 2.55 (s, 3H), 3.25-3.34 (m, 5H), 3.75 (s, 3H), 5.48, (septet, 1H, J=6.2 Hz), 7.17 (d, 1H, J=7.8 Hz), 7.85 (d, 1H, J=7.8 Hz), 8.35 (d, 1H, J=2.0 Hz), 8.85 (d, 1H, J=2.0 Hz).

Step H: 5-(5-(5-Chloro-6-isopropoxypyridin-3-yl)-1,2,4-oxadiazol-3-yl)-4-methylindane-2-carboxylic acid Lithium hydroxide (3.3 mg, 0.0795 mmol) was added to a solution of methyl 5-(5-(5-chloro-6-isopropoxypyridin-3-yl)-1,2,4-oxadiazol-3-yl)-4-methylindane-2-carboxylate (17.0 mg, 0.0397 mmol, from Step G) in THF (1.0 mL) and H$_2$O (300 μL) and heated to 50° C. After 30 min, the reaction mixture was concentrated in vacuo and partitioned between EtOAc (5 mL) and 5% citric acid (2 mL). The layers were separated and organic layer was washed with H$_2$O (3×2 mL), brine (1×2 mL) and dried over MgSO$_4$. The mixture was filtered and the filtrated concentrated in vacuo. Purification of the residue by flash chromatography (3% CH$_3$OH/CH$_2$Cl$_2$/1% HCO$_2$H) on SiO$_2$ afforded 15.2 mg of the title compound as a white solid: $^1$H NMR (500 MHz, CD$_3$OD) δ 1.41 (d, 6H, J=6.2 Hz), 2.51 (s, 3H), 3.19-3.41 (m, 5H), 5.49 (septet, 1H, J=6.2 Hz), 7.17 (d, 1H, J=8.0 Hz), 7.78 (d, 1H, J=7.8 Hz), 8.39 (s, 1H), 8.83 (s, 1H); HPLC A: rt=4.11 min, m/z=414.3 (M+H)$^+$.

Example 115

(R/S)-5-[5-(5-Chloro-6-(morpholin-4-yl)pyridin-3-yl]-1,2,4-oxadiazol-3-yl]-4-methylindane-2-carboxylic acid The title compound was prepared using procedures analogous to those described in EXAMPLE 114 substituting 5-chloro-6-(morpholin-4-yl)nicotinic acid for 5-chloro-6-isopropoxynicotinic acid in Step G: $^1$H NMR (500 MHz, DMSO) δ 2.46 (s, 3H), 3.09-3.68 (m, 13H), 7.22 (d, 1H, J=8.0 Hz), 7.75 (d, 1H, J=7.8 Hz), 8.26 (d, 1H, J=2.3 Hz), 8.36 (s, 1H), 13.0 (br, s, 1H); HPLC A: rt=2.83 min, m/z=441.3 (M+H)$^+$.

Example 116

(5-(5-(3-Cyano-4-isopropoxyphenyl)-1,2,4-oxadiazol-3-yl)-6-methylindan-1-yl)acetic acid Step A:
3'-Chloro-3-methyl-4-methoxypropiophenone A suspension of 5.0 g (37.5 mmol) of aluminum chloride in 100 mL of CH$_2$Cl$_2$ at −2° C. was treated with 3.6 mL (37.7 mmol) of 3-chloropropionyl chloride. The resulting mixture was stirred cold for 15 min at which time it was homogeneous. The solution was treated with 4.2 mL (34 mmol) of 2-methylanisole and stirred cold for 30 min. The reaction mixture was poured onto 175 g of ice. Conc. HCl (~5 mL) was added and the mixture was extracted with 400 mL of ether. The extract was washed with 150 mL of sat'd NaHCO$_3$, dried and concentrated. Recrystallization from hexanes afforded 6.11 g of the title compound: $^1$H NMR (500 MHz, CDCl$_3$) δ 2.25 (s, 3H), 3.41 (t, J=6.5, 2H), 3.90 (s, 3H), 3.92 (t, J=6.5, 2H), 6.86 (d, J=8.5, 1H), 7.77 (d, J=1.5, 1H), 7.83 (dd, J=1.5, 8.5).

Step B: 5-Methoxy-6-methylindanone

A mixture of 5.24 g (24.6 mmol) of 3'-chloro 3-methyl-4-methoxypropiophenone (from Step A) and 50 mL of conc. H$_2$SO$_4$ was stirred at 90° C. for 20 h. The mixture was cooled and poured onto 300 g of ice. The mixture was extracted with 300 mL of EtOAc. The extract was dried and concentrated. Chromatography on a Biotage 40 M cartridge using 9:1 v/v hexanes/EtOAc, the 7:3 v/v hexanes/EtOAc as the eluant afforded 2.55 g of impure product. Recrystallization from hexanes afforded 1.94 of pure title compound: $^1$H NMR (500 MHz, CDCl$_3$) δ 2.22 (s, 3H), 2.64-2.66 (m, 2H), 3.06 (app t, J=5.5, 2H), 3.91 (s, 3H), 6.83 (s, 1H), 7.52 (s, 1H).

Step C: Ethyl (5-methoxy-6-methyl-2,3-dihydro-1H-inden-1-ylidene)acetate

To a mixture of activated Zn dust (1.46 g, 22.3 mmol) in THF (10 mL), a solution of 5-methoxy-6-methylindanone (2.62 g, 14.8 mmol, from Step B) from and ethyl bromoacetate (2.14 mL, 19.3 mmol) in THF (15 mL) were added dropwise via cannula. The reaction was heated to reflux for 45 min and cooled to ambient temperature. The reaction was quenched into 2 N HCl and extracted with EtOAc. The organic layer was washed with H$_2$O, brine, dried over MgSO$_4$, and filtered. Solvents were removed in vacuo, and the residue was purified by flash chromatography (5% EtOAc/hexanes) on SiO$_2$ to afford 2.64 g that was recrystallized from hexanes to afford 2.02 g of the title compound as a white solid: $^1$H NMR (500 MHz, CDCl$_3$) δ 1.35 (t, 3H, J=7.2 Hz), 2.24 (s, 3H), 3.04-3.06 (m, 2H), 3.29-3.31 (m, 2H), 3.88 (s, 3H), 4.23, (q, 2H, J=7.1 Hz), 6.16 (t, 1H, J=2.4 Hz), 6.79 (d, 1H, J=8.8 Hz), 7.38 (d, 1H, J=8.5 Hz).

Step D: Methyl (5-hydroxy-6-methylindan-1-yl)acetate

A solution of ethyl (5-methoxy-6-methyl-2,3-dihydro-1H-inden-1-ylidene)acetate (407 mg, 1.75 mmol, from Step C) in methanol (5 mL) was added to 10% Pd—C (41 mg) under N$_2$. To the resultant mixture, 1 atm H$_2$ was applied. After 2 hr, the mixture was filtered and concentrated in vacuo to afford 385 mg of a colorless liquid, which was dissolved in dichloromethane (3 mL) and cooled to 0° C. A 1.0 M solution of BBr$_3$ (8.22 mL) was added and the reaction mixture warmed to ambient temperature. After 2 hr, the reaction mixture was slowly added to ice-cold methanol (10 mL), and warmed to ambient temperature. The reaction mixture was concentrated in vacuo and azeotroped with methanol (2×5 mL), and partitioned between EtOAc and sat NaH$_2$PO$_4$. The organic layer was then washed with H$_2$O, brine, dried over MgSO$_4$, filtered and concentrated in vacuo. Purification by flash chromatography (5% EtOAc/hexanes) on SiO$_2$ gave 295 mg of the title compound as a white solid: $^1$H NMR (500 MHz, CDCl$_3$) δ 1.66-1.89 (m, 1H), 2.26 (s, 3H), 2.34-2.50 (m, 2H), 2.72-2.93 (m, 3H), 3.47-3.58 (m, 1H), 3.81 (s, 3H), 6.69 (s, 1H), 6.97 (s, 1H).

Step E: Methyl (5-trifluoromethylsulfonyloxy-6-methylindan-1-yl)acetate

To a solution of pyridine (0.13 mL, 1.61 mmol) in dichloromethane (1.0 mL) cooled to 0° C. trifluoromethanesulfonic anhydride (0.25 mL, 1.47 mmol) was added. The resultant mixture was stirred for 5 min and methyl (5-hydroxy-6-methylindan-1-yl)acetate (295 mg, 1.34 mmol, from Step D) was added as a solid. The reaction mixture was warmed to ambient temperature, stirred for 30 min and diluted with dichloromethane. The organic layer was washed with H$_2$O, brine and dried over MgSO$_4$. The mixture was filtered and concentrated in vacuo. Purification by flash chromatography (10% EtOAc/hexanes) on SiO$_2$ gave 405 mg of the title compound as a pale yellow liquid: $^1$H NMR (500 MHz, CDCl$_3$) δ 1.69-1.91 (m, 1H), 2.33 (s, 3H), 2.38-2.56 (m, 2H), 2.69-2.79 (m, 1H), 2.79-3.01 (m, 2H), 3.49-3.65 (m, 1H), 3.76 (s, 3H), 7.09 (s, 2H).

Step F: Methyl (5-cyano-6-methylindan-1-yl)acetate

To a solution of methyl (5-trifluoromethylsulfonyloxy-6-methylindan-1-yl)acetate (405 mg, 1.15 mmol, from Step E)

in N-methylpyrrolidinone (5 mL), Pd$_2$dba$_3$ (5.00 mg, 0.00546 mmol), dppf (7 mg, 0.0127 mmol) and Zn(CN)$_2$ were added under Ar. The reaction mixture was heated to 100° C. for 15 hr, cooled to ambient temperature and diluted with EtOAc. The organic layer was washed several times with H$_2$O, dried (brine, MgSO$_4$), filtered and concentrated in vacuo. Purification by flash chromatography (10% EtOAc/hexanes) on SiO$_2$ afforded the 176 mg of the title compound as a white solid: $^1$H NMR (500 MHz, CDCl$_3$) δ 1.71-1.90 (m, 1H), 2.36-2.60 (m, 5H), 2.71-2.82 (m, 1H), 2.82-2.96 (m, 2H), 3.55-3.68 (m, 1H), 3.76 (s, 3H), 7.11 (s, 1H), 7.47 (s, 1H).

Step G: Methyl (5-(N-hydroxycarboxamidinyl)-6-methylindan-1-yl)acetate

To a solution of methyl (5-cyano-6-methylindan-1-yl)acetate (176 mg, 0.770 mmol, from Step F) in methanol (3 mL) hydroxylamine hydrochloride (69.0 mg, 0.001 mmol) and triethylamine (160 μL, 0.0012 mmol) were added and heated to reflux. After 14 hr, the reaction mixture was cooled to ambient temperature and concentrated in vacuo. The residue was purified by flash chromatography (10, 30, 50% EtOAc/hexanes) on SiO$_2$ to give 85 mg of starting material and 105 mg of the title compound, as an inseparable 2:1 mixture of the amidoxime and primary amide by $^1$H NMR. For amidoxime: $^1$H NMR (500 MHz, CDCl$_3$) δ 1.69-1.84 (m, 1H), 2.36-2.57 (m, 5H), 2.75-3.06 (m, 3H), 3.51-3.69 (m, 1H), 3.78 (s, 3H), 4.83 (s, 2H), 7.07 (s, 1H), 7.29 (s, 1H).

Step H: Methyl (5-(5-(3-cyano-4-isopropoxyphenyl)-1,2,4-oxadiazol-3-yl)-6-methylindan-1-yl)acetate To a solution of 4-isopropoxy-3-(trifluoromethyl)benzoic acid (34.0 mg, 0.114 mmol) in acetonitrile (2.0 mL), EDC·HCl (22.0 mg, 0.114 mmol) was added. The resultant solution was stirred at ambient temperature for 30 min and methyl (5-(N-hydroxycarboxamidinyl)-6-methylindan-1-yl)acetate (30.0 mg, 0.114 mmol, from Step G). After 1 hr, the reaction mixture was concentrated in vacuo. The residue was dissolved in EtOAc and washed with H$_2$O, brine, and dried over MgSO$_4$. The mixture was filtered, concentrated in vacuo and dissolved in THF (1.5 mL). A solution of TBAF 1.0 M in THF (120 μL) was added and the resultant yellow solution was stirred at ambient temperature for 15 hr. The reaction mixture was concentrated in vacuo, dissolved in EtOAc and washed with H$_2$O, brine, and dried over MgSO$_4$. The mixture was filtered, concentrated in vacuo and purified by flash chromatography (10% EtOAc/hexanes) on SiO$_2$ to give 27.0 mg of the title compound as white solid: $^1$H NMR (500 MHz, CDCl$_3$) δ 1.51 (d, 6H, J=5.9 Hz), 1.82-1.87 (m, 1H), 2.45-2.50 (m, 1H), 2.52 (dd, 1H, J=8.9, 15.6 Hz), 2.68 (s, 3H), 2.85 (dd, 1H, J=5.7, 15.6 Hz), 2.94-3.01 (m, 2H), 3.66-3.77 (m, 1H), 3.79 (s, 3H), 4.84, (septet, 1H, J=6.2 Hz), 7.16 (d, 1H, J=9.0 Hz), 7.19 (s, 1H), 7.95 (s, 1H), 8.37 (dd, 1H, J=2.0, 8.9 Hz), 8.47 (d, 1H, J=2.3 Hz).

Step I: (5-(5-(3-Cyano-4-isopropoxyphenyl)-1,2,4-oxadiazol-3-yl)-6-methylindan-1-yl)acetic acid To a solution of methyl (5-(5-(3-cyano-4-isopropoxyphenyl)-1,2,4-oxadiazol-3-yl)-6-methyl indan-1-yl)acetate (23.0 mg, 0.053 mmol, from Step H) in THF (2 mL) and H$_2$O (0.7 mL) lithium hydroxide monohydrate (4.0 mg, 0.107 mmol) was added. The reaction mixture was heated to 50° C. for 3 hr, cooled to ambient temperature and partitioned between EtOAc and 5% citric acid. The organic layer was washed with H$_2$O, brine, dried over MgSO$_4$, filtered and concentrated in vacuo. Purification of the residue by flash chromatography (2% CH$_3$OH/CH$_2$Cl$_2$/0.2% HCO$_2$H) on SiO$_2$ afforded 28.0 mg of the title compound as a white film: $^1$H NMR (500 MHz, DMSO-d$_6$) δ 1.34 (d, 6H, J=5.9 Hz), 1.60-1.74 (m, 1H), 2.25-2.39 (m, 2H), 2.55 (s, 3H), 2.64-2.92 (m, 3H), 3.42-3.47 (m, 1H), 4.85-5.05 (m, 1H), 7.32 (s, 1H), 7.56 (d, 1H, J=9.4 Hz), 7.86 (s, 1H), 8.38 (d, 1H, J=9.6 Hz), 8.51 (s, 1H); HPLC A: rt=3.84 min, m/z=418.5 (M+H)$^+$.

Example 117

The following example was prepared using procedures analogous to those described in EXAMPLE 116 substituting the appropriate carboxylic acid for 4-isopropoxy-3-(trifluoromethyl)benzoic acid in Step H.

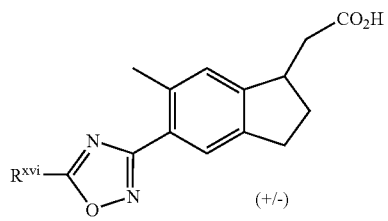

(+/-)

| EXAMPLE | Rxvi | HPLC A (min) | ESI-MS (M + H)$^+$ |
|---|---|---|---|
| 117 | Cl, i-PrO pyridine | 4.35 | 428.2 |

$^1$H NMR (500 MHz, DMSO-d$_6$) δ 1.38(d, 6H, J = 6.2 Hz), 1.69-1.73(m, 1H), 2.32-2.40(m, 2H), 2.55(s, 3H), 2.76(dd, 1H, J = 5.5, 15.8 Hz), 2.82-2.94(m, 2H), 3.42-3.47(m, 1H), 5.44(septet, 1H, J = 6.2 Hz), 7.28(s, 1H), 7.85(s, 1H), 8.54(d, 1H, J = 2.3 Hz), 8.91(d, 1H, J = 2.1 Hz).

Biological Activity

The S1P$_1$/Edg1, S1P$_3$/Edg3, S1P$_2$/Edg5, S1P$_4$/Edg6 or S1P$_5$/Edg8 activity of the compounds of the present invention can be evaluated using the following assays:

Ligand Binding to Edg/S1P Receptors Assay $^{33}$P-sphingosine-1-phosphate was synthesized enzymatically from $\gamma^{33}$P-ATP and sphingosine using a crude yeast extract with sphingosine kinase activity in a reaction mix containing 50 mM KH$_2$PO$_4$, 1 mM mercaptoethanol, 1 mM Na$_3$VO$_4$, 25 mM KF, 2 mM semicarbazide, 1 mM Na$_2$ TA, 5 mM MgCl$_2$, 50 mM sphingosine, 0.1% TritonX-114, and 1 mCi $\gamma^{33}$P-ATP (NEN; specific activity 3000 Ci/mmol). Reaction products were extracted with butanol and $^{33}$P-sphingosine-1-phosphate was purified by HPLC.

Cells expressing EDG/S1P receptors were harvested with enzyme-free dissociation solution (Specialty Media, Lavallette, N.J.). They were washed once in cold PBS and suspended in binding assay buffer consisting of 50 mM HEPES-Na, pH 7.5, 5 mM MgCl$_2$, 1 mM CaCl$_2$, and 0.5% fatty acid-free BSA. $^{33}$P-sphingosine-1-phosphate was sonicated with 0.1 nM sphingosine-1-phosphate in binding assay buffer; 100 µl of the ligand mixture was added to 100 µl cells (1×10$^6$ cells/ml) in a 96 well microtiter dish. Binding was performed for 60 min at room temperature with gentle mixing. Cells were then collected onto GF/B filter plates with a Packard Filtermate Universal Harvester. After drying the filter plates for 30 min, 40 µl of Microscint 20 was added to each well and binding was measured on a Wallac Microbeta Scintillation Counter. Non-specific binding was defined as the amount of radioactivity remaining in the presence of 0.5 µM cold sphingosine-1-phosphate.

Alternatively, ligand binding assays were performed on membranes prepared from cells expressing Edg/S1P receptors. Cells were harvested with enzyme-free dissociation solution and washed once in cold PBS. Cells were disrupted by homogenization in ice cold 20 mM HEPES pH 7.4, 10 mM EDTA using a Kinematica polytron (setting 5, for 10 seconds). Homogenates were centrifuged at 48,000×g for 15 min at 4° C. and the pellet was suspended in 20 mM HEPES pH 7.4, 0.1 mM EDTA. Following a second centrifugation, the final pellet was suspended in 20 mM HEPES pH 7.4, 100 mM NaCl, 10 mM MgCl$_2$. Ligand binding assays were performed as described above, using 0.5 to 2 µg of membrane protein.

Agonists and antagonists of Edg/S1P receptors can be identified in the $^{33}$P-sphingosine-1-phosphate binding assay. Compounds diluted in DMSO, methanol, or other solvent, were mixed with probe containing $^{33}$P-sphingosine-1-phosphate and binding assay buffer in microtiter dishes. Membranes prepared from cells expressing Edg/S1P receptors were added, and binding to $^{33}$P-sphingosine-1-phosphate was performed as described. Determination of the amount of binding in the presence of varying concentrations of compound and analysis of the data by non-linear regression software such as MRLCalc (Merck Research Laboratories) or PRISM (GraphPad Software) was used to measure the affinity of compounds for the receptor. Selectivity of compounds for Edg/S1P receptors was determined by measuring the level of $^{33}$P-sphingosine-1-phosphate binding in the presence of the compound using membranes prepared from cells transfected with each respective receptor (S1P$_1$/Edg1, S1P$_3$/Edg3, S1P$_2$/Edg5, S1P$_4$/Edg6, S1P$_5$/Edg8).

$^{35}$S-GTPγS Binding Assay

Functional coupling of S1P/Edg receptors to G proteins was measured in a $^{35}$S-GTPγS binding assay. Membranes prepared as described in the *Ligand Binding to Edg/S1P Receptors Assay* (1-10 µg of membrane protein) were incubated in a 200 µl volume containing 20 mM HEPES pH 7.4, 100 mM NaCl, 10 mM MgCl$_2$, 5 µM GDP, 0.1% fatty acid-free BSA (Sigma, catalog A8806), various concentrations of sphingosine-1-phosphate, and 125 pM $^{35}$S-GTPγS (NEN; specific activity 1250 Ci/mmol) in 96 well microtiter dishes. Binding was performed for 1 hour at room temperature with gentle mixing, and terminated by harvesting the membranes onto GF/B filter plates with a Packard Filtermate Universal Harvester. After drying the filter plates for 30 min, 40 µl of Microscint 20 was added to each well and binding was measured on a Wallac Microbeta Scintillation Counter.

Agonists and antagonists of S1P/Edg receptors can be discriminated in the $^{35}$S-GTPγS binding assay. Compounds diluted in DMSO, methanol, or other solvent, were added to microtiter dishes to provide final assay concentrations of 0.01 nM to 10 µM. Membranes prepared from cells expressing S1P/Edg receptors were added, and binding to $^{35}$S-GTPγS was performed as described. When assayed in the absence of the natural ligand or other known agonist, compounds that stimulate $^{35}$S-GTPγS binding above the endogenous level were considered agonists, while compounds that inhibit the endogenous level of $^{35}$S-GTPγS binding were considered inverse agonists. Antagonists were detected in a $^{35}$S-GTPγS binding assay in the presence of a sub-maximal level of natural ligand or known S1P/Edg receptor agonist, where the compounds reduced the level of $^{35}$S-GTPγS binding. Determination of the amount of binding in the presence of varying concentrations of compound was used to measure the potency of compounds as agonists, inverse agonists, or antagonists of S1P/Edg receptors. To evaluate agonists, percent stimulation over basal was calculated as binding in the presence of compound divided by binding in the absence of ligand, multiplied by 100. Dose response curves were plotted using a non-linear regression curve fitting program MRLCalc (Merck Research Laboratories), and EC$_{50}$ values were defined to be the concentration of agonist required to give 50% of its own maximal stimulation. Selectivity of compounds for S1P/Edg receptors was determined by measuring the level of $^{35}$S-GTPγS binding in the presence of compound using membranes prepared from cells transfected with each respective receptor.

Intracellular Calcium Flux Assay

Functional coupling of S1P/Edg receptors to G protein associated intracellular calcium mobilization was measured using FLIPR (Fluorescence Imaging Plate Reader, Molecular Devices). Cells expressing S1P/Edg receptors were harvested and washed once with assay buffer (Hanks Buffered Saline Solution (BRL) containing 20 mM HEPES, 0.1% BSA and 710 µg/ml probenicid (Sigma)). Cells were labeled in the same buffer containing 500 nM of the calcium sensitive dye Fluo-4 (Molecular Probes) for 1 hour at 37° C. and 5% CO$_2$. The cells were washed twice with buffer before plating 1.5× 10$^5$ per well (90 µl) in 96 well polylysine coated black microtiter dishes. A 96-well ligand plate was prepared by diluting sphingosine-1-phosphate or other agonists into 200 µl of assay buffer to give a concentration that was 2-fold the final test concentration. The ligand plate and the cell plate were loaded into the FLIPR instrument for analysis. Plates were equilibrated to 37° C. The assay was initiated by transferring an equal volume of ligand to the cell plate and the calcium flux was recorded over a 3 min interval. Cellular response was quantitated as area (sum) or maximal peak height (max). Agonists were evaluated in the absence of natural ligand by dilution of compounds into the appropriate solvent and transfer to the Fluo-4 labeled cells. Antagonists were evaluated by pretreating Fluo-4 labeled cells with varying concentrations of compounds for 15 min prior to the initiation of calcium flux by addition of the natural ligand or other S1P/Edg receptor agonist.

Preparation of Cells Expressing S1P/Edg Receptors

Any of a variety of procedures may be used to clone $S1P_1$/Edg1, $S1P_3$/Edg3, $S1P_2$/Edg5, $S1P_4$/Edg6 or $S1P_5$/Edg8. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence; (2) direct functional expression of the Edg/S1P cDNA following the construction of an S1P/Edg-containing cDNA library in an appropriate expression vector system; (3) screening an S1P/Edg-containing cDNA library constructed in a bacteriophage or plasmid shuttle vector with a labeled degenerate oligonucleotide probe designed from the amino acid sequence of the S1P/Edg protein; (4) screening an S1P/Edg-containing cDNA library constructed in a bacteriophage or plasmid shuttle vector with a partial cDNA encoding the S1P/Edg protein. This partial cDNA is obtained by the specific PCR amplification of S1P/Edg DNA fragments through the design of degenerate oligonucleotide primers from the amino acid sequence known for other proteins which are related to the S1P/Edg protein; (5) screening an S1P/Edg-containing cDNA library constructed in a bacteriophage or plasmid shuttle vector with a partial cDNA or oligonucleotide with homology to a mammalian S1P/Edg protein. This strategy may also involve using gene-specific oligonucleotide primers for PCR amplification of S1P/Edg cDNA; or (6) designing 5' and 3' gene specific oligonucleotides using the S1P/Edg nucleotide sequence as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding S1P/Edg.

It is readily apparent to those skilled in the art that other types of libraries, as well as libraries constructed from other cell types—or species types, may be useful for isolating an S1P/Edg-encoding DNA or an S1P/Edg homologue. Other types of libraries include, but are not limited to, cDNA libraries derived from other cells.

It is readily apparent to those skilled in the art that suitable cDNA libraries may be prepared from cells or cell lines which have S1P/Edg activity. The selection of cells or cell lines for use in preparing a cDNA library to isolate a cDNA encoding S1P/Edg may be done by first measuring cell-associated S1P/Edg activity using any known assay available for such a purpose.

Preparation of cDNA Libraries can be Performed by Standard Techniques Well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

An expression vector containing DNA encoding an S1P/Edg-like protein may be used for expression of S1P/Edg in a recombinant host cell. Such recombinant host cells can be cultured under suitable conditions to produce S1P/Edg or a biologically equivalent form. Expression vectors may include, but are not limited to, cloning vectors, modified cloning vectors, specifically designed plasmids or viruses. Commercially available mammalian expression vectors may be suitable for recombinant S1P/Edg expression.

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines.

The nucleotide sequences for the various S1P/Edg receptors are known in the art. See, for example, the following:

$S1P_1$/Edg1 Human

Hla, T. and T. Maciag 1990 An abundant transcript induced in differentiating human endothelial cells encodes a polypeptide with structural similarities to G-protein coupled receptors. J. Biol. Chem. 265:9308-9313, hereby incorporated by reference in its entirety.

WO91/15583, published on Oct. 17, 1991, hereby incorporated by reference in its entirety.

WO99/46277, published on Sep. 16, 1999, hereby incorporated by reference in its entirety.

$S1P_1$/Edg1 Mouse

WO0059529, published Oct. 12, 2000, hereby incorporated by reference in its entirety.

U.S. Pat. No. 6,323,333, granted Nov. 27, 2001, hereby incorporated by reference in its entirety.

$S1P_1$/Edg1 Rat

Lado, D. C., C. S. Browe, A. A. Gaskin, J. M. Borden, and A. J. MacLennan. 1994 Cloning of the rat edg-1 immediate-early gene: expression pattern suggests diverse functions. Gene 149: 331-336, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

$S1P_3$/Edg3 Human

An, S., T. Bleu, W. Huang, O. G. Hallmark, S. R. Coughlin, E. J. Goetzl 1997 Identification of cDNAs encoding two G protein-coupled receptors for lysosphingolipids FEBS Lett. 417:279-282, hereby incorporated by reference in its entirety.

WO 99/60019, published Nov. 25, 1999, hereby incorporated by reference in its entirety.

U.S. Pat. No. 6,130,067, granted Oct. 10, 2000, hereby incorporated by reference in its entirety.

$S1P_3$/Edg3 Mouse

WO 01/11022, published Feb. 15, 2001, hereby incorporated by reference in its entirety.

$S1P_3$/Edg3 Rat

WO 01/27137, published Apr. 19, 2001, hereby incorporated by reference in its entirety.

$S1P_2$/Edg5 Human

An, S., Y. Zheng, T. Bleu 2000 Sphingosine 1-Phosphate-induced cell proliferation, survival, and related signaling events mediated by G Protein-coupled receptors Edg3 and Edg5. J. Biol. Chem. 275: 288-296, hereby incorporated by reference in its entirety.

WO 99/35259, published Jul. 15, 1999, hereby incorporated by reference in its entirety.

WO99/54351, published Oct. 28, 1999, hereby incorporated by reference in its entirety.

WO 00/56135, published Sep. 28, 2000, hereby incorporated by reference in its entirety.

S1P$_2$/Edg5 Mouse

WO 00/60056, published Oct. 12, 2000, hereby incorporated by reference in its entirety.

S1P$_2$/Edg5 Rat

Okazaki, H., N. Ishizaka, T. Sakurai, K. Kurokawa, K. Goto, M. Kumada, Y. Takuwa 1993 Molecular cloning of a novel putative G protein-coupled receptor expressed in the cardiovascular system. Biochem. Biophys. Res. Comm. 190: 1104-1109, hereby incorporated by reference in its entirety.

MacLennan, A. J., C. S. Browe, A. A. Gaskin, D. C. Lado, G. Shaw 1994 Cloning and characterization of a putative G-protein coupled receptor potentially involved in development. Mol. Cell. Neurosci. 5: 201-209, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

S1P$_4$/Edg6 Human

Graler, M. H., G. Bernhardt, M. Lipp 1998 EDG6, a novel G-protein-coupled receptor related to receptors for bioactive lysophospholipids, is specifically expressed in lymphoid tissue. Genomics 53: 164-169, hereby incorporated by reference in its entirety.

WO 98/48016, published Oct. 29, 1998, hereby incorporated by reference in its entirety.

U.S. Pat. No. 5,912,144, granted Jun. 15, 1999, hereby incorporated by reference in its entirety.

WO 98/50549, published Nov. 12, 1998, hereby incorporated by reference in its entirety.

U.S. Pat. No. 6,060,272, granted May 9, 2000, hereby incorporated by reference in its entirety.

WO 99/35106, published Jul. 15, 1999, hereby incorporated by reference in its entirety.

WO 00/15784, published Mar. 23, 2000, hereby incorporated by reference in its entirety.

WO 00/14233, published Mar. 16, 2000, hereby incorporated by reference in its entirety.

S1P$_4$/Edg6 Mouse

WO 00/15784, published Mar. 23, 2000, hereby incorporated by reference in its entirety.

S1P$_5$/Edg8 Human

Im, D.-S., J. Clemens, T. L. Macdonald, K. R. Lynch 2001 Characterization of the human and mouse sphingosine 1-phosphate receptor, S1P$_5$ (Edg-8): Structure-Activity relationship of sphingosine 1-phosphate receptors. Biochemistry 40:14053-14060, hereby incorporated by reference in its entirety.

WO 00/11166, published Mar. 2, 2000, hereby incorporated by reference in its entirety.

WO 00/31258, published Jun. 2, 2000, hereby incorporated by reference in its entirety.

WO 01/04139, published Jan. 18, 2001, hereby incorporated by reference in its entirety.

EP 1 090 925, published Apr. 11, 2001, hereby incorporated by reference in its entirety.

S1P$_5$/Edg8 Rat

Im, D.-S., C. E. Heise, N. Ancellin, B. F. O'Dowd, G.-J. Shei, R. P. Heavens, M. R. Rigby, T. Hla, S. Mandala, G. McAllister, S. R. George, K. R. Lynch 2000 Characterization of a novel sphingosine 1-phosphate receptor, Edg-8. J. Biol. Chem. 275: 14281-14286, hereby incorporated by reference in its entirety.

WO 01/05829, published Jan. 25, 2001, hereby incorporated by reference in its entirety.

Measurement of Cardiovascular Effects

The effects of compounds of the present invention on cardiovascular parameters can be evaluated by the following procedure:

Adult male rats (approx. 350 g body weight) were instrumented with femoral arterial and venous catheters for measurement of arterial pressure and intravenous compound administration, respectively. Animals were anesthetized with Nembutal (55 mg/kg, ip). Blood pressure and heart rate were recorded on the Gould Po-Ne-Mah data acquisition system. Heart rate was derived from the arterial pulse wave. Following an acclimation period, a baseline reading was taken (approximately 20 minutes) and the data averaged. Compound was administered intravenously (either bolus injection of approximately 5 seconds or infusion of 15 minutes duration), and data were recorded every 1 minute for 60 minutes post compound administration. Data are calculated as either the peak change in heart rate or mean arterial pressure or are calculated as the area under the curve for changes in heart rate or blood pressure versus time. Data are expressed as mean ±SEM. A one-tailed Student's paired t-test is used for statistical comparison to baseline values and considered significant at $p<0.05$.

The S1P effects on the rat cardiovascular system are described in Sugiyama, A., N. N. Aye, Y. Yatomi, Y. Ozaki, K. Hashimoto 2000

Effects of Sphingosine-1-Phosphate, a naturally occurring biologically active lysophospholipid, on the rat cardiovascular system. Jpn. J. Pharmacol. 82: 338-342, hereby incorporated by reference in its entirety.

Measurement of Mouse Acute Toxicity

A single mouse is dosed intravenously (tail vein) with 0.1 ml of test compound dissolved in a non-toxic vehicle and is observed for signs of toxicity. Severe signs may include death, seizure, paralysis or unconciousness. Milder signs are also noted and may include ataxia, labored breathing, ruffling or reduced activity relative to normal. Upon noting signs, the dosing solution is diluted in the same vehicle. The diluted dose is administered in the same fashion to a second mouse and is likewise observed for signs. The process is repeated until a dose is reached that produces no signs. This is considered the estimated no-effect level. An additional mouse is dosed at this level to confirm the absence of signs.

Assessment of Lymphopenia

Compounds are administered as described in Measurement of Mouse Acute Toxicity and lymphopenia is assessed in mice at three hours post dose as follows. After rendering a mouse unconscious by $CO_2$ to effect, the chest is opened, 0.5 ml of blood is withdrawn via direct cardiac puncture, blood is immediately stabilized with EDTA and hematology is evaluated using a clinical hematology autoanalyzer calibrated for performing murine differential counts (H2000, CARESIDE, Culver City Calif.). Reduction in lymphocytes by test treatment is established by comparison of hematological parameters of three mice versus three vehicle treated mice. The dose used for this evaluation is determined by tolerability using a modification of the dilution method above. For this purpose, no-effect is desirable, mild effects are acceptable and severely toxic doses are serially diluted to levels that produce only mild effects.

In Vitro Activity of Examples

The examples disclosed herein have utility as immunoregulatory agents as demonstrated by their activity as potent and selective agonists of the S1P$_1$/Edg1 receptor over the S1PR$_3$/Edg3 receptor as measured in the assays described above. In particular, the examples disclosed herein possess a selectivity for the S1P$_1$/Edg1 receptor over the S1PR$_3$/Edg3 receptor of more than 100 fold as measured by the ratio of EC$_{50}$ for the S1P$_1$/Edg1 receptor to the EC$_{50}$ for the S1P$_3$/Edg3 receptor as evaluated in the $^{35}$S-GTPγS binding assay described above and possess an EC$_{50}$ for binding to the S1P$_1$/Edg1 receptor of less than 50 nM as evaluated by the $^{35}$S-GTPγS binding assay described above.

An alternate method for making EXAMPLE 110 is described below:

Alternate Method

Example 110

(R)-(5-(5-(5-Chloro-6-isopropoxypyridin-3-yl))-1,2,4-oxadiazol-3-yl)-4-methyl-indan-1-yl)acetic acid Step A: Ethyl 3-(3-methoxy-2-methylphenyl)-3-oxopropanoate Thionyl chloride (118 mL) was added to 3-methoxy-2-methyl benzoic acid (98.8 g, 595 mmol) and heated to reflux. After 2 hr, the reaction mixture was cooled to ambient temperature and concentrated in vacuo. The residue was azeotroped with toluene (2×300 mL) and the resultant solid set aside. A suspension of ethyl malonate potassium salt (208 g, 1.22 mol) in acetonitrile (1.50 L) cooled to 5° C., triethylamine (166 mL, 1.49 mol) were added followed by MgCl$_2$ (142 g, 1.49 mol). The cooling bath was removed and the mixture stirred for 3.5 hr at ambient temperature. The mixture was re-cooled to 5° C. and a solution of the aforementioned acid chloride in acetonitrile (100 mL) was added over 10 min. The mixture was warmed to ambient temperature, stirred for 15 hr, concentrated in vacuo and azeotroped with toluene (2×mL). The residue was suspended in EtOAc (750 mL) and toluene (750 mL), cooled in an ice bath and 4 N HCl (750 mL) was added slowly. The cooling bath was removed and the biphasic mixture was stirred vigorously for 30 min. The layers were separated, and the organic layer was washed with sat NaHCO$_3$ (2×1.0 L) and dried over MgSO$_4$. The mixture was filtered, concentrated in vacuo, and purified by flash chromatography (5, 10% EtOAc/heptane) on SiO$_2$ to afford 138 g of the title compound as a pale yellow liquid: $^1$H NMR (500 MHz, CDCl$_3$) indicated a mixture of keto ester and enol in a 2.5 1 ratio. For keto ester: δ 1.23 (t, 3H, J=7.2 Hz), 2.34 (s, 3H), 3.85 (s, 3H), 3.89 (s, 2H), 4.17 (q, 2H, J=7.1 Hz), 6.97 (d, 1H, J=7.8 Hz), 7.14 (d, 1H, J=8.7 Hz), 7.22 (d, 1H, J=7.9 Hz).

Step B: Ethyl 3-(3-methoxy-2-methylphenyl)propanoate

To a solution ethyl 3-(3-methoxy-2-methylphenyl)-3-oxopropanoate (137.2 g, 595 mmol, from Step A) in ethyl alcohol (924 mL), 10% Pd—C (13.7 g) was added and 3 atm of hydrogen were applied. The mixture was heated to 60° C. for 20 hr, cooled to ambient temperature and filtered through Celite®. The filtrate was concentrated in vacuo and the residue purified by flash chromatography (2% EtOAc/hexanes) on SiO$_2$ to afford 110.8 g of the title compound as a pale yellow liquid: $^1$H NMR (500 MHZ, CDCl$_3$) δ 1.25 (t, 3H, J=7.1 Hz), 2.19 (s, 3H), 2.55 (t, 2H, J=8.0 Hz), 2.95 (t, 2H, J=8.0 Hz), 3.82 (s, 3H), 4.14 (q, 2H, J=7.1 Hz), 6.73 (d, 1H, J=8.2 Hz), 6.78 (d, 1H, J=7.6 Hz), 7.10 (d, 1H, J=7.9 Hz).

Step C: 3-Methoxy-2-methylphenylpropionic acid

A solution of ethyl 3-(3-methoxy-2-methylphenyl)propanoate (36.3 g, 165 mmol, from Step B) in abs. EtOH (200 mL) and 5 N NaOH (99 mL) was heated to reflux for 30 min and cooled to ambient temperature. The reaction mixture was concentrated in vacuo, and the resultant solid mass was dissolved in H$_2$O (100 mL) and cooled in an ice bath. Concentrated HCl (50 mL) was then added dropwise. At pH=4, an additional 300 mL H$_2$O was added to facilitate stirring. The acidified mixture was stirred for 30 min, filtered, and the solids washed with H$_2$O (2×100 mL) and Et$_2$O (2×100 mL). After 3 hr, the solids were dried over P$_2$O$_5$ in vacuo overnight to give 29.3 g of the title compound as a white solid: $^1$H NMR (500 MHz, CD$_3$OD) δ 2.15 (s, 3H), 2.50 (t, 2H, J=7.9 Hz), 2.90 (t, 2H, J=7.9 Hz), 3.78 (s, 3H), 6.75 (d, 2H, J=8.0 Hz), 7.05 (t, 1H, J=8.0 Hz).

Step D: 5-Methoxy-4-methylindan-1-one

SOCl$_2$ (144 mL) was added to 3-methoxy-2-methylphenylpropionic acid (from Step C) and the mixture was heated to reflux. After 2 hr, the reaction mixture was concentrated in vacuo and azeotroped with dichloroethane (2×50 mL). The resultant acid chloride was dissolved in dichloromethane (250 mL), cooled in an ice bath and a 1.0 M solution of SnCl$_4$ in dichloromethane (155 mL, 155 mmol) was added dropwise. The purple reaction mixture was warmed to ambient temperature for 1 hr and quenched into 300 mL H$_2$O/300 g crushed ice. The layers were separated and the organic layer was washed with 2N HCl (2×150 mL) H$_2$O (2×150 mL) brine (2×150 mL), dried over MgSO$_4$, filtered and concentrated in vacuo. Purification of the residue by flash chromatography (10, 30% EtOAc/heptane), on SiO$_2$ gave an amber solid that was triturated with hexanes (100 mL) at 0° C. to give 16.6 g of the title compound as an off-white powder. The hexanes filtrate was purified further purified by flash chromatography as above to afford an additional 1.00 g of an off-white solid: $^1$H NMR (500 MHz, CDCl$_3$) δ 2.18 (s, 3H), 2.67-2.69 (m, 2H), 2.98-3.01 (m, 2H), 3.92 (s, 3H), 6.89 (d, 1H, J=8.5 Hz), 7.63 (d, 1H, J=8.5 Hz).

Step E: Ethyl (5-methoxy-4-methyl-2,3-dihydro-1H-1-inden-1-ylidene)acetate

To a mixture of activated Zn dust (556 mg, 8.51 mmol) in THF (2.5 mL), a solution of 5-methoxy-4-methylindan-1-one (1.00 g, 5.68 mmol, rom Step D) and ethyl bromoacetate (819 μL, 7.38 mmol) in THF (5 mL) were added dropwise via cannula. The reaction was initiated by immersing in a 60° C. oil bath for 1 min. After 10 min, the reaction was quenched into 2 N HCl (10 mL) and extracted with EtOAc (10 mL). The organic layer was washed with H$_2$O (1×10 mL), brine (1×10 mL), dried over MgSO$_4$, and filtered. Solvents were removed in vacuo, and the residue was purified by flash chromatography (2, 5% EtOAc/hexanes) on SiO$_2$ to afford 1.26 g that was recrystallized from hexanes to afford 1.01 g of the title compound as a white solid: $^1$H NMR (500 MHz, CDCl$_3$) δ 1.32 (t, 3H, J=7.1 Hz), 2.15 (s, 3H), 2.94-2.97 (m, 2H), 3.29-3.32 (m, 2H), 3.87 (s, 3H), 4.20, (q, 2H, J=7.1 Hz), 6.17 (t, 1H, J=2.5 Hz), 6.79 (d, 1H, J=8.8 Hz), 7.43 (d, 1H, J=8.5 Hz).

Step F: (2E-)-(5-Methoxy-4-methyl-2,3-dihydro-1H-inden-1-ylidene)acetic acid To solution of ethyl (5-methoxy-4-methyl-2,3-dihydro-1H-1-inden-1-ylidene)acetate (8.28 g, 33.6 mmol, from Step E) in 3:2:1 THF:CH$_3$OH:H$_2$O (83 mL) 5.0 N NaOH (14.8 mL, 74.0) was added and the resultant solution was heated to reflux. After 2 hr, the reaction mixture was concentrated in vacuo, dissolved in H$_2$O (150 mL) and cooled to 0° C. The aqueous layer was made acidic (pH<2) by the addition of concentrated HCl and the resultant precipitate was filtered, washed with H$_2$O (150 mL) and dried over P$_2$O$_5$ in vacuo. A total of 6.75 g of the title compound was isolated as a white solid: $^1$H NMR (500 MHz, CD$_3$OD) δ 2.18 (s, 3H), 3.22-3.29 (m, 2H), 3.50-3.52 (m, 2H), 3.80 (s, 3H), 6.26 (s, 1H), 6.82 (d, 1H, J=8.2 Hz), 7.12 (d, 1H, J=8.3 Hz).

Step G: Methyl (R)-(5-methoxy-4-methyl-indan-1-yl)acetate

To a solution of (2E-)-(5-methoxy-4-methyl-2,3-dihydro-1H-inden-1-ylidene)acetic acid (1.0 g, 4.58 mmol, from Step F) in methanol (10 mL) was added [(S)-(−)-2,2'bis(diphenylphosphino)-1,1'-binaphthyl]ruthenium (II) (36.0 mg, 0.0458 mmol) and triethylamine (64 μL, 0.458 mmol). The resultant mixture was subjected to 3 atm H$_2$ and was shaken at ambient temperature for 24 hr. The reaction mixture was filtered through Celite®, and concentrated in vacuo. The residue was dissolved in THF (5 mL) and methanol (5 mL) and treated with TMSCHN$_2$ (6.51 mL, 13.0 mmol) at ambient temperature. After 1 hr, the reaction mixture was concentrated in vacuo and purified by flash chromatography (3% EtOAc/hexanes) on SiO$_2$ to give 828 mg of the title compound as a colorless liquid: $^1$H NMR (500 MHz, CDCl$_3$) δ 1.71-1.78 (m, 1H), 2.15 (s, 3H), 2.37-2.46 (m, 2H), 2.73-2.81 (m, 2H), 2.86-2.92 (m, 1H), 3.53-3.59 (m, 1H), 3.73 (s, 3H), 3.82 (s, 3H), 6.69 (d, 1H, J=8.2 Hz), 6.96 (d, 1H, J=8.2 Hz).

Step H: Methyl (R)-(5-hydroxy-4-methyl-indan-1-yl)acetate

A 1.0 M solution of boron tribromide in dichloromethane (16.2 mL, 16.2 mmol) was added to an ice-cold solution methyl (R)-(5-methoxy-4-methyl-indan-1-yl)acetate (1.52 g, 6.49 mmol, from Step F) in dichloromethane (5 mL). The cooling bath was removed and the reaction mixture stirred at ambient temperature. After 1 hr, the reaction mixture was slowly transferred to an ice-old solution of methanol (50 mL). Methanol was removed in vacuo, and the residue was partitioned between EtOAc and sat. NaH$_2$PO$_4$. The organic layer was washed with H$_2$O, brine, and dried over MgSO$_4$. The mixture was filtered, concentrated in vacuo and purified by flash chromatography (5, 10% EtOAc/hexanes) on SiO$_2$ to afford 1.22 g of the title compound as a white solid: $^1$H NMR (500 MHz, CDCl$_3$) δ 1.71-1.78 (m, 1H), 2.16 (s, 3H), 2.35-2.44 (m, 2H), 2.71-2.79 (m, 2H), 2.86-2.90 (m, 1H), 3.54 (p, 1H, J=7.3 Hz), 3.72 (s, 3H), 4.83 (s, 1H), 6.61 (d, 1H, J=8.0 Hz), 6.85 (d, 1H, J=8.0 Hz).

Step I: Methyl (R)-(5-Trifluoromethylsulfonyloxy-4-methyl-indan-1-yl)acetate To a solution of pyridine (440 μL, 5.45 mmol) in dichloromethane (5.0 mL) cooled to 0° C. trifluoromethanesulfonic anhydride (840 μL, 4.99 mmol) was added. The resultant mixture was stirred for 5 min, and methyl (R)-(5-hydroxy-4-methyl-indan-1-yl)acetate (1.00 g, 1.34 mmol, from Step H) was added as a solid. The reaction mixture was warmed to ambient temperature, stirred for 1 hr and diluted with dichloromethane. The organic layer was washed with H$_2$O, brine and dried over MgSO$_4$. The mixture was filtered and concentrated in vacuo. Purification by flash chromatography (10% EtOAc/hexanes) on SiO$_2$ gave 1.46 g of the title compound as a pale yellow liquid: $^1$H NMR (500 MHz, CDCl$_3$) δ 1.69-1.91 (m, 1H), 2.33 (s, 3H), 2.38-2.56 (m, 2H), 2.69-2.79 (m, 1H), 2.79-3.01 (m, 2H), 3.49-3.65 (m, 1H), 3.76 (s, 3H), 7.09 (s, 2H).

Step J: Methyl (R)-(5-Cyano-4-methyl-indan-1-yl)acetate

To a solution of methyl (R)-(5-Trifluoromethylsulfonyloxy-4-methyl-indan-1-yl)acetate (1.00 g, 2.84 mmol, from Step I) in N-methyl pyrrolidinone (13 mL) under argon, zinc cyanide (267 mg, 2.27 mmol), Pd$_2$dba$_3$ (13.0 mg, 14.2 μmol) and dppf (19.0 mg, 34.1 μmol) and the reaction mixture was heated to 100° C. After 16 hr, the reaction mixture was concentrated in vacuo and partitioned between EtOAc and H$_2$O. The layers were separated and the organic layer was washed with H$_2$O, brine and dried over MgSO$_4$. The mixture was filtered, the filtrate concentrated in vacuo, and the residue purified by flash chromatography (5, 10% EtOAc/hexanes) on SiO$_2$ to give 553 mg of the title compound as a white solid: $^1$H NMR (500 MHz, CDCl$_3$) δ 1.76-1.80 (m, 1H), 2.41-2.50 (m, 5H), 2.73 (dd, 1H, J=5.8, 15.8 Hz), 2.78-2.84 (m, 1H), 2.91 (ddd, 1H, J=4.8, 8.7, 13.5 Hz) 3.61-3.67 (m, 1H), 3.71 (s, 3H), 7.07 (d, 1H, J=7.8 Hz), 7.43 (d, 1H, J=7.7 Hz).

Step K: Methyl (R)-(5-(N-hydroxycarboxamidinyl)-4-methyl-indan-1-yl)acetate

To a solution of methyl (R)-(5-Cyano-4-methyl-indan-1-yl)acetate (724 mg, 3.16 mmol, from Step J) in methanol (10 mL), hydroxylamine hydrochloride (285 mg, 4.11 mmol) and triethylamine (660 μL, 474 mmol) were added and heated to reflux. After 14 hr, the reaction mixture was cooled to ambient temperature and concentrated in vacuo. The residue was purified by flash chromatography (10, 30, 50% EtOAc/hexanes) on SiO$_2$ to give 318 mg of starting material and 352 mg of the title compound, as an inseparable 2:1 mixture of the amidoxime and primary amide by $^1$H NMR. For amidoxime: $^1$H NMR (500 MHz, CDCl$_3$) δ 1.72-1.84 (m, 1H), 2.37 (s, 3H), 2.43-2.51 (m, 2H), 2.76-2.87 (m, 2H), 2.90-2.96 (m, 1H), 3.64 (p, 1H, J=7.2 Hz), 3.76 (s, 3H), 4.85, (br, s, 2H), 7.05 (d, 1H, J=7.5 Hz), 7.31 (d, 1H, J=8.0 Hz).

Step L: Methyl (R)-(5-(5-(5-chloro-6-isopropoxypyridin-3-yl))-1,2,4-oxadiazol-3-yl)-4-methyl-indan-1-yl)acetate To a solution of 5-chloro-6-isopropoxynicotinic acid (289 mg, 1.34 mmol) in acetonitrile (5.0 mL), EDC-HCl (257 mg, 1.34 mmol) was added. The resultant solution was stirred at ambient temperature for 30 min and methyl (R)-(5-(N-hydroxycarboxamidinyl)-4-methyl-indan-1-yl)acetate (352 mg, from Step K) was added. After 1 hr, the reaction mixture was concentrated in vacuo. The residue was dissolved in EtOAc and washed with H$_2$O, brine, and dried over MgSO$_4$. The mixture was filtered, concentrated in vacuo and dissolved in THF (1.5 mL). A solution of TBAF 1.0 M in THF (1.34 mL) was added and the resultant yellow solution was stirred at ambient temperature for 1.5 hr. The reaction mixture was concentrated in vacuo, dissolved in EtOAc and washed with H$_2$O, brine, and dried over MgSO$_4$. The mixture was filtered, concentrated in vacuo and purified by flash chromatography (10% EtOAc/hexanes) on SiO$_2$ to give 277 mg of the title compound as white solid. This material was recrystallized from hexanes to give 176 mg that was >99% ee: $^1$H NMR (500 MHz, CDCl$_3$) δ 1.44 (d, 6H, J=6.2 Hz), 1.78-1.85 (m, 1H), 2.43-2.46 (m, 1H), 2.49 (dd, 1H, J=9.3, 15.6 Hz), 2.56 (s, 3H), 2.81 (dd, 1H, J=5.5, 15.5 Hz), 2.86-2.93 (m, 1H), 3.73 (s, 3H), 5.49, (septet, 1H, J=6.2 Hz), 7.14 (d, 1H, J=7.8 Hz), 7.85 (d, 1H, J=7.8 Hz), 8.38 (d, 1H, J=2.3 Hz), 8.85 (d, 1H, J=2.3 Hz).

Step M: (R)-(5-(5-(5-Chloro-6-isopropoxypyridin-3-yl))-1,2,4-oxadiazol-3-yl)-4-methyl-indan-1-yl)acetic acid To a solution of methyl (R)-(5-(5-(5-chloro-6-isopropoxypyridin-3-yl))-1,2,4-oxadiazol-3-yl)-4-methyl-indan-1-yl)acetate (176 mg, 0.398 mmol, from Step L) in THF (3 mL) and H$_2$O (1 mL) lithium hydroxide monohydrate (167 mg, 3.98 mmol) was added. The reaction mixture was heated to 50° C. for 3 hr, cooled to ambient temperature and partitioned between EtOAc and 5% citric acid. The organic layer was washed with H$_2$O, brine, dried over MgSO$_4$, filtered and concentrated in vacuo. Purification of the residue by flash chromatography (2% CH$_3$OH/CH$_2$Cl$_2$/0.2% HCO$_2$H) on SiO$_2$ afforded 154 mg of the title compound as a white solid: $^1$H NMR (500 MHz, DMSO-d$_6$) δ 1.37 (d, 6H, J=6.2 Hz), 1.69-1.73 (m, 1H), 2.31-2.38 (m, 2H), 2.49 (s, 3H), 2.72 (dd, 1H, J=5.6, 15.6 Hz), 2.81-2.85 (m, 1H), 2.92-2.96 (m, 1H), 3.50-3.52 (m, 1H), 5.43 (septet, 1H, J=6.1 Hz), 7.30 (d, 1H, J=8.0 Hz), 7.77 (d, 1H, J=7.8 Hz), 8.48 (s, 1H), 8.89 (s, 1H); HPLC A: rt=4.32 min, m/z=428.2 (M+H)$^+$.

An embodiment of the invention encompasses a compound represented by Formula A:

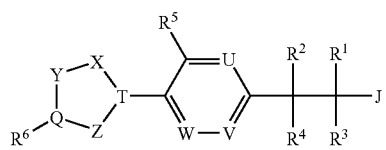

A or a pharmaceutically acceptable salt thereof, wherein:
$R^1$, $R^2$, $R^3$ and $R^4$ are each independently selected from the group consisting of: —H, —F, —Cl, —Br, —I, —CN, —OH, $C_{1-6}$alkyl, $C_{2-6}$alkenyl, $C_{2-6}$alkynyl and $C_{1-5}$alkoxy,
wherein said $C_{1-6}$alkyl, $C_{2-6}$alkenyl, $C_{2-6}$alkynyl and $C_{1-5}$alkoxy are each optionally substituted with one to three substituents independently selected from the group consisting of: —F, —Cl, —Br, —I, —OH, $C_{1-8}$alkoxy and —CO$_2$H,
and any two of $R^1$, $R^2$, $R^3$ and $R^4$ may be joined together with the atoms to which they are attached to form a saturated monocyclic ring of 3 to 8 atoms optionally containing 1 or 2 oxygen atoms;
$R^5$ is selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy,
wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;
$R^6$ is selected from the group consisting of: phenyl, pyridinyl, pyrimidinyl, pyrazinyl, pyridizinyl and thienyl, each optionally substituted with one to three substituents independently selected from the group consisting of: —F, —Cl, —Br, —I, —CN, —OH, —NR$^7$R$^8$, —NO$_2$, phenyl, thienyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{2-4}$acyloxy,
wherein said phenyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I, —OH and $C_{1-8}$alkoxy, and
$R^6$ may be substituted on two adjacent atoms to form a fused partially aromatic bicyclic ring of 9 to 12 atoms optionally containing one or two oxygen or sulfur groups, or both, and optionally substituted with one to three substituents independently selected from the group consisting of: —F, —Cl, —Br, —I, —CN, —OH, and $C_{1-4}$alkyl;
$R^7$ and $R^8$ are independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy, and
$R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy;
U, V and W are independently selected from the group consisting of: —C(R$^9$)— and —N—;
each R$^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy,
wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;
For U or V, R$^9$ and R$^1$ or R$^9$ and R$^2$ may be joined together with the atoms to which they are attached to form a 4 to 8 membered ring, optionally containing 1 or 2 oxygen, sulfur or N(R$^{10}$) atoms, thus forming a fused partially aromatic bicyclic ring system of 8 to 12 atoms with the 6-membered aromatic ring to which R$^9$ is attached;
X, Y and Z are independently selected from —C(R$^{11}$)=, —O—, —N=, —N(R$^{12}$)— and —S— such that the resulting ring together with Q and T form an aromatic heterocycle;
Q and T are independently selected from

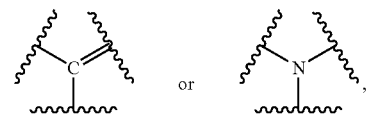

with the proviso that both Q and T are not

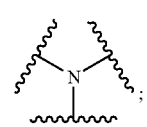

$R^{10}$, $R^{11}$ and $R^{12}$ are each independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy;

J is selected from the group consisting of: —$CO_2H$, —$PO_3H_2$, —$PO_2H_2$, —$SO_3H$, —$CONHSO_2R^{13}$, —$PO(R^{13})OH$,

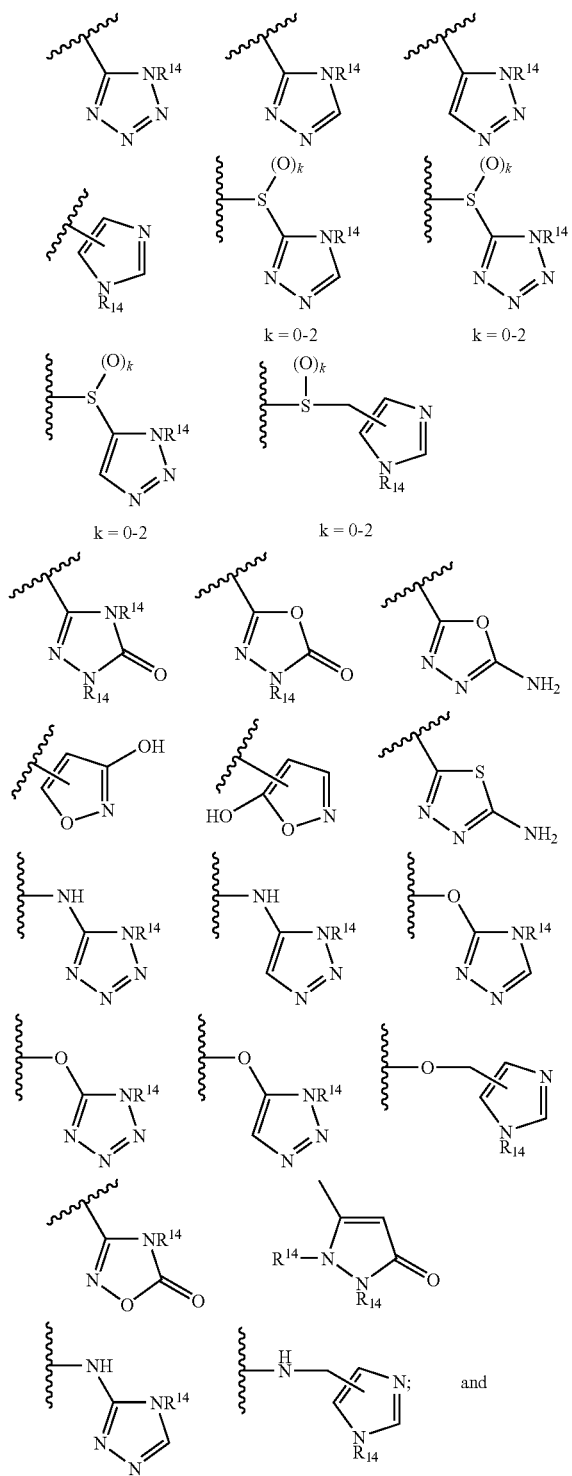

$R^{13}$ is selected from the group consisting of: $C_1$-$C_4$ alkyl, phenyl, —$CH_2OH$ and $CH(OH)$-phenyl; and each $R^{14}$ is independently selected from the group consisting of: —H and —$CH_3$.

Another embodiment of the invention encompasses a compound of Formula If:

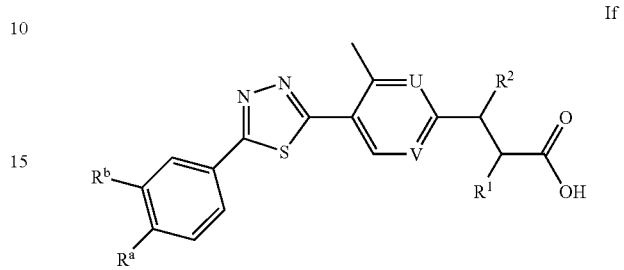

If or a pharmaceutically acceptable salt thereof, wherein:
$R^1$ and $R^2$ are —H, or $R^1$ and $R^2$ may be joined together with the atoms to which they are attached to form cyclopropyl;
U and V are —$C(R^9)$—;
each $R^9$ is —H, or
For U or V, $R^9$ and $R^1$ or $R^9$ and $R^2$ may be joined together with the atoms to which they are attached to form a 5 membered ring, thus forming a fused partially aromatic bicyclic ring system of 9 atoms with the phenyl ring to which $R^9$ is attached;
$R^a$ is selected from the group consisting of: $C_{1-4}$alkoxy and $C_{3-6}$cycloalkoxy, said $C_{1-4}$alkoxy and $C_{3-6}$cycloalkoxy groups optionally substituted from one up to the maximum number of substitutable positions with fluoro; and
$R^b$ is selected from the group consisting of: $C_{1-4}$alkyl and $C_{2-4}$alkenyl.

Another embodiment of the invention encompasses a compound of Formula Ig:

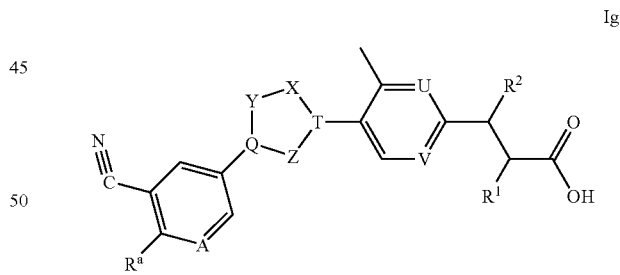

Ig or a pharmaceutically acceptable salt thereof, wherein:
A is selected from —N— or —CH—;
the group

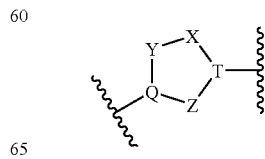

is selected from the group consisting of:

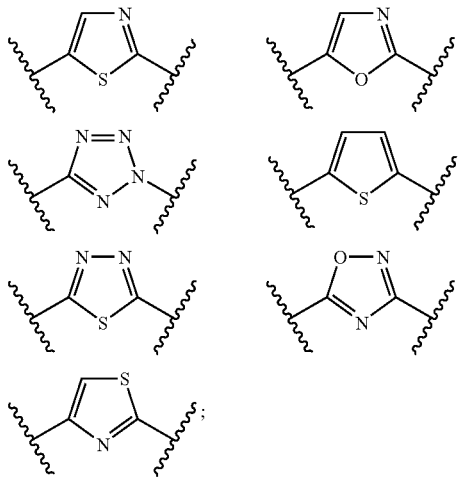

$R^1$ and $R^2$ are —H, or $R^1$ and $R^2$ may be joined together with the atoms to which they are attached to form cyclopropyl;

U and V are —C($R^9$)—;

each $R^9$ is —H, or

For U or V, $R^9$ and $R^1$ or $R^9$ and $R^2$ may be joined together with the atoms to which they are attached to form a 5 membered ring, thus forming a fused partially aromatic bicyclic ring system of 9 atoms with the phenyl ring to which $R^9$ is attached;

$R^a$ is selected from the group consisting of: thienyl, $NR^7R^8$, $C_{1-4}$alkyl, $C_{3-6}$cycloalkyl, $C_{1-4}$alkoxy and $C_{3-6}$cycloalkoxy, wherein said $C_{1-4}$alkyl, $C_{3-6}$cycloalkyl, $C_{1-4}$alkoxy and $C_{3-6}$cycloalkoxy are each optionally substituted from one up to the maximum number of substitutable positions with fluoro;

$R^7$ and $R^8$ are independently selected from the group consisting of: —H and $C_{1-6}$alkyl, optionally substituted with one to three fluoro groups, and $R^7$ and $R^8$ may be joined together with the nitrogen atom to which they are attached to form a saturated monocyclic ring of 3 to 8 atoms, said ring is optionally substituted with one to three fluoro groups.

Another embodiment of the invention encompasses a compound according to of Formula Ih:

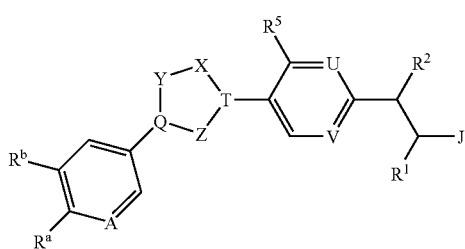

Ih or a pharmaceutically acceptable salt thereof, wherein:

A is selected from —N— or —CH—;

the group

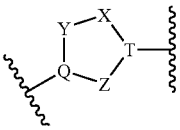

is selected from the group consisting of:

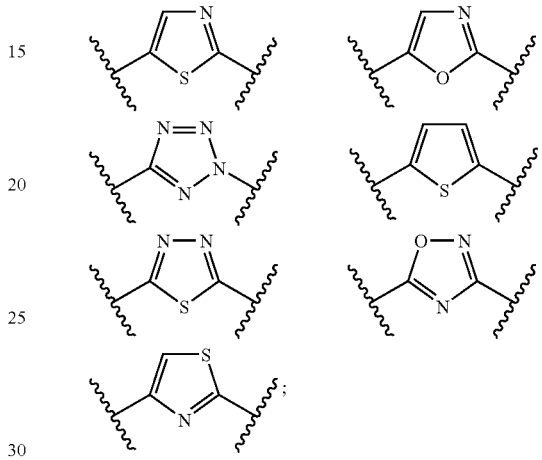

$R^1$ and $R^2$ are —H, or $R^1$ and $R^2$ may be joined together with the atoms to which they are attached to form cyclopropyl;

$R^5$ is —H or —$CH_3$;

U and V are —C($R^9$)—;

each $R^9$ is —H, or

For U or V, $R^9$ and $R^1$ or $R^9$ and $R^2$ may be joined together with the atoms to which they are attached to form a 5 membered ring, thus forming a fused partially aromatic bicyclic ring system of 9 atoms with the phenyl ring to which $R^9$ is attached;

$R^a$ is selected from the group consisting of: —F, $NR^7R^8$, $C_{1-4}$alkyl, $C_{3-6}$cycloalkyl, $C_{1-4}$alkoxy and $C_{3-6}$cycloalkoxy, wherein said $C_{1-4}$alkyl, $C_{3-6}$cycloalkyl, $C_{1-4}$alkoxy and $C_{3-6}$cycloalkoxy are each optionally substituted from one up to the maximum number of substitutable positions with fluoro;

$R^7$ and $R^8$ are independently selected from the group consisting of: —H and $C_{1-6}$alkyl, optionally substituted with one to three fluoro groups, and $R^7$ and $R^8$ may be joined together with the nitrogen atom to which they are attached to form a saturated monocyclic ring of 3 to 8 atoms, said ring is optionally substituted with one to three fluoro groups;

$R^b$ is Cl or I;

J is selected from the group consisting of: —$CO_2H$, —$PO_3H_2$, —$PO_2H_2$, —$SO_3H$, —$CONHSO_2R^{13}$, —PO($R^{13}$)OH,

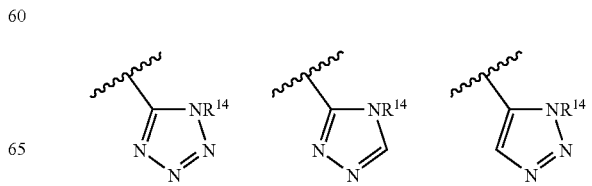

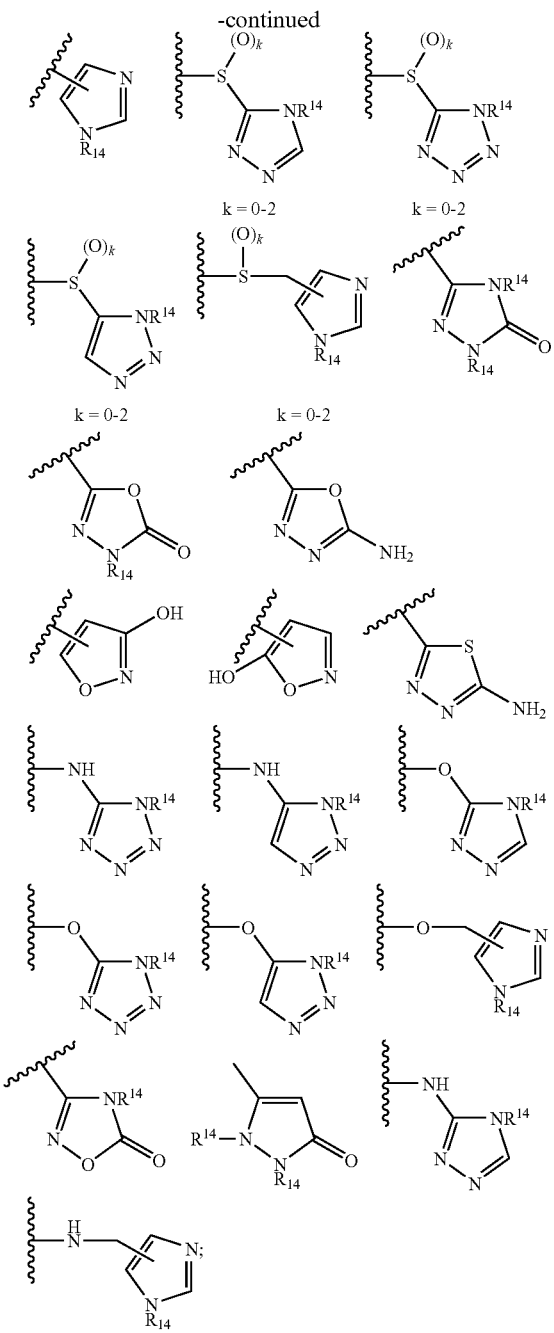

$R^{13}$ is selected from the group consisting of: $C_1$-$C_4$ alkyl, phenyl, —CH$_2$OH and CH(OH)-phenyl; and
each $R^{14}$ is independently selected from the group consisting of: —H and —CH$_3$.

Within this embodiment is encompassed a compound of Formula Ih, wherein:

For U, $R^9$ and $R^1$ are joined together with the atoms to which they are attached to form a 5 membered ring, thus forming a fused partially aromatic bicyclic ring system of 9 atoms with the phenyl ring to which $R^9$ is attached;

$R^5$ is CH$_3$;

$R^b$ is Cl; and

J is selected from the group consisting of: —CO$_2$H, wherein each $R^{14}$ is independently selected from the group consisting of: —H and —CH$_3$.

Additional examples of the invention are as follows:

Example 118

3-(4-(5-(3-Cyano-4-(2-thienyl)phenyl)-1,2,4-thiadiazol-3-yl)-3-methylphenyl)propanoic acid Step A: (3-Cyano-4-(2-thienyl)phenyl boronic acid, pinacol ester The title compound was prepared from 5-bromo-2-iodobenzonitrile using procedures analogous to those described in EXAMPLE 104, Steps E and F substituting 2-thienylzinc bromide for isobutylzinc bromide in Step E: ESI-MS (m/z) 312.3; HPLC A: 4.13 min.

Step B: tert-Butyl 3-(4-(5-(3-Cyano-4-(2-thienyl)phenyl)-1,2,4-thiadiazol-3-yl)-3-methylphenyl)propanoate The title compound was prepared using a procedure analogous to that described in EXAMPLE 104, Step G substituting (3-cyano-4-(2-thienyl)phenyl)boronic acid, pinacol ester (from Step A) for (3-cyano-4-(2-methylphenyl)phenyl)boronic acid, pinacol ester: ESI-MS (m/z) 488.2; HPLC A: 4.47 min.

Step C: 2-(4-(5-(3-Cyano-4-(2-thienyl)phenyl-1,3,4-thiadiazol-3-yl)-5-methylphenyl)propionic acid The title compound was prepared from tert-butyl 3-(4-(5-(3-cyano-4-(2-thienyl)phenyl)-1,2,4-thiadiazol-3-yl)-3-methylphenyl)propanoate (from Step B) using a procedure analogous to that described in EXAMPLE 104, Step H. ESI-MS (m/z) 432.2; HPLC A: 3.69 min.

Example 119

3-(4-(5-(3-Ethyl-4-ethoxyphenyl)-1,2,4-thiadiazol-3-yl)-3-methylphenyl)propanoic acid Step A: 5-Bromo-2-ethoxystyrene Methyltriphenylphosphonium bromide (1.09 g, 3.05 mmol) was added to a solution of potassium t-butoxide (0.5 g, 2.29 mmol) in THF (8 mL). The resulting reaction mixture turned bright yellow and was stirred for 40 min after which, it was cooled to −78° C. 5-bromo-2-ethoxybenzaldehyde was dissolved in THF (2 mL) and added to the reaction which was stirred for 2 h. The reaction was warmed to rt, diluted with ether and filtered through celite. The filtrate was washed with brine, dried over magnesium sulfate, filtered and concentrated in vacuo. Silica gel chromatography eluting with 15% EtOAc/hexanes yielded 320 mg of the desired product: $^1$H NMR (500 MHZ, CDCl$_3$) δ 7.58 (d, J=2.5 Hz, 1H), 7.31 (dd, J=6.4, 2.4 Hz, 1H), 6.96-7.04 (m, 1H), 6.74 (d, J=8.7 Hz, 1H), 5.77 (d, 1H), 5.32 (d, 1H), 4.03-4.07 (m, 2H), 1.45 (t, J=7.0 Hz, 3H).

Step B: (4-Ethoxy-3-vinylphenyl)boronic acid, pinacol ester

The title compound was prepared using a procedure analogous to that described in EXAMPLE 104, Step F substituting 5-bromo-2-ethoxysyrene (from Step A) for 2-(2-ethylpropyl)-5-bromobenzonitrile: ESI-MS (m/z) 275.2; HPLC A: 4.17 min.

Step C: tert-Butyl 3-(4-(5-(4-ethoxy-3-vinylphenyl)-1,2,4-thiadiazol-3-yl)-3-methylphenyl)propanoate The title compound was prepared using a procedure analogous to that described in EXAMPLE 104, Step G substituting (4-ethoxy-3-vinylphenyl)boronic acid, pinacol ester (from Step B) for (3-cyano-4-(2-methylphenyl)phenyl)boronic acid, pinacol ester: ESI-MS (m/z) 451.3; HPLC A: 4.63 min.

Step D: 3-(4-(5-(3-Ethyl-4-ethoxyphenyl)-1,2,4-thiadiazol-3-yl)-3-methylphenyl)propanoic acid A solution of tert-Butyl 3-(4-(5-(4-ethoxy-3-vinylphenyl)-1,2,4-thiadiazol-3-yl)-3-methylphenyl)propanoate (0.01 g, 0.025 mmol) in methanol (1.5 mL) and ethyl acetate (1.5 mL) was degassed with nitrogen. 10% Palladium/Carbon (0.01 g) was added to the reaction mixture which was stirred under a balloon of hydrogen for 30 min. The reaction was filtered through a disposable frit and concentrated in vacuo. The resulting oil was dissolved in 20% solution of trifluoroacetic acid in dichloromethane (4 mL) and stirred at rt for 2 h after which the reaction was concentrated in vacuo. Silica gel chromatography eluting with 2% methanol/methylene chloride afforded 4.5 mg of the title compound: $^1$H NMR (500 MHZ, CDCl$_3$) δ 7.86 (s, 1H), 7.83 (d, J=8.5 Hz, 1H), 7.69 (d, J=7.8 Hz, 1H), 7.23 (s, 1H), 7.19 (d, J=7.5 Hz, 1H), 6.93 (d, J=8.2 Hz, 1H), 4.20-4.30 (m, 2H), 3.00-3.08 (m, 2H), 2.70-2.79 (m, 4H), 2.65 (s, 3H), 1.48-1.52 (m, 3H), 1.23-1.32 (m, 3H), ESI-MS (m/z) 453.3; HPLC A: 4.68 min.

Example 120

3-(4-(5-(4-Ethoxy-3-vinylphenyl)-1,2,4-thiadiazol-3-yl)-3-methylphenyl)propanoic acid The title compound was prepared from tert-butyl 3-(4-(5-(4-ethoxy-3-vinylphenyl)-1,2,4-thiadiazol-3-yl)-3-methylphenyl)propanoate (Example 119, Step C) using a procedure analogous to that described in EXAMPLE 104, Step H: $^1$H NMR (500 MHZ, CDCl$_3$) δ 8.15 (s, 1H), 7.90 (d, J=7.8 Hz, 1H), 7.69 (d, J=7.8 Hz, 1H), 7.24 (s, 1H), 7.19 (d, J=7.3 Hz, 1H), 7.18-7.40 (m, 1H), 6.96-7.04 (m, 1H), 5.92 (d, 1H), 5.39 (d, 1H), 4.15-4.22 (m, 2H), 3.00-3.08 (m, 2H), 2.72-2.81 (m, 2H), 2.65 (s, 3H), 1.50-1.58 (m, 3H).

Example 121

3-(4-(5-(3-Cyano-4-(2-fluoro-1-fluoromethylethoxy)phenyl)-1,2,4-thiadiazol-3-yl)-3-ethylphenyl)propanoic acid

Step A: tert-Butyl 3-(4-(2-Bromo-1,3,4-thiadiazol-5-yl)-3-methylphenyl)propenoate The title compound was prepared using a procedure analogous to those described in EXAMPLE 104, Step D, substituting tert-butyl 3-(4-(2-amino-1,3,4-thiadiazol-5-yl)-3-methylphenyl)propenoate (from EXAMPLE 104, Step B) for tert-butyl 3-(4-(2-amino-1,3,4-thiadiazol-5-yl)-3-methylphenyl)propanoate. ESI-MS (m/z) 383.0; HPLC A: 4.10 min.

Step B: 3-Cyano-4-fluorophenyl boronic acid

Trimethylborate (1.37 mL, 12 mmol) was added to a solution of 5-bromo-2-fluorobenzonitrile (2.0 g, 10 mmol) in toluene (16 mL) and THF (4 mL) at −78° C. n-Butyl lithium (2.5M in hexane; 4.8 mL) was slowly added over 1 h and the solution was stirred for 30 min after which it was warmed to rt for 1 h. The reaction was cooled to 0° C. and quenched with 20 mL of 1 N HCl. The product was extracted with ethyl acetate (2×200 mL), dried over magnesium sulfate, filtered and concentrated in vacuo. Silica gel chromatography eluting with 5% methanol/methylene chloride afforded 0.33 g of the desired product.

Step C: tert-Butyl 3-(4-(3-(3-Cyano-4-fluorophenyl)-1,3,4-thiadiazol-5-yl)-3-methylphenyl)propenoate tert-Butyl 3-(4-(2-Bromo-1,3,4-thiadiazol-5-yl)-3-methylphenyl)propenoate (0.15 g, 0.39 mmol, from Step A), 3-cyano-4-fluorophenyl boronic acid (0.097 g, 0.59 mmol, from Step B) and sodium carbonate (0.21 g, 1.95 mmol) were dissolved in DMF (6 mL) and water (0.2 mL). The reaction mixture was degassed for 5 min with a balloon of argon after which tetrakis(triphenylphosphine) palladium (0.1 g) was added. The reaction was heated at 80° C. for 3 h. The reaction was diluted with water and extracted with ethyl acetate (2×100 mL). The combined organics were dried over magnesium sulfate, filtered and concentrated in vacuo. Silica gel chromatography eluting with 10% ethyl acetate/hexane afforded 0.05 g of product: ESI-MS (m/z) 422.2; HPLC A: 4.21 min.

Step D: tert-Butyl 3-(4-(3-(3-Cyano-4-fluorophenyl)-1,3,4-thiadiazol-5-yl)-3-methylphenyl)cyclopropanecarboxylate The title compound was prepared using a procedure analogous to that described in EXAMPLE 78, Step B substituting tert-butyl 3-(4-(3-(3-cyano-4-fluorophenyl)-1,3,4-thiadiazol-5-yl)-3-methylphenyl)propenoate for methyl (2Z)-3-(4-(5-(3-cyano-4-isopropoxyphenyl)-1,2,4-oxadiazol-3-yl)-3-methylphenyl)propenoate: ESI-MS (m/z) 436.2; HPLC A: 4.22 min.

Step E: 3-(4-(3-(3-Cyano-4-(2-fluoro-1-fluoromethylethoxy phenyl))-1,3,4-thiadiazol-5-yl)-3-methylphenyl)cyclopropanecarboxylic acid The title compound was prepared from tert-butyl 3-(4-(3-(3-cyano-4-fluorophenyl)-1,3,4-thiadiazol-5-yl)-3-methylphenyl)cyclopropanecarboxylate (from Step D) and 1,3-difluoro-2-propanol using procedures analogous to those described in EXAMPLE 105, Step C and EXAMPLE 104, Step H: $^1$H NMR (500 MHZ, CDCl$_3$) δ 8.28 (d, 1H), 8.24 (s, 1H), 7.71 (d, J=8.0 Hz, 1H), 7.27 (s, 1H), 7.14 (s, 1H), 7.09 (d, J=7.8 Hz, 1H), 4.93-5.04 (m, 1H), 4.84 (d, J=4.8 Hz, 2H), 4.74 (d, J=4.8 Hz, 2H), 2.66 (s, 3H), 1.98-2.05 (m, 1H), 1.72-1.78 (m, 1H), 1.46-1.52 (m, 1H), 1.26-1.30 (m, 1H) ESI-MS (m/z) 456.1; HPLC A: 3.44 min.

Examples 122-123

The following examples were prepared using procedures analogous to those described for EXAMPLE 121 substituting the appropriate alcohol for 1,3-difluoro-2-propanol in Step E.

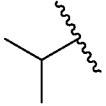

| EXAMPLE | R | HPLC A (min) | ESI-MS (M + H) |
|---|---|---|---|
| 122 |  | 3.71 | 420.1 |

¹H NMR (500 MHz, CDCl₃) δ 8.25(dd, J = 7.1, 1.9 Hz, 1H), 8.18(d, J = 1.8 Hz, 1H), 7.71(d, J = 7.8 Hz, 1H), 7.13(d, J = 5.2 Hz, 2H), 7.08(d, J = 7.7 Hz, 1H), 4.75-4.82(m, 1H), 2.66(s, 3H), 2.00-2.05(m, 1H), 1.71-1.79(m, 1H), 1.60-1.65(m, 1H), 1.49(d, J = 5.9 Hz, 6H)

| 123 | F₃C— | 3.73 | 460.0 |

Example 124

3-(4-(5-(3-Cyano-4-(2-propyloxy)phenyl)-1,3-thiazol-5-yl)-3-methylphenyl)propanoic acid

Step A: 2-(4-bromo-2-methylphenyl)-1,3-thiazole

A solution of 5-bromo-2-iodotoluene (0.15 g, 1.18 mmol) and 2-tributylstannylthiazole (0.45 g, 1.18 mmol) in THF (4 mL) in a sealed tube was degassed with a balloon of argon for 5 min. Bis(triphenylphosphine)palladium(II) chloride (1.18 mmol) was added, the reaction was capped and heated at 90° C. for 6 h. Silica gel chromatography eluting with 100% hexanes yielded 0.12 g of desired product: ¹H NMR (500 MHZ, CDCl₃) δ 7.95 (d, J=3.0 Hz, 1H), 7.63 (d, J=8.3 Hz, 1H), 7.50 (s, 1H), 7.44 (d, J=2.8 Hz, 2H), 2.60 (s, 3H).

Step B: (5-Bromo-2-(4-bromo-2-methylphenyl))-1,3-thiazole 2-(4-Bromo-2-methylphenyl)-1,3-thiazole (0.12 g, 0.47 mmol, from Step A) was dissolved in acetic acid (1 mL). 1 mL of 2% bromine in acetic acid was added and the reaction was heated at 60° C. for 1.5 h. The reaction was diluted with methylene chloride (100 mL) and washed with saturated sodium bicarbonate (1×100 mL). The organic layer was dried over magnesium sulfate, filtered and concentrated in vacuo. Silica gel chromatography eluting with 15% ethyl acetate/hexanes yielded 0.11 g of the desired product: ¹H NMR (500 MHZ, CDCl₃) δ 7.82 (s, 1H), 7.57 (d, J=8.3 Hz, 1H), 7.50 (s, 1H), 7.44 (d, J=8.0 Hz, 1H), 2.57 (s, 3H).

Step C: 5-(3-Cyano-4-fluorophenyl)-2-(4-bromo-2-methyphenyl)-1,3-thiazole

The title compound was prepared using a procedure analogous to that described in EXAMPLE 121, Step C substituting 5-bromo-2-(4-bromo-2-methylphenyl))-1,3-thiazole (from Step B) for tert-butyl 3-(4-(2-bromo-1,3,4-thiadiazol-5-yl)-3-methylphenyl) propenoate: ¹H NMR (500 MHZ, CDCl₃) δ 8.07 (s, 1H), 7.87 (s, 2H), 7.68 (d, J=8.0 Hz, 1H), 7.54 (s, 1H), 7.48 (d, J=7.8 Hz, 1H), 7.32-7.36 (m, 1H), 2.66 (s, 3H).

Step D: 5-(3-Cyano-4-isopropyloxyphenyl)-2-(4-bromo-2-methyphenyl)-1,3-thiazole The title compound was prepared using a procedure analogous to that described in EXAMPLE 105, Step C substituting 5-(3-cyano-4-fluorophenyl)-2-(4-bromo-2-methyphenyl)-1,3-thiazole (EXAMPLE 124, Step C) for tert-butyl 3-(4-(3-(3-cyano-4-fluorophenyl)-1,3,4-thiadiazol-5-yl)-3-methylphenyl)propanoate and 2-propanol for glycolonitrile: ¹H NMR (500 MHZ, CDCl₃) δ 8.00 (s, 1H), 7.80 (d, J=1.8 Hz, 1H), 7.75 (dd, J=6.6, 2.1 Hz, 1H), 7.67 (d, J=8.5 Hz, 1H), 7.52 (s, 1H), 7.46 (d, J=8.5 Hz, 1H), 7.06 (d, J=8.7 Hz, 1H), 4.70-4.78 (m, 1H), 2.65 (s, 3H), 1.47 (d, J=6.0 Hz, 6H).

Step E: Ethyl 3-(4-(5-(3-cyano-4-isopropyloxyphenyl)-1,3-thiazol-2-yl)-3-methylphenyl)propanoate The title compound was prepared using a procedure analogous to that described in EXAMPLE 91, Step D substituting 5-(3-cyano-4-isopropyloxyphenyl)-2-(4-bromo-2-methyphenyl)-1,3-thiazole (from Step D) for 2-(3-cyano-4-isopropylthiophenyl)-5-(4-bromo-2-methyphenyl)-1,3,4-thiadiazole: ¹H NMR (500 ME, CDCl₃) δ 8.00 (s, 1H), 7.81 (s, 1H), 7.76 (dd, J=6.8, 2.0 Hz, 1H), 7.73 (d, J=8.0 Hz, 1H), 7.21 (s, 1H), 7.18 (d, J=8.0 Hz, 1H), 7.06 (d, J=8.7 Hz, 1H), 4.70-4.78 (m, 1H), 4.15-4.25 (m, 2H), 3.02 (t, J=7.7 Hz, 2H), 2.70 (t, J=7.7 Hz, 3H), 2.66 (s, 3H0, 1.48 (d, J=6.0 Hz, 6H), 1.28-1.38 (m, 3H).

Step F: 3-(4-(5-(3-Cyano-4-(2-propyloxy)phenyl)-1,3-thiazol-2-yl)-3-methylphenyl)propanoic acid A solution of 2 mg of LiOH in 1 mL water and 1 mL THF was added to ethyl 3-(4-(5-(3-cyano-4-isopropyloxyphenyl)-1,3-thiazol-2-yl)-3-methylphenyl)propanoate (0.003 g, from Step E) and the reaction was heated at 50° C. for 2 h. The reaction was acidified with 0.5 M HCl (25 mL) and the product was extracted with ethyl acetate (25 mL). The organic layer was dried over magnesium sulfate, filtered and concentrated in vacuo. Silica gel chromatography eluting with 10% methanol/methylene chloride yielded 1.8 mg of the title compound: ¹H NMR (500 MHZ, CDCl₃) δ 7.99 (s, 1H), 7.79 (d, J=2.0 Hz, 1H), 7.75 (dd, J=6.9, 2.0 Hz, 1H), 7.72 (d, J=8.0 Hz, 1H), 7.20 (s, 1H), 7.18 (d, J=8.0 Hz, 1H), 7.05 (d, J=8.7 Hz, 1H), 4.70-4.77 (m, 1H), 3.02 (t, J=7.7 Hz, 2H), 2.76 (t, J=7.7 Hz, 2H), 2.64 (s, 3H), 1.47 (d, J=6.0 Hz, 6H).

Example 125

3-(4-(5-(3-Cyano-4-(2-propyloxy)phenyl)-1,3-oxazol-2-yl)-3-methylphenyl)propanoic acid

Step A: 2-(4-Bromo-2-methylphenyl)-4,5-dihydro-1,3-oxazole

Oxalyl chloride (5 mL) was added to a solution of 4-bromo-2-methylbenzoic acid (1.1 g, 4.72 mmol) in methylene chloride (20 mL) and DMF (2 drops) and stirred at rt for 1 h. The reaction mixture was concentrated and dried. 2-Bromoethylamine hydrobromide (0.88 g, 4.29 mmol) was dissolved in benzene (20 mL) and triethylamine (3.01 mL; 21.45 mmol) was added. The acid chloride was slowly added to the reaction mixture which was stirred vigorously at 90° C. for 18 h. The reaction mixture was poured into 50 mL of water and the product was extracted with methylene chloride (2×200 mL). The combined organics were dried over magnesium sulfate, filtered and concentrated in vacuo. Silica gel chromatography eluting with 10% ethyl acetate/hexanes, then 15% ethyl acetate/hexanes yielded 0.33 g of the desired product: $^1$H NMR (500 MHz, CDCl$_3$) δ 7.71 (d, J=8.3 Hz, 1H), 7.43 (s, 1H), 7.39 (d, J=8.4 Hz, 1H), 4.41 (t, J=9.5 Hz, 2H), 4.11 (t, J=9.6 Hz, 2H), 2.60 (s, 3H).

Step B:
2-(4-Bromo-2-methylphenyl)-5-bromooxazole 2-(4-Bromo-2-methylphenyl)-4,5-dihydro-1,3-oxazole (0.33 g, 1.38 mmol, from Step A) was dissolved in carbon tetrachloride. AIBN (0.003 g) and N-bromosuccinimide (0.18 g, 4.14 mmol) were sequentially added, the mixture was degassed with argon for 5 min and then heated at 85° C. for 24 h. The reaction was filtered, diluted with methylene chloride (200 mL) and washed with saturated sodium bisulfite (2×100 mL). The organic layer was dried over magnesium sulfate, filtered and concentrated in vacuo. Silica gel chromatography eluting with 3% ethyl acetate/hexanes yielded 60 mg of the desired product: $^1$H NMR (500 MHz, CDCl$_3$) δ 7.83 (d, J=8.5 Hz, 1H), 7.49 (s, 1H), 7.45 (d, J=8.2 Hz, 1H), 7.16 (s, 1H), 2.67 (s, 3H).

Step C: 3-(4-(5-(3-Cyano-4-(2-propyloxy)phenyl)-1,3-oxazol-2-yl)-3-methylphenyl)propanoic acid The title compound was prepared using procedures analogous to those described in EXAMPLE 124, Steps C-F substituting 2-(4-bromo-2-methylphenyl)-5-bromooxazole (from Step B) for 5-bromo-2-(4-bromo-2-methylphenyl))-1,3-thiazole in EXAMPLE 124, Steps C: $^1$H NMR (500 MHZ, CDCl$_3$) δ 7.99 (d, J=7.8 Hz, 1H), 7.90 (s, 1H), 7.83 (d, J=8.4 Hz, 1H), 7.42 (s, 1H), 7.20 (s, 2H), 7.06 (d, J=8.7 Hz, 1H), 4.70-4.78 (m, 1H), 2.98-3.05 (m, 2H), 2.70-2.78 (m, 5H), 1.46 (d, J=6.0 Hz, 6H).

Example 126

3-(4-(5-(3-Cyano-4-(2-propyloxy)phenyl)-1,2,3,4-tetrazol-5-yl)-3-methylphenyl)propanoic acid Step A: 3-Cyano-4-fluorobenzaldehyde, p-toluenesulfonhydrazone 3-Cyano-4-fluorobenzaldehyde (1.0 g, 6.71 mmol) and p-toluenesulfonylhydrazine (1.37 g, 7.38 mmol) were dissolved in 2-propanol (25 mL) and heated at 50° C. for 1 h. The reaction mixture was concentrated in vacuo. Silica gel chromatography eluting with 100% ethyl acetate afforded the desired product: ESI-MS (m/z) 318.1; HPLC A: 3.10 min.

Step B: 5-(3-Cyano-4-fluorophenyl)-2-(4-bromo-2-methyphenyl)-1,2,3,4-tetrazole

4-Bromo-2-methylaniline (1.25 g, 6.71 mmol) was dissolved in 50% aqueous ethanol (15 mL) and concentrated HCl (2 mL) and cooled to −10° C. Sodium nitrite (0.46; 6.71 mmol) was dissolved in water (1 mL) and slowly added to the reaction which was then stirred for 1 h at rt. In a separate flask, 3-cyano-4-fluorobenzaldehyde p-toluenesulfonhydrazone (1.25 g, 6.71 mmol, from Step A) was dissolved in pyridine (50 mL) and cooled to −10° C. The diazonium salt mixture was slowly added to the p-toluenesulfonyl hydrazone solution at −10° C., the resulting mixture was stirred cold for 30 min then warmed to rt for 30 min. The reaction was then diluted with methylene chloride (200 mL) and washed with water (1×100 mL), 1N HCl and aqueous sodium bicarbonate (1×100 mL). The aqueous layer was dried over magnesium sulfate, filtered and concentrated in vacuo. Silica gel chromatography eluting with 10% ethyl acetate/hexanes yielded 0.5 g of desired product: ESI-MS (m/z) 359.1; HPLC A: 3.13 min.

Step C: 3-(4-(5-(3-Cyano-4-(2-propyloxy)phenyl)-1,2,3,4-tetrazol-2-yl)-3-methylphenyl)propanoic acid The title compound was prepared using procedures analogous to those described in EXAMPLE 124, Steps C-F substituting 5-(3-cyano-4-fluorophenyl)-2-(4-bromo-2-methyphenyl)-1,2,3,4-tetrazole (from Step B) for 5-bromo-2-(4-bromo-2-methylphenyl))-1,3-thiazole in EXAMPLE 124, Steps C: $^1$H NMR (500 MHZ, CDCl$_3$) δ 8.44 (s, 1H), 8.41 (dd, J=7.1, 1.7 Hz, 1H), 7.61 (d, J=8.0 Hz, 1H), 7.31 (s, 1H), 7.14 (d, J=9.0 Hz, 1H), 4.78-4.82 (m, 1H), 3.08 (t, J=7.6 Hz, 2H), 2.79 (t, J=7.6 Hz, 2H), 2.43 (s, 3H), 1.49 (d, J=6.0 Hz, 6H)

Example 127

3-(4-(5-(3-Cyano-4-(2-propyloxy)phenyl)thien-2-yl)-3-methylphenyl)propanoic acid Step A: 2-(4-Bromo-2-methylphenyl)thiophene 4-Bromo-2-methyliodobenzene (1.0 mmol) was combined with THF solution of 2-thienylzinc bromide (2.0 mmol) in an oven-dried tube under argon. The resulting solution was degassed with a steady stream of argon for 10 min at rt. To this mixture, solid (Ph$_3$P)$_4$Pd (0.1 mmol) was added and the mixture was degassed with argon for 2 min after which it was stirred at rt for 8 h. The reaction mixture was combined with 1M HCl (100 mL) and ethyl acetate (200 mL). Organic layer was separated, washed sequentially with 1M hydrochloric acid (50 mL) and brine (50 mL), and dried over sodium sulfate. The desired product was isolated by flash chromatography on silica gel using hexanes as the eluant: $^1$H NMR (CDCl$_3$) 7.45 (d, J=1.0, 1H), 7.39 (d, J=5.6, 1H), 7.37 (dd, J=1.0, 5.0, 1H), 7.28 (d, J=5.0, 1H), 7.13 (m, 1H), 7.08 (d, J=5.6, 1H); HPLC A 4.09 min; ESI-MS (m/z)=252, 254.

Step B:
5-Bromo-2-(4-bromo-2-methylphenyl)thiophene

To a stirred homogeneous solution of 2-(4-bromo-2-methylphenyl)thiophene (5.0 mmol, from Step A) and sodium acetate (10 mmol) in acetic acid (25 mL), bromine (5.0 mmol) was added dropwise via syringe at rt over 20-30 min and the resulting mixture was stirred for 1 h. The reaction mixture was combined with 1 M sodium hydroxide (250 mL) and ethyl acetate (250 mL). Organic layer was separated, washed sequentially with 1M sodium hydroxide (100 mL) and brine (100 mL), and dried over sodium sulfate. Silica gel chromatography using hexanes as the eluant afforded the title compound: $^1$H NMR (CDCl$_3$) 7.46 (d, J=0.6, 1H), 7.38 (dd, J=3.9, 0.6, 1H), 7.24 (d, J=3.9, 1H), 7.09 (d, J=2.9, 1H), 6.83 (d, J=2.9, 1H), 2.43 (s, 3H); HPLC A 4.41 min, ESI-MS (m/z)= 334.

Step C: 5-(3-Cyano-4-fluorophenyl)-2-(4-bromo-2-methylphenyl)thiophene

The title compound was prepared using a procedure analogous to that described in EXAMPLE 127, Step A substituting 5-bromo-2-(4-bromo-2-methylphenyl)thiophene (from Step B) for 4-bromo-2-methyliodobenzene and 3-cyano-4-fluorophenylzincbromide for 2-thienylzinc bromide: $^1$H NMR (CDCl$_3$) 7.85 (m, 2H), 7.47 (d, J=2.0, 1H), 7.40 (dd, J=2.0, 9.0, 1H), 7.29 (m, 3H), 7.07 (d, J=6.5, 1H), 2.47 (s, 3H). HPLC A 4.20 min.

Step D: 5-(3-Cyano-4-(2-isopropyloxy)phenyl)-2-(4-bromo-2-methylphenyl)thiophene 5-(3-Cyano-4-fluorophenyl)-2-(4-bromo-2-methylphenyl)thiophene (0.2 mmol, from Step C) was combined in an oven-dried vessel with 2-propanol (0.1 mL), tetrahydrofuran (2 mL) and sodium hydride (50 mg). The reaction vessel was sealed with a Teflon pressure lid and the reaction mixture was heated sealed 2 h. The resulting mixture was combined with 50 mL of ethyl acetate and washed with 50 mL of water, dried over sodium sulfate and concentrated. Flash chromatography on silica gel afforded the title compound: $^1$H NMR (CDCl$_3$) 7.80 (d, J=2.0, 1H), 7.75 (dd, J=2.0, 9.0, 1H), 7.47 (d, J=1.0, 1H), 7.37 (dd, J=1.0, 8.5, 1H), 7.31 (d, J=8.0, 1H), 7.22 (d, J=6.0, 1H), 7.04 (d, J=6.0, 1H), 7.02 (d, J=9.0, 1H), 4.71 (sep, J=1.0, 1H), 2.47 (s, 3H), 1.46 (d, J=1, 6H). HPLC A 4.54 min. ESI-MS (m/z)=412, 414.

Step E: Ethyl (4-(5-(3-cyano-4-(2-propyloxy)phenyl)-thien-2-yl)-3-methylphenyl)propanoate The title compound was prepared using a procedure analogous to that described in EXAMPLE 127, Step A substituting 5-(3-cyano-4-(2-isopropyloxy)phenyl)-2-(4-bromo-2-methylphenyl)thiophene (from Step D) for 4-bromo-2-methyliodobenzene and 2-ethoxycarbonyl-1-ethylzinc bromide for 2-thienylzinc bromide: HPLC A 4.33 min; ESI-MS (m/z)= 434.

Step F: (4-(5-(3-Cyano-4-(2-propyloxy)phenyl)-thien-2-yl)-3-methylphenyl)propanoic acid Ethyl (4-(5-(3-cyano-4-(2-propyloxy)phenyl)-thien-2-yl)-3-methylphenyl)propanoate (from STEP E) was combined with 200 mg of lithium hydroxide, 3 mL of tetrahydrofuran and 1 mL of water. The reaction mixture was heated to 55° C. for 6 h, combined with 50 mL of ethyl acetate, 50 mL of 1 M solution of hydrochloric acid. The organic layer was separated, washed with brine, dried over sodium sulfate and concentrated. The title compound was isolated by flash chromatography on silica gel using 10% methanol in dichloromethane as the eluent: $^1$H NMR (CDCl$_3$) 7.81 (d, J=2.0, 1H), 7.74 (dd, J=2.0, 9.0, 1H), 7.38 (d, J=8.0, 1H), 7.22 (d, J=4.0, 1H), 7.16 (d, J=1.0, 1H), 7.11 (dd, J=1.0, 8.0, 1H), 7.03 (d, J=4.0, 1H), 7.00 (d, J=8.0, 1H), 4.70 (sep, J=1.0, 1H), 3.00 (t, J=1.5, 2H), 2.75 (t, J=1.5, 2H), 2.47 (s, 3H), 1.42 (d, J=1.0, 6H); HPLC A 3.78 min; ESI-MS (m/z)=406.

Example 128

(R)-(5-(5-(5-Chloro-6-isopropoxypyridin-3-yl))-1,3,4-thiadiazol-2-yl)-4-methyl-indan-1-yl)acetic acid

Step A: 2-(2-(R)-(5-Cyano-4-methyl-2,3-dihydro-1-H-indan-1-yl))ethanol

Methyl (R)-(5-cyano-methyl-indan-1-yl)acetate (600 mg, 2.65 mmol, from EXAMPLE 110, Step J) was dissolved in 10 mL of anhydrous dichloromethane in an oven-dried round-bottomed flask under argon atmosphere. To this solution, diisobutylaluminum hydride (2.65 mmol) was added drop wise at −78° C. The reaction was allowed to warm up to rt and the reaction mixture was combined with 100 mL of 1M solution of hydrochloric acid and 100 mL of dichloromethane. Organic layer was separated, washed with brine, dried over sodium sulfate and concentrated. The crude oil was dissolved in 30 mL of methanol, and solid sodium borohydride was added at −78° C. in one portion. The resulting mixture was allowed to reach rt over 2 h, diluted with 100 mL of 1 M solution of hydrochloric acid and 100 mL of dichloromethane. The organic layer was separated, washed with brine, dried over sodium sulfate and concentrated. The desired product was isolated by silica gel chromatography (eluent: hexanes/ethyl acetate=2/1): $^1$HNMR (CDCl$_3$) 7.47 (d, J=3.5, 1H), 7.13 (d, J=3.5, 1H), 3.82 (m, 2H), 3.38 (m, 1H), 2.95 (m, 1H), 2.82 (m, 1H), 2.47 (s, 3H), 2.42 (m, 1H), 2.18 (m, 1H), 1.80 (m, 1H), 1.75 (m, 1H), 1.39 (m, 1H).

Step B: 2-(2-(R)-(5-Cyano-4-methyl-2,3-dihydro-1-H-indan-1-yl)-1-benzyloxyethane 2-(2-(R)-(5-Cyano-4-methyl-2,3-dihydro-1-H-indan-1-yl))ethanol (400 mg, 2.0 mmol, from Step A) was combined with benzyl bromide (3.0 mmol) and 10 mL of anhydrous tetrahydrofuran in an oven-dried round-bottomed-flask under argon atmosphere. To this mixture, sodium hydride was added at rt and the reaction was then heated to 55° C. for 2 h. The reaction was diluted with 100 mL of 1 M solution of hydrochloric acid and 100 mL of dichloromethane. The organic layer was separated, washed with brine, dried over sodium sulfate and concentrated. The desired product was isolated by silica gel chromatography (eluent: hexanes/ethyl acetate=10/1): $^1$H NMR (CDCl$_3$) 7.44 (d, J=3.5, 1H), 7.38 (m, 4H), 7.32 (m, 1H), 7.11 (d, J=3.5, 1H), 4.56 (dd, J=4.0, 8.5), 3.61 (m, 2H), 3.36 (m, 1H), 2.89 (m, 1H), 2.81 (m, 1H), 2.47 (s, 3H), 2.35 (m, 1H), 2.18 (m, 1H), 1.77 (m, 2H).

Step C: 2-(2-(R)-(5-Formyl-4-methyl-2,3-dihydro-1-H-indan-1-yl)-1-benzyloxyethane 2-(2-(R)-(5-Cyano-4-methyl-2,3-dihydro-1-H-indan-1-yl)-1-benzyloxyethane (600 mg, 2.06 mmol, from Step B) was dissolved in 10 mL of anhydrous dichloromethane in an oven-dried round-bottomed flask under argon atmosphere. To this solution, diisobutylaluminum hydride (2.30 mmol) was added dropwise at −78° C. The reaction was allowed to warm up to rt and the reaction mixture was combined with 100 mL of 1 M solution of hydrochloric acid and 100 mL of dichloromethane. The organic layer was separated, washed with brine, dried over sodium sulfate and concentrated. The desired product was isolated by silica gel chromatography (eluent: hexanes/ethyl acetate=10/1): $^1$H NMR (CDCl$_3$) 10.25 (s, 1H), 7.66 (d, J=3.5, 1H), 7.38 (m, 4H), 7.32 (m, 1H), 7.22 (d, J=3.5, 1H), 4.58 (dd, J=4.0, 8.5), 3.60 (m, 2H), 3.38 (m, 1H), 2.95 (m, 1H), 2.83 (m, 1H), 2.47 (s, 3H), 2.37 (m, 1H), 2.22 (m, 1H), 1.78 (m, 2H).

Step D: 2-(2-(R)-(5-Carboxy-4-methyl-2,3-dihydro-1-H-indan-1-yl)-1-benzyloxyethane 2-(2-(R)-(5-Formyl-4-methyl-2,3-dihydro-1-H-indan-1-yl)-1-benzyloxyethane (500 mg, from Step C) was combined with 20 mL of acetonitrile, 0.5 mL of 30% aqueous hydrogen peroxide, 0.16 g of sodium dihydrophosphate, and 2 mL of water. To this mixture, a solution of 0.8 g of sodium hypochlorite in 7 mL of water was added over 30 min at 10° C. The mixture was stirred at 10° C. for 1 h and then at rt for 1 h. Solid sodium bisulfite (1 g) was added and the mixture was stirred for 5 min. The reaction was combined with 100 mL of 1 M solution of hydrochloric acid and 100 mL of ethyl acetate. Organic layer was separated, washed with brine, dried over sodium sulfate and concentrated to give the title compound: $^1$H NMR (CDCl$_3$) 7.90 (d, J=3.5, 1H), 7.39 (m, 4H), 7.30 (m, 1H), 7.11 (d, J=3.5, 1H), 4.58 (dd, J=4.0, 8.5), 3.63 (m, 2H), 3.36 (m, 1H), 2.97 (m, 1H), 2.86 (m, 1H), 2.57 (s, 3H), 2.32 (m, 1H), 2.21 (m, 1H), 1.76 (m, 2H).

Step E: 2-(R)-(5-(5-(5-Chloro-6-isopropoxypyridin-3-yl))-1,3,4-thiadiazol-2-yl)-4-methyl-indan-1-yl)-1-benzyloxyethane The title compound was prepared using procedures analogous to those described in EXAMPLE 87, Steps A and B and EXAMPLE 127, Step D substituting 2-(2-(R)-(5-carboxy-4-methyl-2,3-dihydro-1-H-indan-1-yl)-1-benzyloxyethane (from Step D) for 3-cyano-4-isopropyloxybenzoic acid and 3-cyano-4-fluorobenzhydrazide for 4-bromo-2-methylbenzhydrazide in EXAMPLE 87, Step A: HPLC A 4.41 min, ESI-MS (m/z)=510.

Step F: 2-(R)-(5-(5-(5-Chloro-6-isopropoxypyridin-3-yl))-1,3,4-thiadiazol-2-yl)-4-methyl-indan-1-yl)ethanol 2-(R)-(5-(5-(5-Chloro-6-isopropoxypyridin-3-yl))-1,3,4-thiadiazol-2-yl)-4-methyl-indan-1-yl)-1-benzyloxyethane (12 mg, from Step G) was dissolved in ethyl acetate, combined with 10 mg of palladium on activated carbon (loading 10% w/w) and the resulting mixture was hydrogenated under 1 atm of hydrogen for 8 h. The reaction mixture was filtered through Celite and concentrated to give the title compound: HPLC A 3.50 min, ESI-MS (m/z)=420.

Step G: 2-(R)-(5-(5-(5-Chloro-6-isopropoxypyridin-3-yl))-1,3,4-thiadiazol-2-yl)-4-methyl-indan-1-yl)acetic acid 2-(R)-(5-(5-(5-Chloro-6-isopropoxypyridin-3-yl))-1,3,4-thiadiazol-2-yl)-4-methyl-indan-1-yl)ethanol (10 mg, from Step F) was combined with 3 mL of acetonitrile, 4 mg of TEMPO, 1.5 mL of pH=7 buffer solution and heated to 35° C. A solution of 0.1 mL of bleach and 0.1 mL of water and 100 mg of sodium hypochlorite in 0.5 mL of water was added simultaneously over 5 min at 35° C. The reaction was heated to 35° C. for 4 h. Solid sodium bisulfite (1 g) was added and the mixture was stirred for 5 min. The reaction was combined with 100 mL of 1 M solution of hydrochloric acid and 100 mL of ethyl acetate. Organic layer was separated, washed with brine, dried over sodium sulfate and concentrated. The desired product was isolated by silica gel chromatography (eluent: 10% methanol in methylene chloride): HPLC A 3.52 min, ESI-MS (m/z)=434.

Example 129

(R)-(5-(5-(5-Chloro-6-(2,2,2-trifluoroethoxy)pyridin-3-yl))-1,2,4-oxadiazol-3-yl)-4-methyl-indan-1-yl)acetic acid

Step A: Methyl (R)-(5-(5-(5,6-dichloropyridin-3-yl))-1,2,4-oxadiazol-3-yl)-4-methyl-indan-1-yl)acetate To a solution of 5,6-dichloronicotinic acid (558 mg, 2.90 mmol) in acetonitrile (5.0 mL) and THF (5.0 mL), EDC-HCl (557 mg, 2.90 mmol) was added. The resultant solution was stirred at ambient temperature for 30 min and methyl (R)-(5-(N-hydroxycarboxamidinyl)-4-methyl-indan-1-yl)acetate (545 mg, 2.90 mmol, from EXAMPLE 110, Step K) was added. After 1 h, the reaction mixture was concentrated in vacuo. The residue was dissolved in EtOAc and washed with H$_2$O, brine, and dried over MgSO$_4$. The mixture was filtered, concentrated in vacuo and dissolved in THF (5 mL). A solution of TBAF 1.0 M in THF (2.08 mL, 2.08 mmol) was added and the resultant yellow solution was stirred at ambient temperature for 16 h. The reaction mixture was then concentrated in vacuo, dissolved in EtOAc and washed with H$_2$O, brine, and dried over MgSO$_4$. The mixture was filtered, concentrated in vacuo and purified by flash chromatography (3, 5% EtOAc/hexanes) on SiO$_2$ to give 482 mg of the title compound as white solid: $^1$H NMR (500 MHz, CDCl$_3$) δ 1.44 (d, 6H, J=6.2 Hz), 1.78-1.85 (m, 1H), 2.43-2.46 (m, 1H), 2.49 (dd, 1H, J=9.3, 15.6 Hz), 2.56 (s, 3H), 2.81 (dd, 1H, J=5.5, 15.5 Hz), 2.86-2.93 (m, 1H), 3.73 (s, 3H), 5.49, (septet, 1H, J=6.2 Hz), 7.14 (d, 1H, J=7.8 Hz), 7.85 (d, 1H, J=7.8 Hz), 8.38 (d, 1H, J=2.3 Hz), 8.85 (d, 1H, J=2.3 Hz).

Step B: (R)-(5-(5-(5-Chloro-6-(2,2,2-trifluoroethoxy)pyridin-3-yl))-1,2,4-oxadiazol-3-yl)-4-methyl-indan-1-yl)acetic acid In a sealed tube, a solution of methyl (R)-(5-(5-(5,6-dichloropyridin-3-yl))-1,2,4-oxadiazol-3-yl)-4-methyl-indan-1-yl)acetate (30 mg, 0.0718 mmol, from Step A) in THF (1 mL) and 2,2,2-trifluoroethanol (150 μL) was treated with 60% sodium hydride (10 mg, 0.144 mmol). The reaction mixture was sealed and heated to 80° C. After 15 h, the mixture was cooled to ambient temperature and partitioned between EtOAc and 5% citric acid. The organic layer was washed with H$_2$O, brine, dried over MgSO$_4$, filtered and concentrated in vacuo. Purification of the residue by HPLC B afforded 25 mg of the title compound: $^1$H NMR (500 MHz, DMSO-d$_6$) δ 1.71-1.75 (m, 1H), 2.34-2.41 (m, 2H), 2.49 (s, 3H), 2.77 (dd, 1H, J=5.5, 15.8 Hz), 2.82-2.85 (m, 1H), 2.93-2.98 (m, 1H), 3.48-3.55 (m, 1H), 5.19-5.24 (m, 2H), 7.25 (d, 1H, J=8.0 Hz), 7.78 (d, 1H, J=8.0 Hz), 8.67 (d, 1H, J=2.1 Hz), 8.95 (d, 1H, J=1.8 Hz); HPLC A: rt=4.01 min, m/z=468.2 (M+H)$^+$, 470.2 (M+H+2)$^+$.

The following examples were prepared using procedures analogous to those described in EXAMPLE 129, substituting the appropriate alcohol for 2,2,2,-trifluoroethanol in Step B:

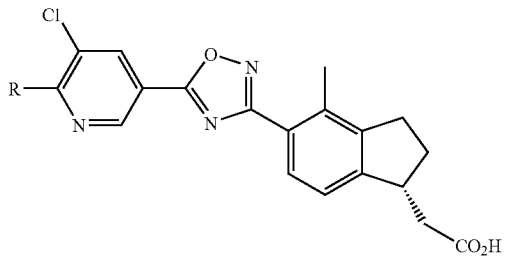

| EXAMPLE | R | HPLC A (min) | ESI-MS (M + H)+ |
|---|---|---|---|
| 130 | 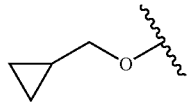 | 4.24 | 440.2, 442.2 |

¹H NMR (500 MHz, DMSO-d₆) δ 0.37-0.40(m, 2H), 0.56-0.60(m, 2H), 1.29-1.32(m, 1H), 1.69-1.73(m, 1H), 2.32-2.39(m, 2H), 2.46(s, 3H), 2.76 (dd, 1H, J =5.5, 15.8 Hz), 2.78-2.85(m, 1H), 2.91-2.96(m, 1H), 3.50-3.53(m, 1H), 4.31(d, 2H, J = 7.3 Hz), 7.24(d, 1H, J = 7.8 Hz), 7.76(d, 1H, J = 7.8 Hz), 8.52(d, 1H, J = 2.0 Hz), 8.87(d, 1H, J = 2.1 Hz).

| 131 | | 4.36 | 454.3, 456.3 |

¹H NMR (500 MHz, CD₃OD) δ 0.36-0.39(m, 1H), 0.49-0.52(m, 1H), 0.55-0.62(m, 2H), 1.20-1.23(m, 1H), 1.47(d, 3H, J = 6.2 Hz), 1.81-1.85(m, 1H), 2.43-2.48(m, 2H), 2.53(s, 3H), 2.80(dd, 1H, J = 5.5, 15.5 Hz), 2.88-2.92(m, 1H), 2.99-3.04(m, 1H), 3.62-3.64(m, 1H), 4.94-4.97(m, 1H), 7.22(d, 1H, J = 7.8 Hz), 7.81(d, 1H, J = 7.8 Hz), 8.45(d, 1H, J = 1.6 Hz), 8.85(d, 1H, J = 1.6 Hz).

| 132 | CF₃ | 4.18 | 482.2 |

¹H NMR (500 MHz, DMSO-d₆) δ 1.55(d, 3H, J = 6.4 Hz), 1.71-1.75(m, 1H), 2.34-2.40(m, 2H), 2.49(s, 3H), 2.76(dd, 1H, J = 5.3, 15.8 Hz), 2.82-2.85(m, 1H), 2.93-2.97(m, 1H), 3.51-3.53(m, 1H), 6.04(q, 1H, J = 6.4, 13.1 Hz), 7.26(d, 1H, J = 8.3 Hz), 7.78(d, 1H, J = 7.8 Hz), 8.67(d, 1H, J = 2.0 Hz), 8.95(d, 1H, J = 2.1 Hz).

| 133 | CF₃, F₃C | 4.23 | 550.0, 552.3 |

¹H NMR (500 MHz, DMSO-d₆) δ 1.71-1.75(m, 1H), 2.33-2.41(m, 2H), 2.49(s, 3H), 2.77(dd, 1H, J = 5.5, 15.8 Hz), 2.82-2.87(m, 1H), 2.94-2.99(m, 1H), 3.51-3.54(m, 1H), 7.28(d, 1H, J = 7.8 Hz), 7.42(t, 1H, J = 6.1, 12.3 Hz), 7.80(d, 1H, J = 7.8 Hz), 8.82(d, 1H, J = 1.8 Hz), 8.99(d, 1H, J = 1.8 Hz).

Example 134

(R)-(5-(5-(5-Chloro-6-(3,3-difluoropyrrolidin-1-yl)pyridin-3-yl))-1,2,4-oxadiazol-3-yl)-4-methyl-indan-1-yl)acetic acid

Step A: Methyl (R)-(5-(5-(5-chloro-6-(3,3-difluoropyrrolidin-1-yl)pyridin-3-yl))-1,2,4-oxadiazol-3-yl)-4-methyl-indan-1-yl)acetate In a sealed tube, a solution of methyl (R)-(5-(5-(5,6-dichloropyridin-3-yl))-1,2,4-oxadiazol-3-yl)-4-methyl-indan-1-yl) acetate (40 mg, 0.0956 mmol, from EXAMPLE 129, Step A) in THF (1 mL), 3,3-difluoropyrrolidine hydrochloride (21 mg, 0.0.144 mmol) and triethylamine (40 µL, 0.287 mmol) were heated to 80° C. for 16 h. The reaction mixture was cooled to ambient temperature, concentrated in vacuo and dissolved in ethyl acetate. The organic layer was washed with water and brine, dried over MgSO₄, filtered and concentrated in vacuo. Purification by flash chromatography (5, 10% EtOAc/hexanes) on SiO₂ afforded 43 mg of the title compound: ¹H NMR (500 MHz, CDCl₃) δ 1.81-1.88 (m, 1H), 2.44-2.54 (m, 4H), 2.58 (s, 3H), 2.83 (dd, 1H, J=5.5, 15.6 Hz), 2.89-2.93 (m, 1H), 3.01-3.06 (m, 1H), 3.68-3.71 (m, 1H), 3.76 (s, 3H), 4.11 (t, 2H, J=7.4 Hz), 4.24 (t, 2H, J=13.0 Hz), 7.17 (d, 1H, J=8.0 Hz), 7.87 (d, 1H, J=7.8 Hz), 8.28 (d, 1H, J=2.1 Hz), 8.88 (d, 1H, J=1.8 Hz).

Step B: (R)-(5-(5-(5-Chloro-6-(3,3-difluoropyrrolidin-1-yl)pyridin-3-yl))-1,2,4-oxadiazol-3-yl)-4-methyl-indan-1-yl)acetic acid To a solution of methyl (R)-(5-(5-(5,6-dichloropyridin-3-yl))-1,2,4-oxadiazol-3-yl)-4-methyl-indan-1-yl)acetate (43 mg, 0.0881 mmol, from STEP A) in THF (2 mL), 1.0 N NaOH (0.88 mmol) was added and the reaction mixture was stirred at ambient temperature. After 15 h, the reaction mixture was concentrated in vacuo and dissolved in ethyl acetate. The organic layer was washed with water and brine, dried over MgSO₄, filtered and concentrated in vacuo. Purification by HPLC B afforded 19 mg of the title compound: ¹H NMR (500 MHz, DMSO-d₆) δ 1.72-1.78 (m, 1H), 2.24-2.39 (m, 2H), 2.50 (s, 3H), 2.54-2.58 (m, 2H), 2.78 (dd, 1H, J=5.5, 15.8 Hz), 2.81-2.87 (m, 1H), 2.91-3.04 (m, 1H), 3.42-3.61 (m, 1H), 4.03 (t, 2H, J=7.3 Hz), 4.21 (t, 2H, J=13.0 Hz), 7.27 (d, 1H, J=8.0 Hz), 7.74 (d, 1H, J=7.8 Hz), 8.31 (s, 1H), 8.86 (s, 1H); HPLC A: rt=3.97 min, m/z=475.1 (M+H)⁺, 477.1 (M+H+2)⁺.

The following compounds were prepared using procedures analogous to those described in EXAMPLE 134 substituting the appropriate amine for 3,3-difluoropyrrolidine in Step A:

| EXAMPLE | X | R | HPLC A (min) | ESI-MS (M + H)+ |
|---|---|---|---|---|
| 135 | I | F, F (3,3-difluoropyrrolidin-1-yl) | 4.04 | 567.0 |

¹H NMR (500 MHz, DMSO-d₆) δ 1.64-1.74(m, 1H), 2.27-2.41(m, 2H), 2.50(s, 3H), 2.52-2.57(m, 2H), 2.75 (dd, 1H, J = 5.5, 15.6 Hz), 2.81-2.85(m, 1H), 2.86-3.02(m, 1H), 3.43-3.63(m, 1H), 3.99 (t, 2H, J = 7.3 Hz), 4.18(t, 2H, J = 13.0 Hz), 7.25(d, 1H, J = 8.0 Hz), 7.76(d, 1H, J = 7.6 Hz), 8.70(d, 1H, J = 2.0 Hz), 8.86(d, 1H, J = 2.0 Hz).

-continued

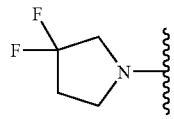

| EXAMPLE | X | R | HPLC A (min) | ESI-MS (M + H)+ |
|---|---|---|---|---|
| 136 | CN | 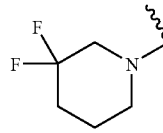 | 3.61 | 466.2 |

$^1$H NMR (500 MHz, DMSO-d$_6$) δ 1.74-1.70(m, 1H), 2.26-2.39(m, 2H), 2.48(s, 3H), 2.52-2.647(m, 2H), 2.75(dd, 1H, J = 5.5, 15.8 Hz), 2.82-2.86(m, 1H), 2.87-2.98(m, 1H), 3.46-3.62(m, 1H), 4.07 (t, 2H, J = 7.4 Hz), 4.23(t, 2H, J = 13.0 Hz), 7.26(d, 1H, J = 8.0 Hz), 7.75(d, 1H, J = 7.6 Hz), 8.65(d, 1H, J = 2.3 Hz), 9.04(d, 1H, J = 2.1 Hz).

| 137 | Cl | 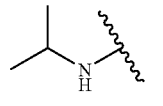 | 4.08 | 489.3, 491.3 |

$^1$H NMR (500 MHz, DMSO-d$_6$) δ 1.70-1.74(m, 1H), 1.89 (s, 2H), 2.06-2.14(m, 2H), 2.34-2.40(m, 2H), 2.49(s, 3H), 2.76(dd, 1H, J = 5.5, 15.8 Hz), 2.81-2.84(m, 1H), 2.94-2.97(m, 1H), 3.50-3.52 (m, 1H), 3.56-3.58(m, 2H), 3.85(t, 2H, J = 11.5, 23.1 Hz), 7.25 (d, 1H, J = 7.8 Hz), 7.77(d, 1H, J = 7.8 Hz), 8.41(d, 1H, J = 2.1 Hz), 8.92(d, 1H, J = 2.0 Hz).

| 138 | Cl | | 4.00 | 427.6, 429.6 |

$^1$H NMR (500 MHz, DMSO-d$_6$) δ 1.23(d, 6H, J = 6.4 Hz), 1.70-1.74(m, 1H), 2.33-2.40(m, 2H), 2.46(s, 3H), 2.76(dd, 1H, J = 5.5, 15.8 Hz), 2.81-2.84(m, 1H), 2.92-2.94(m, 1H), 3.50-3.52(m, 1H), 4.38-4.42(m, 1H), 7.07(d, 1H, J = 8.0 Hz), 7.24(d, 1H, J = 8.0 Hz), 7.75(d, 1H, J = 8.0 Hz), 8.17(d, 1H, J = 2.1 Hz), 8.76(d, 1H, J = 1.9 Hz).

Example 139

(R)-(5-(5-(5-Chloro-6-isopropoxypyridin-3-yl))-1,2,4-oxadiazol-3-yl)-4-methyl-1-(1H-tetrazol-5-yl)methylindane Step A: (R)-(5-(5-(5-Chloro-6-isopropoxypyridin-3-yl))-1,24-oxadiazol-3-yl)-4-methyl-indan-1-yl)acetamide To a solution of (R)-(5-(5-(5-chloro-6-isopropoxypyridin-3-yl))-1,2,4-oxadiazol-3-yl)-4-methyl-indan-1-yl)acetic acid (934 mg, 2.00 mmol, from EXAMPLE 110) in dichloromethane (10 mL) and DMF (1 drop), oxalyl chloride was added (570 µL, 1.17 mmol). After 45 min, the reaction mixture was concentrated in vacuo, and the residue azeotroped with benzene (3×5 mL). The resultant crude acid chloride was dissolved in EtOAc (5 mL) and treated with concentrated NH$_4$OH (7 mL). After 15 min, the reaction mixture was concentrated in vacuo and azeotroped with EtOAc (3×5 mL). The residue was dissolved in EtOAc (15 mL), washed with H$_2$O, dried (MgSO$_4$), filtered and concentrated in vacuo to afford 871 mg of the title compound: $^1$H NMR (500 MHz, CD$_3$OD) δ 1.45 (d, 6H, J=6.2 Hz), 1.72-1.81 (m, 1H), 2.35-2.43 (m, 2H), 2.55 (s, 3H), 2.72 (dd, 1H, J=6.2, 14.2 Hz), 2.88-2.95 (m, 1H), 3.01-3.08 (m, 1H), 3.63-3.69 (m, 1H), 5.54 (septet, 1H, J=1H), 7.25 (d, 1H, J=7.8 Hz), 7.84 (d, 1H, J=8.0 Hz), 8.46 (d, 1H, J=2.1 Hz), 8.89 (d, 1H, J=2.0 Hz); HPLC A: rt=3.89 min, m/z=427.0 (M+H)+, 429.0 (M+H+2)+.

Step B: (R)-(5-(5-(5-Chloro-6-isopropoxypyridin-3-yl))-1,2,4-oxadiazol-3-yl)-methyl-indan-1-yl)acetonitrile To an ice-cold solution of (R)-(5-(5-(5-chloro-6-isopropoxypyridin-3-yl))-1,2,4-oxadiazol-3-yl)-4-methyl-indan-1-yl)acetamide (871 mg, 2.00 mmol, from Step A) in dichloromethane (6 mL) and triethylamine (625 µL, 4.48 mmol), trifluoroacetic acetic anhydride (320 µL, 2.24 mmol) was added and the reaction mixture was warmed to ambient temperature. After 30 min, dichloromethane (10 mL) was added and the organic layer was washed with sat. NaHCO$_3$ (1×5 mL), brine (1×5 mL), dried (MgSO$_4$), filtered and concentrated in vacuo. The residue was purified by flash chromatography (10% EtOAc/hexanes) on SiO$_2$ to afford 728 mg of the title compound: $^1$H NMR (500 MHz, CDCl$_3$) δ 1.47 (d, 6H, J=5.7 Hz), 1.95-2.03 (m, 1H), 2.52-2.66 (m, 5H), 0.77 (dd, 1H, J=5.8, 16.8 Hz), 2.94-3.05 (m, 1H), 3.07-3.13 (m, 1H), 3.59-3.64 (m, 1H), 5.53 (septet, 1H, J=1H), 7.29 (d, 1H, J=7.8 Hz), 7.93 (d, 1H, J=7.8 Hz), 8.41 (s, 1H), 8.89 (s, 1H); HPLC A: rt=4.37 min, m/z=409.0 (M+H)+, 411.0 (M+H+2)+.

Step C: (R)-(5-(5-(5-Chloro-6-isopropoxypyridin-3-yl))-1,2,4-oxadiazol-3-yl)-4-methyl-1-(1H-tetrazol-5-yl)methylindane A solution of (R)-(5-(5-(5-chloro-6-isopropoxypyridin-3-yl))-1,2,4-oxadiazol-3-yl)-4-methyl-indan-1-yl)acetonitrile (500 mg, 1.22 mmol, from Step B), n-tributyltin oxide (152 mg, 0.611 mmol) and trimethylsilyl azide (1.62 mL, 12.0 mmol) in toluene (5 mL) was heated to reflux. After 15 h, the reaction mixture was cooled to ambient temperature and concentrated in vacuo. The residue was purified by flash chromatography (1.3% CH$_3$OH/CH$_2$Cl$_2$/1% NH$_4$OH) on SiO$_2$ to afford 257 mg of the title compound as a white solid: $^1$H NMR (500 MHz, DMSO-d$_6$) δ 1.38 (d, 6H, J=6.4 Hz), 1.78-1.83 (m, 1H), 2.23-2.26 (m, 1H), 2.49 (s, 3H), 2.81-2.88 (m, 1H), 2.93-2.99 (m, 1H), 3.06 (dd, 1H, J=8.9, 14.9 Hz), 3.40 (dd, 1H, J=5.7, 14.9 Hz), 3.66-3.69 (m, 1H), 5.44 (septet, 1H, J=5.5, 5.9 Hz), 7.15 (d, 1H, J=8.0 Hz), 7.77 (d, 1H, J=7.8 Hz), 8.53 (d, 1H, J=1.9 Hz), 8.91 (d, 1H, J=2.1 Hz); HPLC A: rt=4.00 min, m/z=452.0 (M+H)+, 454.0 (M+H+2)+.

Examples 140 and 141

(R)-(5-(5-(5-Chloro-6-isopropoxypyridin-3-yl))-1,2,4-oxadiazol-3-yl)-4-methyl-1-(1-methyltetrazol-5-yl) methylindane and (R)-(5-(5-(5-Chloro-6-isopropoxypyridin-3-yl))-1,2,4-oxadiazol-3-yl)-4-methyl-1-(2-methyltetrazol-5-yl)methylindane To a solution of (R)-(5-(5-(5-chloro-6-isopropoxypyridin-3-yl))-1,2,4-oxadiazol-3-yl)-4-methyl-1-(1H-tetrazol-5-yl) methylindane (50 mg, 0.111 mmol, from EXAMPLE 139) in DMF (2 mL), 60% sodium hydride (4.6 mg, 0.116 mmol) was added. After 10 min, methyl iodide was added and the reaction mixture was stirred at ambient temperature. After 15 h, the reaction mixture was partitioned between Et$_2$O and H$_2$O. The organic layer was dried (MgSO$_4$), filtered, and concentrated in vacuo. Purification by HPLC B afforded two N-methyl tetrazole regioisomers. For R)-(5-(5-(5-Chloro-6-isopropoxypyridin-3-yl))-1,2,4-oxadiazol-3-yl)-4-methyl-1-(1-methyltetrazol-5-yl)methylindane: 10.5 mg; $^1$H NMR (500 MHz, CDCl$_3$) δ 1.48 (d, 6H, J=6.1 Hz), 1.97-2.01 (m, 1H), 2.45-2.53 (m, 1H), 2.60 (s, 3H), 2.98-3.01 (m, 2H), 3.11 (dd, 1H, J=8.5, 15.1 Hz), 3.26 (dd, 1H, J=6.4, 15.1 Hz), 3.86 (s, 3H), 3.88-3.91 (m, 1H), 5.53 (septet, 1H, J=6.0, 6.2 Hz), 7.00 (d, 1H, J=7.8 Hz), 7.88 (d, 1H, J=7.8 Hz), 8.41 (d, 1H, J=1.8 Hz), 8.90 (d, 1H, J=1.6 Hz); HPLC A: rt=4.33 min, m/z=466.3 (M+H)$^+$, 468.3 (M+H+2)$^+$. For (R)-(5-(5-(5-Chloro-6-isopropoxypyridin-3-yl))-1,2,4-oxadiazol-3-yl)-4-methyl-1-(2-methyltetrazol-5-yl)methylindane: 7.7 mg; $^1$H NMR (500 MHz, CDCl$_3$) δ 1.47 (d, 6H, J=6.4 Hz), 1.91-1.99 (m, 1H), 2.33-2.40 (m, 1H), 2.58 (s, 3H), 2.88-2.94 (m, 1H), 3.01-3.04 (m, 1H), 3.08 (dd, 1H, J=9.7, 14.7 Hz), 3.41 (dd, 1H, J=5.0, 14.9 Hz), 3.75-3.81 (m, 1H), 4.36 (s, 3H), 5.51 (septet, 1H, J=6.2, 6.4 Hz), 7.19 (d, 1H, J=8.0 Hz), 7.88 (d, 1H, J=7.8 Hz), 8.40 (d, 1H, J=2.3 Hz), 8.89 (d, 1H, J=2.0 Hz); HPLC A: rt=4.33 min. m/z=466.3 (M+H)$^+$, 468.3 (M+H+2)$^+$.

Example 142

(R)-(5-(5-(5-Chloro-6-isopropoxypyridin-3-yl))-1,2,4-oxadiazol-3-yl)-4-methyl-1-(5-oxo-1,2,4-oxadiazol-3-yl)methylindane Step A: N-Hydroxy (R)-(5-(5-(5-chloro-6-isopropoxypyridin-3-yl))-1,2,4-oxadiazol-3-yl)-4-methyl-indan-1-yl)acetamidine To a solution of (R)-(5-(5-(5-chloro-6-isopropoxypyridin-3-yl))-1,2,4-oxadiazol-3-yl)-4-methyl-indan-1-yl)acetonitrile (100 mg, 0.245 mmol, from EXAMPLE 139, Step B) in methanol (3 mL) hydroxylamine hydrochloride (22 mg, 0.318 mmol) and triethylamine (51 µL, 0.367 mmol) were added and the reaction mixture was heated to reflux. After 15 h, the reaction was concentrated in vacuo and purified by flash chromatography (60, 80% EtOAc/hexanes) to afford 60 mg of starting material and 13 mg of the title compound. Subjection of the recovered starting material to the aforementioned reaction conditions afforded an additional 5.6 mg of the title compound (18.6 mg total): $^1$H NMR (500 MHz, CDCl$_3$) δ 1.46 (d, 6H, J=6.2 Hz), 1.78-1.95 (m, 1H), 2.33-2.44 (m, 2H), 2.56 (s, 3H), 2.65 (dd, 1H, J=5.6, 14.5 Hz), 2.86-2.92 (m, 1H), 2.98-3.04 (m, 1H), 3.52-3.58 (m, 1H), 4.68 (brs, 2H), 5.50 (septet, 1H, J=6.2 Hz), 7.22 (d, 1H, J=8.0 Hz), 7.87 (d, 1H, J=8.0 Hz), 8.38 (d, 1H, J=2.1 Hz), 8.87 (d, 1H, J=2.1 Hz).

Step B: (R)-(5-(5-(5-Chloro-6-isopropoxypyridin-3-yl))-1,2,4-oxadiazol-3-yl)-4-methyl-1-(5-oxo-1,2,4-oxadiazol-3-yl)methylindane A solution of N-hydroxy (R)-(5-(5-(5-chloro-6-isopropoxypyridin-3-yl))-1,2,4-oxadiazol-3-yl)-4-methyl-indan-1-yl)acetamidine (17 mg, 0.0385 mmol, from Step A) and 1,1'-carbonyldiimidazole (CDI) (38.5 mg, 0.237 mmol) were heated in a sealed tube at 80° C. After 15 h, an additional 62 mg of CDI was added and the reaction mixture was heated at 100° C. for another 15 h. The reaction mixture was concentrated in vacuo and purified by flash chromatography (4% CH$_3$OH/CH$_2$Cl$_2$/0.1% HCO$_2$H) to afford 5.1 mg of the title compound: $^1$H NMR (500 MHz, CDCl$_3$) δ 1.47 (d, 6H, J=6.2 Hz), 1.90-1.93 (m, 1H), 2.47-2.51 (m, 1H), 2.60 (s, 3H), 2.86 (dd, 1H, J=8.2, 15.4 Hz), 2.97-3.00 (m, 1H), 3.02-3.05 (m, 1H), 3.10 (dd, 1H, J=5.2, 15.4 Hz), 3.67-3.70 (m, 1H), 5.52 (septet, 1H, J=6.0, 6.4 Hz), 7.22 (d, 1H, J=7.7 Hz), 7.95 (d, 1H, J=7.8 Hz), 8.41 (d, 1H, J=2.1 Hz) 8.70 (s, 1H), 8.90 (d, 1H, J=2.1 Hz); HPLC A: rt=4.19 min, m/z=468.0 (M+H)$^+$, 470.0 (M+H+2)$^+$.

Example 143

(R)-(5-(5-(5-Chloro-6-isopropoxypyridin-3-yl))-1,2,4-oxadiazol-3-yl)-4-methyl-1-(1H-3-hydroxypyrazol-5-yl)methylindane To a solution of (R)-(5-(5-(5-chloro-6-isopropoxypyridin-3-yl))-1,2,4-oxadiazol-3-yl)-4-methyl-indan-1-yl)acetic acid (121 mg, 0.283 mmol, from EXAMPLE 110) in THF (1 mL), 1,1'-carbonyldiimidazole (53 mg, 0.325 mmol) and DMAP (1 crystal) was added and the resultant solution was stirred for 16 h at ambient temperature (solution A). In a separate flask, potassium ethyl malonate (53 mg, 0.311 mmol) was dissolved acetonitrile (1 mL), treated with trimethylsilyl chloride (39 µL, 0.311 mmol) and stirred at ambient temperature (solution B). After 15 h, the contents of solution B were cooled to 0° C. and treated with 1,8-diazabicyclo (5.4.0)undec-7-ene (92 µL, 0.616 mmol), followed by the contents of solution A. The reaction mixture was then warmed to ambient temperature, stirred for 16 h and partitioned between EtOAc and 5% Citric acid. The organic layer was washed with H$_2$O, sat. NaHCO$_3$, dried over MgSO$_4$ and concentrated in vacuo. Purification by flash chromatography (10% EtOAc/hexanes) on SiO$_2$ afforded 23 mg of a colorless film, which was dissolved in EtOH (1 mL) and treated with hydrazine (4 drops) and stirred at ambient temperature. After 15 h, the mixture was filtered, treated with methanol and filtered to afford 2.0 mg of the title compound: $^1$H NMR (500 MHz, DMSO-d$_6$) δ 1.38 (d, 6H, J=6.2 Hz), 1.73-1.75 (m, 1H), 2.20-2.22 (m, 1H), 2.49 (s, 3H), 2.62-2.70 (m, 1H), 2.80-2.84 (m, 1H), 2.90-2.95 (m, 2H), 3.46-3.49 (m, 1H), 5.44 (septet, 1H, J=6.2 Hz), 7.16 (d, 1H, J=6.6 Hz), 7.77 (d, 1H, J=7.5 Hz), 8.53 (d, 1H, J=2.0 Hz), 8.91 (d, 1H, J=2.1 Hz); HPLC A: rt=3.63 min, m/z=466.1 (M+H)$^+$, 468.1 (M+H+2)$^+$.

Example 144

(R)-(5-(5-(5-Chloro-6-isopropoxypyridin-3-yl))-oxazol-2-yl)-4-methyl-indan-1-yl)acetic acid Step A:
2-Isopropoxy-3-chloro-5-(2-chloroacetyl)pyridine A mixture of 5-chloro-6-isopropoxynicotinic acid (1.0 g, 4.64 mmol) and thionyl chloride (5 mL) was heated to reflux. After 1.5 hr, the reaction mixture was cooled to ambient temperature, concentrated in vacuo and azeotroped with toluene (2×10 mL). The resultant acid chloride was then added to an ethereal solution of diazomethane (~8.8 mmol) at 0° C. The reaction mixture was stirred for 1.5 hr at 0° C., warmed to ambient temperature, then recooled to 0° C. A solution of 4.0 M HCl in dioxane (4 mL) was added dropwise and the reaction warmed to ambient temperature. The organic layer was washed with 2.0 N HCl (2×10 mL), saturated NaHCO$_3$ (2×10 mL), brine (1×10 mL), and then dried over MgSO$_4$. The mixture was filtered, the filtrate concentrated in vacuo, and the residue purified by flash chromatography (5% EtOAc/hexanes) on SiO$_2$ to give 1.15 g of the title compound as a white solid: $^1$H NMR (500 MHz, CDCl$_3$) δ 1.41 (d, 6H, J=6.2

Hz), 4.58 (s, 2H), 5.46 (septet, 1H, J=6.2 Hz), 8.18 (d, 1H, J=2.3 Hz), 8.64 (d, 1H, J=2.3 Hz).

Step B:
2-Isopropoxy-3-chloro-5-(2-aminoacetyl)pyridine, hydrochloride salt

To a solution of 2-isopropoxy-3-chloro-5-(2-chloroacetyl) pyridine (275 mg, 1.11 mmol, from Step A) in DMF (2.5 mL), lithium azide (60 mg, 1.22 mmol) was added in one portion and the resultant solution was stirred at ambient temperature. After 1.5 hr, the reaction mixture was diluted with EtOAc (10 mL) and washed with $H_2O$ (5×3 mL) and brine (1×3 mL). The organic layer was dried over $MgSO_4$, filtered and concentrated in vacuo to afford the α-azido ketone as a white solid, 217 mg. To this material and 10% Pd—C (40 mg), methanol (5 mL) was added followed by 1.0 M $HCl/Et_2O$ (1.0 mL) and one atmosphere of $H_2$. After 15 min, the mixture was filtered through Celite® and concentrated in vacuo. The residue was triturated with $Et_2O$ to give 214 mg of the title compound as a white powder: $^1H$ NMR (500 MHz, $CD_3OD$) δ 1.40 (d, 6H, J=6.2 Hz), 4.54 (s, 2H), 5.51 (septet, 1H, J=6.2 Hz), 8.30 (d, 1H, J=2.1 Hz), 8.74 (d, 1H, J=2.3 Hz).

Step C: Methyl (R)-(5-formyl-4-methyl-indan-1-yl) acetate

To a solution of methyl (R)-(5-cyano-4-methyl-indan-1-yl)acetate (1.00 g, 4.36 mmol, from EXAMPLE 110, Step J) in pyridine (28 mL), acetic acid (15 mL), $H_2O$ (15 mL) and $NaH_2PO_2$ (3.07 g, 34.9 mmol) Rainey nickel was added (1.0 g) and the mixture was heated to 50° C. After 5 hr, the reaction was concentrated in vacuo and filtered through Celite®. The filtrate was concentrated in vacuo and partitioned between EtOAc (150 mL) and $H_2O$ (50 mL). The organic layer was washed with 5.0 N HCl (7×50 mL), sat. $NaHCO_3$ (2×50 mL), brine (1×50 mL) and dried ($MgSO_4$). The mixture was filtered, concentrated in vacuo and purified by flash chromatography (10% EtOAc/hexanes) to give 882 mg of the title compound as a white solid: $^1H$ NMR (500 MHz, $CDCl_3$) δ 1.76-1.84 (m, 1H), 2.41-2.51 (m, 2H), 2.57 (s, 3H), 2.78 (dd, 1H, J=5.5, 15.6 Hz), 2.81-2.87 (m 1H), 2.93-2.99 (m, 1H), 3.61-3.67 (m, 1H), 3.72 (s, 3H), 7.16 (d, 1H, J=7.8 Hz), 7.63 (d, 1H, 7.8 Hz), 10.2 (s, 1H).

Step D: Methyl (R)-(5-carboxy-4-methyl-indan-1-yl) acetate

To an ice-cold solution of methyl (R)-(5-formyl-4-methyl-indan-1-yl)acetate (872 mg, 3.76 mmol, from Step C), $NaH_2PO_4$ (150 mg) and 30% $H_2O_2$ (500 μL) in acetonitrile (10 mL) and $H_2O$ (2.5 mL), a solution of $NaClO_2$ (615 mg) in $H_2O$ (4 mL) was added dropwise and the reaction mixture was allowed to warm to ambient temperature over 1 hr. After another hour, $NaHSO_3$ (1.0 g) was added and the mixture was partitioned between EtOAc (30 mL) and 2.0 N HCl (15 mL). The layers were separated and the organic layer was washed with $H_2O$ (2×15 mL), brine (1×15 mL) dried ($MgSO_4$) and filtered. The filtrate was concentrated in vacuo to give 854 mg of the title compound as a white solid: $^1H$ NMR (500 MHz, $CDCl_3$) δ 1.74-1.82 (m, 1H), 2.40-2.50 (m, 2H), 2.56 (s, 3H), 2.78 (dd, 1H, J=5.5, 15.5 Hz), 2.82-2.93 (m, 1H), 2.94-2.99 (m, 1H), 3.61-3.66 (m, 1H), 3.73 (s, 3H), 7.07 (d, 1H, J=7.8 Hz), 7.89 (d, 1H, J=8.0 Hz), 10.8-12.0 (br, s 1H); HPLC A: rt=2.74 min, m/z=249 $(M+H)^+$.

Step E: Methyl (R)-(5-(N-((5-chloro-6-isopropoxy) nicotinoyl)methyl)carboxamido)-4-methyl-indan-1-yl)acetate To a solution of methyl (R)-(5-carboxy-4-methyl-indan-1-yl)acetate (103 mg, 0.415 mmol, from Step D) in $CH_2Cl_2$ (2 mL) and 1 drop DMF cooled to 0° C., $COCl_2$ (1.06 μL, 1.25 mmol) was added. After 30 min, the reaction mixture was concentrated in vacuo and azeotroped with benzene (3×1 mL). The resultant residue was dissolved in $CH_2Cl_2$ (2 mL) and cooled to 0° C. 2-Isopropoxy-3-chloro-5-(2-aminoacetyl)pyridine, hydrochloride salt (116 mg, 0.436 mmol, from Step B) and pyridine (71 μL, 0.872 mmol) were added and the cooling bath removed. After 15 hr, the reaction mixture was concentrated in vacuo and the residue dissolved in EtOAc (10 mL). The organic layer was washed with 1.0 N HCl (2×3 mL), sat. $NaHCO_3$ (1×3 mL), brine (1×3 mL) and dried ($MgSO_4$). The mixture was filtered, concentrated in vacuo and purified by flash chromatography (15, 30% EtOAc/Hexanes) on $SiO_2$ to afford 134 mg of the title compound as a pale-yellow solid: $^1H$ NMR (500 MHz, $CDCl_3$) δ 1.43 (d, 6H, J=6.2 Hz), 1.74-1.82 (m, 1H), 2.38 (s, 3H), 2.39-2.49 (m, 2H), 2.76 (dd, 1H, J=5.5, 15.5 Hz), 2.80-2.85 (m, 1H), 2.89-2.95 (m, 1H), 3.60-3.66 (m, 1H), 3.73 (s, 3H), 4.87 (d, 2H, J=4.4 Hz), 5.48 (septet, 1H, J=6.2 Hz), 6.76 (t, 1H, J=4.2 Hz), 7.05 (d, 1H, J=7.8 Hz), 7.31 (d, 1H, J=7.7 Hz), 8.21 (d, 1H, J=2.1 Hz), 8.69 (d, 1H, J=2.0 Hz).

Step F: Methyl (R)-(5-(5-(5-chloro-6-isopropoxypyridin-3-yl))-oxazol-2-yl)-4-methyl-indan-1-yl)acetate To a solution of methyl (R)-(5-(N-((5-chloro-6-isopropoxy)nicotinoyl)methyl)carboxamido)-4-methyl-indan-1-yl)acetate (32.0 mg, 0.0697 mmol, from Step E) in toluene (1.0 mL), pyridine (56 μL, 0.139 mmol) and Burgess' reagent (33 mg, 0.697 mmol) were added and the reaction mixture was heated to 100° C. After 2 hr, additional pyridine (56 μL) and Burgess' reagent (33 mg) were added. The reaction mixture was heated at 80° C. for another 2 hr, and cooled to ambient temperature. The residue was dissolved in EtOAc (5 mL) and washed with 2.0 N HCl (2×2 mL), sat. $NaHCO_3$ (1×2 mL), brine (1×2 mL) and dried ($MgSO_4$). The mixture was filtered, concentrated in vacuo and purified by preparative tlc (5% EtOAc/Hexanes) to afford 17.0 mg of the title compound as a white solid: $^1H$ NMR ($CDCl_3$) δ 1.42 (d, 6H, J=6.2 Hz), 1.77-1.85 (m, 1H), 2.43-2.52 (m, 2H), 2.63 (s, 3H), 2.80 (dd, 1H, J=5.5, 15.5 Hz), 2.86-2.91 (m, 1H), 2.92-3.03 (m, 1H), 3.65-3.70 (m, 1H), 3.74 (s, 3H), 5.40 (septet, 1H, J=6.2 Hz), 7.13 (d, 1H, J=8.0 Hz), 7.39 (s, 1H), 7.86 (d, 1H, J=7.8 Hz), 7.90 (d, 1H, J=2.0 Hz), 8.39 (d, 1H, J=2.3 Hz); HPLC/MS 441 $(M+H)^+$, 442 $(M+H+2)^+$.

Step G: (R)-(5-(5-(5-Chloro-6-isopropoxypyridin-3-yl))-oxazol-2-yl)-4-methyl-indan-1-yl)acetic acid To a solution of methyl (R)-(5-(5-(5-chloro-6-isopropoxy-pyridin-3-yl))-oxazol-2-yl)-4-methyl-indan-1-yl)acetate (17.0 mg, 0.0386 mmol, from Step F) in THF (2.0 mL), 5.0 N NaOH was added (50 μL) and the reaction mixture was heated to reflux. After 2 hr, the reaction mixture was cooled to ambient temperature and partitioned between EtOAc (3 mL) and 5% citric acid (3 mL). The layers were separated and the organic layer was washed with $H_2O$ (3×1 mL), brine (1×1 mL), dried over $MgSO_4$, filtered and concentrated in vacuo. The residue was purified by HPLC B to afford 17.0 mg of the title compound as a lemon-yellow solid: $^1H$ NMR (500 MHz, $CD_3OD$) δ 1.39 (d, 6H, J=6.1 Hz), 1.77-1.85 (m, 1H), 2.40-2.47 (m, 2H), 2.58 (s, 3H), 2.78 (dd, 1H, J=5.5, 15.5 Hz), 2.85-2.91 (m, 1H), 2.98-3.04 (m, 1H), 3.59-3.62 (m, 1H), 5.41 (septet, 1H, J=6.2 Hz), 7.20 (d, 1H, J=8.0 Hz), 7.59 (s, 1H), 7.79 (d, 1H, J=8.0 Hz), 8.10 (d, 1H, J=2.3 Hz), 8.45 (d, 1H, J=2.3 Hz); HPLC A: rt=4.02 min, m/z=427 (M+H)$^+$, 429 (M+H+2)$^+$.

Example 145

(R)-(5-(5-(5-Chloro-6-isopropoxypyridin-3-yl))-thiazol-2-yl)-4-methyl-indan-1-yl)acetic acid Step A: Methyl (R)-(5-(5-(5-Chloro-6-isopropoxypyridin-3-yl))-thiazol-2-yl)-4-methyl-indan-1-yl)acetate In a sealed tube, Lawesson's reagent (189 mg, 0.466 mmol) was added to a solution methyl (R)-(5-(N-((5-chloro-6-isopropoxy)nicotinoyl)methyl)carboxamido)-4-methyl-indan-1-yl)acetate (214 mg, 0.466 mmol, from EXAMPLE 144, Step E) in THF (3.5 mL). The contents were sealed and heated to 100° C. After 20 hr, the reaction mixture was concentrated in vacuo and purified by flash chromatography (0, 2, 4% acetone/hexanes) on SiO$_2$ to afford the 103 mg of the title compound as an off-white solid: $^1$H NMR (CDCl$_3$) δ 1.40 (d, 6H, J=6.2 Hz), 1.76-1.84 (m, 1H), 2.40-2.49 (m, 5H), 2.77 (dd, 1H, J=5.6, 15.5 Hz), 2.82-2.88 (m, 1H), 2.93-2.98 (m, 1H), 3.62-3.72 (m, 1H), 3.72 (s, 3H), 5.37 (septet, 1H, J=6.2 Hz), 7.07 (d, 1H, J=7.8 Hz), 7.49 (d, 1H, J=8.0 Hz), 7.82 (d, 1H, J=2.0 Hz), 7.93 (s, 1H), 8.25 (d, 1H, J=2.0 Hz).

Step B: (R)-(5-(5-(5-Chloro-6-isopropoxypyridin-3-yl))-thiazol-2-yl)-4-methyl-indan-1-yl)acetic acid The title compound was prepared from methyl (R)-(5-(5-(5-chloro-6-isopropoxypyridin-3-yl))-thiazol-2-yl)-4-methyl-indan-1-yl)acetate (from Step A) using a procedure analogous to that described in EXAMPLE 144, Step G: $^1$H NMR (500 MHz, CD$_3$OD) δ 1.38 (d, 6H, J=6.1 Hz), 1.78-1.86 (m, 1H), 2.41-2.47 (m, 2H), 2.49 (s, 3H), 2.77 (dd, 1H, J=5.8, 15.8 Hz), 2.85-2.91 (m, 1H), 2.98-3.04 (m, 1H), 3.58-3.64 (m, 1H), 5.41 (septet, 1H, J=6.2 Hz), 7.16 (d, 1H, J=8.0 Hz), 7.49 (d, 1H, J=7.8 Hz), 7.84 (s, 1H), 8.27 (d, 1H, J=2.3 Hz), 8.65 (d, 1H, J=2.3 Hz); HPLC A: rt=4.19 min, m/z=443 (M+H)$^+$, 445 (M+H+2)$^+$.

Example 146

(R)-(5-(4-(5-Chloro-6-isopropoxypyridin-3-yl))-thiazol-2-yl)-4-methyl-indan-1-yl)acetic acid Step A: Methyl/ethyl (R)-(5-thiocarboxamido-4-methyl-indan-1-yl)acetate In a scintillation vial, methyl (R)-(5-cyano-4-methyl-indan-1-yl)acetate (1.12 g, 4.88 mmol, from EXAMPLE 110, Step J) was dissolved in diethyldithiophosphate (3.0 mL), H$_2$O, (6 drops), sealed and heated to 50° C. After 15 h, the reaction mixture was diluted with EtOAc (15 mL) and washed with saturated NaHCO$_3$ (5×5 mL), brine (1×5 mL), and then dried over MgSO$_4$. The mixture was filtered, the filtrate concentrated in vacuo, and the residue purified by flash chromatography (10, 20, 30% EtOAc/hexanes) on SiO$_2$ to give 1.01 g of the title compound as a white solid: $^1$H NMR (500 MHz, CDCl$_3$) indicated a 4:1 mixture of methyl:ethyl esters. For methyl ester: δ 1.72-1.79 (m, 1H), 2.36 (s, 3H), 2.37-2.40 (m, 1H), 2.41 (dd, 1H, J=9.2, 15.6 Hz), 2.73 (dd, 1H, J=5.5, 15.6 Hz) 2.74-2.81 (m, 1H), 2.88 (ddd, 1H, J=5.1, 8.7, 13.8 Hz), 3.55-3.61, (m, 1H), 3.71 (s, 3H), 6.94 (brs, 1H), 7.01 (d, 1H, J=7.8 Hz), 7.22 (d, 1H, J=7.8 Hz), 7.77 (br, s, 1H).

Step B: Methyl (R)-(5-(4-(5-chloro-6-isopropoxypyridin-3-yl))-thiazol-2-yl)-4-methyl-indan-1-yl)acetate In a sealed tube, a solution of methyl/ethyl (R)-(5-thiocarboxamido-4-methyl-indan-1-yl)acetate (45.0 mg, 0.171 mmol, from Step A) in dioxane (1.5 mL) was treated with 2-isopropoxy-3-chloro-5-(2-chloroacetyl)pyridine (47.0 mg, 0.188 mmol, from EXAMPLE 144, Step A). The resulting mixture was stirred for 1 h at 50° C., and at reflux for 15 h. The reaction was cooled to ambient temperature, concentrated in vacuo, and purified by flash chromatography (2.4% EtOAc/hexanes) on SiO$_2$ to afford 54.5 mg of the title compound as a colorless film. $^1$H NMR (500 MHz, CDCl$_3$), (For methyl ester): δ 1.42 (d, 6H, J=6.2 Hz), 1.77-1.84 (m, 1H), 2.41-2.51 (m, 2H), 2.53 (s, 3H), 2.79 (dd, 1H, J=5.7, 15.4 Hz), 2.85-2.90 (m, 1H), 2.91-3.02 (m, 1H), 3.63-3.70 (m, 1H), 3.73 (s, 3H), 5.41 (septet, 1H, J=6.2 Hz), 7.09 (d, 1H, J=8.0 Hz), 7.42 (s, 1H), 7.53 (d, 1H, J=7.8 Hz), 8.20 (d, 1H, J=2.1 Hz), 8.62 (d, 1H, J=2.0 Hz).

Step C: (R)-(5-(4-(5-Chloro-6-isopropoxypyridin-3-yl))-thiazol-2-yl)-4-methyl-indan-1-yl)acetic acid To a solution of methyl (R)-(5-(4-(5-chloro-6-isopropoxypyridin-3-yl))-thiazol-2-yl)-4-methyl-indan-1-yl)acetate (54.5 mg, 0.119 mmol, from Step B) in THF (1.0 mL), 1.0 N sodium hydroxide (358 μL, 0.358 mmol) was added and the reaction mixture was heated to reflux. After 4 h, the reaction mixture was cooled to ambient temperature and concentrated in vacuo. The residue was partitioned between EtOAc (5 mL) and 5% citric acid (2 mL), and the organic layer was washed with H$_2$O (2×2 mL), brine (1×2 mL), dried (MgSO$_4$), filtered and concentrated in vacuo. Purification by HPLC B afforded 27.0 mg of the title compound as a white solid: $^1$H NMR (500 MHz, CD$_3$OD) δ 1.38 (d, 6H, J=6.1 Hz), 1.78-1.86 (m, 1H), 2.41-2.47 (m, 2H), 2.49 (s, 3H), 2.77 (dd, 1H, J=5.8, 15.8 Hz), 2.85-2.91 (m, 1H), 2.98-3.04 (m, 1H), 3.58-3.64 (m, 1H), 5.41 (septet, 1H, J=6.2 Hz), 7.16 (d, 1H, J=8.0 Hz), 7.49 (d, 1H, J=7.8 Hz), 7.84 (s, 1H), 8.27 (d, 1H, J=2.3 Hz), 8.65 (d, 1H, J=2.1 Hz).

Example 147

(R)-(5-(5-(3-Cyano-4-isopropoxyphenyl)thiazol-2-yl)-4-methyl-indan-1-yl)acetic acid Step A: Methyl/ethyl (R)-(5-(thiazol-2-yl)-4-methyl-indan-1-yl)acetate To a solution of methyl/ethyl (R)-(5-thiocarboxamido-4-methyl-indan-1-yl)acetate (542 mg, ~2.00 mmol, from EXAMPLE 146, Step A) in dimethoxyethane (2.0 mL) chloroacetaldehyde (45% in H$_2$O, 8.00 mmol, 1.43 mL) and potassium bicarbonate (824 mg, 8.00 mmol) were added and the resulting mixture was stirred at ambient temperature. After 15 h, the reaction mixture was filtered and the filtrate was concentrated in vacuo. The residue was dissolved in EtOAc (15 mL) and washed with H$_2$O (3×5 mL), brine (1×5 mL) and dried over MgSO$_4$. The mixture was filtered, and the filtrate dissolved in CH$_2$Cl$_2$ (5 mL) and cooled to 0° C. Triethylamine (613 μL, 4.40 mmol) was added followed by dropwise addition of trifluoroacetic anhydride (311 μL, 2.20 mmol). After 15 min, the organic layer was washed with NaHCO3 (1×5 mL), brine (1×5 mL), dried over MgSO$_4$ and concentrated in vacuo. The residue was purified by flash chromatography (5, 7% EtOAc/hexanes) on SiO$_2$ to give 583 mg the title compound as a yellow film. For methyl ester: $^1$H NMR (500 MHz, CDCl$_3$) δ 1.76-1.83 (m, 1H), 2.40-2.50 (m, 5H), 2.79 (dd, 1H, J=5.7, 15.4 Hz), 2.83-2.89, (m, 1H), 2.94-3.03 (m, 1H), 3.62-3.68 (m, 1H), 3.72 (s, 3H), 7.07 (d, 1H, J=7.8 Hz), 7.35 (d, 1H, J=3.2 Hz), 7.47 (d, 1H, J=7.8 Hz), 7.89 (d, 1H, J=3.2 Hz).

Step B: Methyl/ethyl (R)-(5-(5-bromo-thiazol-2-yl)-4-methyl-indan-1-yl)acetate To a solution of methyl/ethyl (R)-(5-(thiazol-2-yl)-4-methyl-indan-1-yl)acetate (379 mg, ~1.44 mmol, from Step B) in acetonitrile (7.0 mL), N-bromosuccinimide (261 mg, ~1.44 mmol) was added and the resulting solution was heated to 50° C. After 1.5 h, the reaction mixture was cooled to ambient temperature and concentrated in vacuo. The residue was dissolved in EtOAc (20 mL) and washed with NaHCO$_3$, (2×10 mL) brine (1×10 mL), and dried over MgSO$_4$. The mixture was filtered, concentrated in vacuo and purified by flash chromatography (2, 5% EtOAc/hexanes) on SiO$_2$ to give 278 mg of the title compound as yellow oil. For the methyl ester: $^1$H NMR (500 MHz, CDCl$_3$) δ 1.76-1.84 (m, 1H), 2.41-2.50 (m, 5H), 2.77 (dd, 1H, J=5.8, 15.6 Hz), 2.82-2.89 (m, 1H), 2.92-3.02 (m, 1H), 3.65-3.71 (m, 1H), 3.73 (s, 3H), 7.08 (d, 1H, J=8.7 Hz), 7.40 (d, 1H, J=8.8 Hz), 7.76 (s, 1H).

Step C: Methyl/ethyl (R)-(5-(5-(3-cyano-4-fluorophenyl)thiazol-2-yl)-4-methyl-indan-1-yl)acetate A solution of methyl/ethyl (R)-(5-(5-bromo-thiazol-2-yl)-4-methyl-indan-1-yl)acetate (252 mg, ~0.690 mmol, from Step B) and 3-cyano-4-fluorophenylboronic acid (125 mg, 0.757 mmol) in THF (10 mL) and 1.0 M aqueous Na$_2$CO$_3$ (2.5 mL), (167 mg, 3.98 mmol) was degassed with argon. Pd(PPh$_3$)$_4$ (4.1 mg, 0.00355 mmol) was added. The reaction mixture was heated to 80° C. After 1.5 h, the reaction mixture was cooled to ambient temperature and partitioned between EtOAc and H$_2$O. The organic layer was washed with H$_2$O, brine, dried over MgSO$_4$, filtered and concentrated in vacuo. Purification of the residue by flash chromatography (5, 10, 15% EtOAc/hexanes) on SiO2 afforded 217 mg of the title compound as a yellow solid. For the methyl ester: $^1$H NMR (500 MHz, CDCl$_3$) δ 1.88-1.85 (m, 1H), 2.42-2.52 (m, 5H), 2.79 (dd, 1H, J=5.8, 15.6 Hz), 2.82-2.91 (m, 1H), 2.96-3.02 (m, 1H), 3.63-3.69 (m, 1H), 3.73 (s, 3H), 7.10 (d, 1H, J=7.7 Hz), 7.28 (t, 1H, J=8.5 Hz), 7.51 (d, 1H, J=7.7 Hz), 7.79-7.83 (m, 2H), 8.01 (s, 1H).

Step D: (R)-(5-(5-(3-cyanoisopropoxyphenyl)thiazol-2-yl)-4-methyl-indan-1-yl)acetic acid In a sealed vial, methyl/ethyl (R)-(5-(5-(3-cyano-4-fluorophenyl)thiazol-2-yl)-4-methyl-indan-1-yl)acetate (from Step C) was dissolved in THF (1.5 mL) and i-PrOH (150 μL). Sodium hydride (60% dispersion in mineral oil, 11.3 mg, 0.283 mmol) was added in one portion, the vial was capped and heated to reflux. After 2 h, the reaction mixture was cooled to ambient temperature and partitioned between EtOAc (5 mL) and 5% citric acid (2 mL). The layers were separated, and the organic layer was washed with H$_2$O (1×2 mL), brine (1×2 mL) and dried MgSO$_4$. The mixture was filtered, concentrated in vacuo, and purified by HPLC B to afford the title compound as a white solid: $^1$H NMR (500 MHz, CD$_3$OD) δ 1.41 (d, 1H, J=6.0 Hz), 1.78-1.85 (m, 1H), 2.43-2.47 (m, 5H), 2.77 (dd, 1H, J=5.7, 15.6 Hz), 2.84-2.90 (m, 1H), 2.97-3.03 (m, 1H), 3.59-3.62 (m, 1H), 4.78-4.82 (m, 1H), 7.17 (d, 1H, J=8.0 Hz), 7.26 (d, 1H, J=8.9 Hz), 7.44 (d, 1H, J=8.7 Hz), 7.89 (dd, 1H, J=2.3, 8.7 Hz), 7.94 (d, 1H, J=2.3 Hz), 8.10 (s, 1H); HPLC B: rt=3.78 min, m/z=433.2 (M+H)$^+$, 434.2 (M+H+2)$^+$.

Examples 148-160

The following compounds were prepared using procedures analogous to those described in Example 147, substituting the appropriate alcohol from isopropanol in Step D.

| EXAMPLE | Ar | HPLC B (min) | ESI-MS (M + H)$^+$ |
|---|---|---|---|
| 148 | 4-MeO, 3-CN phenyl | 3.48 | 405.2 |

$^1$H NMR (500 MHz, CD$_3$OD) δ 1.79-1.86(m, 1H), 2.41-2.48(m, 5H), 2.77(dd, 1H, J = 5.8, 15.8 Hz), 2.84-2.91(m, 1H), 2.96-3.03(m, 1H), 3.59-3.62(m, 1H), 4.00(s, 3H), 7.17(d, 1H, J = 8.0 Hz), 7.27(d, 1H, J = 8.7 Hz), 7.45(d, 1H, J = 8.8 Hz), 7.92(dd, 1H, J = 2.3, 8.7 Hz), 7.97(d, 1H, J = 2.3 Hz), 8.11(s, 1H).

| 149 | 4-(F$_3$CCH$_2$O), 3-CN phenyl | 3.62 | 473.1 |

$^1$H NMR (500 MHz, DMSO-d$_6$) δ 1.71-1.76(m, 1H), 2.32-2.45(m, 5H), 2.74-2.85(m, 2H), 2.91-2.97(m, 1H), 5.04(q, 2H, J = 8.6 Hz), 7.19(d, 1H, J = 7.8 Hz), 7.47(d, 1H, J = 8.8 Hz), 7.51(d, 1H, J = 7.8Hz), 8.03(d, 1H, J = 2.0 Hz), 8.04(dd, 1H, J = 2.0, 8.8 Hz), 8.23(d, 1H, J = 2.0 Hz), 8.37(s, 1H).

| EXAMPLE | Ar | HPLC B (min) | ESI-MS (M + H)+ |
|---|---|---|---|
| 150 | 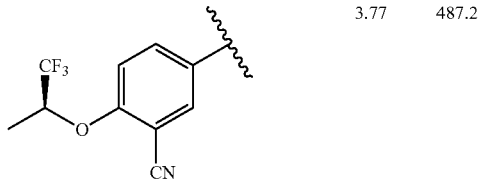 | 3.77 | 487.2 |

¹H NMR (500 MHz, DMSO-d₆) δ 1.50(d, 3H, J = 6.4 Hz), 1.67-1.75(m, 1H), 2.31-2.40 (m, 2H), 2.45(s, 3H), 2.75 dd, 1H, J = 5.9, 15.9 Hz), 2.79-2.84(m, 1H), 2.91-2.96(m, 1H), 3.47-3.53(m, 1H), 5.55(septet, 1H, J = 6.4 Hz), 7.19(d, 1H, J = 7.7 Hz), 7.51(d, 1H, J = 7.8 Hz), 7.57(d, 1H, J = 8.9 Hz), 8.00(dd, 1H, J = 2.3, 9.0 Hz), 8.21(d, 1H, J = 2.3 Hz), 8.37(s, 1H).

| 151 | 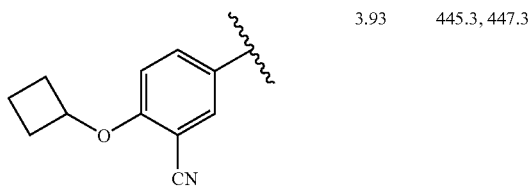 | 3.93 | 445.3, 447.3 |

¹H NMR (500 MHz, acetone-d₆) δ 1.74-1.85(m, 3H), 1.89-1.93(m, 1H), 2.19-2.25(m, 3H), 2.42-2.50(m, 1H), 2.52(s, 3H), 2.54-2.59(m, 1H), 2.85(dd, 1H, J = 5.2, 16.0 Hz), 2.87-2.92(m, 1H), 2.99-3.03(m, 1H), 3.60-3.63(m, 1H), 4.95-4.97(m, 1H), 7.18 (d, 1H, J = 8.7 Hz), 7.24(d, 1H, J = 7.8 Hz), 7.57(d, 1H, J = 7.8 Hz), 7.93(dd, 1H, J = 2.0, 8.7 Hz), 8.05(d, 1H, J = 2.1 Hz), 8.16(s, 1H).

| 152 | 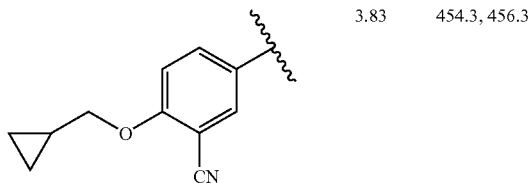 | 3.83 | 454.3, 456.3 |

¹H NMR (500 MHz, acetone-d₆) δ 0.45(d, 2H, J = 2.5 Hz), 0.67(d, 2H, J = 6.2 Hz), 0.87-0.89(m, 1H), 1.81-1.85(m, 1H), 2.45-2.50(m, 2H), 2.53(s, 3H), 2.71-2.91(m, 2H), 2.92-3.02(m, 1H), 3.61-3.64(m, 1H), 4.11(d, 2H, J = 6.1 Hz), 7.25(d, 1H, J = 7.3 Hz), 7.32(d, 1H, J = 9.4 Hz), 7.58(d, 1H, J = 8.0 Hz), 7.95(d, 1H, J = 6.2 Hz), 8.05(s, 1H), 8.24(s, 1H).

| 153 | 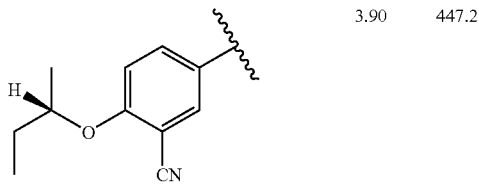 | 3.90 | 447.2 |

¹H NMR (500 MHz, CD₃OD) δ 1.01(t, 3H, J = 7.4 Hz), 1.34(d, 3H, J = 6.2 Hz), 1.67-1.81(m, 3H), 2.37-2.43(m, 5H), 2.74(dd, 1H, J = 5.8, 15.8 Hz), 2.78-2.84(m, 1H), 2.91-2.97(m, 1H), 3.52-3.59(m, 1H), 4.55(sextet, 1H, J = 6.1 Hz), 7.10(d, 1H, J = 7.7 Hz), 7.18(d, 1H, J = 8.9 Hz), 7.38(d, 1H, J = 8.7 Hz), 7.79(dd, 1H, J = 2.4, 8.7 Hz), 7.85(d, 1H, J = 8.7 Hz), 8.03(s, 1H).

| 154 | 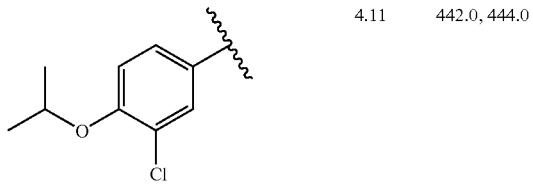 | 4.11 | 442.0, 444.0 |

¹H NMR (500 MHz, CD₃OD) δ 1.37(d, 6H, J = 6.2 Hz), 1.78-1.85(m, 1H), 2.42(s, 3H), 2.43-2.47(m, 2H), 2.77(dd, 1H, J = 5.9, 15.7 Hz), 2.83-2.90(m, 1H), 2.96-3.03 (m, 1H), 3.57-3.63(m, 1H), 4.69(septet, 1H, J = 6.2 Hz), 7.13(d, 1H, J = 8.4 Hz), 7.16(d, 1H, J = 7.7 Hz), 7.43(d, 1H, J = 7.8 Hz), 7.54(dd, 1H, J = 2.3, 8.7 Hz), 7.70 (d, 1H, J = 2.3 Hz), 8.05(s, 1H).

| EXAMPLE | Ar | HPLC B (min) | ESI-MS (M + H)+ |
|---|---|---|---|
| 155 | 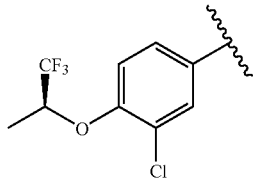 | 4.11 | 496.1, 498.1 |

$^1$H NMR (500 MHz, DMSO-d$_6$) δ 1.50(d, 3H, J = 6.4 Hz), 1.79-1.83(m, 1H), 2.33-2.52(m, 2H), 2.43(s, 3H), 2.76(dd, 1H, J = 5.7, 15.3 Hz), 2.81-2.94(m, 1H), 2.95-3.08(m, 1H), 3.59-3.62(m, 1H), 5.00-5.10(m, 1H), 7.17(d, 1H, J = 7.8 Hz), 7.27(d, 1H, J = 8.7 Hz), 7.44(d, 1H, J = 7.8 Hz), 7.59(dd, 1H, J = 2.5, 8.9 Hz), 7.76(d, 1H, J = 2.3 Hz), 8.08(s, 1H).

| | | | |
|---|---|---|---|
| 156 | 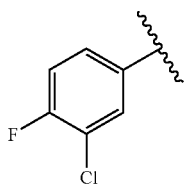 | 3.95 | 402.1, 404.1 |

$^1$H NMR (500 MHz, DMSO-d$_6$) δ 1.79-1.94(m, 1H), 2.41-2.48(m, 2H), 2.44(s, 3H), 2.78(dd, 1H, J = 5.7, 15.8 Hz), 2.84-2.90(m, 1H), 2.97-3.03(m, 1H), 3.60-3.63(m, 1H), 7.18(d, 1H, J = 7.8 Hz), 7.33(t, 1H, J = 8.8 Hz), 7.45(d, 1H, J = 8.0 Hz), 7.62-7.65(m, 1H), 7.83(dd, 1H, J = 2.3, 6.8 Hz), 8.13(s, 1H).

| | | | |
|---|---|---|---|
| 157 | 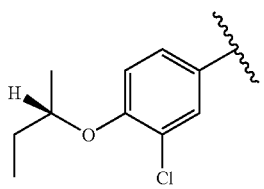 | 4.28 | 458.1, 460.1 |

$^1$H NMR (500 MHz, DMSO-d$_6$) δ 1.03(t, 3H, J = 7.4 Hz), 1.34(d, 3H, J = 6.0 Hz), 1.69-1.81(m, 1H), 1.82-1.85(m, 2H), 2.46-2.48(m, 2H), 2.44(s, 3H), 2.79(dd, 1H, J = 5.7, 15.8 Hz), 2.86-2.90(m, 1H), 2.98-3.01(m, 1H), 3.60-3.63(m, 1H), 4.47-4.51(m, 1H), 7.14(d, 1H, J = 8.7 Hz), 7.18(d, 1H, J = 7.8 Hz), 7.45(d, 1H, J = 7.7 Hz), 7.55(dd, 1H, J = 2.3, 8.5 Hz), 7.71(d, 1H, J = 2.3 Hz), 8.05(s, 1H).

| | | | |
|---|---|---|---|
| 158 | 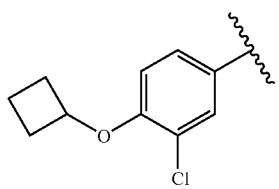 | 4.28 | 454.2, 456.2 |

$^1$H NMR (500 MHz, CD$_3$OD) δ 1.73-1.84(m, 3H), 1.86-1.90(m, 1H), 2.16-2.22(m, 3H), 2.42(s, 3H), 2.44-2.49(m, 1H), 2.50-2.54(m, 1H), 2.76(dd, 1H, J = 5.7, 15.3 Hz), 2.85-2.90(m, 1H), 2.96-3.01(m, 1H), 3.59-3.62(m, 1H), 4.77-4.82(m, 1H), 6.97(d, 1H, J = 8.7 Hz), 7.17(d, 1H, J = 7.8 Hz), 7.43(d, 1H, J = 7.7 Hz), 7.52(dd, 1H, J = 2.3, 8.7 Hz), 7.69(d, 1H, J = 2.0 Hz), 8.02(s, 1H).

| | | | |
|---|---|---|---|
| 159 | 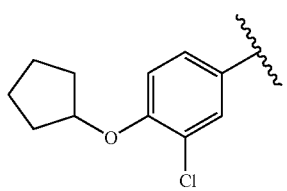 | 4.44 | 468.2, 470.2 |

$^1$H NMR (500 MHz, DMSO-d$_6$) δ 1.66-1.69(m, 2H), 1.79-1.86(m, 6H), 1.88-1.98(m, 1H), 2.42(s, 3H), 2.43-2.47(m, 2H), 2.77(dd, 1H, J = 5.7, 15.5 Hz), 2.83-2.89(m, 1H), 2.96-3.02(m, 1H), 3.58-3.61(m, 1H), 4.85-4.93(m, 1H), 7.10(d, 1H, J = 8.7 Hz), 7.16(d, 1H, J = 7.8 Hz), 7.42(d, 1H, J = 7.8 Hz), 7.52(dd, 1H, J = 2.3, 8.7 Hz), 7.67(d, 1H, J = 2.3 Hz), 8.01(s, 1H).

| EXAMPLE | Ar | HPLC B (min) | ESI-MS (M + H)⁺ |
|---|---|---|---|
| 160 | (4-(2,2,2-trifluoroethoxy)-3-chlorophenyl group) | 3.98 | 482.0, 484.0 |

¹H NMR (500 MHz, DMSO-d₆) δ 1.70-1.85(m, 1H), 2.41-2.46(m, 2H), 2.44(s, 3H), 2.76(dd, 1H, J = 6.2, 15.6 Hz), 2.86-2.89(m, 1H), 2.98-3.01(m, 1H), 3.60-3.63(m, 1H), 4.69(q, 2H, J = 8.3, 16.6 Hz), 7.19(d, 1H, J = 7.3 Hz), 7.24(d, 1H, J = 8.5 Hz), 7.45(d, 1H, J = 7.8 Hz), 7.61-7.64(m, 1H), 7.79(d, 1H, J = 2.3 Hz), 8.10(s, 1H).

Example 161

(R)-(5-(5-(5-Chloro-6-isopropoxypyridin-3-yl))-thiazol-2-yl)-4-methyl-1-(1H-tetrazol-5-yl)methylindane

Step A: (R)-(5-(5-(5-Chloro-6-isopropoxypyridin-3-yl))-thiazol-2-yl)-4-methyl-indan-1-yl)acetamide To a solution of (R)-(5-(5-(5-chloro-6-isopropoxypyridin-3-yl))-thiazol-2-yl)-4methyl-indan-1-yl)acetic acid (101 mg, 0.221 mmol, from EXAMPLE 145) in dichloromethane (2 mL) and DMF (1 drop), oxalyl chloride was added (100 µL, 1.17 mmol). After 45 min. the reaction mixture was concentrated in vacuo, and the residue azeotroped with benzene (3×1 mL). The resulting crude acid chloride was dissolved in THF (5 mL) and treated with concentrated NH₄OH (1.0 mL). After 15 min, the reaction mixture was concentrated in vacuo and azeotroped with EtOAc (3×5 mL). The residue was dissolved in EtOAc (5 mL), dried (MgSO₄), filtered and concentrated in vacuo to afford 88 mg of the title compound: ¹H NMR (500 MHz, CDCl₃) δ 1.42 (d, 6H, J=6.1 Hz), 1.66-1.86 (m, 1H), 2.40 (dd, 1H, J=8.6, 14.8 Hz), 2:45-2.50 (m, 4H), 2.68 (dd, 1H, J=5.9, 14.6 Hz), 2.86-2.92 (m, 1H), 2.95-3.01 (m, 1H), 3.69-3.74 (m, 1H), 5.36-5.41 (m, 3H), 7.15 (d, 1H, J=8.0 Hz), 7.51 (d, 1H, J=8.0 Hz), 7.84 (d, 1H, J=2.3 Hz), 7.94 (s, 1H), 8.27 (d, 1H, J=2.3 Hz).

Step B: (R)-(5-(5-(5-Chloro-6-isopropoxypyridin-3-yl))-thiazol-2-yl)-4-methyl-indan-1-yl)acetonitrile To a ice-cold solution of (R)-(5-(5-(5-chloro-6-isopropoxypyridin-3-yl))-thiazol-2-yl)-4-methyl-indan-1-yl)acetamide (86 mg, 0.202 mmol, from Step A) in dichloromethane (1.5 mL) and triethylamine (62 µL, 0.444 mmol), trifluoroacetic acetic anhydride (32 µL, 0.222 mmol) was added and the reaction mixture was warmed to ambient temperature. After 30 min, dichloromethane (10 mL) was added and the organic layer was washed with sat. NaHCO₃ (1×3 mL), brine (1×3 mL), dried (MgSO₄), filtered and concentrated in vacuo. The residue was purified by flash chromatography (10, 20% EtOAc/hexanes) on SiO₂ to afford 70 mg of the title compound as a yellow film: ¹H NMR (500 MHz, CDCl₃) δ 1.42 (d, 6H, J=6.2 Hz), 1.92-1.98 (m, 1H), 2.51-2.55 (m, 4H), 2.60 (dd, 1H, J=7.6, 16.7 Hz), 2.72 (dd, 1H, J=6.1, 16.8 Hz), 2.89-2.96 (m, 1H), 3.02-3.08 (m, 1H), 3.55-3.60 (m, 1H), 5.39 (septet, 1H, J=6.2 Hz), 7.21 (d, 1H, J=7.8 Hz), 7.56 (d, 1H, J=7.8 Hz), 7.84 (d, 1H, J=2.1 Hz), 7.95 (s, 1H), 8.26 (d, 1H, J=2.3 Hz).

Step C: (R)-(5-(5-(5-Chloro-6-isopropoxypyridin-3-yl))-thiazol-2-yl)-4-methyl-1-(1H-tetrazol-5-yl)methylindane A solution of (R)-(5-(5-(5-Chloro-6-isopropoxypyridin-3-yl))-thiazol-2-yl)-4-methyl-indan-1-yl)acetonitrile (67 mg, 0.158 mmol, from Step B), n-tributyltin oxide (20 mg, 0.0790 mmol) and trimethylsilyl azide (210 µL, 1.58 mmol) in toluene (2 mL) was heated to reflux. After 15 h, the reaction mixture was cooled to ambient temperature and concentrated in vacuo. The residue was purified by flash chromatography (1.3% CH₃OH/CH₂Cl₂/1% NH₄OH) on SiO₂ followed by recrystallization from hot methanol (1.25 mL) to afford 25.0 mg of the title compound as a white solid: ¹H NMR (500 MHz, CD₃OD) δ 1.38 (d, 6H, J=6.2 Hz), 1.85-1.92 (m, 1H), 2.31-2.36 (m, 1H), 2.43 (s, 3H), 2.86-2.92 (m, 1H), 2.95-3.01 (m, 1H), 3.11 (dd, 1 H, J=8.9, 14.9 Hz), 3.40 (dd, 1H, J=6.0, 14.9 Hz), 3.69-3.74 (m, 1H), 5.39 (septet, 1H, J=6.2 Hz), 7.01 (d, 1H, J=7.8 Hz), 7.45 (d, 1H, J=8.0 Hz), 8.08 (d, 1H, J=2.1 Hz), 8.10 (s, 1H), 8.35 (d, 1H, J=2.1 Hz); HPLC B: rt=4.00 min, m/z=467.1 (M+H)⁺, 469.0 (M+H+2)⁺.

Example 162

(R/S)-(5-(5-(5-Chloro-6-isopropoxypyridin-3-yl))-1,2,4-oxadiazol-3-yl)-4-methylindan-2-yl)acetic acid

Step A: (R/S) 5-Cyano-4-methylindane-2-carboxylic acid

To a solution of methyl 5-cyano-4-methylindane-2-carboxylate (121 mg, 0.562 mmol) in methanol (2 mL), 1.0 N NaOH (1.69 mL, 1.69 mmol) was added and the reaction mixture was stirred overnight. The reaction mixture was acidified, extracted with EtOAc and the organic layer was washed with H₂O, brine, dried (MgSO₄), filtered and concentrated in vacuo to afford 98 mg of the title compound: ¹H NMR (CDCl₃) δ 2.48 (s, 3H), 3.26-3.48 (m, 5H), 7.16 (d, 1H, J=7.7 Hz), 7.47 (d, 1H, J=7.8 Hz).

Step B: Methyl (R/S)-(5-cyano-4-methylindan-2-yl)acetate

To a solution of (R/S) 5-cyano-4-methylindane-2-carboxylic acid (98 mg, 0.487 mmol, from Step A) in THF (1.5 mL) cooled to 0° C., triethylamine (68 µL, 0.487 mmol) was added followed by dropwise addition of ethyl chloroformate (46 µL, 0.487 mmol). After 30 min, a solution of diazomethane (~1.46 mmol) in Et₂O (2 mL) was added. The reaction mixture was warmed to ambient temperature and stirred for 45 min and concentrated in vacuo. The residue was dissolved in EtOAc and washed with sat. NaHCO$_3$, H$_2$O, brine, dried over MgSO$_4$, filtered and concentrated in vacuo. Purification by flash chromatography afforded 44 mg of the desired α-diazoketone. $^1$H NMR (CDCl$_3$) δ 2.49 (s, 3H), 3.15-3.27 (m, 3H), 3.33-3.37 (m, 2H), 5.38 (brs, 1H), 7.15 (d, 1H, J=8.0 Hz), 7.47 (d, 1H, J=7.8 Hz). This material (44 mg, 0.194 mmol) was dissolved in methanol (1 mL), triethylamine (140 µL, 0.972 mmol) and cooled to 0° C. Silver (1) Benzoate was added and the reaction mixture was stirred in the dark for 1 h at ambient temperature. The reaction mixture was concentrated in vacuo, the residue was dissolved in EtOAc and washed with sat. NaHCO$_3$, H$_2$O, brine, dried over MgSO$_4$, filtered and concentrated in vacuo. Purification by flash chromatography afforded 33 mg of the title compound: $^1$H NMR (CDCl$_3$) δ 2.46 (s, 3H), 2.55 (d, 2H, J=7.6 Hz), 2.63 (dd, 1H, J=7.1, 16.2 Hz), 2.75 (dd, 1H, J=7.4, 16.2 Hz), 2.93-2.99 (m, 1H), 3.18 (dd, 1H, J=8.2, 15.9 Hz), 3.24 (dd, 1H, J=8.5, 16.5 Hz), 3.74 (s, 3H), 7.13 (d, 1H, J=7.8 Hz), 7.45 (d, 1H, J=7.6 Hz).

Step C: Methyl (R/S)-(5-(5-(5-chloro-6-isopropoxy-pyridin-3-yl))-1,2,4-oxadiazol-3-yl)-4-methyl-indan-2-yl)acetate To a solution of methyl (R/S)-(5-cyano-4-methylindan-2-yl)acetate (33 mg, 0.149 mmol, from Step B) in methanol, hydroxylamine (13 mg, 0.187 mmol) and triethylamine (30 µL, 0.216 mmol) were added and the reaction mixture was heated to reflux. After 15 h, the reaction mixture was cooled and concentrated in vacuo. The residue was dissolved in dichloromethane (5 mL) and washed with 1.0 N HCl (2.5 mL). The organic layer was dried (MgSO$_4$), filtered and concentrated in vacuo to give 27 mg of starting material. The aqueous layer was neutralized with 1.0 N NaOH (2.5 mL) and extracted into EtOAc (5 mL). The EtOAc layer was washed with sat. NaHCO$_3$ (2.5 mL), brine (2.5 mL), dried over MgSO$_4$, filtered and concentrated in vacuo to afford 3.5 mg of the corresponding amidoxime. Subjection of the recovered starting material to the conditions as described above led to the isolation of an additional 6.7 mg of amidoxime and 15 mg of starting material respectively.

To a solution of 5-chloro-6-isopropoxynicotinic acid (10.0 mg, 0.0467 mmol) in acetonitrile (1.0 mL), EDC-HCl (9.0 mg, 0.0467 mmol) was added. After 30 min, the aforementioned amidoxime (10.2 mg, 0.0389 mmol) was added and the reaction mixture was stirred at ambient temperature for 1 h. The reaction mixture was then concentrated in vacuo and partitioned between EtOAc (5 mL) and H$_2$O (2.5 mL). The organic layer was washed with sat. NaHCO$_3$ (2.5 mL), brine (2.5 mL), dried over MgSO$_4$, filtered and concentrated in vacuo. The resulting residue was dissolved in THF (1.0 mL) and tetrabutylammonium fluoride (TBAF, 40 mL, 0.0389 mmol) was added. After 15 h, the reaction mixture was concentrated in vacuo and purified by flash chromatography (5% EtOAc/hexanes) on SiO$_2$ to afford 7.3 mg of the title compound.

Step D: (R/S)-(5-(5-(5-Chloro-6-isopropoxypyridin-3-yl))-1,2,4-oxadiazol-3-yl)-4-methyl-indan-2-yl)acetic acid To a solution of methyl (R/S)-(5-(5-(5-chloro-6-isopropoxypyridin-3-yl))-1,2,4-oxadiazol-3-yl)-4-methyl-indan-2-yl)acetate (7.3 mg, 0.0165 mmol, from Step C) in THF (1.0 mL) and H$_2$O (300 µL), lithium hydroxide was added (7.0 mg, 0.0165 mmol) and the reaction mixture was heated to 50° C. After 15 h, the reaction mixture was cooled to ambient temperature and concentrated in vacuo. The residue was partitioned between EtOAc and 5% citric acid. The layers were separated and the organic layer was washed with H$_2$O, brine, dried over MgSO$_4$, filtered, and concentrated in vacuo. Purification by RP-HPLC afforded 2.9 mg of the title compound: $^1$H NMR (DMSO-d$_6$) δ 1.38 (d, 6H, J=6.1 Hz), 2.43-2.45 (m, 2H), 2.49 (s, 3H), 3.13 (m, 2H), 5.43 (septet, 1H, J=6.2 Hz), 7.22 (d, 1H, J=7.7 Hz), 7.76 (d, 1H, J=7.8 Hz), 8.52 (d, 1H, J=2.1 Hz), 8.90 (d, 1H, J=2.0 Hz); HPLC A: rt=4.19 min, m/z=428 M+H)$^+$, 430 (M+H+2)$^+$.

Example 163

(R/S)-(5-(5-(5-Chloro-6-isopropoxypyridin-3-yl))-1,24-oxadiazol-3-yl)indan-1-yl)acetic acid Step A: Methyl (2E)-(5-methoxy-2,3-dihydro-1H-inden-1-ylidene)acetate A solution of 5-methoxy-1-indanone (2.50 g, 15.4 mmol) and methyl bromoacetate (1.84 mL, 20.0 mmol) in THF (15 mL) was added dropwise to a mixture of activated zinc dust (1.51 g, 23.1 mmol) in THF (10 mL). During the addition the reaction mixture reached reflux temperature, which was maintained for an additional hour after the addition was completed. After cooling to ambient temperature, the reaction mixture was poured into ice-cold 2.0 N HCl and extracted into EtOAc. The organic layer was washed with H$_2$O, brine, dried over MgSO$_4$, filtered and concentrated in vacuo. Purification by flash chromatography (10% EtOAc/hexanes) on SiO$_2$ afforded 2.45 g of the title compound: $^1$H NMR (CDCl$_3$) δ 3.04-3.07 (m, 2H), 3.30-3.33 (m, 2H), 3.77 (s, 3H), 3.85 (s, 3H), 6.19 (t, 1H, J=2.5 Hz), 6.83 (dd, 1H, J=2.3, 8.7 Hz), 6.85 (s, 1H), 7.52 (d 1H J=8.5 Hz).

Step B: Methyl (R/S)-(5-methoxy-indan-1-yl)acetate

To a mixture of 10% Pd—C (200 mg) in methanol (10 mL) under an atmosphere of nitrogen, methyl (2E)-(5-methoxy-2,3-dihydro-1H-inden-1-ylidene)acetate (2.00 g, 9.16 mmol, from Step A) was added as a solid. The mixture was evacuated and filled with 1 atmosphere of H$_2$. After 1 hr, the mixture was filtered through a pad of Celite® and the filtrate concentrated in vacuo. The residue was azeotroped with toluene to afford 2.00 g of the title compound: $^1$H NMR (CDCl$_3$) δ 1.78-1.84 (m, 1H), 2.40-2.50 (m, 2H), 2.79 (dd, 1H, J=5.7, 15.3 Hz), 2.87-2.98 (m, 2H), 3.57-3.60 (m, 1H), 3.77 (s, 3H), 3.83 (s, 3H), 6.77 (dd, 1H, J=2.3, 8.2 Hz), 6.83 (d, 1H, J=1.9 Hz), 7.12 (d, 1H, J=8.2 Hz).

Step C: Methyl (R/S)-(5-hydroxy-indan-1-yl)acetate

A 1.0 M solution of boron tribromide in dichloromethane (22.7 mL, 22.7 mmol) was added to an ice-cold solution of methyl (R/S)-(5-methoxy-indan-1-yl)acetate (2.00 g, 9.08 mmol, from Step B) in dichloromethane (15 mL). The cooling bath was removed and the reaction mixture stirred at ambient temperature. After 1 hr, the reaction mixture was slowly transferred to an ice-cold solution of methanol (50 mL). Methanol was removed in vacuo, and the residue was partitioned between EtOAc and sat. NaH$_2$PO$_4$. The organic layer was washed with H$_2$O, brine, and dried over MgSO$_4$. The mixture was filtered, concentrated in vacuo and purified by flash chromatography (15, 20% EtOAc/hexanes) on SiO$_2$ to afford 1.74 g of the title compound: $^1$H NMR (CDCl$_3$) δ 1.72-1.79 (m, 1H), 2.35-2.42 (m, 1H), 2.46 (dd, 1H, J=8.5, 15.3 Hz), 2.76 (dd, 1H, J=5.9, 15.3 Hz), 2.80-2.92 (m, 2H), 3.50-3.55 (m, 1H), 3.75 (s, 3H), 5.63-5.86 (brs, 1H), 6.67 (dd, 1H, J=2.4, 8.1 Hz), 6.74 (d, 1H, J=2.0 Hz), 7.01 (d, 1H, J=8.3 Hz).

Step D: Methyl (R/S)-(5-trifluoromethylsulfonyloxy-indan-1-yl)acetate

To a solution of pyridine (820 µL, 10.1 mmol) in dichloromethane (10 mL) cooled to 0° C. trifluoromethanesulfonic anhydride (1.56 mL, 9.28 mmol) was added. The resulting mixture was stirred for 5 min, and methyl (R/S)-(5-hydroxy-indan-1-yl)acetate (1.74 g, 8.44 mmol, from Step C) was added. The reaction mixture was warmed to ambient temperature, stirred for 1 hr and diluted with dichloromethane. The organic layer was washed with $H_2O$, brine and dried over $MgSO_4$. The mixture was filtered and concentrated in vacuo. Purification by flash chromatography (10% EtOAc/hexanes) on $SiO_2$ gave 2.63 g of the title compound as a pale yellow liquid: $^1$H NMR (CDCl$_3$) δ 1.83-1.88 (m, 1H), 2.47-2.55 (m, 2H), 2.78 (dd, 1H, J=6.0, 15.8 Hz), 2.92-3.01 (m, 2H), 3.62-3.65 (m, 1H), 3.76 (s, 3H), 7.09 (dd, 1H, J=2.3, 8.3 Hz), 7.16 (s, 1H), 7.25 (d, 1H, J=8.2 Hz).

Step E: Methyl (R/S)-(5-cyano-indan-1-yl)acetate

To a solution methyl (R/S)-(5-trifluoromethylsulfonyloxy-indan-1-yl)acetate (2.63 g, 7.80 mmol, from Step D) in N-methylpyrrolidinone (20 mL) under argon, zinc cyanide (733 mg, 6.24 mmol), Pd$_2$dba$_3$ (36 mg, 39.0 µmol) and dppf (52.0 mg, 93.6 µmol) were added, and the reaction mixture was heated to 100° C. After 16 hr, the reaction mixture was concentrated iji vacuo and partitioned between EtOAc and $H_2O$. The layers were separated and the organic layer was washed with $H_2O$, brine and dried over $MgSO_4$. The mixture was filtered, the filtrate concentrated in vacuo, and the residue purified by flash chromatography (5, 10% EtOAc/hexanes) on $SiO_2$ to give 1.40 g of the title compound as a white solid: $^1$H NMR (CDCl$_3$) δ 1.80-1.84 (m, 1H), 2.43-2.48 (m, 1H), 2.52 (dd, 1H, J=8.5, 15.8 Hz), 2.77 (dd, 1H, J=6.0, 15.8 Hz), 2.92-3.00 (m, 2H), 3.62-3.66 (m, 1H), 3.74 (s, 3H), 7.27 (d, 1H, J=5.5 Hz), 7.47 (d, 1H, J=7.8 Hz), 7.51 (s, 1H).

Step F: Methyl (R/S)-(5-(N-hydroxyamidino-indan-1-yl)acetate

To a solution of methyl (R/S)-(5-cyano-indan-1-yl)acetate (724 mg, 3.16 mmol, Step E) in methanol (10 mL) hydroxylamine hydrochloride (285 mg, 4.11 mmol) and triethylamine (660 mL, 474 mmol) were added and heated to reflux. After 14 hr, the reaction mixture was cooled to ambient temperature and concentrated in vacuo. The residue was purified by flash chromatography (50, 60% EtOAc/hexanes) on $SiO_2$ to afford 1.40 g of the title compound: $^1$H NMR (CDCl$_3$) δ 1.76-1.80 (m, 1H), 2.40-2.49 (m, 2H), 2.78 (dd, 1H, J=5.8, 15.6 Hz), 2.87-2.96 (m, 2H), 3.59-3.62 (m, 1H), 3.74 (s, 3H), 4.94 (s, 2H), 7.20 (d, 1H, J=7.8 Hz), 7.45 (d, 1H, J=7.7 Hz), 7.51 (s, 1H).

Step G: Methyl (R/S)-(5-(5-(5-Chloro-6-isopropoxy-pyridin-3-yl))-1,2,4-oxadiazol-3-yl)indan-1-yl)acetate To a solution of 5-chloro-6-isopropoxynicotinic acid (52 mg, 0.242 mmol) in acetonitrile (3.0 mL), EDC-HCl (46 mg, 0.242 mmol) was added. The resulting solution was stirred at ambient temperature for 30 min and methyl (R/S)-(5-(N-hydroxyamidino-indan-1-yl)acetate (60 mg, 0.242 mmol, from Step F) was added. After 1 hr, the reaction mixture was concentrated in vacuo. The residue was dissolved in EtOAc and washed with $H_2O$, brine, and dried over $MgSO_4$. The mixture was filtered, concentrated in vacuo and dissolved in THF (3.0 mL). A solution of TBAF 1.0 M in THF (242 µL, 0.242 mmol) was added and the resulting yellow solution was stirred at ambient temperature for overnight. The reaction mixture was concentrated in vacuo, dissolved in EtOAc and washed with $H_2O$, brine, and dried over $MgSO_4$. The mixture was filtered, concentrated in vacuo and purified by flash chromatography (5% EtOAc/hexanes) on $SiO_2$ to give 59 mg of the title compound as white solid: $^1$H NMR (500 MHz, CDCl$_3$) δ 1.49 (d, 6H, J=6.2 Hz), 1.84-1.90 (m, 1H), 2.47-2.51 (m, 2H), 2.86 (dd, 1H, J=5.8, 15.6 Hz), 2.98-3.09 (m, 2H), 3.68-3.71 (m, 1H), 3.78 (s, 3H), 5.53, (septet, 1H, J=6.2 Hz), 7.35 (d, 1H, J=8.0 Hz), 8.01 (d, 1H, J=7.8 Hz), 8.04 (s, 1H), 8.43 (d, 1H, J=2.1 Hz), 8.90 (d, 1H, J=2.3 Hz).

Step H: (R/S)-(5-(5-(5-Chloro-6-isopropoxypyridin-3-yl))-1,2,4-oxadiazol-3-yl)indan-1-yl)acetic acid To a solution of methyl (R/S)-(5-(5-(5-chloro-6-isopropoxypyridin-3-yl))-1,2,4-oxadiazol-3-yl)indan-1-yl)acetate (59 mg, 0.138 mmol, from Step G) in THF (3 mL) and $H_2O$ (1 mL) lithium hydroxide monohydrate (58 mg, 1.38 mmol) was added. The reaction mixture was heated to 50° C. for 3 hr, cooled to ambient temperature and partitioned between EtOAc and 5% citric acid. The organic layer was washed with $H_2O$, brine, dried over $MgSO_4$, filtered and concentrated in vacuo. Purification of the residue by preparative tlc (2% $CH_3OH/CH_2Cl_2$/0.2% $HCO_2H$) on SiO2 afforded 36 mg of the title compound as a white solid: $^1$H NMR (500 MHz, DMSO-d$_6$) δ 1.40 (d, 6H, J=6.2 Hz), 1.70-1.78 (m, 1H), 2.30-2.46 (m, 2H), 2.78 (dd, 1H, J=5.6, 15.9 Hz), 2.84-2.95 (m, 1H), 2.96-3.06 (m, 1H), 3.45-3.57 (m, 1H), 5.45 (septet, 1H, J=6.1 Hz), 7.45 (d, 1H, J=7.7 Hz), 7.91 (d, 1H, J=7.7 Hz), 7.94 (s, 1H), 8.50 (d, 1H, J=2.1 Hz), 8.92 (d, 1H, J=1.8 Hz); HPLC A: rt=4.16 nm in, m/z=414.1 (M+H)$^+$, 416.1 (M+H)$^+$.

The following example was prepared using procedures analogous to those described in EXAMPLE 163 substituting 3-cyano-4-(2-trifluoromethylethoxy)benzoic acid for 5-chloro-6-isopropoxybenzoic acid in Step G:

| EXAMPLE | Ar | HPLC A (min) | ESI-MS (M + H)$^+$ |
|---|---|---|---|
| 164 | 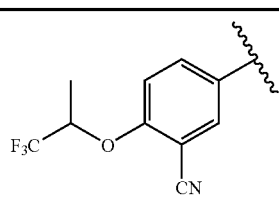 | 3.67 | 404.1 |

$^1$H NMR (500 MHz, DMSO-d$_6$) δ 1.39(d, 6H, J = 6.2 Hz), 1.66-1.82(m, 1H), 2.29-2.46(m, 2H), 2.78(dd, 1H, J = 5.6, 15.9 Hz), 2.84-2.94(m, 1H), 2.95-3.07(m, 1H), 3.47-3.62(m, 1H), 4.97(septet, 1H, J = 6.0 Hz), 7.41(d, 1H, J = 7.8 Hz), 7.55(d, 1H, J = 9.1 Hz), 7.90(d, 1H, J = 7.7 Hz), 7.92(s, 1H), 8.37(dd, 1H, J = 2.1, 9.1 Hz), 8.48 (d, 1H, J = 2.3 Hz).

What is claimed is:

1. A compound represented by Formula A:

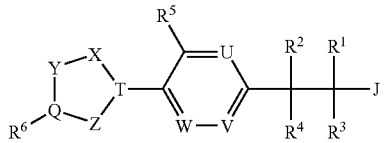

or a pharmaceutically acceptable salt thereof, wherein:
- $R^1$, $R^2$, $R^3$ and $R^4$ are each independently selected from the group consisting of: —H, —F, —Cl, —Br, —I, —CN, —OH, $C_{1-6}$alkyl, $C_{2-6}$alkenyl, $C_{2-6}$alkynyl and $C_{1-5}$alkoxy,
  wherein said $C_{1-6}$alkyl, $C_{2-6}$alkenyl, $C_{2-6}$alkynyl and $C_{1-5}$alkoxy are each optionally substituted with one to three substituents independently selected from the group consisting of: —F, —Cl, —Br, —I, —OH, $C_{1-8}$alkoxy and —CO$_2$H,
  and any two of $R^1$, $R^2$, $R^3$ and $R^4$ may be joined together with the atoms to which they are attached to form a saturated monocyclic ring of 3 to 8 atoms optionally containing 1 or 2 oxygen atoms;
- $R^5$ is selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy,
  wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;
- $R^6$ is selected from the group consisting of: phenyl and pyridinyl, each optionally substituted with one to three substituents independently selected from the group consisting of: —F, —Cl, —Br, —I, —CN, —OH, —NR$^7$R$^8$, —NO$_2$, phenyl, thienyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{2-4}$acyloxy,
  wherein said phenyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I, —OH and $C_{1-8}$alkoxy,
- $R^7$ and $R^8$ are independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy, and
- $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy;
- U, V and W are each; —C($R^9$)—;
- each $R^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy,
  wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;
- For U or V, $R^9$ and $R^1$ or $R^9$ and $R^2$ may be joined together with the atoms to which they are attached to form a 5 membered ring, thus forming a fused partially aromatic bicyclic ring system of 9 atoms with the 6-membered aromatic ring to which $R^9$ is attached;
the ring

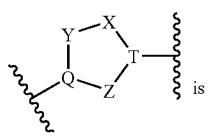 is 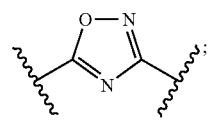;

J is selected from the group consisting of: —CO$_2$H,

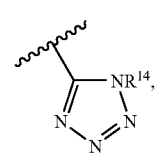 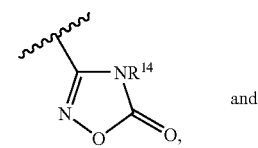 and

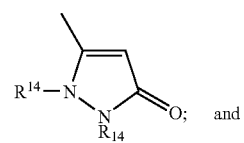 and each $R^{14}$ is independently selected from the group consisting of: —H and —CH$_3$.

2. A compound in accordance with claim 1 represented by Formula I

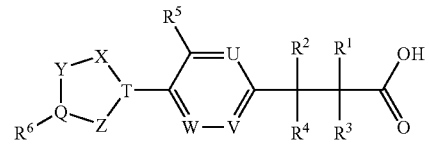

or a pharmaceutically acceptable salt thereof, wherein:
- $R^1$, $R^2$, $R^3$ and $R^4$ are each independently selected from the group consisting of: —H, —F, —Cl, —Br, —I, —CN, —OH, $C_{1-6}$alkyl, $C_{2-6}$alkenyl, $C_{2-6}$alkynyl and $C_{1-5}$alkoxy,
  wherein said $C_{1-6}$alkyl, $C_{2-6}$alkenyl, $C_{2-6}$alkynyl and $C_{1-5}$alkoxy are each optionally substituted with one to three substituents independently selected from the group consisting of: —F, —Cl, —Br, —I, —OH, $C_{1-8}$alkoxy and —CO$_2$H,
  and any two of $R^1$, $R^2$, $R^3$ and $R^4$ may be joined together with the atoms to which they are attached to form a saturated monocyclic ring of 3 to 8 atoms optionally containing 1 or 2 oxygen atoms;

$R^5$ is selected from the group consisting of: —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;

$R^6$ is selected from the group consisting of: phenyl and pyridinyl each optionally substituted with one to three substituents independently selected from the group consisting of: —F, —Cl, —Br, —I, —CN, —OH, —NR$^7$R$^8$, —NO$_2$, phenyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{2-4}$acyloxy, wherein said phenyl, $C_{1-4}$alkyl, $C_{3-6}$cycloalkyl, $C_{2-4}$alkenyl, $C_{2-4}$alkynyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I, —OH and $C_{1-8}$alkoxy $R^7$ and $R^8$ are independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy;

U, V and W are each —C(R$^9$)—;

each $R^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy;

For U or V, $R^9$ and $R^1$ or $R^9$ and $R^2$ may be joined together with the atoms to which they are attached to form a 5 membered ring, thus forming a fused partially aromatic bicyclic ring system of 9 atoms with the 6-membered aromatic ring to which $R^9$ is attached; and the ring

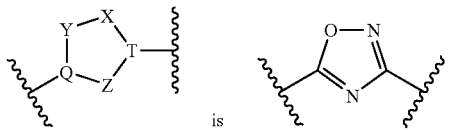

is

3. A compound according to claim 2 wherein $R^5$ is methyl.

4. A compound according to claim 2 wherein $R^6$ is selected from the group consisting of: phenyl and pyridinyl, each optionally substituted with one to three substituents independently selected from the group consisting of: —F, —Cl, —Br, —I, —CN, —OH, —NR$^7$R$^8$, —NO$_2$, $C_{1-4}$alkyl, $C_{3-6}$cycloalkyl, $C_{2-4}$alkenyl, $C_{2-4}$alkynyl, $C_{1-4}$alkoxy, $C_{1-4}$alkylthio, $C_{3-6}$cycloalkoxy and $C_{1-4}$acyloxy, wherein said $C_{1-4}$alkyl, $C_{3-6}$cycloalkyl, $C_{2-4}$alkenyl, $C_{2-4}$alkynyl, $C_{1-4}$alkoxy, $C_{1-4}$alkylthio, $C_{3-6}$cycloalkoxy and $C_{1-4}$acyloxy are each optionally substituted from one up to the maximum number of substitutable positions with a substituent independently selected from the group consisting of: —F, —Cl, —Br, —I, —OH and $C_{1-8}$alkoxy; and $R^7$ and $R^8$ are independently selected from the group consisting of: —H, $C_{1-6}$alkyl, $C_{2-6}$alkenyl and $C_{2-6}$alkynyl, wherein said $C_{1-6}$alkyl, $C_{2-6}$alkenyl and $C_{2-6}$alkynyl are each optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy.

5. A compound according to claim 2 wherein V and W are —CH—.

6. A compound according to claim 2 of Formula Ia

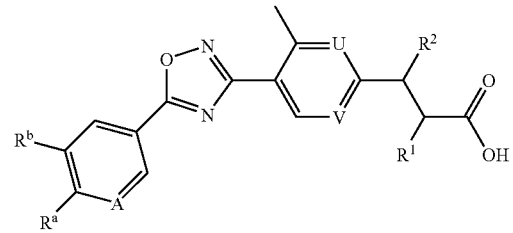

Ia or a pharmaceutically acceptable salt thereof, wherein:

$R^1$ and $R^2$ are independently selected from the group consisting of: —H, —OH and methyl or $R^1$ and $R^2$ may be joined together with the atoms to which they are attached to form cyclopropyl;

U and V are each —C(R$^9$)—;

each $R^9$ is independently selected from the group consisting of: —H, —F, —Cl, —Br, —I, —CN, —OH, $C_{1-4}$alkyl, $C_{2-4}$alkenyl, $C_{2-4}$alkynyl and $C_{1-4}$alkoxy, wherein said $C_{1-4}$alkyl, $C_{2-4}$alkenyl, $C_{2-4}$alkynyl and $C_{1-4}$alkoxy are each optionally substituted with one to three substituents independently selected from the group consisting of: —F, —Cl, —Br, —I, —OH and $C_{1-8}$alkoxy, and For U or V, $R^9$ and $R^1$ or $R^9$ and $R^2$ may be joined together with the atoms to which they are attached to form a 5 membered ring, thus forming a fused partially aromatic bicyclic ring system of 9 atoms with the 6-membered aromatic ring to which $R^9$ is attached;

A is selected from the group consisting of: —N— and —C(R$^{13}$)—, wherein R$^{13}$ is selected from the group consisting of: —H, —F, —Cl, —Br, —I, —CN, —CH$_3$, —OCH$_3$, —CF$_3$, ethynyl, —NO$_2$ and —NH$_2$;

$R^a$ is selected from the group consisting of: NR$^7$R$^8$, $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy, wherein said $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I and —OH;

$R^7$ and $R^8$ are independently selected from the group consisting of: —H and $C_{1-6}$alkyl, optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy; and $R^b$ is selected from the group consisting of: —H, —F, —Cl, —Br, —I, —CN, —CH$_3$, —OCH$_3$, —CF$_3$, ethynyl, —NO$_2$ and —NH$_2$.

7. A compound according to claim 2 of Formula Ib

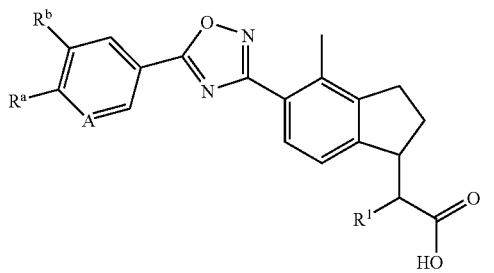

or a pharmaceutically acceptable salt thereof, wherein:

$R^1$ is selected from the group consisting of: —H, —OH and methyl;

A is selected from the group consisting of: —N— and —C($R^{13}$)—, wherein $R^{13}$ is selected from the group consisting of: —H, —F, —Cl, —Br, —I, —CN, —CH$_3$, —OCH$_3$, —CF$_3$, ethynyl, —NO and —NH$_2$;

$R^a$ is selected from the group consisting of: NR$^7$R$^8$, $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy, wherein said $C_{1-4}$alkyl, $C_{3-6}$cycloalkyl, $C_{1-4}$alkoxy, $C_{3-6}$cycloalkoxy, $C_{1-4}$alkylthio and $C_{1-4}$acyloxy are each optionally substituted from one up to the maximum number of substitutable positions with a substituent independently selected from the group consisting of: —F, —Cl, —Br, —I and —OH;

$R^7$ and $R^8$ are independently selected from the group consisting of: —H and $C_{1-6}$alkyl, optionally substituted with one to three substituents independently selected from the group consisting of: —F, —Cl, —Br, —I, —OH and $C_{1-5}$alkoxy, and $R^7$ and $R^8$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy; and $R^b$ is selected from the group consisting of: —H, —F, —Cl, —Br, —I, —CN, —CH$_3$, —OCH$_3$, —CF$_3$, ethynyl, —NO$_2$ and —NH$_2$.

8. A compound according to claim 2 selected from the following table:

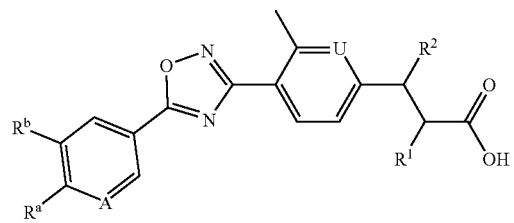

| Ex. | $R^a$ | $R^b$ | A | U | $R^2$ | $R^1$ |
|---|---|---|---|---|---|---|
| 1 | i-PrO— | —CN | —CH= | =CH— | H | H |
| 2 | i-PrO— | Cl— | —CH= | =CH— | H | H |
| 3 | i-PrO— | Br— | —CH= | =CH— | H | H |
| 4 | i-PrO— | MeO— | —CH= | =CH— | H | H |
| 5 | i-PrO— | Me— | —CH= | =CH— | H | H |
| 6 | i-PrO— | F— | —CH= | =CH— | H | H |
| 8 | i-PrO— | —CF$_3$ | —CH= | =CH— | $R^2$ and $R^1$ joined to form cyclopropyl | |
| 9 | i-PrO— | —CF$_3$ | —CH= | =CH— | H | Me |
| 10 | i-PrO— | —CN | —CH= | =CH— | H | Me |
| 11 | i-PrO— | —CH3 | —CH= | =CH— | H | Me |
| 12 | i-PrO— | —CF$_3$ | —CH= | =CH— | Me | H |
| 13 | i-PrO— | —CN | —CH= | =CH— | Me | H |

-continued

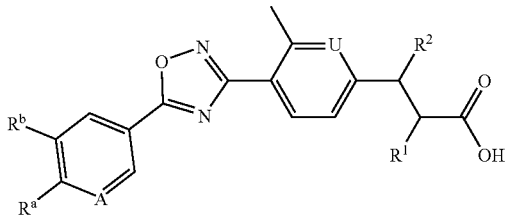

Ie

| Ex. | $R^a$ | $R^b$ | A | U | $R^2$ | $R^1$ |
|---|---|---|---|---|---|---|
| 14 | i-PrO— | —CH3 | —CH= | =CH— | Me | H |
| 15 | i-PrO— | Cl— | —N= | =CH— | H | H |
| 16 | i-Pr-NH— | Cl— | —N= | =CH— | H | H |
| 17 | 2,2-trifluoro-1-methylethoxy | Cl— | —N= | =CH— | H | H |
| 18 | pyrrolidinyl | Cl— | —N= | =CH— | H | H |
| 19 | morpholin-4-yl | Cl— | —N= | =CH— | H | H |
| 20 | i-Pr-N(Me)— | Cl— | —N= | =CH— | H | H |
| 21 | 2,2,2-trifluoroethoxy | Cl— | —N= | =CH— | Me | H |
| 22 | 2,2,2-trifluoro-1-methylethoxy | Cl— | —N= | =CH— | Me | H |
| 23 | 3,3,-difluoro piperidinyl | Cl— | —N= | =CH— | Me | H |
| 24 | 3,3,-difluoro pyrrolidinyl | Cl— | —N= | =CH— | Me | H |
| 25 | morpholin-4-yl | —CF3 | —N= | =CH— | Me | H |
| 26 | 3,3,-difluoro pyrrolidinyl | Cl— | —N= | =CH— | $R^2$ and $R^1$ joined to form cyclopropyl | |
| 27 | 2,2,2-trifluoroethoxy | Cl— | —N= | =CH— | $R^2$ and $R^1$ joined to form cyclopropyl | |
| 28 | 2,2,2-trifluoro-1-methylethoxy | Cl— | —N= | =CH— | $R^2$ and $R^1$ joined to form cyclopropyl | |
| 29 | 1-Me-n-PrO— | Cl— | —N= | =CH— | $R^2$ and $R^1$ joined to form cyclopropyl | |
| 30 | i-PrO— | Cl— | —N= | =CH— | $R^2$ and $R^1$ joined to form cyclopropyl | |
| 31 | i-Bu— | Cl— | —N= | =CH— | H | H |
| 32 | i-Pr-N(Me)— | I— | —N= | =CH— | H | H |
| 33 | i-Pr-N(Me)— | —CN | —N= | =CH— | H | H |
| 34 | 3,3,-difluoro pyrrolidinyl | I | —N= | =CH— | H | H |
| 35 | 3,3,-difluoro pyrrolidinyl | —CN | —N= | =CH— | H | H |
| 36 | i-PrO— | —CN | —CH= | =CH— | $R^2$ and $R^1$ joined to form cyclopropyl | |
| 37 | 2,2,2-trifluoro-1-methylethoxy | —CN | —CH= | =CH— | $R^2$ and $R^1$ joined to form cyclopropyl | |
| 38 | i-PrO— | MeO— | —CH= | =CH— | $R^2$ and $R^1$ joined to form cyclopropyl | |
| 39 | 2,2,2-trifluoroethoxy | —CN | —CH= | =CH— | $R^2$ and $R^1$ joined to form cyclopropyl | |
| 40 | 2,2,2-trifluoro-1-trifluoromethyl ethoxy | —CN | —CH= | =CH— | $R^2$ and $R^1$ joined to form cyclopropyl | |
| 43 | 1-Me-n-PrO— | —CN | —CH= | =CH— | $R^2$ and $R^1$ joined to form cyclopropyl | |
| 44 | 2,2,2-trifluoro-1-methylethoxy | —CN | —N= | =CH— | $R^2$ and $R^1$ joined to form cyclopropyl | |
| 45 | i-PrO— | I | —N= | =CH— | $R^2$ and $R^1$ joined to form cyclopropyl | |
| 48 | Ethoxy | —CN | —N= | =CH— | H | H |
| 49 | 2,2,2-trifluoro-1-methylethoxy | —CN | —N= | =CH— | H | H |
| 50 | 2-Me-n-Pr— | —CN | —N= | =CH— | H | H |
| 51 | 2-methyl-1,1-difluoro-n-Propyl | H | —CH= | =CH— | H | H |
| 52 | 2,2,2-trifluoro-1-methylethoxy | I— | —N= | =CH— | H | H |
| 53 | Cyclopentyloxy | Cl— | —CH= | =CH— | H | H |
| 54 | 2-Me-n-Pro— | Cl— | —CH= | =CH— | H | H |
| 55 | 2,2,2-trifluoro-1-methylethoxy | —CN | —CH= | =CH— | H | H |
| 56 | 2,2,2-trifluoro-1-methylethoxy | Cl— | —CH= | =CH— | H | H |

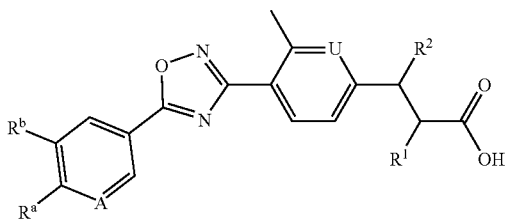

| Ex. | $R^a$ | $R^b$ | A | U | $R^2$ | $R^1$ |
|---|---|---|---|---|---|---|
| 57 | i-PrO— | Cl— | —C(Cl)= | =CH— | H | H |
| 58 | cyclopropylmethoxy | Cl— | —CH= | =CH— | H | H |
| 60 | 2,2,2-trifluoro-1-methylethoxy | —NO₂ | —CH= | =CH— | H | H |
| 61 | 2,2,2-trifluoroethoxy | —CN | —CH= | =CH— | H | H |
| 62 | 2,2,2-trifluoro-1-trifluoromethyl ethoxy | —CN | —CH= | =CH— | H | H |
| 63 | 1-Me-n-PrO— | —CN | —CH= | =CH— | H | H |
| 65 | 2,2,2-trifluoro-1-methylethoxy | —NH₂ | —CH= | =CH— | H | H |
| 66 | 1-Me-n-PrO— | —CN | —CH= | =CH— | Me | H |
| 67 | 2,2,2-trifluoro-1-trifluoromethyl ethoxy | —CN | —CH= | =CH— | Me | H |
| 68 | 2,2,2-trifluoromethoxy | —CN | —CH= | =CH— | Me | H |
| 75 | i-PrO— | —CF₃ | —CH= | =CH— | H | H |
| 79 | i-PrO— | —CN | —CH= | =CH— | OH | OH |
| 80 | i-PrO— | —CN | —CH= | =CH— | OH | OH | or a pharmaceutically acceptable salt of any of the compounds above.

9. A compound according to claim 2 selected from the following table:

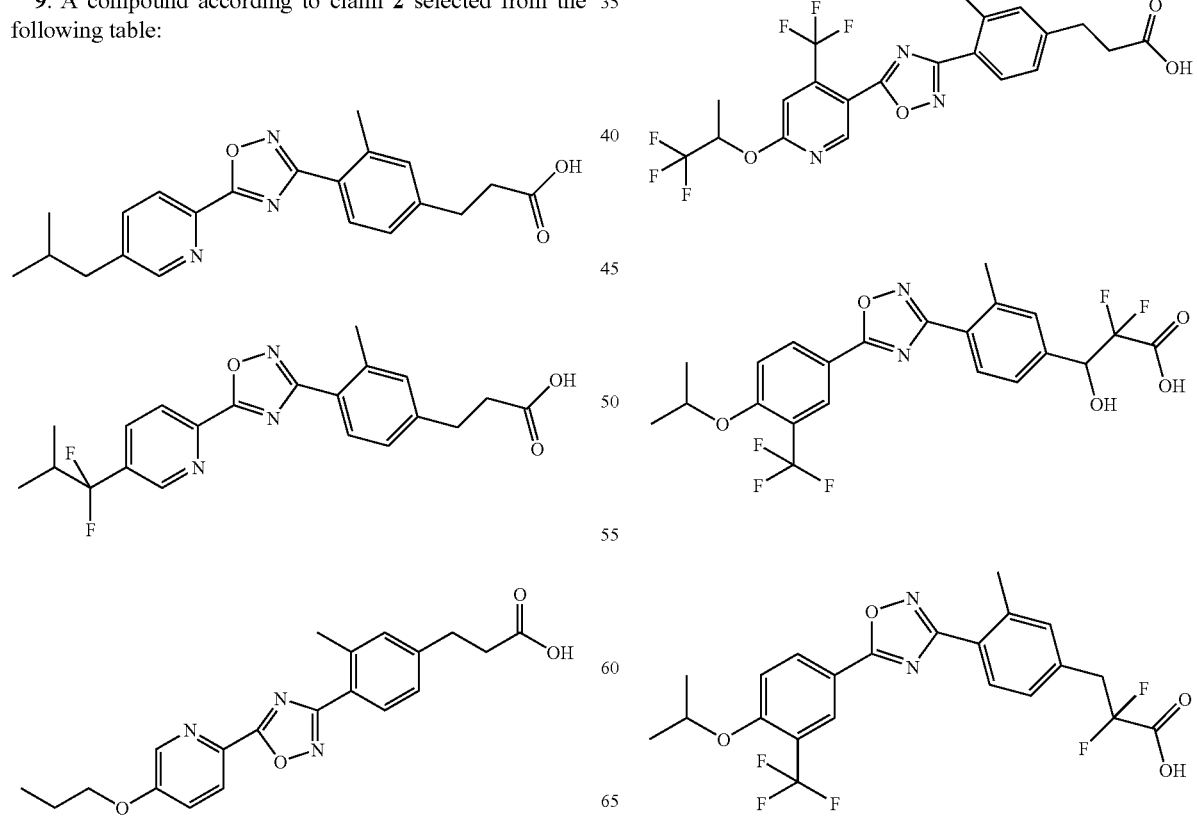

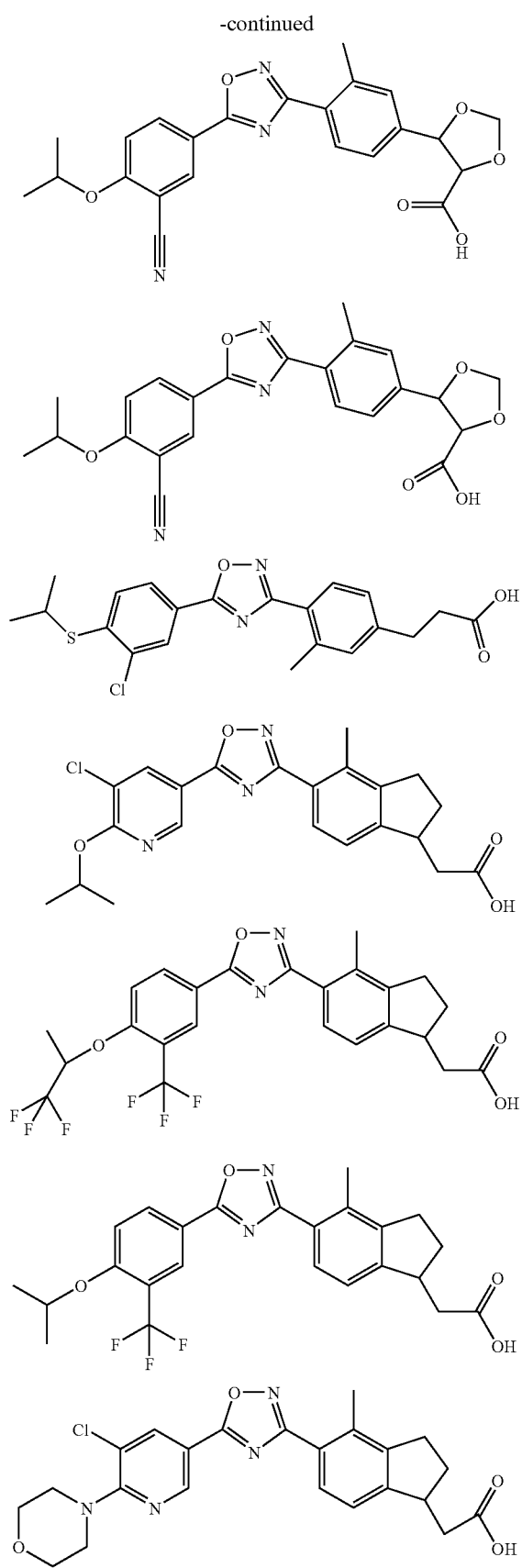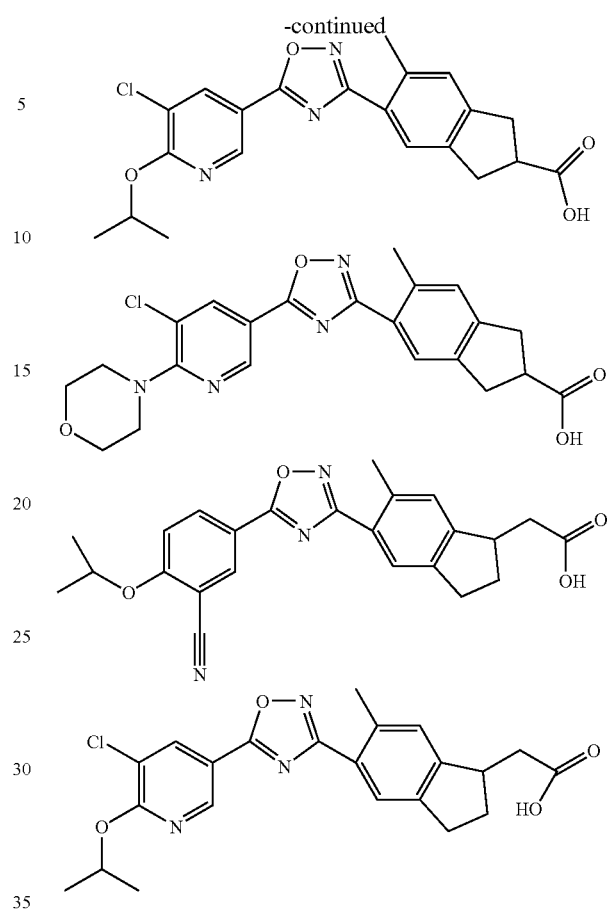
or a pharmaceutically acceptable salt of any of the compounds above.
10. A pharmaceutical composition comprised of a compound in accordance with claim 1 in combination with a pharmaceutically acceptable carrier.
11. A compound according to claim 1 of Formula Ig:
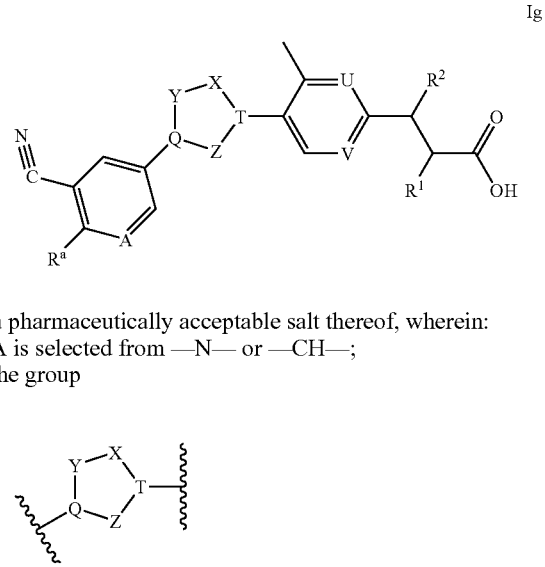
or a pharmaceutically acceptable salt thereof, wherein:
A is selected from —N— or —CH—;
the group
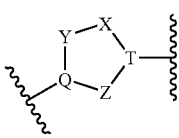

is:

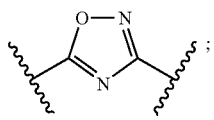

R¹ and R² are —H, or R¹ and R² may be joined together with the atoms to which they are attached to form cyclopropyl;

U and V are —C(R⁹)—;

each R⁹ is —H, or

For U or V, R⁹ and R¹ or R⁹ and R² may be joined together with the atoms to which they are attached to form a 5 membered ring, thus forming a fused partially aromatic bicyclic ring system of 9 atoms with the phenyl ring to which R⁹ is attached;

R$^a$ is selected from the group consisting of: thienyl, NR⁷R⁸, $C_{1-4}$alkyl, $C_{3-6}$cycloalkyl, $C_{1-4}$alkoxy and $C_{3-6}$cycloalkoxy, wherein said $C_{1-4}$alkyl, $C_{3-6}$cycloalkyl, $C_{1-4}$alkoxy and $C_{3-6}$cycloalkoxy are each optionally substituted from one up to the maximum number of substitutable positions with fluoro;

R⁷ and R⁸ are independently selected from the group consisting of: —H and $C_{1-6}$alkyl, optionally substituted with one to three fluoro groups, and R⁷ and R⁸ may be joined together with the nitrogen atom to which they are attached to form a saturated monocyclic ring of 3 to 8 atoms, said ring is optionally substituted with one to three fluoro groups.

12. A compound according to claim 11 selected from the group consisting of:

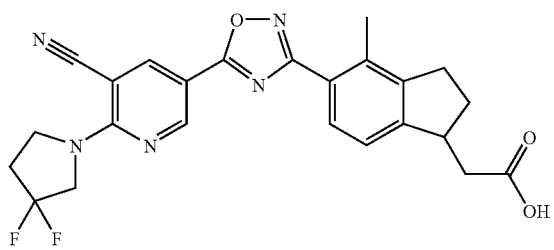

or a pharmaceutically acceptable salt of any of the above.

13. A compound according to claim 1 of Formula Ih:

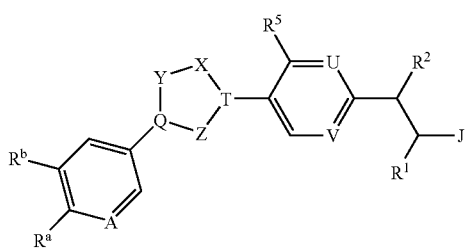

Ih or a pharmaceutically acceptable salt thereof, wherein:

A is selected from —N— or —CH—;

the group

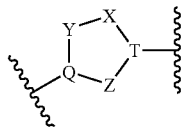

is:

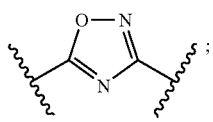

R¹ and R² are —H, or R¹ and R² may be joined together with the atoms to which they are attached to form cyclopropyl;

R⁵ is —H or —CH₃;

U and V are —C(R⁹)—;

each R⁹ is —H, or

For U or V, R⁹ and R¹ or R⁹ and R² may be joined together with the atoms to which they are attached to form a 5 membered ring, thus forming a fused partially aromatic bicyclic ring system of 9 atoms with the phenyl ring to which R⁹ is attached;

R$^a$ is selected from the group consisting of: —F, NR⁷R⁸, $C_{1-4}$alkyl, $C_{3-6}$cycloalkyl, $C_{1-4}$alkoxy and $C_{3-6}$cycloalkoxy, wherein said $C_{1-4}$alkyl, $C_{3-6}$cycloalkyl, $C_{1-4}$alkoxy and $C_{3-6}$cycloalkoxy are each optionally substituted from one up to the maximum number of substitutable positions with fluoro;

R⁷ and R⁸ are independently selected from the group consisting of: —H and $C_{1-6}$alkyl, optionally substituted with one to three fluoro groups, and R⁷ and R⁸ may be joined together with the nitrogen atom to which they are attached to form a saturated monocyclic ring of 3 to 8 atoms, said ring is optionally substituted with one to three fluoro groups;

R$^b$ is Cl or I;

J is selected from the group consisting of: —CO₂H,

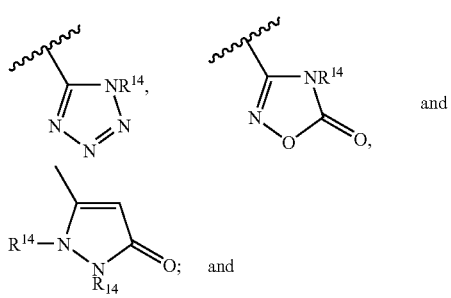

and each R¹⁴ is independently selected from the group consisting of: —H and CH₃.

14. A compound according to claim 13, wherein:

For U, R⁹ and R¹ are joined together with the atoms to which they are attached to form a 5 membered ring, thus forming a fused partially aromatic bicyclic ring system of 9 atoms with the phenyl ring to which $R^9$ is attached;
$R^5$ is $CH_3$;
$R^b$ is Cl; and
J is selected from the group consisting of: —$CO_2H$,
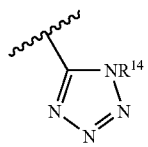 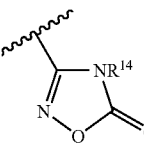 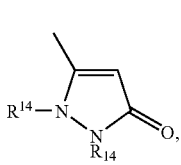
wherein each $R^{14}$ is independently selected from the group consisting of: —H and —$CH_3$.
15. A compound according to claim 13 selected from the group consisting of:
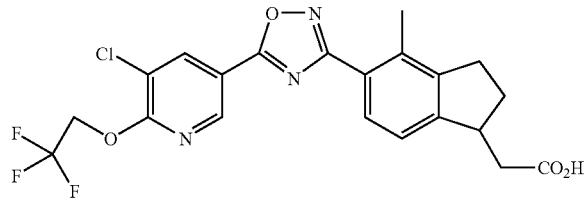
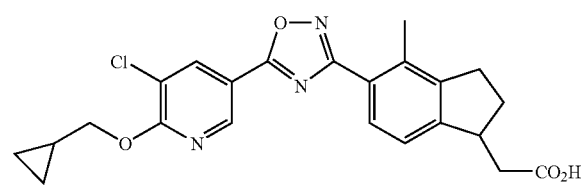
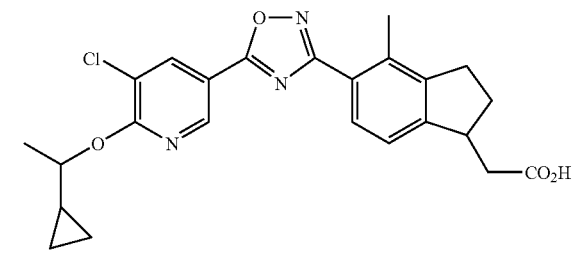
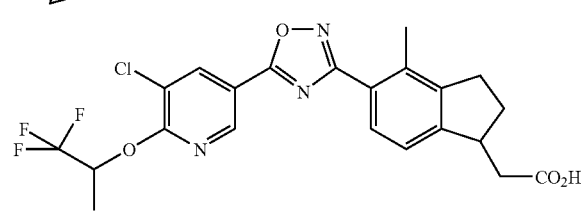
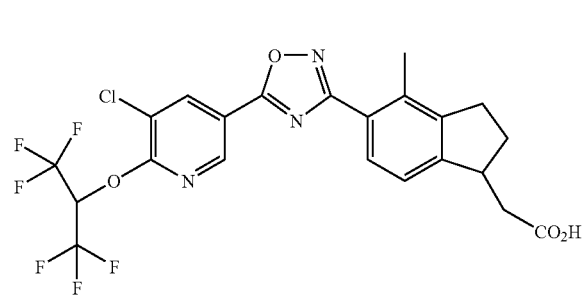
-continued
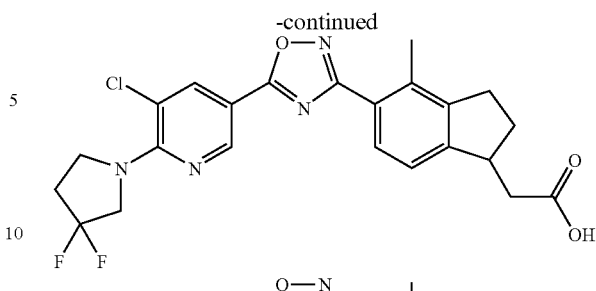
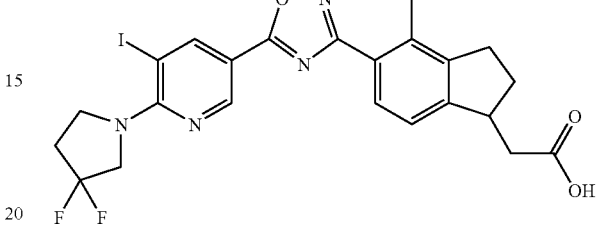
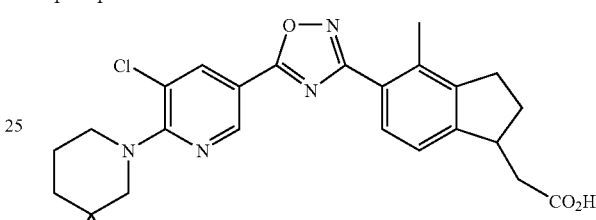
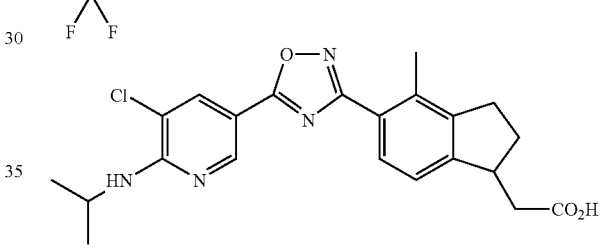
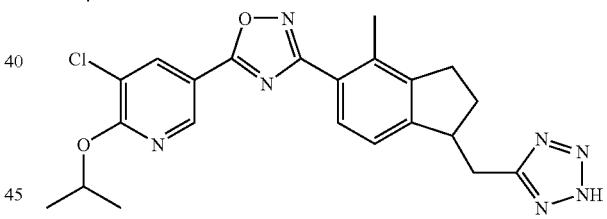
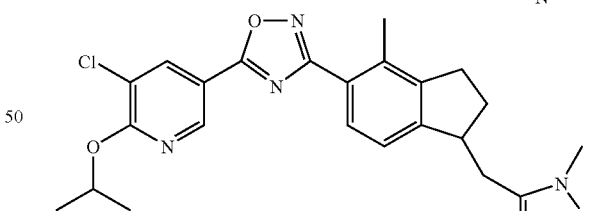
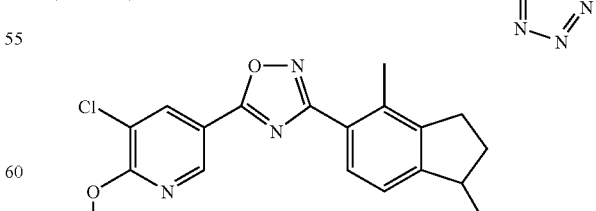

171
-continued
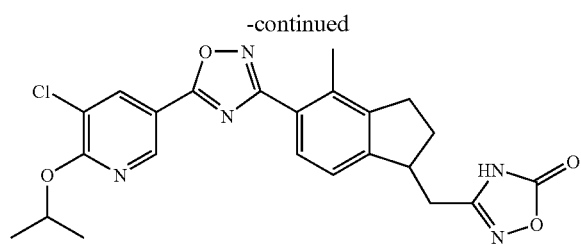
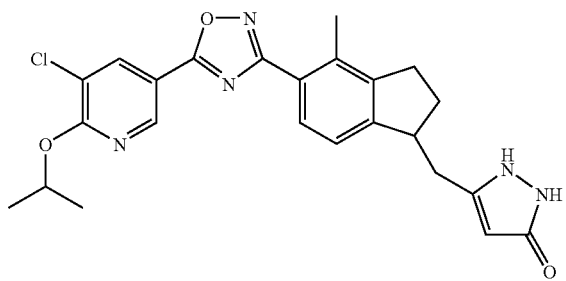
172
-continued
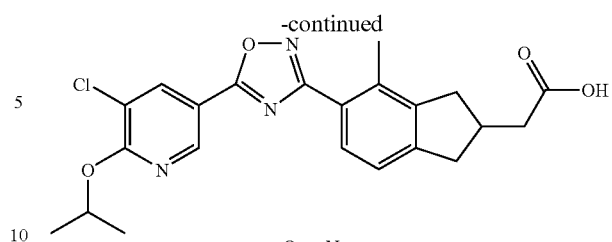
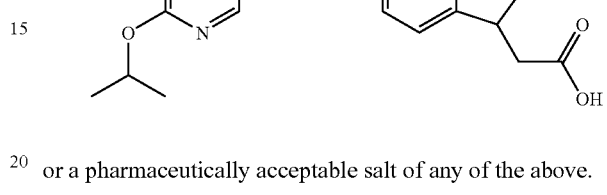
or a pharmaceutically acceptable salt of any of the above.
* * * * *